(12) United States Patent
Lin et al.

(10) Patent No.: US 11,208,416 B2
(45) Date of Patent: *Dec. 28, 2021

(54) SELECTIVE INHIBITORS OF PROTEIN ARGININE METHYTRANSTERASE 5 (PRMT5)

(71) Applicant: Prelude Therapeutics, Incorporated, Wilmington, DE (US)

(72) Inventors: Hong Lin, Exton, PA (US); Juan Luengo, Phoenixville, PA (US); Rupa Shetty, Blue Bell, PA (US); Michael Hawkins, Ambler, PA (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/985,643

(22) Filed: Aug. 5, 2020

(65) Prior Publication Data

US 2020/0361946 A1 Nov. 19, 2020

Related U.S. Application Data

(63) Continuation of application No. 16/744,771, filed on Jan. 16, 2020, which is a continuation of application No. 16/059,909, filed on Aug. 9, 2018, now Pat. No. 10,570,140.

(60) Provisional application No. 62/543,141, filed on Aug. 9, 2017, provisional application No. 62/630,581, filed on Feb. 14, 2018, provisional application No. 62/664,442, filed on Apr. 30, 2018.

(51) Int. Cl.
    C07D 487/04      (2006.01)
    C07H 19/14       (2006.01)
    A61K 31/7064     (2006.01)
    A61P 35/02       (2006.01)
    C07D 519/00      (2006.01)

(52) U.S. Cl.
    CPC ........ *C07D 487/04* (2013.01); *A61K 31/7064* (2013.01); *A61P 35/02* (2018.01); *C07D 519/00* (2013.01); *C07H 19/14* (2013.01)

(58) Field of Classification Search
    CPC .... C07D 487/04; C07D 519/00; C07H 19/14; A61K 31/7064; A61P 35/02
    See application file for complete search history.

(56) References Cited

U.S. PATENT DOCUMENTS 10,570,140 B2 * 2/2020 Lin ...................... C07D 487/04
2016/0244475 A1   8/2016 Tatlock et al.

FOREIGN PATENT DOCUMENTS

WO    2012075500 A2    6/2012
WO    2012097000 A1    7/2012
WO    2015200680 A2    12/2015
WO    2016178870 A1    11/2016
WO    2017032840 A1    3/2017
WO    2017153186 A1    9/2017
WO    2017218802 A1    12/2017
WO    2018065365 A1    4/2018
WO    2018075601 A1    4/2018
WO    2018085818 A1    5/2018
WO    2018085833 A2    5/2018
WO    2018152501 A1    8/2018
WO    2018152548 A1    8/2018
WO    2018160824 A1    9/2018
WO    2018160855 A1    9/2018
WO    2019032859 A1    2/2019
WO    2019084470 A1    5/2019

OTHER PUBLICATIONS

Chung et al., "Protein Arginine Methyltransferase 5 (PRMT5) Inhibition Induces Lymphoma Cell Death through Reactivation of the Retinoblastoma Tumor Suppressor Pathway and Polycomb Repressor Complex 2 (PRC2) Silencing", Journal of Biological Chemistry, Dec. 2013, vol. 288, No. 49, 35534-35547 [Cited in related U.S. Appl. No. 16/059,909].
Hsu et al., "The spliceosome is a therapeutic vulnerability in MYC-driven cancer", Nature, Sep. 2015, 525(7569), 384-388 [Cited in related U.S. Appl. No. 16/059,909].
Hulpia et al., "Synthesis of a 3-C-ethynyl-[beta]-d-ribofuranose purine nucleoside library: Discovery of C7-deazapurine analogs as potent antiproliferative nucleosides", European Journal of Medicinal Chemistry, Jul. 29, 2018, vol. 157, 248-267 [Cited in related U.S. Appl. No. 16/059,909].
Koh et al., "MYC regulates the core pre-mRNA splicing machinery as an essential step in lymphomagenesis", Nature, May 2015, 523(7558), 96-100 [Cited in related U.S. Appl. No. 16/059,909].
Pal et al., "Human SWI/SNF-Associated PRMT5 Methylates Histone H3 Arginine 8 and Negatively Regulates Expression of ST7 and NM23 Tumor Suppressor Genes", Molecular Cellular Biology, Nov. 2004, 9630-9645 [Cited in related U.S. Appl. No. 16/059,909].

(Continued)

Primary Examiner — Tracy Vivlemore
Assistant Examiner — Ebenezer O Sackey
(74) Attorney, Agent, or Firm — BakerHostetler

(57) ABSTRACT

The disclosure is directed to compounds of Formula I

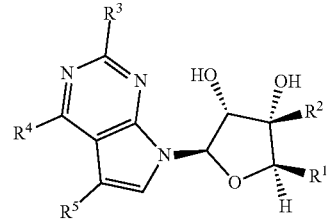

Pharmaceutical compositions comprising compounds of Formula I, as well as methods of their use and preparation, are also described.

37 Claims, No Drawings

(56) References Cited

OTHER PUBLICATIONS

Pal et al., "mSin3A/Histone Deacetylase 2- and PRMT5-Containing Brg1 Complex Is Involved in Transcriptional Repression of the Myc Target Gene cad", Molecular and Cellular Biology, Nov. 2003, vol. 23, No. 21, 7475-7487 [Cited in related U.S. Appl. No. 16/059,909].
Wang et al., "Protein Arginine Methyltransferase 5 Suppresses the Transcription of the RB Family of Tumor Suppressors in Leukemia and Lymphoma Cells", Molecular and Cellular Biology, Oct. 2008, 6262-6277 [Cited in related U.S. Appl. No. 16/059,909].
Zhao et al., "PRMT5-mediated methylation of histone H4R3 recruits DNMT3A, coupling histone and DNA methylation in gene silencing", Nature Structural Molecular Biology, Feb. 2009, 16, 304-311 [Cited in related U.S. Appl. No. 16/059,909].

* cited by examiner

SELECTIVE INHIBITORS OF PROTEIN ARGININE METHYTRANSFERASE 5 (PRMT5)

CROSS-REFERENCE TO RELATED APPLICATIONS

This application is a continuation of U.S. patent application Ser. No. 16/744,771, filed Jan. 16, 2020, which is a continuation of U.S. patent application Ser. No. 16/059,909, filed Aug. 9, 2018, now U.S. Pat. No. 10,570,140, which claims the benefit of priority to U.S. Provisional Patent Application No. 62/543,141, filed Aug. 9, 2017, U.S. Provisional Patent Application No. 62/630,581, filed Feb. 14, 2018, and U.S. Provisional Patent Application No. 62/664,442, filed Apr. 30, 2018. The entirety of each of these applications is incorporated by reference herein.

TECHNICAL FIELD

The disclosure is directed to PRMT5 inhibitors and methods of their use.

BACKGROUND

Protein arginine methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG, N'G symmetric dimethylarginine (SDMA). The formation of methylated arginines is catalyzed by the protein arginine methyl transferases (PRMTs) family of methyltransferases. Currently, there are nine PRMTs annotated in the human genome. The majority of these enzymes are Type I enzymes (PRMT1, -2, -3, -4, -6, -8) that are capable of mono- and asymmetric dimethylation of arginine, with S-adenosylmethionine (SAM) as the methyl donor. PRMT-5, -7 and -9 are considered to be Type II enzymes that catalyze symmetric dimethylation of arginines. Each PRMT species harbors the characteristic motifs of seven beta strand methyltransferases (Katz et al., 2003), as well as additional "double E" and "THW" sequence motifs particular to the PRMT subfamily.

PRMT5 is as a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Role of PRMTs in Cancer

Aberrant expression of PRMTs has been identified in human cancers, and PRMTs are considered to be therapeutic targets. Global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. Pal et al., Mol. Cell. Biol. 2003, 7475; Pal et al. Mol. Cell. Biol. 2004, 9630; Wang et al. Mol. Cell. Biol. 2008, 6262; Chung et al. J Biol Chem 2013, 5534. In addition to its well-documented oncogenic functions in transcription and translation, the transcription factor MYC also safeguards proper pre-messenger-RNA splicing as an essential step in lymphomagenesis. Koh et al. Nature 2015, 523 7558; Hsu et al. Nature 2015 525, 384.

The discovery of cancer dependencies has the potential to inform therapeutic strategies and to identify putative drug targets. Integrating data from comprehensive genomic profiling of cancer cell lines and from functional characterization of cancer cell dependencies, it has been recently discovered that loss of the enzyme methylthioadenosine phosphorylase (MTAP) confers a selective dependence on protein arginine methyltransferase 5 (PRMT5) and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. Together, these findings reveal PRMT5 as a potential vulnerability across multiple cancer lineages augmented by a common "passenger" genomic alteration.

Role of PRMT5 in Hemoglobinopathies

The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by the protein arginine methyltransferase PRMT5. Zhao et al. Nat Struct Mol Biol. 2009 16, 304. PRMT5-mediated methylation of histone H4R3 recruits DNMT3A, coupling histone and DNA methylation in gene silencing.

PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These studies provide the basis for developing PRMT5 inhibitors as targeted therapies for thalassemia and SCD.

SUMMARY

The disclosure is directed to compounds of Formula I:

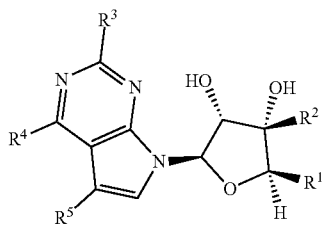

or a pharmaceutically acceptable salt or solvate thereof; wherein

R¹ is —C₀-C₆alk-C₁-C₆alkyl, —C₀-C₆alk-C₁-C₆haloalkyl, —C₁-C₆alk-O—C₁-C₆alkyl, —C₁-C₆alk-S—C₁-C₆alkyl, —C₁-C₆alk-S—C₁-C₆alk-CO₂H, —C₁-C₆alk-aryl, —C₁-C₆alk-O-aryl, —C₁-C₆alk-NH-aryl, —C₁-C₆alk-S-aryl, —C₀-C₆alk-heteroaryl, —C₁-C₆alk-O-heteroaryl, —C₁-C₆alk-S-heteroaryl, —C₁-C₆alk-NH-heteroaryl, or —C(O)NH-aryl;

R² is —C₁-C₆alkyl, —C₁-C₆haloalkyl, —C₂-C₆alkenyl, or —C₂-C₆alkynyl;

R³ is H, halo, NH₂, or —C₁-C₆alkyl;

R⁴ is H, halo, —C₁-C₆alkyl, —C₁-C₆alk-O—C₁-C₆alkyl, —NR⁶R⁶', —NHC(O)NR⁶R⁶', —NHC(S)NR⁶R⁶', —NH—O—R⁶, or —NH—NR⁶R⁶';

R⁵ is H, halo, —C₁-C₆alkyl, —C₁-C₆haloalkyl, —C₂-C₆alkenyl, —C₂-C₆alkynyl, or —C₁-C₆alk-OH; and R⁶ and R⁶' are each independently H, C₁-C₆alkyl, or —C₁-C₆alk-OC₁-C₆alkyl;

or R⁶ and R⁶', together with the atom to which they are attached, form a C₃-C₆heterocycloalkyl ring.

Stereoisomers of the compounds of Formula I, and the pharmaceutical salts and solvates thereof, are also described. Methods of using compounds of Formula I are described, as well as pharmaceutical compositions including the compounds of Formula I.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "alkyl," when used alone or as part of a substituent group, refers to a straight- or branched-chain hydrocarbon group having from 1 to 12 carbon atoms ("C₁-C₁₂"), preferably 1 to 6 carbons atoms ("C₁-C₆"), in the group. Examples of alkyl groups include methyl (Me, C₁alkyl), ethyl (Et, C₂alkyl), n-propyl (C₃alkyl), isopropyl (C₃alkyl), butyl (C₄alkyl), isobutyl (C₄alkyl), sec-butyl (C₄alkyl), tert-butyl (C₄alkyl), pentyl (C₅alkyl), isopentyl (C₅alkyl), tert-pentyl (C₅alkyl), hexyl (C₆alkyl), isohexyl (C₆alkyl), and the like.

The term "halo" when used alone or as part of a substituent group refers to chloro, fluoro, bromo, or iodo.

The term "haloalkyl" when used alone or as part of a substituent group refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl (—CF₃), chloromethyl (—CH₂Cl), and the like.

The term "cycloalkyl" when used alone or as part of a substituent group refers to cyclic-containing, non-aromatic hydrocarbon groups having from 3 to 10 carbon atoms ("C₃-C₁₀"), preferably from 3 to 6 carbon atoms ("C₃-C₆"). Examples of cycloalkyl groups include, for example, cyclopropyl (C₃), cyclobutyl (C₄), cyclopropylmethyl (C₄), cyclopentyl (C₅), cyclohexyl (C₆), 1-methylcyclopropyl (C₄), 2-methylcyclopentyl (C₄), adamantanyl (C₁₀), and the like.

The term "heterocycloalkyl" when used alone or as part of a substituent group refers to any three to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "alkenyl" when used alone or as part of a substituent group refers to a straight- or branched-chain group having from 2 to 12 carbon atoms ("C₂-C₁₂"), preferably 2 to 4 carbons atoms ("C₂-C₄"), in the group, wherein the group includes at least one carbon-carbon double bond. Examples of alkenyl groups include vinyl (—CH=CH₂; C₂alkenyl) allyl (—CH₂—CH=CH₂; C₃alkenyl), propenyl (—CH=CHCH₃; C₃alkenyl); isopropenyl (—C(CH₃)=CH₂; C₃alkenyl), butenyl (—CH=CHCH₂CH₃; C₄alkenyl), sec-butenyl (—C(CH₃)=CHCH₃; C₄alkenyl), iso-butenyl (—CH=C(CH₃)₂; C₄alkenyl), 2-butenyl (—CH₂CH=CHCH₃; C₄alkyl), pentenyl (—CH=CHCH₂CH₂CH₃; C₅alkenyl), and the like.

The term "alkynyl" when used alone or as part of a substituent group refers to a straight- or branched-chain group having from 1 to 12 carbon atoms ("C₁-C₁₂"), preferably 1 to 4 carbons atoms ("C₂-C₄"), in the group, and wherein the group includes at least one carbon-carbon triple bond. Examples of alkynyl groups include ethynyl (—C≡CH; C₂alkynyl); propargyl (—CH₂—C≡CH; C₃alkynyl), propynyl (—C≡CCH₃; C₃alkynyl); butynyl (—C≡CCH₂CH₃; C₄alkynyl), pentynyl (—C≡CCH₂CH₂CH₃; C₅alkynyl), and the like.

The term "aryl" when used alone or as part of a substituent group refers to a mono- or bicyclic-aromatic hydrocarbon ring structure having 6 or 10 carbon atoms in the ring, wherein one or more of the carbon atoms in the ring is optionally substituted with a halogen atom, a —C₁-C₃ alkyl group, an amino-substituted —C₁-C₃ alkyl group, a C₁-C₃haloalkyl group, an amino group (i.e., —NH₂), or a substituted amino group. The term "aryl" when used alone or as part of a substituent group also refers to a mono- or bicyclic-aromatic hydrocarbon ring structure having 6 or 10 carbon atoms in the ring, wherein one or more of the carbon atoms in the ring is optionally substituted with a halogen atom, a —C₁-C₃ alkyl group, an amino-substituted —C₁-C₃ alkyl group, an alkylamino-substituted —C₁-C₃ alkyl group, a hydroxy-substituted —$C_1$-$C_3$ alkyl group, a $C_1$-$C_3$haloalkyl group, an —O—$C_1$-$C_3$haloalkyl group, an amino group (i.e., —$NH_2$), or a substituted amino group. Halogen atoms include chlorine, fluorine, bromine, and iodine. Amino-substituted —$C_1$-$C_3$ alkyl groups include —$CH_2$—$NH_2$, —$CH_2CH_2$—$NH_2$, and the like. Alkylamino-substituted —$C_1$-$C_3$ alkyl groups include —$CH_2$—$NHCH_3$ and the like. $C_1$-$C_3$haloalkyl groups include, for example, —$CF_3$, —$CH_2CF_3$, and the like. Substituted amino groups include, for example, —NH—C(O)—$NH_2$. Hydroxy-substituted —$C_1$-$C_3$ alkyl groups include —$CH_2$—OH and the like. The term "aryl" also includes a mono- or bicyclic-aromatic hydrocarbon ring structure having 6 or 10 carbon atoms in the ring, wherein two adjacent carbon atoms in the ring are optionally substituted such that said two adjacent carbon atoms and their respective substituents form a heterocyclic ring. Thus, aryl groups include, for example, 2,3-dihydrobenzofuran and 1,3-benzodioxole. Examples of aryl groups (substituted and unsubstituted) include phenyl, aminomethylphenyl, 3-(aminomethyl)phenyl, phenylurea, methylchlorophenyl, 3-methyl-4-chlorophenyl, fluorochlorophenyl, 3-fluoro-4-chlorophenyl, naphtyl, fluorophenyl, trifluoromethylphenyl, 4-trifluoromethylphenyl, fluoro-triflouromethylphenyl, 3-fluoro-4-trifluoromethylphenyl, 4-fluoro-3-trifluoromethylphenyl, difluorophenyl, 3,4-difluorophenyl, chlorophenyl, 4-chlorophenyl, 4-chloro-2-(hydroxymethyl)phenyl, 2-(aminomethyl)-4-chlorophenyl, 4-chloro-2-((methylamino)methyl)phenyl, dichlorophenyl, 3,4-dichlorophenyl, bromophenyl, iodophenyl, chlorofluorophenyl, fluoronaphthyl, difluoronaphthyl, chloronaphthyl, bromonaphthyl, iodonaphthyl, methylphenyl, ethylphenyl, 4-isopropylphenyl, 4-(trifluoromethoxy)phenyl, benzo[d][1,3]dioxolyl, and the like.

The term "heteroaryl" when used alone or as part of a substituent group refers to a mono- or bicyclic-aromatic ring structure including carbon atoms as well as up to four heteroatoms selected from nitrogen, oxygen, and sulfur. Heteroaryl rings can include a total of 5, 6, 9, or 10 ring atoms. The heteroaryl moiety can be unsubstituted, or one or more of the carbon atoms in the ring can be substituted with a halogen atom; an amino group; a substituted amino group, including an amino group substituted with a —$C_1$-$C_6$ cycloalkyl group, a —O—$C_1$-$C_3$alkyl group, or a —$C_1$-$C_6$ alkyl group; or a —$C_1$-$C_3$ alkyl group. Halogen atoms include chlorine, fluorine, bromine, and iodine. Examples of heteroaryl groups include but are not limited to, pyrrolyl, furyl, thiophenyl (thienyl), oxazolyl, imidazolyl, purazolyl, isoxazolyl, isothiazolyl, triazolyl, thiadiazolyl, pyrazolyl, pyridyl, pyridazinyl, pyrimidinyl, pyrazinyl, pyranyl, furazanyl, indolizinyl, indolyl, indol-6-yl, isoindolinyl, indazolyl, indazol-6-yl, benzofuranyl, benzothiophenyl, benzimidazolyl, benzthiazolyl, purinyl, quinolizinyl, quinolinyl, aminoquinolinyl, aminohaloquinolinyl, quinolin-7-yl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, 2-(methoxyamino)quinolin-7-yl, 2-aminoquinolin-7-yl, isoquinolinyl, isothiazolyl, cinnolinyl, phthalazinyl, quinazolinyl, quinoxalinyl, naphthyridinyl, pteridinyl, imidazo[1,2-a]pyridinyl, substituted imidazo[1,2-a]pyridinyl, 3-methylimidazo[1,2-a]pyridin-7-yl, and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond. In some aspects, the $C_1$-$C_6$alk can be substituted with one or more —OH, —$NH_2$, or halo (e.g., —F, —Cl, —Br, with —F being preferred) substituents.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I as described herein, as well as their subgenera, which expression includes the stereoisomers (e.g., entaniomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

The disclosure is directed to compounds of Formula I

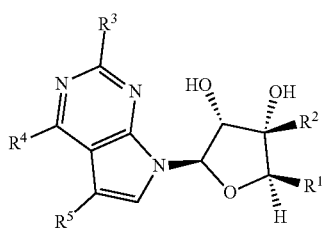

I

According to the disclosure, $R^1$ in Formula I is $R^1$—$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-CO$_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl. In some aspects, $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-CO$_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, —$C_1$-$C_6$alk-NH-heteroaryl, or —C(O)NH-aryl.

In some aspects, $R^1$ is —$C_0$-$C_6$alk-$C_1$-$C_6$alkyl, for example, —$C_0$alk-$C_1$alkyl, —$C_1$alk-$C_1$alkyl, —$C_2$alk-$C_1$alkyl, —$C_3$alk-$C_1$alkyl, —$C_4$alk-$C_1$alkyl, —$C_5$alk-$C_1$alkyl, —$C_0$alk-$C_1$alkyl, —$C_0$alk-$C_2$alkyl, —$C_1$alk-$C_2$alkyl, —$C_2$alk-$C_2$alkyl, —$C_3$alk-$C_2$alkyl, —$C_4$alk-$C_2$alkyl, —$C_5$alk-$C_2$alkyl, —$C_6$alk-$C_2$alkyl, —$C_0$alk-$C_3$alkyl, —$C_1$alk-$C_3$alkyl, —$C_2$alk-$C_3$alkyl, —$C_3$alk-$C_3$alkyl, —$C_4$alk-$C_3$alkyl, —$C_5$alk-$C_3$alkyl, —$C_6$alk-$C_3$alkyl, —$C_0$alk-$C_4$alkyl, —$C_1$alk-$C_4$alkyl, —$C_2$alk-$C_4$alkyl, —$C_3$alk-$C_4$alkyl, —$C_4$alk-$C_4$alkyl, —$C_5$alk-$C_4$alkyl, —$C_6$alk-$C_4$alkyl, —$C_0$alk-$C_5$alkyl, —$C_1$alk-$C_5$alkyl, —$C_2$alk-$C_5$alkyl, —$C_3$alk-$C_5$alkyl, —$C_4$alk-$C_5$alkyl, —$C_5$alk-$C_5$alkyl, —$C_6$alk-$C_5$alkyl, —$C_0$alk-$C_6$alkyl, —$C_1$alk-$C_6$alkyl, —$C_2$alk-$C_6$alkyl, —$C_3$alk-$C_6$alkyl, —$C_4$alk-$C_6$alkyl, —$C_5$alk-$C_6$alkyl, —$C_0$alk-$C_6$alkyl, methyl, ethyl, propyl, isopropyl, butyl, isobutyl, s-butyl, t-butyl, pentyl, —CH(OH)—$C_1$-$C_6$alkyl (for example, —CH(OH)— methyl, —CH(OH)-ethyl, —CH(OH)-propyl, —CH(OH)-isopropyl, —CH(OH)-pentyl, —CH(OH)-butyl, and the like), —CH(F)—$C_1$-$C_6$alkyl, —CH(NH$_2$)—$C_1$-$C_6$alkyl, —CH(Me)—$C_1$-$C_6$alkyl, —C(Me)(OH)—$C_1$-$C_6$alkyl, and the like.

In other aspects, $R^1$ is —$C_0$-$C_6$alk-$C_1$-$C_6$haloalkyl, for example, —$C_0$alk-$C_1$haloalkyl, —$C_1$alk-$C_1$haloalkyl, —$C_2$alk-$C_1$haloalkyl, —$C_3$alk-$C_1$haloalkyl, —$C_4$alk-$C_1$haloalkyl, —$C_5$alk-$C_1$haloalkyl, —$C_6$alk-$C_1$haloalkyl, —$C_0$alk-$C_2$haloalkyl, —$C_1$alk-$C_2$haloalkyl, —$C_2$alk-$C_2$haloalkyl, —$C_3$alk-$C_2$haloalkyl, —$C_4$alk-$C_2$haloalkyl, —$C_5$alk-$C_2$haloalkyl, —$C_6$alk-$C_2$haloalkyl, —$C_0$alk-$C_3$haloalkyl, —$C_1$alk-$C_3$haloalkyl, —$C_2$alk-$C_3$haloalkyl, —$C_3$alk-$C_3$haloalkyl, —$C_4$alk-$C_3$haloalkyl, —$C_5$alk-$C_3$haloalkyl, —$C_6$alk-$C_3$haloalkyl, —$C_0$alk-$C_4$haloalkyl, —$C_1$alk-$C_4$haloalkyl, —$C_2$alk-$C_4$haloalkyl, —$C_3$alk-$C_4$haloalkyl, —$C_4$alk-$C_4$haloalkyl, —$C_5$alk-$C_4$haloalkyl, —$C_6$alk-$C_4$haloalkyl, —$C_0$alk-$C_5$haloalkyl, —$C_1$alk-$C_5$haloalkyl, —$C_2$alk-$C_5$haloalkyl, —$C_3$alk-$C_5$haloalkyl, —$C_4$alk-$C_5$haloalkyl, —$C_5$alk-$C_5$haloalkyl, —$C_6$alk-$C_5$haloalkyl, —$C_0$alk-$C_6$haloalkyl, —$C_1$alk-$C_6$haloalkyl, —$C_2$alk-$C_6$haloalkyl, —$C_3$alk-$C_6$haloalkyl, —$C_4$alk-$C_6$haloalkyl, —$C_5$alk-$C_6$haloalkyl, —$C_6$alk-$C_6$haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, —CH(OH)—$C_1$-$C_6$ haloalkyl (e.g., —CH(OH)-fluoromethyl, —CH(OH)-fluoroethyl, —CH(OH)-fluoropropyl, —CH(OH)-fluoroisopropyl, —CH(OH)-fluoropentyl, —CH(OH)-fluorobutyl), —CH(F)—$C_1$-$C_6$haloalkyl, —CH(NH$_2$)—$C_1$-$C_6$ haloalkyl, —CH(Me)—$C_1$-$C_6$ haloalkyl, —C(Me)(OH)—$C_1$-$C_6$ haloalkyl, and the like. Thus, in some aspects, $R^1$ is chloromethyl (i.e., —CH$_2$—Cl.)

In some aspects, $R^1$ is —$C_1$-$C_6$alk-O—$C_1$-$C_6$alkyl, for example, —$C_1$alk-O—$C_1$alkyl, —$C_2$alk-O—$C_1$alkyl, —$C_3$alk-O—$C_1$alkyl, —$C_4$alk-O—$C_1$alkyl, —$C_5$alk-O—$C_1$alkyl, —$C_6$alk-O—$C_1$alkyl, —$C_1$alk-O—$C_2$alkyl, —$C_2$alk-O—$C_2$alkyl, —$C_3$alk-O—$C_2$alkyl, —$C_4$alk-O—$C_2$alkyl, —$C_5$alk-O—$C_2$alkyl, —$C_6$alk-O—$C_2$alkyl, —$C_1$alk-O—$C_3$alkyl, —$C_2$alk-O—$C_3$alkyl, —$C_3$alk-O—$C_3$alkyl, —$C_4$alk-O—$C_3$alkyl, —$C_5$alk-O—$C_3$alkyl, —$C_6$alk-O—$C_3$alkyl, —$C_1$alk-O—$C_4$alkyl, —$C_2$alk-O—$C_4$alkyl, —$C_3$alk-O—$C_4$alkyl, —$C_4$alk-O—$C_4$alkyl, —$C_5$alk-O—$C_4$alkyl, —$C_6$alk-O—$C_4$alkyl, —$C_1$alk-O—$C_5$alkyl, —$C_2$alk-O—$C_5$alkyl, —$C_3$alk-O—$C_5$alkyl, —$C_4$alk-O—$C_5$alkyl, —$C_5$alk-O—$C_5$alkyl, —$C_6$alk-O—$C_5$alkyl, —$C_1$alk-O—$C_6$alkyl, —$C_2$alk-O—$C_6$alkyl, —$C_3$alk-O—$C_6$alkyl, —$C_4$alk-O—$C_6$alkyl, —$C_5$alk-O—$C_6$alkyl, or —$C_6$alk-O—$C_6$alkyl. In some embodiments, $R^1$ is —$CH_2$—O—$CH_3$.

In some aspects, $R^1$ is —$C_1$-$C_6$alk-S—$C_1$-$C_6$alkyl, for example, —$C_1$alk-S—$C_1$alkyl, —$C_2$alk-S—$C_1$alkyl, —$C_3$alk-S—$C_1$alkyl, —$C_4$alk-S—$C_1$alkyl, —$C_5$alk-S—$C_1$alkyl, —$C_6$alk-S—$C_1$alkyl, —$C_1$alk-S—$C_2$alkyl, —$C_2$alk-S—$C_2$alkyl, —$C_3$alk-S—$C_2$alkyl, —$C_4$alk-S—$C_2$alkyl, —$C_5$alk-S—$C_2$alkyl, —$C_6$alk-S—$C_2$alkyl, —$C_1$alk-S—$C_3$alkyl, —$C_2$alk-S—$C_3$alkyl, —$C_3$alk-S—$C_3$alkyl, —$C_4$alk-S—$C_3$alkyl, —$C_5$alk-S—$C_3$alkyl, —$C_6$alk-S—$C_3$alkyl, —$C_1$alk-S—$C_4$alkyl, —$C_2$alk-S—$C_4$alkyl, —$C_3$alk-S—$C_4$alkyl, —$C_4$alk-S—$C_4$alkyl, —$C_5$alk-S—$C_4$alkyl, —$C_6$alk-S—$C_4$alkyl, —$C_1$alk-S—$C_5$alkyl, —$C_2$alk-S—$C_5$alkyl, —$C_3$alk-S—$C_5$alkyl, —$C_4$alk-S—$C_5$alkyl, —$C_5$alk-S—$C_5$alkyl, —$C_6$alk-S—$C_5$alkyl, —$C_1$alk-S—$C_6$alkyl, —$C_2$alk-S—$C_6$alkyl, —$C_3$alk-S—$C_6$alkyl, —$C_4$alk-S—$C_6$alkyl, —$C_5$alk-S—$C_6$alkyl, or —$C_6$alk-S—$C_6$alkyl. In some embodiments, $R^1$ is —$CH_2$—S—$CH_3$.

In some aspects, $R^1$ is —$C_1$-$C_6$alk-S—$C_1$-$C_6$alk-$CO_2$H, for example, —$C_1$alk-S— $C_1$-$C_6$alk-$CO_2$H, —$C_2$alk-S—$C_1$-$C_6$alk-$CO_2$H, —$C_3$alk-S—$C_1$-$C_6$alk-$CO_2$H, —$C_4$alk-S—$C_1$-$C_6$alk-$CO_2$H, —$C_5$alk-S—$C_1$-$C_6$alk-$CO_2$H, —$C_6$alk-S—$C_1$-$C_6$alk-$CO_2$H, —$C_1$-$C_6$alk-S— $C_1$alk-$CO_2$H, —$C_1$-$C_6$alk-S— $C_2$alk-$CO_2$H, —$C_1$-$C_6$alk-S—$C_3$alk-$CO_2$H, —$C_1$-$C_6$alk-S—$C_4$alk-$CO_2$H, —$C_1$-$C_6$alk-S— $C_5$alk-$CO_2$H, —$C_1$-$C_6$alk-S— $C_6$alk-$CO_2$H, and the like. In some embodiments, $R^1$ is —$CH_2$—S—$CH_2CH_2$CH($NH_2$)—$CO_2$H.

In some aspects, $R^1$ is —$C_1$-$C_6$alk-aryl, for example, —$C_1$alk-aryl, —$C_2$alk-aryl, —$C_3$alk-aryl, —$C_4$alk-aryl, —$C_5$alk-aryl, —$C_6$alk-aryl, —$CH_2$aryl, —CH(OH)-aryl, —CH(F)-aryl, —CH($NH_2$)-aryl, —CH(Me)-aryl, —C(Me)(OH)-aryl, and the like.

In some embodiments wherein $R^1$ is —$C_1$-$C_6$alk-aryl, the -aryl is a mono- or bicyclic-aromatic hydrocarbon ring structure having 6 or 10 carbon atoms in the ring, wherein one or more of the carbon atoms in the ring is optionally substituted with a halogen atom, a —$C_1$-$C_3$ alkyl group, an amino-substituted —$C_1$-$C_3$ alkyl group, a $C_1$-$C_3$haloalkyl group, an amino group (i.e., —$NH_2$), or a substituted amino group.

In other embodiments wherein $R^1$ is —$C_1$-$C_6$alk-aryl, the -aryl is a mono- or bicyclic-aromatic hydrocarbon ring structure having 6 or 10 carbon atoms in the ring, wherein one or more of the carbon atoms in the ring is optionally substituted with a halogen atom, a —$C_1$-$C_3$ alkyl group, an amino-substituted —$C_1$-$C_3$ alkyl group, an alkylamino-substituted —$C_1$-$C_3$ alkyl group, a hydroxy-substituted —$C_1$-$C_3$ alkyl group, a $C_1$-$C_3$haloalkyl group, an —O—$C_1$-$C_3$haloalkyl group, an amino group (i.e., —$NH_2$), or a substituted amino group.

In some embodiments wherein $R^1$ is —$C_1$-$C_6$alk-aryl, the -aryl is -4-chlorophenyl, 4-chloro-2-(hydroxymethyl)phenyl, 4-chloro-2-(aminomethyl)phenyl, 4-chloro-2-((methylamino)methyl)phenyl, -3,4-dichlorophenyl, -3,4-difluorophenyl, -3-fluoro-4-chlorophenyl, 3-methyl-4-chlorophenyl, 3-fluoro-4-trifluoromethylphenyl, 4-trifluoromethylphenyl, 4-(trifluoromethoxy)phenyl, 4-fluoro-3-trifluoromethylphenyl, benzo[d][1,3]dioxazole, 4-isopropylphenyl, or -3-chloro-4-fluorophenyl. Thus in some embodiments, $R^1$ is —$CH_2$-difluorophenyl, —$CH_2$-3,4-difluorophenyl, —$CH_2$-4-chlorophenyl, —$CH_2$-(4-chloro-2-(hydroxymethyl)phenyl), —$CH_2$-(4-chloro-2-(aminomethyl)phenyl), —$CH_2$-(4-chloro-2-((methylamino)methyl)phenyl), —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3,4-difluorophenyl, —$CH_2$-3-methyl-4-chlorophenyl, —$CH_2$-4-trifluoromethylphenyl, —$CH_2$-4-(trifluoromethoxy)phenyl, —$CH_2$-3-fluoro-4-trifluoromethylphenyl, —$CH_2$-4-fluoro-3-trifluoromethylphenyl, benzo[d][1,3]dioxazol-5-ylmethyl, —$CH_2$-4-isopropylphenyl, —CH(OH)-4-chlorophenyl, —CH(OH)-4-chloro-2-(hydroxymethyl)phenyl, —CH(OH)-4-chloro-2-(aminomethyl)phenyl, —CH(OH)-4-chloro-2-((methylamino)methyl)phenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-4-trifluoromethylphenyl, —CH(OH)-4-(trifluoromethoxy)phenyl, —CH(OH)-3-fluoro-4-trifluoromethylphenyl, —CH(OH)-4-fluoro-3-trifluoromethylphenyl, —CH(OH)-benzo[d][1,3]dioxazol-5-yl, —CH(OH)-4-isopropylphenyl, —CH(F)-4-chlorophenyl, —CH(F)-4-chloro-2-(hydroxymethyl)phenyl, —CH(F)-4-chloro-2-(aminomethyl)phenyl, —CH(F)-4-chloro-2-((methylamino)methyl)phenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-4-trifluoromethylphenyl, —CH(F)-4-(trifluoromethoxy)phenyl, —CH(F)-3-fluoro-4-trifluoromethylphenyl, —CH(F)-4-fluoro-3-trifluoromethylphenyl, —CH(F)-benzo[d][1,3]dioxazol-5-yl, —CH(F)-4-isopropylphenyl, —CH($NH_2$)-4-chlorophenyl, —CH($NH_2$)-4-chloro-2-(hydroxymethyl)phenyl, —CH($NH_2$)-4-chloro-2-(aminomethyl)phenyl, —CH($NH_2$)-4-chloro-2-((methylamino)methyl)phenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-4-trifluoromethylphenyl, —CH($NH_2$)-4-(trifluoromethoxy)phenyl, —CH($NH_2$)-3-fluoro-4-trifluoromethylphenyl, —CH($NH_2$)-4-fluoro-3-trifluoromethylphenyl, —CH($NH_2$)-benzo[d][1,3]dioxazol-5-yl, —CH($NH_2$)-4-isopropylphenyl, —CH(Me)-4-chlorophenyl, —CH(Me)-4-chloro-2-(hydroxymethyl)phenyl, —CH(Me)-4-chloro-2-(aminomethyl)phenyl, —CH(Me)-4-chloro-2-((methylamino)methyl)phenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-4-trifluoromethylphenyl, —CH(Me)-4-(trifluoromethoxy)phenyl, —CH(Me)-3-fluoro-4-trifluoromethylphenyl, —CH(Me)-4-fluoro-3-trifluoromethylphenyl, —CH(Me)-benzo[d][1,3]dioxazol-5-yl, —CH(Me)-4-isopropylphenyl, —C(Me)(OH)-4-chlorophenyl, —C(Me)(OH)-4-chloro-2-(hydroxymethyl)phenyl, —C(Me)(OH)-4-chloro-2-(aminomethyl)phenyl, —C(Me)(OH)-4-chloro-2-((methylamino)methyl)phenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, —C(Me)(OH)-4-trifluoromethylphenyl, —C(Me)(OH)-4-(trifluoromethoxy)phenyl, —C(Me)(OH)-3-fluoro- 4-trifluoromethylphenyl, —C(Me)(OH)-4-fluoro-3-trifluoromethylphenyl, —C(Me)(OH)-4-isopropylphenyl, or —C(Me)(OH)-benzo[d][1,3]dioxazol-5-yl.

In some embodiments wherein $R^1$ is —$C_1$-$C_6$alk-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, benzo[d][1,3]dioxazole, or -3-chloro-4-fluorophenyl. Thus in some embodiments, $R^1$ is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, benzo[d][1,3]dioxazol-5-ylmethyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(OH)-benzo[d][1,3]dioxazol-5-yl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH(F)-benzo[d][1,3]dioxazol-5-yl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH($NH_2$)-benzo[d][1,3]dioxazol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —CH(Me)-benzo[d][1,3]dioxazol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, —C(Me)(OH)-3-fluoro-4-trifluoromethylphenyl, or —C(Me)(OH)-benzo[d][1,3]dioxazol-5-yl.

In other embodiments wherein $R^1$ is —$C_1$-$C_6$alk-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, or -3-chloro-4-fluorophenyl. Thus in some embodiments, $R^1$ is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, or —C(Me)(OH)-3-fluoro-4-trifluoromethylphenyl.

In some aspects, $R^1$ is —$C_1$-$C_6$alk-O-aryl, for example, —$C_1$alk-O-aryl, —$C_2$alk-O-aryl, —$C_3$alk-O-aryl, —$C_4$alk-O-aryl, —$C_5$alk-O-aryl, —$C_6$alk-O-aryl, —$CH_2$—O-aryl, and the like. In some embodiments wherein $R^1$ is —$C_1$-$C_6$alk-O-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, -3-chloro-4-fluorophenyl, -phenyl, -3-(aminomethyl)phenyl, 3-(urea)phenyl, 3-methyl-4-chlorophenyl, 3-fluoro-4-chlorophenyl, -3-fluoro-4-trifluoromethylphenyl, difluorophenyl, chlorophenyl, 4-chlorophenyl, dichlorophenyl, 3,4-dichlorophenyl, bromophenyl, iodophenyl, or chlorofluorophenyl. Thus in some embodiments, $R^1$ is —$CH_2$—O-phenyl, —$CH_2$—O-difluorophenyl, —$CH_2$—O-3,4-difluorophenyl, —$CH_2$—O-4-chlorophenyl, —$CH_2$—O-3-chloro-4-fluorophenyl, —$CH_2$—O-4-chloro-3-fluorophenyl, —$CH_2$—O-dichlorophenyl, —$CH_2$—O-3,4-dichlorophenyl, —$CH_2$—O-3-methyl-4-chlorophenyl, —$CH_2$—O-3-fluoro-4-trifluoromethylphenyl, —$CH_2$—O-3-(aminomethyl)phenyl, —$CH_2$—O-3-(urea)phenyl. In some embodiments wherein $R^1$ is —$C_1$-$C_6$alk-O-aryl, the -aryl is -4-chloro-2-(hydroxymethyl)phenyl, -4-chloro-2-(aminomethyl)phenyl, -4-chloro-2-((methylamino)methyl)phenyl, -4-trifluoromethylphenyl, -4-(trifluoromethoxy)phenyl, 4-fluoro-3-trifluoromethylphenyl, or -4-isopropylphenyl.

In some aspects, $R^1$ is —$C_1$-$C_6$alk-NH-aryl, for example, —$C_1$alk-NH-aryl, —$C_2$alk NH-aryl, —$C_3$alk-NH-aryl, —$C_4$alk-NH-aryl, —$C_5$alk-NH-aryl, —$C_6$alk-NH-aryl, —$CH_2$—NH-aryl, and the like. In some embodiments wherein $R^1$ is —$C_1$-$C_6$alk-NH-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, -3-chloro-4-fluorophenyl, -phenyl, -3-(aminomethyl)phenyl, 3-(urea)phenyl, 3-methyl-4-chlorophenyl, 3-fluoro-4-chlorophenyl, -3-fluoro-4-trifluoromethylphenyl, difluorophenyl, chlorophenyl, 4-chlorophenyl, dichlorophenyl, 3,4-dichlorophenyl, bromophenyl, iodophenyl, chlorofluorophenyl. Thus in some embodiments, $R^1$ is —$CH_2$—NH-difluorophenyl, —$CH_2$—NH-3,4-difluorophenyl, —$CH_2$—NH-4-chlorophenyl, —$CH_2$—NH-3-chloro-4-fluorophenyl, —$CH_2$—NH-4-chloro-3-fluorophenyl, —$CH_2$—NH-dichlorophenyl, —$CH_2$—NH-3,4-dichlorophenyl, —$CH_2$—NH-3-methyl-4-chlorophenyl, —$CH_2$—NH-3-fluoro-4-trifluoromethylphenyl, —$CH_2$—NH-3-(aminomethyl)phenyl, —$CH_2$—NH-3-(urea)phenyl. In some embodiments wherein $R^1$ is —$C_1$-$C_6$alk-NH-aryl, the -aryl is 4-chloro-2-(hydroxymethyl)phenyl, -4-chloro-2-(aminomethyl)phenyl, -4-chloro-2-((methylamino)methyl)phenyl, -4-trifluoromethylphenyl, -4-(trifluoromethoxy)phenyl, 4-fluoro-3-trifluoromethylphenyl, -4-isopropylphenyl.

In some aspects, $R^1$ is —$C_1$-$C_6$alk-S-aryl, for example, —$C_1$alk-S-aryl, —$C_2$alk-S-aryl, —$C_3$alk-S-aryl, —$C_4$alk-S-aryl, —$C_5$alk-S-aryl, —$C_6$alk-S-aryl, —$CH_2$—S-aryl, and the like. In some embodiments wherein $R^1$ is —$C_1$-$C_6$alk-S-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, -3-chloro-4-fluorophenyl, -phenyl, -3-(aminomethyl)phenyl, 3-(urea)phenyl, 3-methyl-4-chlorophenyl, 3-fluoro-4-chlorophenyl, -3-fluoro-4-trifluoromethylphenyl, difluorophenyl, chlorophenyl, 4-chlorophenyl, dichlorophenyl, 3,4-dichlorophenyl, bromophenyl, iodophenyl, chlorofluorophenyl. Thus in some embodiments, $R^1$ is —CH$_2$—S-difluorophenyl, —CH$_2$—S-3,4-difluorophenyl, —CH$_2$—S-4-chlorophenyl, —CH$_2$—S-3-chloro-4-fluorophenyl, —CH$_2$—S-4-chloro-3-fluorophenyl, —CH$_2$—S-dichlorophenyl, —CH$_2$—S-3,4-dichlorophenyl, —CH$_2$—S-3-methyl-4-chlorophenyl, —CH$_2$—S-3-fluoro-4-trifluoromethylphenyl, —CH$_2$—S-3-(aminomethyl)phenyl, —CH$_2$—S-3-(urea)phenyl. In some embodiments wherein $R^1$ is —C$_1$-C$_6$alk-S-aryl, the -aryl-4-chloro-2-(hydroxymethyl)phenyl, -4-chloro-2-(aminomethyl)phenyl, -4-chloro-2-((methylamino)methyl)phenyl, -4-trifluoromethylphenyl, -4-(trifluoromethoxy)phenyl, 4-fluoro-3-trifluoromethylphenyl, or -4-isopropylphenyl.

In some aspects, $R^1$ is —C$_0$-C$_6$alk-heteroaryl, for example, —C$_0$alk-heteroaryl, —C$_1$alk-heteroaryl, —C$_2$alk-heteroaryl, —C$_3$alk-heteroaryl, —C$_4$alk-heteroaryl, —C$_5$alk-heteroaryl, and —C$_6$alk-heteroaryl. In some embodiments wherein $R^1$ is —C$_0$-C$_6$alk-heteroaryl, the heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl. Thus, in some embodiments, $R^1$ is 2-(2-amino-3-bromoquinolin-7-yl)ethyl (i.e., —CH$_2$CH$_2$-(2-amino-3-bromoquinolin-7-yl)), 2-(2-amino-3-chloroquinolin-7-yl)ethyl, 2-(2-amino-3-fluoroquinolin-7-yl)ethyl, 2-(2-((cyclopropylmethyl)amino)quinolin-7-yl)ethyl, 2-(2-(methylamino)quinolin-7-yl)ethyl, 2-(2-aminoquinolin-7-yl)ethyl, (indol-6-yl)ethyl, or (indazol-6-yl)ethyl. In some embodiments wherein $R^1$ is —C$_0$-C$_6$alk-heteroaryl, the heteroaryl is 3-methylimidazo[1,2-a]pyridin-7-yl, and $R^1$ is (3-methylimidazo[1,2-a]pyridin-7-yl)ethyl.

In some aspects, $R^1$ is —C$_1$-C$_6$alk-O-heteroaryl, for example, —C$_1$alk-O-heteroaryl, —C$_2$alk-O-heteroaryl, —C$_3$alk-O-heteroaryl, —C$_4$alk-O-heteroaryl, —C$_5$alk-O-heteroaryl, and —C$_0$alk-O-heteroaryl. In some embodiments wherein $R^1$ is —C$_1$-C$_6$alk-O-heteroaryl, the heteroaryl is indolyl, indol-6-yl, indazolyl, indazol-6-yl, quinolinyl, quinolin-7-yl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, 2-(methoxyamino)quinolin-7-yl, 3-methylimidazo[1,2-a]pyridin-7-yl, or 2-aminoquinolin-7-yl. Thus, in some embodiments, $R^1$ is ((2-amino-3-bromoquinolin-7-yl)oxy)methyl (i.e., —CH$_2$—O-(2-amino-3-bromoquinolin-7-yl)), ((2-amino-3-chloroquinolin-7-yl)oxy)methyl, ((2-amino-3-fluoroquinolin-7-yl) oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, (2-(methoxyamino)quinolin-7-yl)oxy)methyl, ((quinolin-7-yl)oxy)methyl, ((indazol-6-yl)oxy)methyl, or ((3-methylimidazo[1,2-a]pyridin-7-yl)oxy)methyl.

In some embodiments wherein $R^1$ is —C$_1$-C$_6$alk-O-heteroaryl, the heteroaryl is indolyl, indol-6-yl, indazolyl, indazol-6-yl, quinolinyl, quinolin-7-yl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, 2-(methoxyamino)quinolin-7-yl, or 2-aminoquinolin-7-yl. Thus, in some embodiments, $R^1$ is ((2-amino-3-bromoquinolin-7-yl)oxy)methyl (i.e., —CH$_2$—O-(2-amino-3-bromoquinolin-7-yl)), ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, 2-(methoxyamino)quinolin-7-yl)oxy)methyl, ((quinolin-7-yl)oxy)methyl or ((indazol-6-yl)oxy)methyl.

In other embodiments wherein $R^1$ is —C$_1$-C$_6$alk-O-heteroaryl, the heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl. Thus, in some embodiments, $R^1$ is ((2-amino-3-bromoquinolin-7-yl)oxy)methyl (i.e., —CH$_2$—O-(2-amino-3-bromoquinolin-7-yl)), ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, or ((indazol-6-yl)oxy)methyl.

In some aspects, $R^1$ is —C$_1$-C$_6$alk-S-heteroaryl, for example, —C$_1$alk-S-heteroaryl, —C$_2$alk-S-heteroaryl, —C$_3$alk-S-heteroaryl, —C$_4$alk-S-heteroaryl, —C$_5$alk-S-heteroaryl, and —C$_6$alk-S-heteroaryl. In some embodiments wherein $R^1$ is —C$_1$-C$_6$alk-S-heteroaryl, the heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl. Thus, in some embodiments, $R^1$ is ((2-amino-3-bromoquinolin-7-yl)thio)methyl (i.e., —CH$_2$—S-(2-amino-3-bromoquinolin-7-yl)), ((2-amino-3-chloroquinolin-7-yl)thio)methyl, ((2-amino-3-fluoroquinolin-7-yl)thio)methyl, ((2-((cyclopropylmethyl)amino)quinolin-7-yl)thio)methyl, ((2-(methylamino)quinolin-7-yl)thio)methyl, ((2-aminoquinolin-7-yl)thio)methyl, ((indol-6-yl) thio)methyl, or ((indazol-6-yl)thio)methyl. In some embodiments wherein $R^1$ is —C$_1$-C$_6$alk-S-heteroaryl, the heteroaryl is 3-methylimidazo[1,2-a]pyridin-7-yl, and $R^1$ is ((3-methylimidazo[1,2-a]pyridin-7-yl)thio)methyl.

In some aspects, $R^1$ is —C$_1$-C$_6$alk-NH-heteroaryl, for example, —C$_1$alk-NH-heteroaryl, —C$_2$alk-NH-heteroaryl, —C$_3$alk-NH-heteroaryl, —C$_4$alk-NH-heteroaryl, —C$_5$alk-NH-heteroaryl, and —C$_6$alk-NH-heteroaryl. In some embodiments wherein $R^1$ is —C$_1$-C$_6$alk-NH-heteroaryl, the heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl. Thus, in some embodiments, $R^1$ is ((2-amino-3-bromoquinolin-7-yl)amino)methyl (i.e., —CH$_2$—NH-(2-amino-3-bromoquinolin-7-yl)), ((2-amino-3-chloroquinolin-7-yl)amino)methyl, ((2-amino-3-fluoroquinolin-7-yl)amino)methyl, ((2-((cyclopropylmethyl)amino)quinolin-7-yl)amino)methyl, ((2-(methylamino)quinolin-7-yl)amino)methyl, ((2-aminoquinolin-7-yl)amino)methyl, ((indol-6-yl) amino)methyl, or ((indazol-6-yl)amino)methyl. In some embodiments wherein $R^1$ is —C$_1$-C$_6$alk-NH-heteroaryl, the heteroaryl is 3-methylimidazo[1,2-a]pyridin-7-yl. Thus, in some embodiments, $R^1$ is ((3-methylimidazo[1,2-a]pyridin-7-yl)amino)methyl.

In some aspects, $R^1$ is -C(O)—NH-aryl. In some embodiments wherein $R^1$ is —C(O)—NH-aryl, the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, or -3-chloro-4-fluorophenyl, -phenyl, -3-(aminomethyl)phenyl, 3-(urea)phenyl, 3-methyl-4-chlorophenyl, 3-fluoro-4-chlorophenyl, -3-fluoro-4-trifluoromethylphenyl, difluorophenyl, chlorophenyl, 4-chlorophenyl, dichlorophenyl, 3,4-dichlorophenyl, bromophenyl, iodophenyl, chlorofluorophenyl, or benzo[d][1,3]dioxazole. In some embodiments wherein $R^1$ is —C(O)—NH-aryl, the -aryl is -4-chloro-2-(hydroxymethyl)phenyl, -4-chloro-2-(aminomethyl)phenyl, -4-chloro-2-((methylamino)methyl)phenyl, -4-trifluoromethylphenyl, 4-fluoro-3-trifluoromethylphenyl, -4-isopropylphenyl, or -4-(trifluoromethoxy)phenyl.

In some aspects, $R^1$ is —$C_1$-$C_6$alk-S(O)aryl, for example, —$C_1$alk-S(O)aryl, —$C_2$alk-S(O)aryl, —$C_3$alk-S(O)aryl, —$C_4$alk-S(O)aryl, —$C_5$alk-S(O)aryl, and —$C_6$alk-S(O)aryl, wherein aryl is phenyl, naphthyl, fluorophenyl, difluorophenyl, fluoronaphthyl, chlorophenyl, bromophenyl, iodophenyl, methylphenyl, and the like.

In some aspects, R is —$C_1$-$C_6$alk-S(O)$_2$aryl, for example, —$C_1$alk-S(O)$_2$aryl, —$C_2$alk-S(O)$_2$aryl, —$C_3$alk-S(O)$_2$aryl, —$C_4$alk-S(O)$_2$aryl, —$C_5$alk-S(O)$_2$aryl, and —$C_6$alk-S(O)$_2$aryl, wherein aryl is phenyl, naphthyl, fluorophenyl, difluorophenyl, fluoronaphthyl, chlorophenyl, bromophenyl, iodophenyl, methylphenyl, and the like.

In some aspects, $R^1$ is —$C_1$-$C_6$alk-S(O)heteroaryl, for example, —$C_1$alk-S(O)heteroaryl, —$C_2$alk-S(O)heteroaryl, —$C_3$alk-S(O)heteroaryl, —$C_4$alk-S(O)heteroaryl, —$C_5$alk-S(O) heteroaryl, and —$C_6$alk-S(O)heteroaryl, wherein heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl.

In some aspects, $R^1$ is —$C_1$-$C_6$alk-S(O)$_2$heteroaryl, for example, —$C_1$alk-S(O)$_2$heteroaryl, —$C_2$alk-S(O)$_2$heteroaryl, —$C_3$alk-S(O)$_2$heteroaryl, —$C_4$alk-S(O)$_2$heteroaryl, —$C_5$alk-S(O)$_2$heteroaryl, and —$C_6$alk-S(O)$_2$heteroaryl, wherein heteroaryl is indolyl, indol-6-yl, indazolyl, indazol-6-yl, quinolinyl, aminoquinolinyl, aminohaloquinolinyl, 2-amino-3-bromoquinolin-7-yl, 2-amino-3-chloroquinolin-7-yl, 2-amino-3-fluoroquinolin-7-yl, 2-((cyclopropylmethyl)amino)quinolin-7-yl, 2-(methylamino)quinolin-7-yl, or 2-aminoquinolin-7-yl.

In compounds of the present disclosure, $R^2$ is —$C_1$-$C_6$alkyl, —$C_1$-$C_6$haloalkyl, —$C_2$-$C_6$alkenyl, or —$C_2$-$C_6$alkynyl.

In some embodiments, $R^2$ is —$C_1$-$C_6$alkyl, —$C_2$-$C_6$alkenyl, or —$C_2$-$C_6$alkynyl.

In some aspects, $R^2$ is —$C_1$-$C_6$alkyl, for example, methyl, ethyl, propyl, isopropyl, butyl, isobutyl, s-butyl, t-butyl, pentyl, and the like. In some embodiments, $R^2$ is methyl.

In other aspects, $R^2$ is —$C_1$-$C_6$haloalkyl, for example, —$CF_3$ or —$CHF_2$. In some embodiments, $R^2$ is —$CF_3$.

In some aspects, $R^2$ is —$C_2$-$C_6$alkenyl, preferably —$C_2$-$C_4$alkenyl, for example, vinyl, allyl, and the like.

In other aspects, $R^2$ is —$C_2$-$C_6$alkynyl, preferably —$C_2$-$C_4$alkynyl, for example, ethynyl, propargyl, and the like.

In compounds of the present disclosure, $R^3$ is H, halo, —$C_1$-$C_6$alkyl, or $NH_2$. Thus in some embodiments, $R^3$ is H. In other embodiments, $R^3$ is halo, for example F, Cl, Br, or I. In other embodiments, $R^3$ is —$C_1$-$C_6$alkyl, for example, methyl, ethyl, propyl, isopropyl, butyl, isobutyl, s-butyl, t-butyl, pentyl, and the like. Thus, in some embodiments, $R^3$ is methyl (Me). In yet other embodiments, $R^3$ is $NH_2$. In the most preferred embodiments, $R^3$ is H.

In compounds of the present disclosure, $R^4$ is H, halo, —$C_1$-$C_6$alkyl, —$C_1$-$C_6$alk-O—$C_1$-$C_6$alkyl, —$NR^6R^{6'}$, —$NHCONR^6R^{6'}$, $NHC(S)NR^6R^{6'}$, —NH—$R^6$, or —NH—$NR^6R^{6'}$. In some embodiments, $R^4$ is halo, —$C_1$-$C_6$alkyl, —$C_1$-$C_6$alk-O—$C_1$-$C_6$alkyl, —$NR^6R^{6'}$, —$NHCONR^6R^{6'}$, $NHC(S)NR^6R^{6'}$, —NH—O—$R^6$, or —NH—$NR^6R^{6'}$.

In some aspects, $R^4$ is H.

In some aspects, $R^4$ is halo, for example chloro, fluoro, bromo, or iodo. In some embodiments, $R^4$ is chloro.

In some aspects, $R^4$ is —$C_1$-$C_6$alkyl, for example, methyl, ethyl, propyl, isopropyl, butyl, isobutyl, s-butyl, t-butyl, pentyl, and the like. In some embodiments, $R^4$ is methyl.

In some aspects, $R^4$ is —$C_1$-$C_6$alk-O—$C_1$-$C_6$alkyl, for example, —$C_1$-$C_6$alk-O—$C_1$-$C_6$alkyl, —$C_1$-$C_5$alk-O—$C_1$-$C_6$alkyl, —$C_1$-$C_4$alk-O—$C_1$-$C_6$alkyl, —$C_1$-$C_3$alk-O—$C_1$-$C_6$alkyl, —$C_1$-$C_2$alk-O—$C_1$-$C_6$alkyl, —$C_1$alk-O—$C_1$-$C_6$alkyl, —$C_1$-$C_6$alk-O—$C_1$-$C_5$alkyl, —$C_1$-$C_6$alk-O—$C_1$-$C_4$alkyl, —$C_1$-$C_6$alk-O—$C_1$-$C_3$alkyl, —$C_1$-$C_6$alk-O—$C_1$-$C_2$alkyl, or —$C_1$-$C_6$alk-O—$C_1$alkyl. In some embodiments, $R^4$ is —$CH_2CH_2$—O—$CH_3$.

In some aspects, $R^4$ is —$NR^6R^{6'}$. Thus, in some embodiments wherein $R^6$ and $R^{6'}$ are both H, $R^4$ is —$NH_2$. In some embodiments wherein $R^6$ and $R^{6'}$ are both methyl, $R^4$ is —$N(CH_3)_2$. In embodiments wherein $R^6$ is H and $R^{6'}$ is methyl, $R^4$ is —$NH(CH_3)$.

In some aspects, $R^4$ is —$NHCONR^6R^{6'}$. Thus, in some embodiments wherein $R^6$ and $R^{6'}$ are both H, $R^4$ is —$NHCONH_2$. In embodiments wherein $R^6$ and $R^{6'}$ are both methyl, $R^4$ is —$NHCON(CH_3)_2$. In embodiments wherein $R^6$ is H and $R^{6'}$ is methyl, $R^4$ is —$NHCONHCH_3$.

In some aspects, $R^4$ is $NHC(S)NR^6R^{6'}$. Thus, in some embodiments wherein $R^6$ and $R^{6'}$ are both H, $R^4$ is —NHC(S)$NH_2$. In embodiments wherein $R^6$ and $R^{6'}$ are both methyl, $R^4$ is —$NHC(S)N(CH_3)_2$. In embodiments wherein $R^6$ is H and $R^{6'}$ is methyl, $R^4$ is —$NHC(S)NHCH_3$.

In some aspects, $R^4$ is —NH—O—$R^6$. In some embodiments wherein $R^6$ is $C_1$-$C_6$alkyl, for example, methyl, $R^4$ is —NH—$OCH_3$. In some embodiments wherein $R^6$ is ethyl, $R^4$ is —NH—$OCH_2CH_3$. In some embodiments wherein $R^6$ is H, $R^4$ is —NH—OH.

In some aspects, $R^4$ is —NH—$NR^6R^{6'}$. In some embodiments wherein $R^6$ and $R^{6'}$ are both H, $R^4$ is —NH—$NH_2$. In embodiments wherein $R^6$ and $R^{6'}$ are both $C_1$-$C_6$alkyl, for example, methyl, $R^4$ is —NH—$N(CH_3)_2$. In embodiments wherein $R^6$ is H and $R^{6'}$ is $C_1$-$C_6$alkyl, for example, methyl, $R^4$ is —NH—$NHCH_3$.

It will be apparent that when $R^4$ is —NH—$R^6$ or —NH—$NR^6R^{6'}$, the compounds of Formula I may exist as tautomers having (E)- or (Z)-geometry at the exocyclic carbon-nitrogen double bond. The compounds of Formula I described and claimed herein are meant to encompass all such tautomers and geometric isomers. The depiction of a particular tautomer or geometric isomer is not intended to be limiting. For example, when $R^4$ is —NH—O—$R^6$, compounds of Formula I may be represented by any of the following equivalent structures:

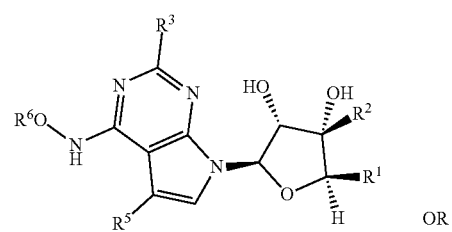

OR

17

-continued

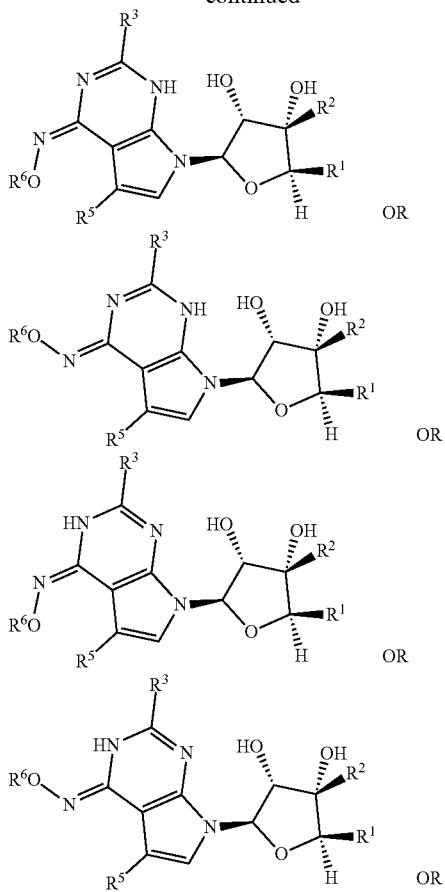

Similarly, when $R^4$ is —NH—NR$^6$R$^{6'}$, compounds of Formula I may be represented by any of the following equivalent structures:

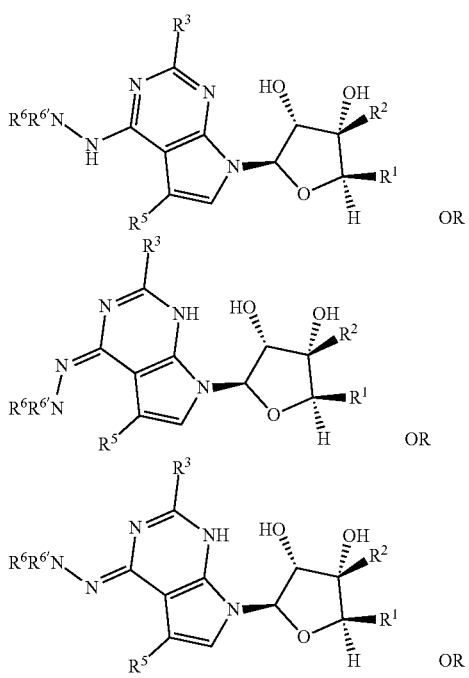

18

-continued

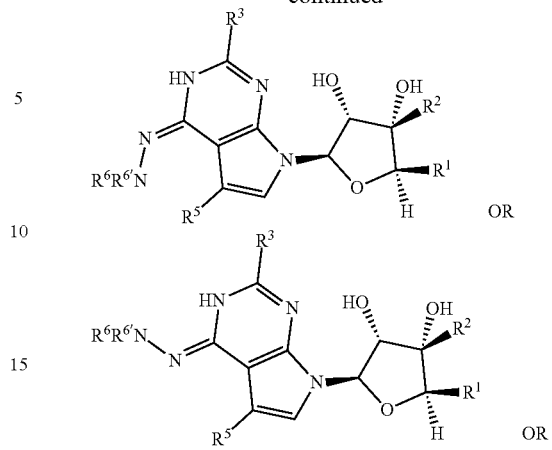

In compounds of the present disclosure, $R^5$ is H, halo, —$C_1$-$C_6$alkyl, —$C_1$-$C_6$haloalkyl, —$C_2$-$C_6$alkenyl, —$C_2$-$C_6$alkynyl, or —$C_1$-$C_6$alk-OH. In some aspects, $R^5$ is H.

In other aspects, $R^5$ is halo, for example, fluoro, chloro, bromo, or iodo. In some embodiments, $R^5$ is fluoro.

In some aspects, $R^5$ is —$C_1$-$C_6$alkyl, for example, methyl, ethyl, propyl, isopropyl, butyl, isobutyl, s-butyl, t-butyl, pentyl, and the like. In other aspects, $R^5$ is —$C_2$-$C_6$alkenyl, preferably —$C_2$-$C_4$alkenyl, for example, vinyl, allyl, and the like. In yet other aspects, $R^5$ is —$C_2$-$C_6$alkynyl, preferably —$C_2$-$C_4$alkynyl, for example, ethynyl, propragyl, and the like.

In other aspects, $R^5$ is —$C_1$-$C_6$haloalkyl, for example, —$CF_3$ or —$CHF_2$. In some embodiments, $R^5$ is —$CF_3$.

In some aspects, $R^5$ is —$C_1$-$C_6$alk-OH, for example, —$C_1$-$C_6$alk-OH, —$C_1$-$C_5$alk-OH, —$C_1$-$C_4$alk-OH, —$C_1$-$C_3$alk-OH, —$C_1$-$C_2$alk-OH, or —$C_1$alk-OH. In some embodiments, $R^5$ is —$CH_2$OH.

In compounds of the present disclosure, $R^6$ and $R^{6'}$ are each independently H, $C_1$-$C_6$alkyl (e.g., methyl, ethyl, propyl, isopropyl, butyl, isobutyl, s-butyl, t-butyl, pentyl, and the like), or —$C_1$-$C_6$alk-O$C_1$-$C_6$alkyl (e.g., $C_1$-$C_6$alk-O$C_1$-$C_6$alkyl, $C_1$-$C_5$alk-O$C_1$-$C_6$alkyl, $C_1$-$C_4$alk-O$C_1$-$C_6$alkyl, $C_1$-$C_3$alk-O$C_1$-$C_6$alkyl, $C_1$-$C_2$alk-O$C_1$-$C_6$alkyl, $C_1$alk-O$C_1$-$C_6$alkyl, $C_1$-$C_6$alk-O$C_1$-$C_5$alkyl, $C_1$-$C_6$alk-O$C_1$-$C_4$alkyl, $C_1$-$C_6$alk-O$C_1$-$C_3$alkyl, $C_1$-$C_6$alk-O$C_1$-$C_2$alkyl, or $C_1$-$C_6$alk-O$C_1$alkyl).

In some embodiments, $R^6$ is H or $C_1$-$C_6$alkyl. In some embodiments, $R^{6'}$ is H or $C_1$-$C_6$alkyl.

In some embodiments, $R^6$ and $R^{6'}$ are each H.

In other embodiments, $R^6$ and $R^{6'}$ are each independently $C_1$-$C_6$alkyl. Thus, in some embodiments $R^6$ is methyl and $R^{6'}$ is methyl.

In some aspects, $R^6$ is $C_1$-$C_6$alkyl and $R^{6'}$ is H. Thus, in some embodiments, $R^6$ is methyl and $R^{6'}$ is H.

In other embodiments, $R^6$ and $R^{6'}$ are each independently —$C_1$-$C_6$alk-O$C_1$-$C_6$alkyl.

In other aspects, $R^6$ is —$C_1$-$C_6$alk-O$C_1$-$C_6$alkyl and $R^{6'}$ is H.

In some embodiments of the disclosure, $R^6$ and $R^{6'}$, together with the atom to which they are attached, form a $C_2$-$C_6$heterocycloalkyl ring, for example, azepanyl, aziridinyl, azetidinyl, pyrrolidinyl, imidazolidinyl, pyrazolidinyl, piperazinyl, piperidinyl, morpholinyl, thiomorpholinyl, oxazepanyl, piperazinyl, and the like. In some preferred embodiments, $R^6$ and $R^{6'}$, together with the atom to which they are attached, form a $C_3$-$C_6$heterocycloalkyl ring, for example, azepanyl, azetidinyl, pyrrolidinyl, imidazolidinyl, pyrazolidinyl, piperazinyl, piperidinyl, morpholinyl, thiomorpholinyl, oxazepanyl, piperazinyl, and the like.

Preferred embodiments are those wherein $R^1$ is —CH$_2$—O—CH$_3$, —CH$_2$—S—CH$_3$, —CH$_2$—S—CH$_2$CH$_2$CH(NH$_2$)—CO$_2$H, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, —C(Me)(OH)-3-fluoro-4-trifluoromethylphenyl, —CH$_2$—O-phenyl, —CH$_2$—O-difluorophenyl, —CH$_2$—O-3,4-difluorophenyl, —CH$_2$—O-4-chlorophenyl, —CH$_2$—O-3-chloro-4-fluorophenyl, —CH$_2$—O-4-chloro-3-fluorophenyl, —CH$_2$—O-dichlorophenyl, —CH$_2$—O-3,4-dichlorophenyl, —CH$_2$—O-3-methyl-4-chlorophenyl, —CH$_2$—O-3-fluoro-4-trifluoromethylphenyl, —CH$_2$—O-3-(aminomethyl)phenyl, —CH$_2$—O-3-(urea)phenyl, ((2-amino-3-bromoquinolin-7-yl)oxy)methyl (i.e., —CH$_2$—O-(2-amino-3-bromoquinolin-7-yl)), ((2-amino-3-chloroquinolin-7-yl)oxy)methyl, ((2-amino-3-fluoroquinolin-7-yl) oxy)methyl, ((2-(methylamino)quinolin-7-yl)oxy)methyl, ((2-aminoquinolin-7-yl)oxy)methyl, ((indol-6-yl) oxy)methyl, ((indazol-6-yl)oxy)methyl, 2-(2-aminoquinolin-7-yl)ethyl, ((2-aminoquinolin-7-yl)thio)methyl, ((2-aminoquinolin-7-yl)amino)methyl. Other preferred embodiments are those wherein R is ((3-methylimidazo[1,2-a]pyridin-7-yl)oxy)methyl (i.e., —CH$_2$—O-3-methylimidazo[1,2-a]pyridin-7-yl), —CH(OH)-4-isopropylphenyl, —CH(OH)-4-trifluoromethylphenyl, —CH(OH)-4-(trifluoromethoxy)phenyl, —CH(OH)-4-fluoro-3-trifluoromethylphenyl, —CH$_2$-(4-chloro-2-(hydroxymethyl)phenyl), —CH$_2$-(4-chloro-2-(aminomethyl)phenyl), or —CH$_2$-(4-chloro-2-((methylamino)methyl)phenyl).

Preferred embodiments are those in which $R^2$ is methyl.

In some aspects, the present disclosure is directed to compounds of Formula I-A

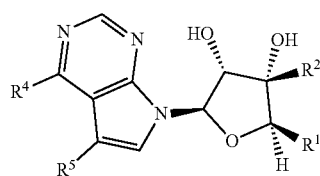

I-A wherein $R^1$ is —C$_0$-C$_6$alk-C$_1$-C$_6$alkyl, —C$_0$-C$_6$alk-C$_1$-C$_6$haloalkyl, —C$_1$-C$_6$alk-O—C$_1$-C$_6$alkyl, —C$_1$-C$_6$alk-S—C$_1$-C$_6$alkyl, —C$_1$-C$_6$alk-S—C$_1$-C$_6$alk-CO$_2$H, —C$_1$-C$_6$alk-aryl, —C$_1$-C$_6$alk-O-aryl, —C$_0$-C$_6$alk-heteroaryl, —C$_1$-C$_6$alk-O-heteroaryl, —C$_1$-C$_6$alk-S-heteroaryl, or —C$_1$-C$_6$alk-NH-heteroaryl; $R^2$ is methyl, trifluoromethyl, ethynyl, or vinyl; $R^4$ is halo, C$_1$-C$_6$alkyl, —NHC(O)NR$^6$R$^{6'}$, —NR$^6$R$^{6'}$, —NH—O—R$^6$ or —NH—NR$^6$R$^{6'}$; $R^5$ is H or F; and $R^6$ and $R^{6'}$ are each independently H or —C$_1$-C$_6$alkyl.

In some embodiments, the compounds of formula I-A are those in which $R^1$ is —C$_0$-C$_6$alk-C$_1$-C$_6$alkyl, —C$_0$-C$_6$alk-C$_1$-C$_6$haloalkyl, —C$_1$-C$_6$alk-O—C$_1$-C$_6$alkyl, —C$_1$-C$_6$alk-S—C$_1$-C$_6$alkyl, —C$_1$-C$_6$alk-S—C$_1$-C$_6$alk-CO$_2$H, —C$_1$-C$_6$alk-aryl, —C$_1$-C$_6$alk-O-aryl, —C$_0$-C$_6$alk-heteroaryl, —C$_1$-C$_6$alk-O-heteroaryl, —C$_1$-C$_6$alk-S-heteroaryl, or —C$_1$-C$_6$alk-NH-heteroaryl; $R^2$ is methyl, ethynyl, or vinyl; $R^4$ is halo, C$_1$-C$_6$alkyl, —NHC(O)NR$^6$R$^{6'}$, —NR$^6$R$^{6'}$, —NH—R$^6$ or —NH—NR$^6$R$^{6'}$; $R^5$ is H or F; and $R^6$ and $R^{6'}$ are each independently H or —C$_1$-C$_6$alkyl.

In some embodiments, the compounds of formula I-A are those in which $R^1$ is —C$_1$-C$_6$alk-aryl or —C$_1$-C$_6$alk-O-heteroaryl; —R$^2$ is methyl, ethynyl, or vinyl; $R^4$ is halo, C$_1$-C$_6$alkyl, —NHC(O)NR$^6$R$^{6'}$, —NR$^6$R$^{6'}$, —NH—R$^6$ or —NH—NR$^6$R$^{6'}$; $R^5$ is H or F; and $R^6$ and $R^{6'}$ are each independently H or —C$_1$-C$_6$alkyl.

In some embodiments, the compounds of formula I-A are those in which $R^1$ is —C$_1$-C$_6$alk-O-heteroaryl; $R^2$ is methyl, ethynyl, or vinyl; $R^4$ is halo, C$_1$-C$_6$alkyl, —NHC(O)NR$^6$R$^{6'}$, —NR$^6$R$^{6'}$, —NH—R$^6$ or —NH—NR$^6$R$^{6'}$; $R^5$ is H or F; and $R^6$ and $R^{6'}$ are each independently H or —C$_1$-C$_6$alkyl.

In some embodiments, the compounds of formula I-A are those in which $R^1$ is —C$_1$-C$_6$alk-aryl; $R^2$ is methyl, ethynyl, or vinyl; $R^4$ is halo, C$_1$-C$_6$alkyl, —NHC(O)NR$^6$R$^{6'}$, —NR$^6$R$^{6'}$, —NH—O—R$^6$ or —NH—NR$^6$R$^{6'}$; $R^5$ is H or F; and $R^6$ and $R^{6'}$ are each independently H or —C$_1$-C$_6$alkyl.

In some embodiments, the compounds of formula I-A are those in which $R^1$ is —C$_1$-C$_6$alk-aryl wherein the aryl is a mono- or bicyclic-aromatic hydrocarbon ring structure having 6 or 10 carbon atoms in the ring, wherein one or more of the carbon atoms in the ring is optionally substituted with a halogen atom, a —C$_1$-C$_3$ alkyl group, an amino-substituted —C$_1$-C$_3$ alkyl group, a C$_1$-C$_3$haloalkyl group, an amino group (i.e., —NH$_2$), or a substituted amino group; —R$^2$ is methyl, ethynyl, or vinyl; $R^4$ is halo, C$_1$-C$_6$alkyl, —NHC(O)NR$^6$R$^{6'}$, —NR$^6$R$^{6'}$, —NH—O—R$^6$ or —NH—NR$^6$R$^{6'}$; $R^5$ is H or F; and $R^6$ and $R^{6'}$ are each independently H or —C$_1$-C$_6$alkyl.

In some aspects, the present disclosure is directed to compounds of Formula I-B

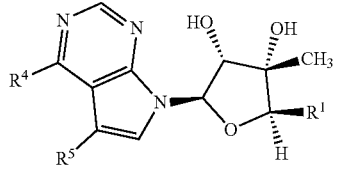

I-B wherein $R^1$ is —C$_0$-C$_6$alk-heteroaryl, —C$_1$-C$_6$alk-O-heteroaryl, —C$_1$-C$_6$alk-S-heteroaryl, or —C$_1$-C$_6$alk-NH-heteroaryl; $R^4$ is —NR$^6$R$^{6'}$, —NH—O—R$^6$ or —NH—NR$^6$R$^{6'}$; $R^5$ is H or F; and $R^6$ and $R^{6'}$ are each independently H or —C$_1$-C$_6$alkyl. In some preferred embodiments, the compounds of Formula I-B are those wherein $R^1$ is —C$_1$-C$_6$alk-O-heteroaryl; $R^4$ is —NR$^6$R$^{6'}$, —NH—O—R$^6$ or —NH—NR$^6$R$^{6'}$; $R^5$ is H or F; and $R^6$ and $R^{6'}$ are each independently H or —C$_1$-C$_6$alkyl.

In some preferred embodiments, the compounds of Formula I-B are those wherein $R^1$ is ((2-amino-3-bromoquinolin-7-yl)oxy)methyl (i.e., —CH$_2$—O-(2-amino-3-bromoquinolin-7-yl)), ((2-amino-3-chloroquinolin-7-yl)oxy) methyl, ((2-amino-3-fluoroquinolin-7-yl) oxy)methyl, ((2-(methylamino)quinolin-7-yl)oxy)methyl, ((2-aminoquinolin-7-yl)oxy)methyl, ((indol-6-yl) oxy)methyl, ((indazol-6-yl)oxy)methyl, 2-(2-aminoquinolin-7-yl)ethyl, ((2-aminoquinolin-7-yl)thio)methyl, or ((2-aminoquinolin-7-yl)amino)methyl; $R^4$ is —$NH_2$, —NH—O—$CH_3$ or —NH—$NHCH_3$; and $R^5$ is H or F.

In some preferred embodiments, the compounds of Formula I-B are those wherein $R^1$ is ((quinolin-7-yl)oxy)methyl, ((2-amino-3-bromoquinolin-7-yl)oxy)methyl (i.e., —$CH_2$—O-(2-amino-3-bromoquinolin-7-yl)), ((2-amino-3-chloroquinolin-7-yl)oxy)methyl, ((2-amino-3-fluoroquinolin-7-yl) oxy)methyl, ((2-(methylamino)quinolin-7-yl)oxy)methyl, ((2-(methoxyamino)quinolin-7-yl)oxy)methyl, ((2-aminoquinolin-7-yl)oxy)methyl, ((indol-6-yl) oxy)methyl, ((indazol-6-yl)oxy)methyl, 2-(2-aminoquinolin-7-yl)ethyl, ((2-aminoquinolin-7-yl)thio)methyl, ((3-methylimidazo[1,2-a]pyridine-7yl)oxy)methyl, or ((2-aminoquinolin-7-yl)amino)methyl; $R^4$ is —$NH_2$, —NH—OH, —NH—O—$CH_3$ or —NH—$NHCH_3$; and $R^5$ is H or F.

In some preferred embodiments, the compounds of Formula I-B are those wherein $R^1$ is ((quinolin-7-yl)oxy)methyl, ((2-amino-3-bromoquinolin-7-yl)oxy)methyl (i.e., —$CH_2$—O-(2-amino-3-bromoquinolin-7-yl)), ((2-amino-3-chloroquinolin-7-yl)oxy)methyl, ((2-amino-3-fluoroquinolin-7-yl)oxy)methyl, ((2-(methylamino)quinolin-7-yl)oxy)methyl, ((2-(methoxyamino)quinolin-7-yl)oxy)methyl, ((2-aminoquinolin-7-yl)oxy)methyl, ((indol-6-yl) oxy)methyl, ((indazol-6-yl)oxy)methyl, 2-(2-aminoquinolin-7-yl)ethyl, ((2-aminoquinolin-7-yl)thio)methyl, ((3-methylimidazo[1,2-a]pyridine-7yl)oxy)methyl, or ((2-aminoquinolin-7-yl)amino)methyl; $R^4$ is —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In some aspects, the present disclosure is directed to compounds of Formula I-B wherein $R^1$ is —$C_1$-$C_6$alk-aryl, $R^4$ is —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In some embodiments, the compounds of Formula I-B are those wherein $R^1$ is —$C_1$-$C_6$alk-aryl wherein the aryl is a mono- or bicyclic-aromatic hydrocarbon ring structure having 6 or 10 carbon atoms in the ring, wherein one or more of the carbon atoms in the ring is optionally substituted with a halogen atom, a —$C_1$-$C_3$ alkyl group, an amino-substituted —$C_1$-$C_3$ alkyl group, a $C_1$-$C_3$haloalkyl group, an amino group (i.e., —$NH_2$), or a substituted amino group; $R^4$ is —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In some preferred embodiments, the compounds of Formula I-B are those wherein $R^1$ is —$C_1$alk-aryl, and $R^4$ is —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In other preferred embodiments, the compounds of Formula I-B are those wherein $R^1$ is —$C_1$alk-aryl, $R^4$ is —$NH_2$, —NH—O—$CH_3$ or —NH—$NHCH_3$; and $R^5$ is H or F.

In other preferred embodiments, the compounds of Formula I-B are those wherein $R^1$ is —CH(OH)-4-chlorophenyl, —CH(OH)-4-chloro-2-(hydroxymethyl)phenyl, —CH(OH)-3,4-dichlorophenyl, —CH(OH)-3,4-difluorophenyl, —CH(OH)-3-fluoro-4-chlorophenyl, —CH(OH)-3-methyl-4-chlorophenyl, —CH(OH)-3-fluoro-4-trifluoromethylphenyl, —CH(OH)-4-trifluoromethylphenyl, —CH(OH)-4-(trifluoromethoxy)phenyl, —CH(OH)-4-fluoro-3-trifluoromethylphenyl, —CH(OH)-benzo[d][1,3]dioxazole, —CH(OH)-4-isopropylphenyl, or —CH(OH)-3-chloro-4-fluorophenyl; $R^4$ is —$NR^6R^{6'}$, —NH—$R^6$ or —NH—$NR^6R^{6'}$; $R^5$ is H or F; and $R^6$ and $R^{6'}$ are each independently H or —$C_1$-$C_6$alkyl.

In other preferred embodiments, the compounds of Formula I-B are those wherein $R^1$ is —CH(OH)-4-chlorophenyl, —CH(OH)-4-chloro-2-(hydroxymethyl)phenyl, —CH(OH)-3,4-dichlorophenyl, —CH(OH)-3,4-difluorophenyl, —CH(OH)-3-fluoro-4-chlorophenyl, —CH(OH)-3-methyl-4-chlorophenyl, —CH(OH)-3-fluoro-4-trifluoromethylphenyl, —CH(OH)-4-trifluoromethylphenyl, —CH(OH)-4-(trifluoromethoxy)phenyl, —CH(OH)-4-fluoro-3-trifluoromethylphenyl, —CH(OH)-benzo[d][1,3]dioxazole, —CH(OH)-4-isopropylphenyl, or —CH(OH)-3-chloro-4-fluorophenyl; $R^4$ is —$NH_2$, —NH—O—$CH_3$ or —NH—$NHCH_3$; and $R^5$ is H or F.

In other preferred embodiments, the compounds of Formula I-B are those wherein $R^1$ is —$CH_2$-4-chloro-2-(hydroxymethyl)phenyl, —$CH_2$-4-chloro-2-(aminomethyl)phenyl, —$CH_2$-(4-chloro-2-(methylamino)methyl)phenyl, —$CH_2$-3,4-dichlorophenyl, —$CH_2$-benzo[d][1,3]dioxazole; $R^4$ is H, —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In other preferred embodiments, the compounds of Formula I-B are those wherein $R^1$ is —$CH_2$-4-chloro-2-(hydroxymethyl)phenyl, —$CH_2$-4-chloro-2-(aminomethyl)phenyl, —$CH_2$-(4-chloro-2-(methylamino)methyl)phenyl, —$CH_2$-3,4-dichlorophenyl, —$CH_2$-benzo[d][1,3]dioxazole; $R^4$ is H, —$NH_2$, —NH—OH, —NH—O—$CH_3$ or —NH—$NHCH_3$; and $R^5$ is H or F.

In other preferred embodiments, the compounds of Formula I-B are those wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, or —C(Me)(OH)-3-fluoro-4-trifluoromethylphenyl; $R^4$ is —$NR^6R^{6'}$, —NH—O—$R^6$ or —NH—$NR^6R^{6'}$; $R^5$ is H or F; and $R^6$ and $R^{6'}$ are each independently H or —$C_1$-$C_6$alkyl.

In yet other preferred embodiments, the compounds of Formula I-B are those wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, or —C(Me)(OH)-3-fluoro-4-trifluoromethylphenyl; $R^4$ is —$NH_2$, —NH—O—$CH_3$ or —NH—$NHCH_3$; and $R^5$ is H or F.

In yet other preferred embodiments, the compounds of Formula I-B are those wherein $R^1$ is —CH(OH)-4-chlorophenyl, —CH(OH)-3,4-dichlorophenyl, or —CH(OH)-3-methyl-4-chlorophenyl; $R^4$ is —$NH_2$, —NH—O—$CH_3$ or —NH—$NHCH_3$; and $R^5$ is H or F. In yet other preferred embodiments, the compounds of Formula I-B are those wherein $R^1$ is —CH(OH)-4-chlorophenyl, —CH(OH)-3,4-dichlorophenyl, or —CH(OH)-3-methyl-4-chlorophenyl; $R^4$ is —$NH_2$, —NH—OH, —NH—O—$CH_3$ or —NH—$NHCH_3$; and $R^5$ is H or F.

In some aspects, the present disclosure is directed to compounds of Formula I-B wherein $R^1$ is —$C_1$-$C_6$alk-aryl, R⁴ is —C₁-C₆alkyl; and R⁵ is H or F. Some preferred embodiments are those in which R¹ is —C₁alk-aryl, and R⁴ is —CH₃; and R⁵ is H or F.

In some aspects, the present disclosure is directed to compounds of Formula I-B wherein R¹ is —C₁-C₆alk-aryl wherein the aryl is a mono- or bicyclic-aromatic hydrocarbon ring structure having 6 or 10 carbon atoms in the ring, wherein one or more of the carbon atoms in the ring is optionally substituted with a halogen atom, a —C₁-C₃ alkyl group, an amino-substituted —C₁-C₃ alkyl group, a C₁-C₃haloalkyl group, an amino group (i.e., —NH₂), or a substituted amino group; R⁴ is —C₁-C₆alkyl; and R⁵ is H or F.

In preferred embodiments, the compounds of Formula I-B are those wherein R¹ is —CH(OH)-4-chlorophenyl, —CH(OH)-4-chloro-2-(hydroxymethyl)phenyl, —CH(OH)-3,4-dichlorophenyl, —CH(OH)-3,4-difluorophenyl, —CH(OH)-3-fluoro-4-chlorophenyl, —CH(OH)-3-methyl-4-chlorophenyl, —CH(OH)-3-fluoro-4-trifluoromethylphenyl, —CH(OH)-4-trifluoromethylphenyl, —CH(OH)-4-(trifluoromethoxy)phenyl, —CH(OH)-4-fluoro-3-trifluoromethylphenyl, —CH(OH)-benzo[d][1,3]dioxazole, —CH(OH)-4-isopropylphenyl, or —CH(OH)-3-chloro-4-fluorophenyl; R⁴ is —CH₃; and R⁵ is H.

In yet other preferred embodiments, the compounds of Formula I-B are those wherein R¹ is —CH(OH)-4-chlorophenyl, —CH(OH)-3,4-dichlorophenyl, or —CH(OH)-3-methyl-4-chlorophenyl; R⁴ is —CH₃; and R⁵ is H or F.

In some preferred embodiments, the compounds of Formula I-B are those wherein R¹ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, or —C(Me)(OH)-3-fluoro-4-trifluoromethylphenyl; R⁴ is —CH₃; and R⁵ is H.

In other preferred embodiments, the compounds of Formula I-B are those wherein R¹ is —CH(OH)-4-chlorophenyl, —CH(OH)-3,4-dichlorophenyl, —CH(OH)-3-methyl-4-chlorophenyl, —CH(OH)-4-trifluoromethylphenyl, —CH(OH)-4-fluoro-3-trifluoromethylphenyl, —CH(OH)-3-fluoro-4-trifluoromethylphenyl, —CH(OH)-4-chloro-2-(hydroxymethyl)phenyl; R⁴ is —CH₃; and R⁵ is H.

In some preferred embodiments, the compounds of Formula I-B are those wherein R¹ is —C₁-C₆alk-O-aryl, and R⁴ is —NR⁶R⁶', —NH—O—R⁶ or —NH—NR⁶R⁶'; R⁵ is H or F; and R⁶ and R⁶' are each independently H or —C₁-C₆alkyl.

In other preferred embodiments, the compounds of Formula I-B are those wherein R¹ is —C₁-C₆alk-O-aryl, R⁴ is —NH₂, —NH—O—CH₃ or —NH—NHCH₃; and R⁵ is H or F.

In other preferred embodiments, the compounds of Formula I-B are those wherein R¹ is —CH₂—O-3-(aminomethyl)phenyl; R⁴ is —NH₂, —NH—O—CH₃ or —NH—NHCH₃; and R⁵ is H or F.

In some aspects, the present disclosure is directed to compounds of Formula I-B wherein R¹ is —C₁-C₆alk-S—C₁-C₆alkyl, R⁴ is —NR⁶R⁶', —NH—O—R⁶ or —NH—NR⁶R⁶'; and R⁶ and R⁶' are each independently H or —C₁-C₆alkyl.

In some aspects, the present disclosure is directed to compounds of Formula I-B wherein R¹ is —C₁-C₆alk-O—C₁-C₆alkyl, R⁴ is —NR⁶R⁶', —NH—O—R⁶ or —NH—NR⁶R⁶'; and R⁶ and R⁶' are each independently H or —C₁-C₆alkyl.

In some preferred embodiments, the present disclosure is directed to compounds of Formula I-C

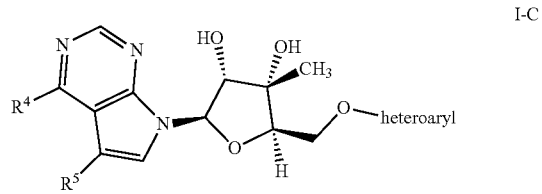

wherein R⁴ is —NR⁶R⁶', —NH—O—R⁶ or —NH—NR⁶R⁶'; R⁵ is H or F; and R⁶ and R⁶' are each independently H or —C₁-C₆alkyl. Other preferred embodiments are compounds of Formula I-C wherein R⁴ is —NR⁶R⁶', —NH—O—R⁶ or —NH—NR⁶R⁶'; R⁵ is H or F; R⁶ and R⁶' are each independently H or —C₁-C₆alkyl, and heteroaryl is quinolinyl, substituted quinolinyl, indolyl, substituted indolyl, indazolyl, or substituted indazolyl.

Other preferred embodiments are compounds of Formula I-C wherein R⁴ is —NH₂, —NH—O—CH₃ or —NH—NHCH₃; and R⁵ is H or F.

Other preferred embodiments are compounds of Formula I-C wherein R⁴ is —NH₂, —NH—OH, —NH—O—CH₃ or —NH—NHCH₃; R⁵ is H or F, R⁶ and R⁶' are each independently H or —C₁-C₆alkyl, and heteroaryl is quinolinyl, substituted quinolinyl, indolyl, substituted indolyl, indazolyl, substituted indazolyl, imidazo[1,2-a]pyridinyl, or substituted imidazo[1,2-a]pyridinyl.

Other preferred embodiments are compounds of Formula I-C wherein heteroaryl is (2-amino-3-bromoquinolin-7-yl), (2-amino-3-chloroquinolin-7-yl), (2-amino-3-fluoroquinolin-7-yl), (2-(methylamino)quinolin-7-yl), (2-aminoquinolin-7-yl), 2-(methoxyamino)quinolin-7-yl, (indol-6-yl), (indazol-6-yl), and R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-C wherein heteroaryl is (2-amino-3-bromoquinolin-7-yl), (2-amino-3-chloroquinolin-7-yl), (2-amino-3-fluoroquinolin-7-yl), (2-(methylamino)quinolin-7-yl), (2-aminoquinolin-7-yl), (indol-6-yl), (indazol-6-yl), and R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-C wherein heteroaryl is quinolinyl, substituted quinolinyl, indolyl, substituted indolyl, indazolyl, substituted indazolyl, imidazo[1,2-a]pyridinyl, or substituted imidazo[1,2-a]pyridinyl; R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-C wherein heteroaryl is quinolin-7-yl, (2-amino-3-bromoquinolin-7-yl), (2-amino-3-chloroquinolin-7-yl), (2-amino-3-fluoroquinolin-7-yl), (2-(methylamino)quinolin-7-yl), (2-aminoquinolin-7-yl), 2-(methoxyamino)quinolin-7-yl, (indol-6-yl), (indazol-6-yl), or (3-methylimidazo[1,2-a]pyridine-7yl); R⁴ is —NR⁶R⁶', —NH—O—R⁶ or —NH—NR⁶R⁶'; R⁵ is H or F; and R⁶ and R⁶' are each independently H or —C₁-C₆alkyl.

In some preferred embodiments, the present disclosure is directed to compounds of Formula I-D

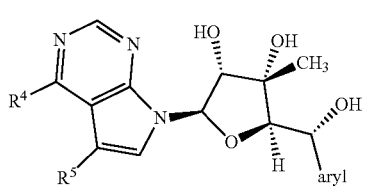

I-D wherein R⁴ is —NR⁶R⁶', —NH—O—R⁶ or —NH—NR⁶R⁶'; R⁵ is H or F; and R⁶ and R⁶' are each independently H or —C₁-C₆alkyl. Other preferred embodiments are compounds of Formula I-D wherein R⁴ is —NR⁶R⁶', —NH—O—R⁶ or —NH—NR⁶R⁶'; R⁵ is H or F; R⁶ and R⁶' are each independently H or —C₁-C₆alkyl, and aryl is phenyl or substituted phenyl.

Some embodiments of compounds of formula I-D are those wherein R⁴ is —NR⁶R⁶', —NH—O—R⁶ or —NH—NR⁶R⁶'; R⁵ is H or F; R⁶ and R⁶' are each independently H or —C₁-C₆alkyl, and aryl is a mono- or bicyclic-aromatic hydrocarbon ring structure having 6 or 10 carbon atoms in the ring, wherein one or more of the carbon atoms in the ring is optionally substituted with a halogen atom, a —C₁-C₃ alkyl group, an amino-substituted —C₁-C₃ alkyl group, a C₁-C₃haloalkyl group, an amino group (i.e., —NH₂), or a substituted amino group.

Other preferred embodiments are compounds of Formula I-D wherein R⁴ is —NH₂, —NH—O—CH₃ or —NH—NHCH₃; and R⁵ is H or F.

Other preferred embodiments are compounds of Formula I-D wherein R⁴ is —NH₂, —NH—OH, —NH—O—CH₃ or —NH—NHCH₃; and R⁵ is H or F, R⁶ and R⁶' are each independently H or —C₁-C₆alkyl, and aryl is phenyl or substituted phenyl.

Other preferred embodiments are compounds of Formula I-D wherein aryl is -4-chlorophenyl, -3,4-dichlorophenyl, -3,4-difluorophenyl, -3-fluoro-4-chlorophenyl, -3-chloro-4-fluorophenyl, -3-methyl-4-chlorophenyl, -3-fluoro-4-trifluoromethylphenyl, R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-D wherein aryl is -4-chlorophenyl, -3,4-dichlorophenyl, -3,4-difluorophenyl, -3-fluoro-4-chlorophenyl, -3-chloro-4-fluorophenyl, -3-methyl-4-chlorophenyl, -3-fluoro-4-trifluoromethylphenyl, or -4-fluoro-3-trifluoromethylphenyl, R⁴ is —NR⁶R⁶', —NH—O—R⁶ or —NH—NR⁶R⁶'; R⁵ is H or F; and R⁶ and R⁶' are each independently H or —C₁-C₆alkyl.

Yet other preferred embodiments are compounds of Formula I-D wherein aryl is -4-chlorophenyl, -3,4-dichlorophenyl, -3,4-difluorophenyl, -3-fluoro-4-chlorophenyl, -3-chloro-4-fluorophenyl, -3-methyl-4-chlorophenyl, or -3-fluoro-4-trifluoromethylphenyl; R⁴ is —NH₂, —NH—O—CH₃ or —NH—NHCH₃; and R⁵ is H or F.

Other preferred embodiments are compounds of Formula I-D wherein aryl is -4-chlorophenyl, -4-chloro-2-(hydroxymethyl)phenyl, -3,4-dichlorophenyl, -3,4-difluorophenyl, -3-fluoro-4-chlorophenyl, -3-methyl-4-chlorophenyl, -3-fluoro-4-trifluoromethylphenyl, -4-trifluoromethylphenyl, -4-(trifluoromethoxy)phenyl, -4-fluoro-3-trifluoromethylphenyl, -benzo[d][1,3]dioxazole, -4-isopropylphenyl, or -3-chloro-4-fluorophenyl; R⁴ is —NH₂, —NH—O—CH₃ or —NH—NHCH₃; and R⁵ is H or F.

In some preferred embodiments, the present disclosure is directed to compounds of Formula I-E

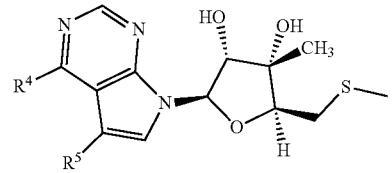

I-E wherein R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-E wherein R⁴ is —NH₂, —NHCH₃, —NH—O—CH₃ or —NH—NHCH₃; and R⁵ is H or F.

In some preferred embodiments, the present disclosure is directed to compounds of Formula I-F

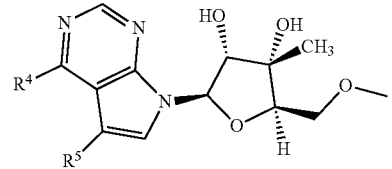

I-F wherein R⁴ is —NR⁶R⁶', —NH—O—R⁶ or —NH—NR⁶R⁶'; R⁵ is H or F; and R⁶ and R⁶' are each independently H or —C₁-C₆alkyl.

Other preferred embodiments are compounds of Formula I-F wherein R⁴ is —NH₂, —NHCH₃, —NH—O—CH₃ or —NH—NHCH₃; and R⁵ is H or F.

In some preferred embodiments, the present disclosure is directed to compounds of Formula I-G

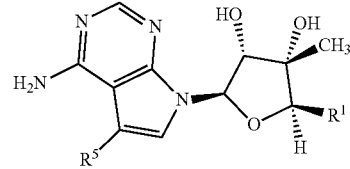

I-G wherein R¹ is —C₀-C₆alk-C₁-C₆alkyl, —C₀-C₆alk-C₁-C₆haloalkyl, —C₁-C₆alk-O—C₁-C₆alkyl, —C₁-C₆alk-S—C₁-C₆alkyl, —C₁-C₆alk-aryl, —C₁-C₆alk-O-aryl, —C₀-C₆alk-heteroaryl, —C₁-C₆alk-O-heteroaryl, —C₁-C₆alk-S-heteroaryl, or —C₁-C₆alk-NH-heteroaryl; and R⁵ is H or F.

In some embodiments, the compounds of Formula I-G are those wherein R¹ is —C₁-C₆alk-aryl or —C₁-C₆alk-O-heteroaryl; and R⁵ is H or F.

In some embodiments, the compounds of Formula I-G are those wherein R¹ is —C₁-C₆alk-aryl and R⁵ is H or F. In some embodiments, the compounds of Formula I-G are those wherein R¹ is —C₁-C₆alk-aryl wherein aryl is a mono- or bicyclic-aromatic hydrocarbon ring structure having 6 or 10 carbon atoms in the ring, wherein one or more of the carbon atoms in the ring is optionally substituted with a halogen atom, a —C₁-C₃ alkyl group, an amino-substituted —$C_1$-$C_3$ alkyl group, a $C_1$-$C_3$haloalkyl group, an amino group (i.e., —$NH_2$), or a substituted amino group; and $R^5$ is H or F.

In some embodiments, the compounds of Formula I-G are those wherein $R^1$ is —$C_1$-$C_6$alk-O-heteroaryl and $R^5$ is H or F.

In other preferred embodiments, the present disclosure is directed to compounds of Formula I-H

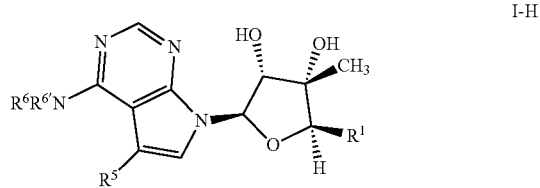

I-H wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-aryl, —$C_1$-$C_6$alk-O-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl; $R^5$ is H or F; and $R^6$ and $R^{6'}$ are each independently H or —$C_1$-$C_6$alkyl.

Some preferred embodiments are compounds of Formula I-H wherein $R^1$ is -$C_1$-$C_6$alk-O—$C_1$-$C_6$alkyl, —$C_1$-$C_6$alk-S—$C_1$-$C_6$alkyl, —$C_1$-$C_6$alk-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl; $R^5$ is H or F; and $R^6$ is H and $R^{6'}$ is methyl.

In some embodiments, the compounds of Formula I-H are those wherein $R^1$ is —$C_1$-$C_6$alk-aryl or —$C_1$-$C_6$alk-O-heteroaryl; and $R^5$ is H or F; and $R^6$ and $R^{6'}$ are each independently H or —$C_1$-$C_6$alkyl.

In some embodiments, the compounds of Formula I-H are those wherein $R^1$ is —$C_1$-$C_6$alk-aryl; $R^5$ is H or F; and $R^6$ and $R^{6'}$ are each independently H or —$C_1$-$C_6$alkyl. In some embodiments, the compounds of Formula I-H are those wherein $R^1$ is —$C_1$-$C_6$alk-aryl wherein aryl is a mono- or bicyclic-aromatic hydrocarbon ring structure having 6 or 10 carbon atoms in the ring, wherein one or more of the carbon atoms in the ring is optionally substituted with a halogen atom, a —$C_1$-$C_3$ alkyl group, an amino-substituted —$C_1$-$C_3$ alkyl group, a $C_1$-$C_3$haloalkyl group, an amino group (i.e., —$NH_2$), or a substituted amino group; $R^5$ is H or F; and $R^6$ and $R^{6'}$ are each independently H or —$C_1$-$C_6$alkyl.

In some embodiments, the compounds of Formula I-H are those wherein $R^1$ is —$C_1$-$C_6$alk-O-heteroaryl; $R^5$ is H or F; and $R^6$ and $R^{6'}$ are each independently H or —$C_1$-$C_6$alkyl.
10.1541 In other preferred embodiments, the present disclosure is directed to compounds of Formula I-J

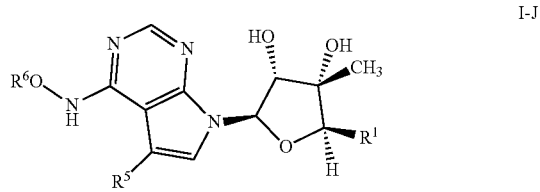

I-J wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-aryl, —$C_1$-$C_6$alk-O-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl; $R^5$ is H or F; and $R^6$ is H or —$C_1$-$C_6$alkyl.

Some preferred embodiments are compounds of Formula I-J wherein $R^1$—$C_1$-$C_6$alk-O—$C_1$-$C_6$alkyl, —$C_1$-$C_6$alk-S—$C_1$-$C_6$alkyl, —$C_1$-$C_6$alk-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl; $R^5$ is H or F; and $R^6$ methyl.

In some embodiments, the compounds of Formula I-J are those wherein $R^1$ is —$C_1$-$C_6$alk-aryl or —$C_1$-$C_6$alk-O-heteroaryl; and $R^5$ is H or F; and $R^6$ and $R^{6'}$ are each independently H or —$C_1$-$C_6$alkyl.

In some embodiments, the compounds of Formula I-J are those wherein $R^1$ is —$C_1$-$C_6$alk-aryl; $R^5$ is H or F; and $R^6$ and $R^{6'}$ are each independently H or —$C_1$-$C_6$alkyl. In some embodiments, the compounds of Formula I-J are those wherein $R^1$ is —$C_1$-$C_6$alk-aryl wherein aryl is a mono- or bicyclic-aromatic hydrocarbon ring structure having 6 or 10 carbon atoms in the ring, wherein one or more of the carbon atoms in the ring is optionally substituted with a halogen atom, a —$C_1$-$C_3$ alkyl group, an amino-substituted —$C_1$-$C_3$ alkyl group, a $C_1$-$C_3$haloalkyl group, an amino group (i.e., —$NH_2$), or a substituted amino group; $R^5$ is H or F; and $R^6$ and $R^{6'}$ are each independently H or —$C_1$-$C_6$alkyl.

In some embodiments, the compounds of Formula I-J are those wherein $R^1$ is —$C_1$-$C_6$alk-O-heteroaryl; $R^5$ is H or F; and $R^6$ and $R^{6'}$ are each independently H or —$C_1$-$C_6$alkyl.

References to Formula I herein also refer to Formulas I-A, I-B, I-C, I-D, I-E, I-F, I-G, I-H, and I-J.

Stereoisomers of compounds of Formula I are also contemplated by the present disclosure. Thus, the disclosure encompasses all stereoisomers and constitutional isomers of any compound disclosed or claimed herein, including all enantiomers and diastereomers.

Pharmaceutically acceptable salts and solvates of the compounds of Formula I are also within the scope of the disclosure.

Isotopic variants of the compounds of Formula I are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11% 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100%, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a PRMT5 inhibitor with an IC50 value of about or less than a predetermined value, as ascertained in an in vitro assay. In some embodiments, the PRMT5 inhibitor inhibits PRMT5 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1. µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the PRMT5 inhibitor selectively inhibits PRMT5 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other PRMTs.

In some embodiments, the PRMT5 inhibitor selectively inhibits PRMT5 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other PRMTs.

The subject methods are useful for treating a disease condition associated with PRMT5. Any disease condition that results directly or indirectly from an abnormal activity or expression level of PRMT5 can be an intended disease condition.

Different disease conditions associated with PRMT5 have been reported. PRMT5 has been implicated, for example, in a variety of human cancers as well as a number of hemoglobinopathies.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, said method is for treating a disease selected from breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In yet other embodiments, said method is for treating a disease selected from CDKN2A deleted cancers; 9P deleted cancers; MTAP deleted cancers; glioblastoma, NSCLC, head and neck cancer, bladder cancer, or hepatocellular carcinoma.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In other aspects, compounds of the disclosure, as well as pharmaceutical compositions comprising them, can be administered to treat any of the described diseases, alone or in combination with one or more other chemotherapeutic agents. Examples of other chemotherapeutic agents include, for example, abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat, and zoledronate, as well as any combination thereof.

In other aspects, the other agent is a therapeutic agent that targets an epigenetic regulator. Examples of epigenetic regulator agents include, for example, bromodomain inhibitors, the histone lysine methyltransferases, histone arginine methyl transferases, histone demethylases, histone deacetylases, histone acetylases, and DNA methyltransferases, as well as any combination thereof. Histone deacetylase inhibitors are preferred in some aspects, and include, for example, vorinostat.

In other methods wherein the disease to be treated is cancer or another proliferative disease, the compounds of the disclosure, as well as pharmaceutical compositions comprising them, can be administered in combination with targeted therapy agents. Targeted therapies include, for example, JAK kinase inhibitors (e.g. Ruxolitinib), PI3 kinase inhibitors (including PI3K-delta selective and broad spectrum PI3K inhibitors), MEK inhibitors, Cyclin Dependent kinase inhibitors (e.g., CDK4/6 inhibitors), BRAF inhibitors, mTOR inhibitors, proteasome inhibitors (e.g., Bortezomib, Carfilzomib), HDAC-inhibitors (e.g., panobinostat, vorinostat), DNA methyl transferase inhibitors, dexamethasone, bromo and extra terminal family members, BTK inhibitors (e.g., ibrutinib, acalabrutinib), BCL2 inhibitors (e.g., venetoclax), MCL1 inhibitors, PARP inhibitors, FLT3 inhibitors, and LSD1 inhibitors, as well as any combination thereof.

In other methods wherein the disease to be treated is cancer or another proliferative disease, the compounds of the disclosure, as well as pharmaceutical compositions comprising them, can be administered in combination with an immune checkpoint inhibitor agents. Immune checkpoint inhibitors include, for example, inhibitors of PD-1, for example, an anti-PD-1 monoclonal antibody. Examples of anti-PD-1 monoclonal antibodies include, for example, nivolumab, pembrolizumab (also known as MK-3475), pidilizumab, SHR-1210, PDR001, and AMP-224, as well as combinations thereof. In some aspects, the anti-PD1 antibody is nivolumab. In some aspects, the anti-PD1 antibody is pembrolizumab. In some aspects, the immunce checkpoint inhibitor is an inhibitor of PD-L1, for example, an anti-PD-L1 monoclonal antibody. In some aspects, the anti-PD-L1 monoclonal antibody is BMS-935559, MEDI4736, MPDL3280A (also known as RG7446), or MSB0010718C, or any combination thereof. In some aspects, the anti-PD-L1 monoclonal antibody is MPDL3280A or MEDI4736. In other aspects, the immune checkpoint inhibitor is an inhibitor of CTLA-4, for example, and anti-CTLA-4 antibody. In some aspects, the anti-CTLA-4 antibody is ipilimumab.

In other methods wherein the disease to be treated is cancer or another proliferative disease, the compounds of the disclosure, as well as pharmaceutical compositions comprising them, can be administered in combination with an alkylating agent (e.g., cyclophosphamide (CY), melphalan (MEL), and bendamustine), a proteasome inhibitor agent (e.g., carfilzomib), a corticosteroid agent (e.g., dexamethasone (DEX)), or an immunomodulatory agent (e.g., lenalidomide (LEN) or pomalidomide (POM)), or any combination thereof.

In some embodiments, the disease to be treated is an autoimmune condition or an inflammatory condition. In these aspects, the compounds of the disclosure, as well as pharmaceutical compositions comprising them, can be administered in combination with a corticosteroid agent such as, for example, triamcinolone, dexamethasone, fluocinolone, cortisone, prednisolone, or flumetholone, or any combination thereof.

In other methods wherein the disease to be treated is an autoimmune condition or an inflammatory condition, the compounds of the disclosure, as well as pharmaceutical compositions comprising them, can be administered in combination with an immune suppressant agent such as, for example, fluocinolone acetonide (RETISERT™), rimexolone (AL-2178, VEXOL™, ALCO™), or cyclosporine (RESTASIS™), or any combination thereof.

In some embodiments, the disease to be treated is beta-thalassemia or sickle cell disease. In these aspects, the compounds of the disclosure, as well as pharmaceutical compositions comprising them, can be administered in combination with one or more agents such as, for example, HYDREA™ (hydroxyurea).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Compounds of the disclosure can be prepared, for example, by reference to the following schemes.

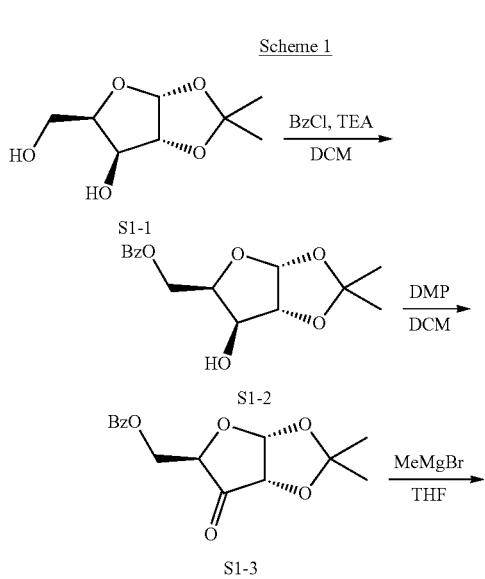

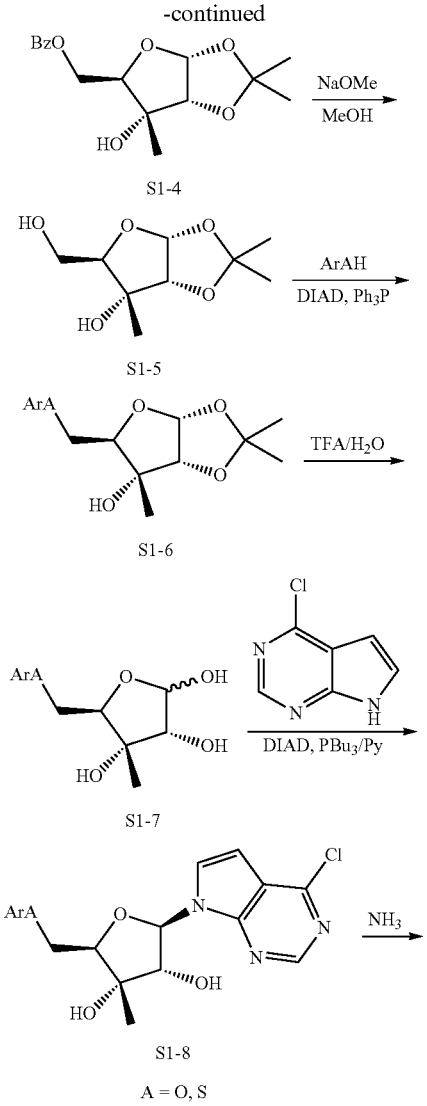
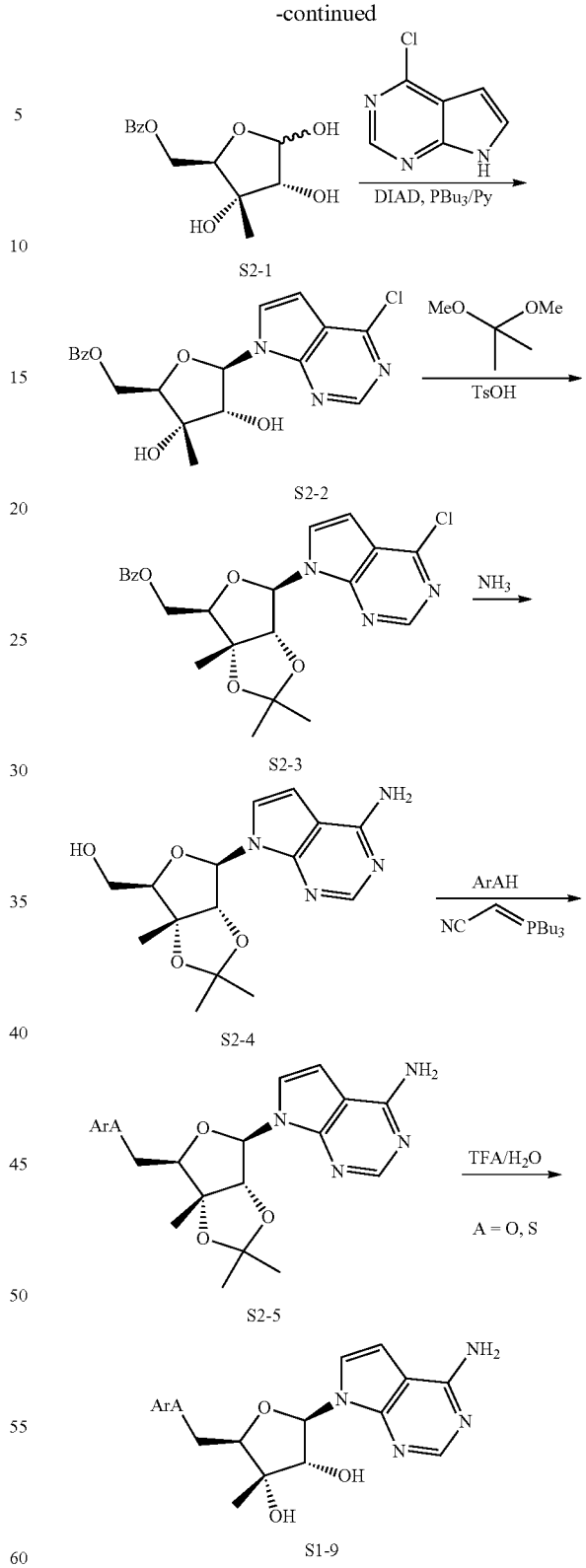
Scheme 2
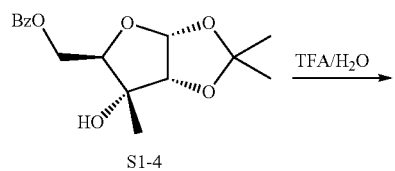
In some aspects, the compounds of the disclosure include synthetic intermediates useful in the preparation of other compounds of the disclosure. In this regard, the compounds of the disclosure include, for example, the compounds of formula SI-1, formula SI-2, formula SI-3, and formula SI-4:

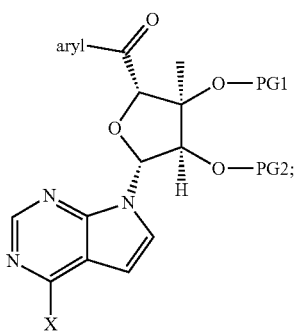
(SI-1)

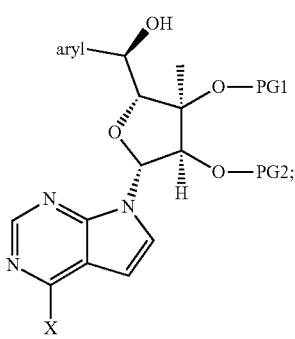
(SI-2)

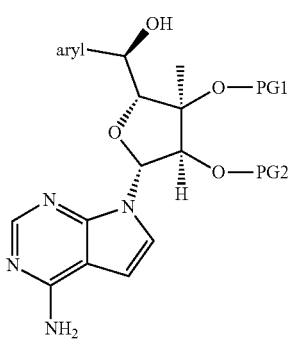
(SI-3)

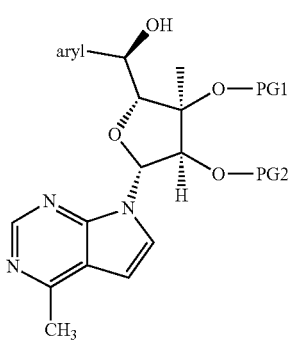
(SI-4)

wherein
aryl is substituted or unsubstituted phenyl;
X is a halogen selected from fluorine, chlorine, or bromine; and
PG1 is a hydroxyl protecting group;
PG2 is a hydroxyl protecting group; or PG1 and PG2, together with the atoms to which they are attached, form a cyclic 1,2-dihydroxyl protecting group.

In some embodiments of the compounds of formula SI-1, SI-2, SI-3, and SI-4, the aryl is -4-chlorophenyl, 4-chloro-2-(hydroxymethyl)phenyl, -3,4-dichlorophenyl, -3,4-difluorophenyl, -3-fluoro-4-chlorophenyl, 3-methyl-4-chlorophenyl, 3-fluoro-4-trifluoromethylphenyl, 4-trifluoromethylphenyl, 4-(trifluoromethoxy)phenyl, 4-fluoro-3-trifluoromethylphenyl, benzo[d][1,3]dioxazole, 4-isopropylphenyl, or -3-chloro-4-fluorophenyl.

In some embodiments of the compounds of formula SI-1 and SI-2, X is chlorine. In other embodiments, X is fluorine. In yet other embodiments, X is bromine.

In some embodiments of the compounds of formula SI-1, SI-2, SI-3, and SI-4, PG1 and PG2 are each a hydroxyl protecting group, or alternatively, PG1 and PG2, together with the atoms to which they are attached, form a cyclic 1,2-dihydroxyl protecting group.

In some embodiments of the compounds of formula SI-1, SI-2, SI-3, and SI-4, PG1 and PG2 are each a hydroxyl protecting group. In other embodiments, PG1 and PG2, together with the atoms to which they are attached, form a cyclic 1,2-dihydroxyl protecting group. Suitable protecting groups are well known to those skilled in the art. See, e.g., Wuts, Peter G M, and Theodora W. Greene. *Greene's protective groups in organic synthesis*. John Wiley & Sons, 2006. In some embodiments PG1 and PG2 together form a ketal. In other embodiments PG1 and PG2 together form a di-alkyl acetal. In some embodiments, PG1 and PG2 together form an acetonide protecting group, and the compounds have the formula SI-1a, SI-2a, SI-3a, and SI-4a:

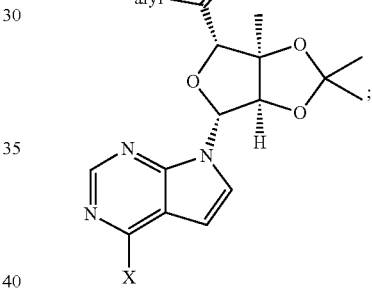
(SI-1a)

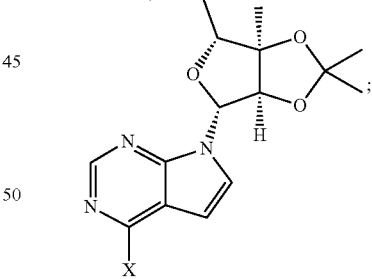
(SI-2a)

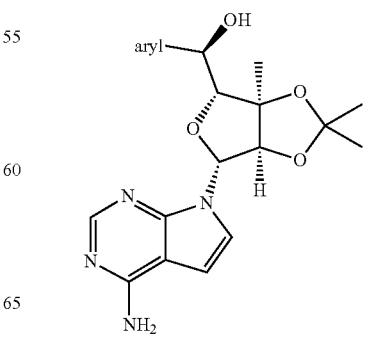
(SI-3a)

-continued

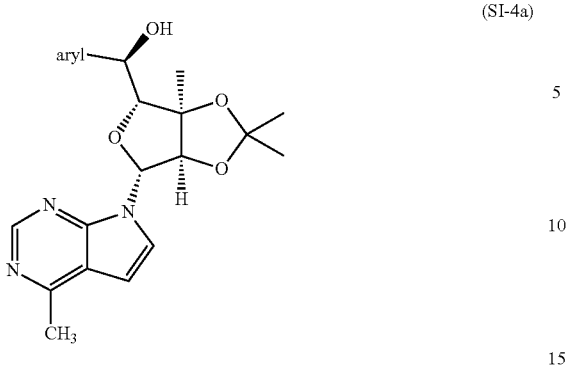

(SI-4a)

Specific embodiments of compounds of formula SI-1, SI-2, SI-3, and SI-4 are described in the Experimental Procedures section set forth below.

Compounds of the disclosure include, for example, the compounds identified in Table A.

TABLE A

| Ex. # | Structures | MW | Name |
|---|---|---|---|
| 1 | 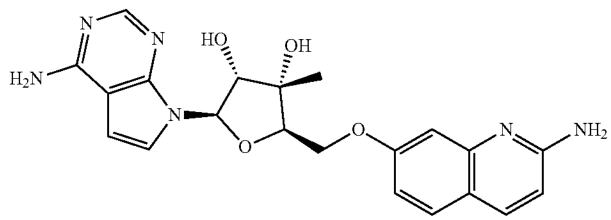 [SMILES: C[C@@]1(O)[C@@H](COc2ccc3ccc(N)nc3c2)O[C@@H](n2ccc3c(N)ncnc32)[C@@H]1O] | 422.445 | (2R,3S,4R,5R)-5-(4-amino-7H-pyrrolo[2,3-d]pyrimidin-7-yl)-2-(((2-aminoquinolin-7-yl)oxy)methyl)-3-methyltetrahydrofuran-3,4-diol |
| 2 | 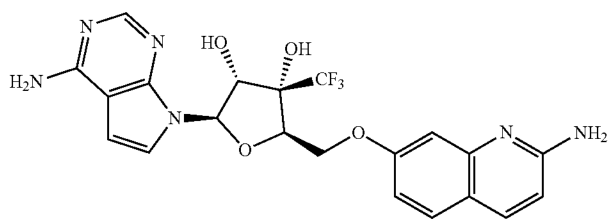 [SMILES: Nc1ccc2ccc(OC[C@H]3O[C@@H](n4ccc5c(N)ncnc54)[C@H](O)[C@@]3(O)C(F)(F)F)cc2n1] | 476.41621 | (2R,3S,4R,5R)-5-(4-amino-7H-pyrrolo[2,3-d]pyrimidin-7-yl)-2-(((2-aminoquinolin-7-yl)oxy)methyl)-3-(trifluoromethyl)tetrahydrofuran-3,4-diol |
| 3 | 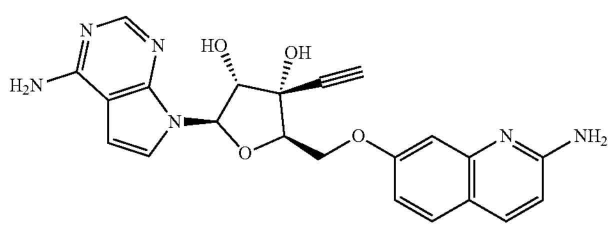 [SMILES: C#C[C@@]1(O)[C@@H](COc2ccc3ccc(N)nc3c2)O[C@@H](n2ccc3c(N)ncnc32)[C@@H]1O] | 432.44 | (2R,3S,4R,5R)-5-(4-amino-7H-pyrrolo-[2,3-d]pyrimidin-7-yl)-2-(((2-aminoquinolin-7-yl)oxy)methyl)-3-ethynyl-tetrahydrofuran-3,4-diol |
| 4 | 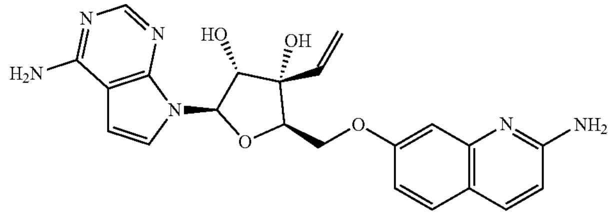 [SMILES: C=C[C@@]1(O)[C@@H](COc2ccc3ccc(N)nc3c2)O[C@@H](n2ccc3c(N)ncnc32)[C@@H]1O] | 434.456 | (2R,3S,4R,5R)-5-(4-amino-7H-pyrrolo-[2,3-d]pyrimidin-7-yl)-2-(((2-aminoquinolin-7-yl)oxy)methyl)-3-vinyltetrahydrofuran-3,4-diol |

TABLE A-continued

| Ex. # | Structures | MW | Name |
|---|---|---|---|
| 5 | 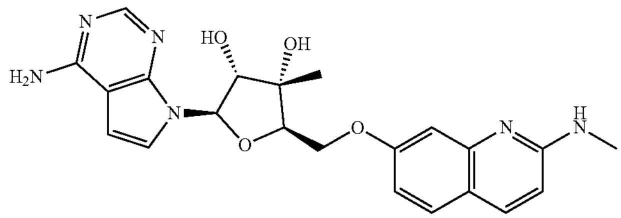 [SMILES: CNc1ccc2ccc(OC[C@H]3O[C@@H](n4ccc5c(N)ncnc54)[C@H](O)[C@]3(C)O)cc2n1] | 436.472 | (2R,3S,4R,5R)-5-(4-amino-7H-pyrrolo-[2,3-d]pyrimidin-7-yl)-3-methyl-2-(((2-(methylamino)-quinolin-7-yl)oxy)-methyl)tetrahydro-furan-3,4-diol |
| 6 | 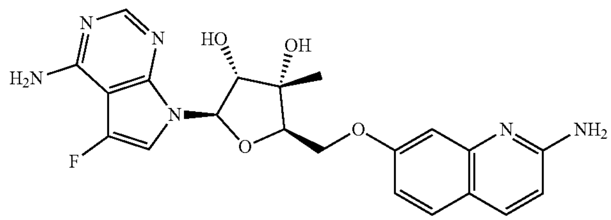 [SMILES: C[C@@]1(O)[C@@H](COc2ccc3ccc(N)nc3c2)O[C@@H](n2cc(F)c3c(N)ncnc32)[C@@H]1O] | 440.435 | (2R,3S,4R,5R)-5-(4-amino-5-fluoro-7H-pyrrolo[2,3-d]-pyrimidin-7-yl)-2-(((2-aminoquinolin-7-yl)oxy)methyl)-3-methyltetrahydro-furan-3,4-diol |
| 7 | 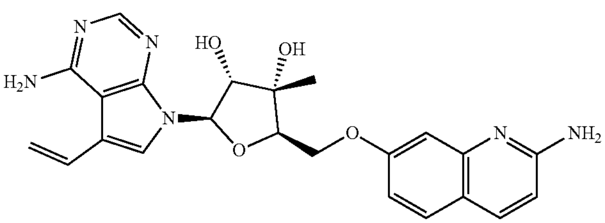 [SMILES: C=Cc1cn([C@@H]2O[C@H](COc3ccc4ccc(N)nc4c3)[C@@](C)(O)[C@H]2O)c2ncnc(N)c12] | 448.483 | (2R,3S,4R,5R)-5-(4-amino-5-vinyl-7H-pyrrolo[2,3-d]-pyrimidin-7-yl)-2-(((2-aminoquinolin-7-yl)oxy)methyl)-3-methyltetrahydro-furan-3,4-diol |
| 8 | 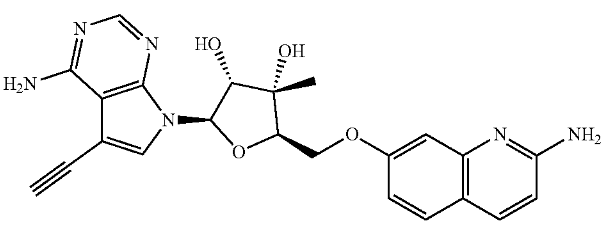 [SMILES: C#Cc1cn([C@@H]2O[C@H](COc3ccc4ccc(N)nc4c3)[C@@](C)(O)[C@H]2O)c2ncnc(N)c12] | 446.467 | (2R,3S,4R,5R)-5-(4-amino-5-ethynyl-7H-pyrrolo[2,3-d]-pyrimidin-7-yl)-2-(((2-aminoquinolin-7-yl)oxy)methyl)-3-methyltetrahydro-furan-3,4-diol |
| 9 | 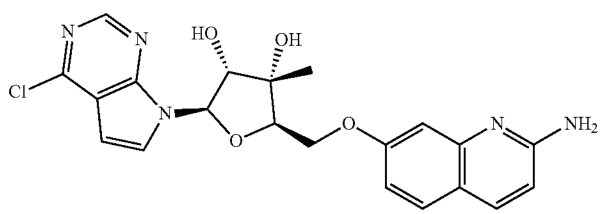 [SMILES: C[C@@]1(O)[C@@H](COc2ccc3ccc(N)nc3c2)O[C@@H](n2ccc3c(Cl)ncnc32)[C@@H]1O] | 441.872 | (2R,3S,4R,5R)-2-(((2-aminoquinolin-7-yl)oxy)methyl)-5-(4-chloro-7H-pyrrolo-[2,3-d]pyrimidin-7-yl)-3-methyltetra-hydrofuran-3,4-diol |
| 10 | 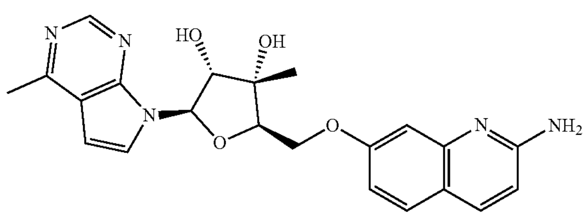 [SMILES: Cc1ncnc2c1ccn2[C@@H]1O[C@H](COc2ccc3ccc(N)nc3c2)[C@@](C)(O)[C@H]1O] | 421.457 | (2R,3S,4R,5R)-2-(((2-aminoquinolin-7-yl)oxy)methyl)-3-methyl-5-(4-methyl-7H-pyrrolo[2,3-d]-pyrimidin-7-yl)tetra-hydrofuran-3,4-diol |
| 11 | 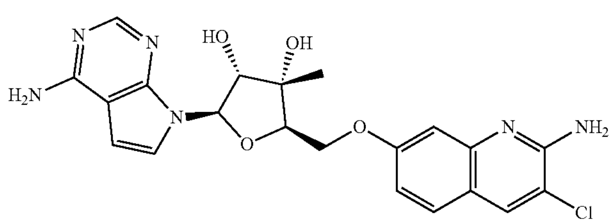 [SMILES: C[C@@]1(O)[C@@H](COc2ccc3cc(Cl)c(N)nc3c2)O[C@@H](n2ccc3c(N)ncnc32)[C@@H]1O] | 456.887 | (2R,3S,4R,5R)-2-(((2-amino-3-chloro-quinolin-7-yl)oxy)-methyl)-5-(4-amino-7H-pyrrolo[2,3-d]-pyrimidin-7-yl)-3-methyltetrahydro-furan-3,4-diol |

TABLE A-continued

| Ex. # | Structures | MW | Name |
|---|---|---|---|
| 12 | 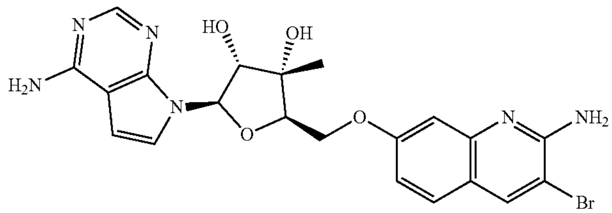 [SMILES: C[C@@]1(O)[C@@H](COc2ccc3cc(Br)c(N)nc3c2)O[C@@H](n2ccc3c(N)ncnc32)[C@@H]1O] | 501.341 | (2R,3S,4R,5R)-2-(((2-amino-3-bromo-quinolin-7-yl)oxy)-methyl)-5-(4-amino-7H-pyrrolo[2,3-d]-pyrimidin-7-yl)-3-methyltetrahydro-furan-3,4-diol |
| 13 | 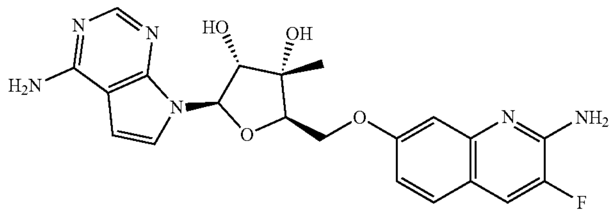 | 440.435 | (2R,3S,4R,5R)-2-(((2-amino-3-fluoro-quinolin-7-yl)oxy)-methyl)-5-(4-amino-7H-pyrrolo[2,3-d]-pyrimidin-7-yl)-3-methyltetrahydro-furan-3,4-diol |
| 14 | 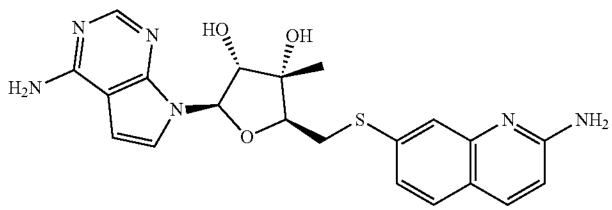 [SMILES: C[C@@]1(O)[C@@H](CSc2ccc3ccc(N)nc3c2)O[C@@H](n2ccc3c(N)ncnc32)[C@@H]1O] | 438.506 | (2S,3S,4R,5R)-5-(4-amino-7H-pyrrolo-[2,3-d]-pyrimidin-7-yl)-2-(((2-amino-quinolin-7-yl)thio)-methyl)-3-methyltetra-hydrofuran-3,4-diol |
| 15 | 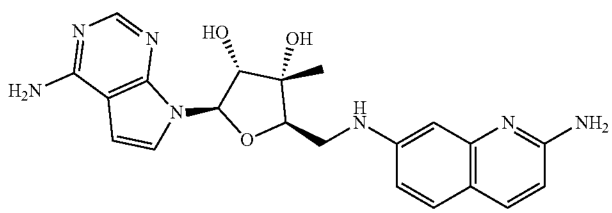 [SMILES: C[C@@]1(O)[C@@H](CNc2ccc3ccc(N)nc3c2)O[C@@H](n2ccc3c(N)ncnc32)[C@@H]1O] | 421.461 | (2R,3S,4R,5R)-5-(4-amino-7H-pyrrolo-[2,3-d]pyrimidin-7-yl)-2-(((2-amino-quinolin-7-yl)amino)-methyl)-3-methyltetra-hydrofuran-3,4-diol |
| 16 | 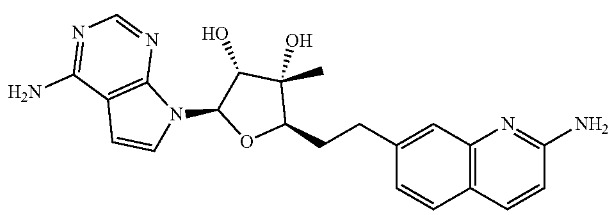 | 420.473 | (2R,3S,4R,5R)-5-(4-amino-7H-pyrrolo-[2,3-d]pyrimidin-7-yl)-2-(2-(2-amino-quinolin-7-yl)ethyl)-3-methyltetrahydro-furan-3,4-diol |
| 17 | 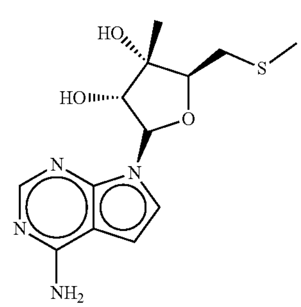 | 310.372 | (2S,3S,4R,5R)-5-(4-amino-7H-pyrrolo-[2,3-d]pyrimidin-7-yl)-3-methyl-2-((methylthio)methyl)-tetrahydrofuran-3,4-diol |
| 18 | 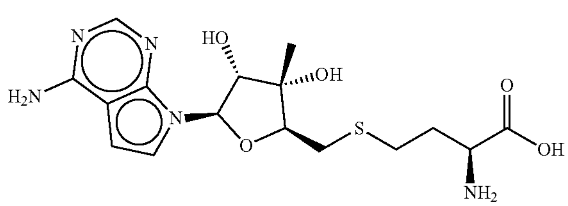 | 397.45 | S-(((2S,3S,4R,5R)-5-(4-amino-7H-pyrrolo[2,3-d]-pyrimidin-7-yl)-3,4-dihydroxy-3-methyl-tetrahydro-furan-2-yl)methyl)-L-homocysteine |

TABLE A-continued

| Ex. # | Structures | MW | Name |
|---|---|---|---|
| 19 | 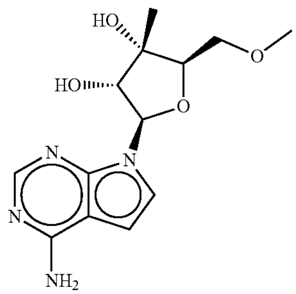 | 294.311 | (2R,3S,4R,5R)-5-(4-amino-7H-pyrrolo-[2,3-d]pyrimidin-7-yl)-2-(methoxymethyl)-3-methyltetrahydrofuran-3,4-diol |
| 20 | 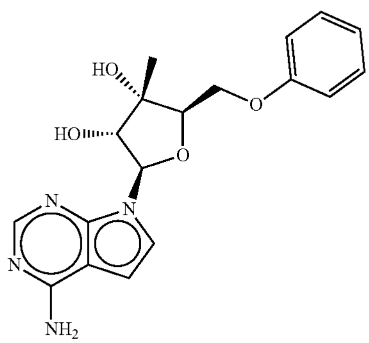 | 356.382 | (2R,3S,4R,5R)-5-(4-amino-7H-pyrrolo-[2,3-d]pyrimidin-7-yl)-3-methyl-2-(phenoxymethyl)-tetrahydrofuran-3,4-diol |
| 21 | 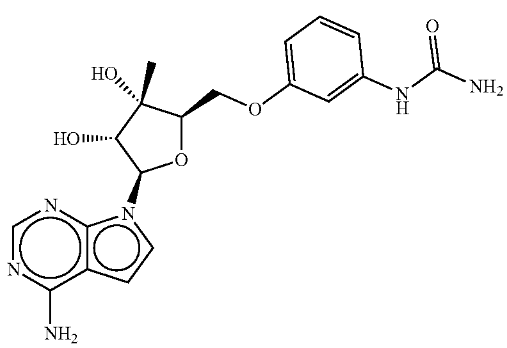 | 414.422 | 1-(3-(((2R,3S,4R,5R)-5-(4-amino-7H-pyrrolo[2,3-d]-pyrimidin-7-yl)-3,4-dihydroxy-3-methyl-tetrahydrofuran-2-yl)-methoxy)phenyl)urea |
| 22 | 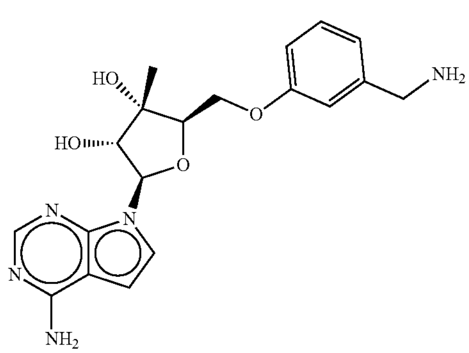 | 385.424 | (2R,3S,4R,5R)-5-(4-amino-7H-pyrrolo-[2,3-d]pyrimidin-7-yl)-2-((3-(aminomethyl)phenoxy)-methyl)-3-methyl-tetrahydrofuran-3,4-diol |

TABLE A-continued

| Ex. # | Structures | MW | Name |
|---|---|---|---|
| 23 | 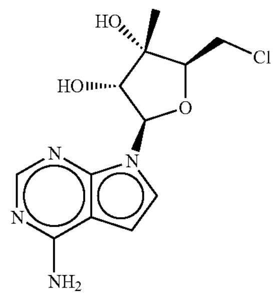 | 298.727 | (2S,3S,4R,5R)-5-(4-amino-7H-pyrrolo-[2,3-d]pyrimidin-7-yl)-2-(chloromethyl)-3-methyltetrahydro-furan-3,4-diol |
| 24 | 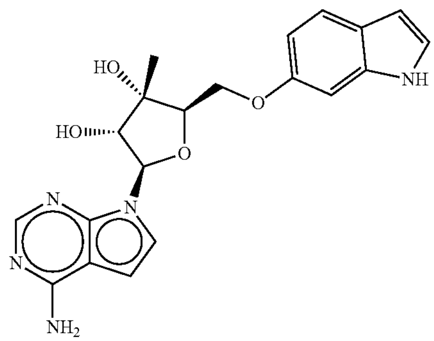 | 395.419 | (2R,3S,4R,5R)-2-(((1H-indol-6-yl)-oxy)methyl)-5-(4-amino-7H-pyrrolo-[2,3-d]pyrimidin-7-yl)-3-methyltetra-hydrofuran-3,4-diol |
| 25 | 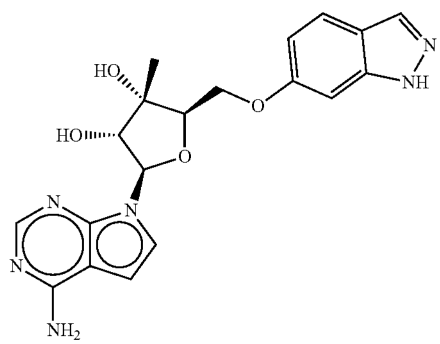 | 396.407 | (2R,3S,4R,5R)-2-(((1H-indazol-6-yl)-oxy)methyl)-5-(4-amino-7H-pyrrolo-[2,3-d]-pyrimidin-7-yl)-3-methyltetra-hydrofuran-3,4-diol |
| 26 | 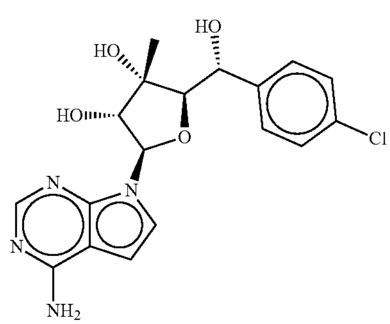 | 390.824 | (2R,3S,4R,5R)-5-(4-amino-7H-pyrrolo-[2,3-d]pyrimidin-7-yl)-2-((R)-(4-chloro-phenyl)(hydroxy)-methyl)-3-methyl-tetrahydrofuran-3,4-diol |

TABLE A-continued

| Ex. # | Structures | MW | Name |
|---|---|---|---|
| 27 | 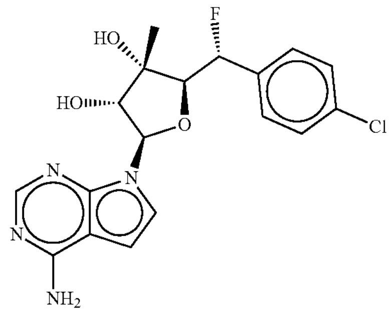 | 392.815 | (2S,3S,4R,5R)-5-(4-amino-7H-pyrrolo-[2,3-d]pyrimidin-7-yl)-2-((R)-(4-chlorophenyl)fluoromethyl)-3-methyltetrahydrofuran-3,4-diol |
| 28 | 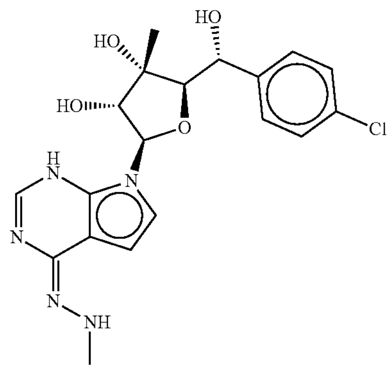 | 419.866 | (2R,3S,4R,5R)-2-((R)-(4-chlorophenyl)-(hydroxy)methyl)-3-methyl-5-(4-(2-methylhydrazineylidene)-1,4-dihydro-7H-pyrrolo[2,3-d]-pyrimidin-7-yl)tetrahydrofuran-3,4-diol |
| 29 | 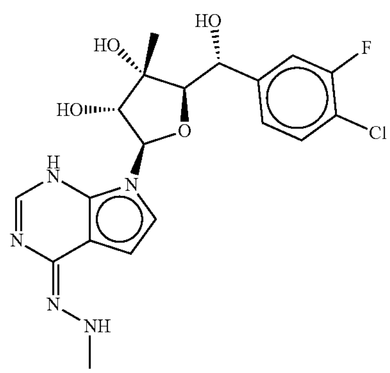 | 437.856 | (2R,3S,4R,5R)-2-((R)-(4-chloro-3-fluorophenyl)-(hydroxy)methyl)-3-methyl-5-(4-(2-methylhydrazineylidene)-1,4-dihydro-7H-pyrrolo[2,3-d]-pyrimidin-7-yl)tetrahydrofuran-3,4-diol |
| 30 | 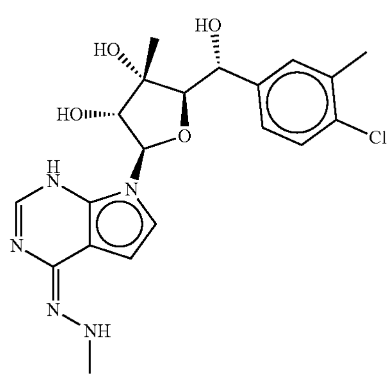 | 433.893 | (2R,3S,4R,5R)-2-((R)-(4-chloro-3-methylphenyl)-(hydroxy)methyl)-3-methyl-5-(-4-(2-methylhydrazineylidene)-1,4-dihydro-7H-pyrrolo[2,3-d]-pyrimidin-7-yl)tetrahydrofuran-3,4-diol |

TABLE A-continued

| Ex. # | Structures | MW | Name |
|---|---|---|---|
| 31 | 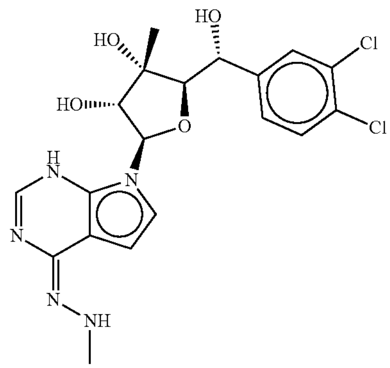 | 454.308 | (2R,3S,4R,5R)-2-((R)-(3,4-dichlorophenyl)(hydroxy)methyl)-3-methyl-5-(4-(2-methylhydrazineylidene)-1,4-dihydro-7H-pyrrolo[2,3-d]pyrimidin-7-yl)-tetrahydrofuran-3,4-diol |
| 32 | 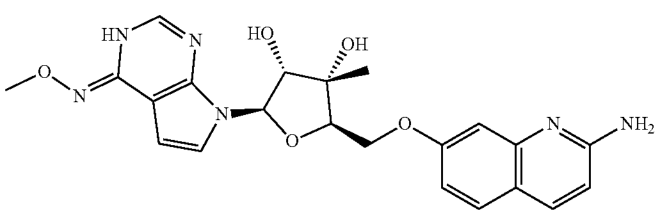 [SMILES: CO/N=c1\[nH]cnc2c1ccn2[C@@H]1O[C@H](COc2ccc3ccc(N)nc3c2)[C@@](C)(O)[C@H]1O] | 452.471 | 7-((2R,3R,4S,5R)-5-(((2-aminoquinolin-7-yl)oxy)methyl)-3,4-dihydroxy-4-methyl-tetrahydrofuran-2-yl)-3,7-dihydro-4H-pyrrolo[2,3-d]-pyrimidin-4-one O-methyl oxime |
| 33 | 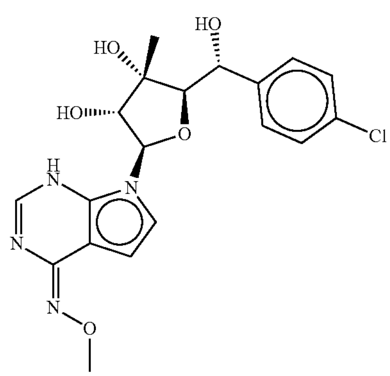 | 420.85 | 7-((2R,3R,4S,5R)-5-((R)-(4-chlorophenyl)-(hydroxy)methyl)-3,4-dihydroxy-4-methyl-tetrahydrofuran-2-yl)-1,7-dihydro-4H-pyrrolo[2,3-d]-pyrimidin-4-one O-methyl oxime |
| 34 | 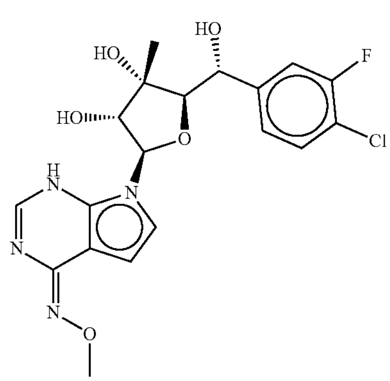 | 438.840 | 7-((2R,3R,4S,5R)-5-((R)-(4-chloro-3-fluorophenyl)-(hydroxy)methyl)-3,4-dihydroxy-4-methyltetrahydrofuran-2-yl)-1,7-dihydro-4H-pyrrolo-[2,3-d]pyrimidin-4-one O-methyl oxime |

TABLE A-continued

| Ex. # | Structures | MW | Name |
|---|---|---|---|
| 35 | 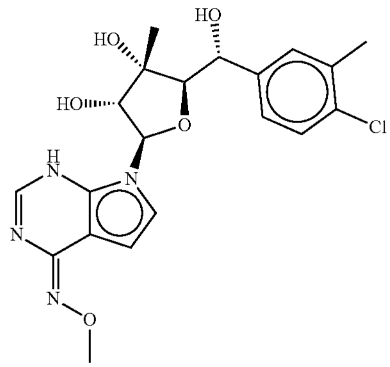 | 434.877 | 7-((2R,3R,4S,5R)-5-((R)-(4-chloro-3-methylphenyl)-(hydroxy)methyl)-3,4-dihydroxy-4-methyltetrahydrofuran-2-yl)-1,7-dihydro-4H-pyrrolo-[2,3-d]pyrimidin-4-one O-methyl oxime |
| 36 | 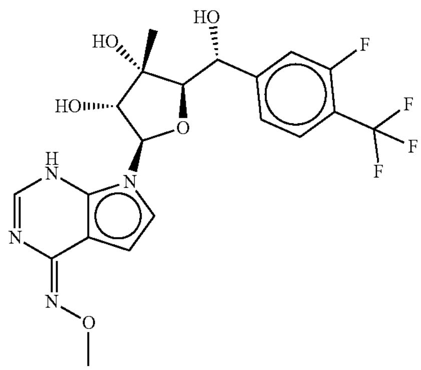 | 472.397 | 7-((2R,3R,4S,5R)-5-((R)-(3-fluoro-4-(trifluoromethyl)-phenyl)(hydroxy)-methyl)-3,4-dihydroxy-4-methyl-tetrahydrofuran-2-yl)-1,7-dihydro-4H-pyrrolo[2,3-d]-pyrimidin-4-one O-methyl oxime |
| 37 | 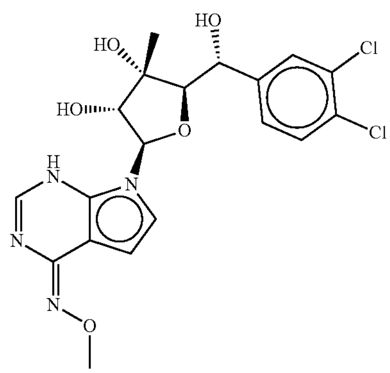 | 455.292 | 7-((2R,3R,4S,5R)-5-((R)-(3,4-dichloro-phenyl)(hydroxy)-methyl)-3,4-dihydroxy-4-methyl-tetrahydrofuran-2-yl)-1,7-dihydro-4H-pyrrolo[2,3-d]-pyrimidin-4-one O-methyl oxime |
| 38 | 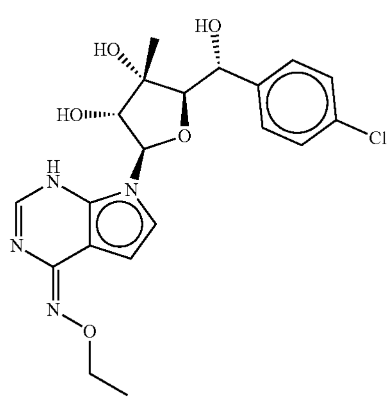 | 434.877 | 7-((2R,3R,4S,5R)-5-((R)-(4-chloro-phenyl)(hydroxy)-methyl)-3,4-dihydroxy-4-methyl-tetrahydrofuran-2-yl)-1,7-dihydro-4H-pyrrolo[2,3-d]-pyrimidin-4-one O-ethyl oxime |

TABLE A-continued

| Ex. # | Structures | MW | Name |
|---|---|---|---|
| 39 | 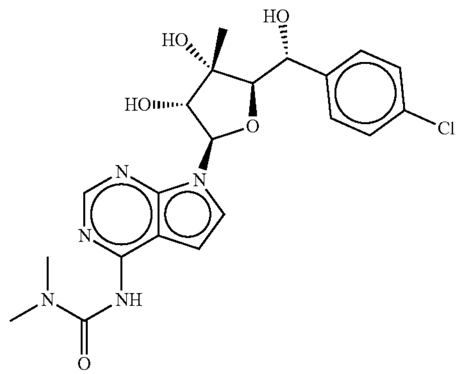 | 461.903 | 3-(7-((2R,3R,4S,5R)-5-((R)-(4-chloro-phenyl)(hydroxy)methyl)-3,4-dihydroxy-4-methyl-tetrahydrofuran-2-yl)-7H-pyrrolo[2,3-d]pyrimidin-4-yl)-1,1-dimethylurea |
| 40 | 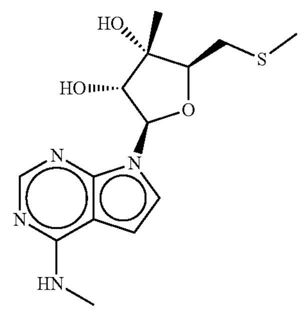 | 324.399 | (2S,3S,4R,5R)-3-methyl-5-(4-(methylamino)-7H-pyrrolo[2,3-d]pyrimidin-7-yl)-2-((methylthio)methyl)tetrahydrofuran-3,4-diol |
| 41 | 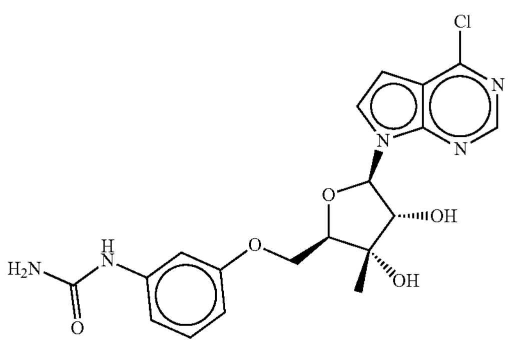 | 433.85 | 1-(3-(((2R,3S,4R,5R)-5-(4-chloro-7H-pyrrolo[2,3-d]pyrimidin-7-yl)-3,4-dihydroxy-3-methyltetrahydrofuran-2-yl)methoxy)phenyl)urea |
| 42 | 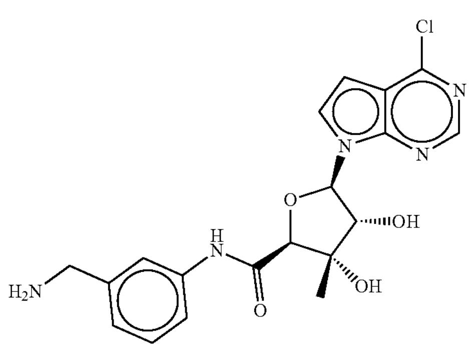 | 417.85 | (2S,3S,4R,5R)-N-(3-(aminomethyl)phenyl)-5-(4-chloro-7H-pyrrolo[2,3-d]pyrimidin-7-yl)-3,4-dihydroxy-3-methyl-tetrahydrofuran-2-carboxamide |

TABLE A-continued

| Ex. # | Structures | MW | Name |
|---|---|---|---|
| 43 | 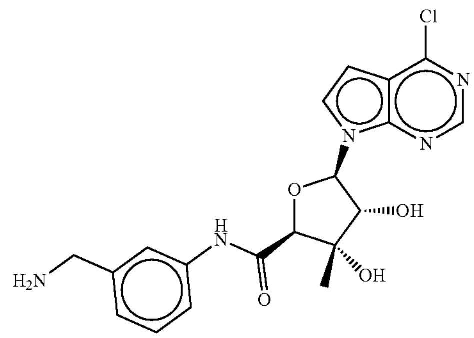 | 398.42 | (2S,3S,4R,5R)-5-(4-amino-7H-pyrrolo[2,3-d]-pyrimidin-7-yl)-N-(3-(aminomethyl)-phenyl)-3,4-dihydroxy-3-methyl-tetrahydrofuran-2-carboxamide |
| 44 | 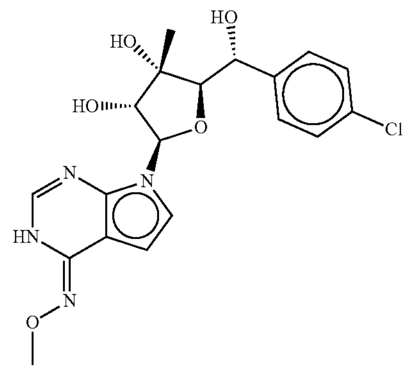 | 420.85 | (Z)-7-((2R,3R,4S,5R)-5-((R)-(4-chloro-phenyl)(hydroxy)-methyl)-3,4-dihydroxy-4-methyl-tetrahydrofuran-2-yl)-3,7-dihydro-4H-pyrrolo[2,3-d]-pyrimidin-4-one O-methyl oxime |
| 45 | 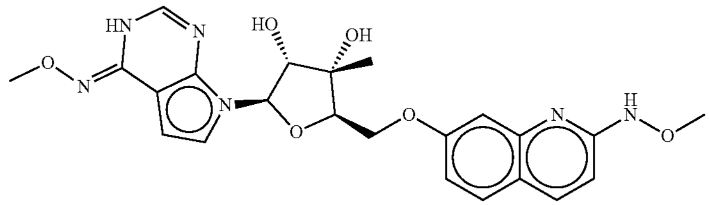 | 482.49 | (Z)-7-((2R,3R,4S,5R)-3,4-dihydroxy-5-(((2-(methoxyamino)-quinolin-7-yl)oxy)-methyl)-4-methyl-tetrahydrofuran-2-yl)-3,7-dihydro-4H-pyrrolo[2,3-d]-pyrimidin-4-one O-methyl oxime |
| 46 | 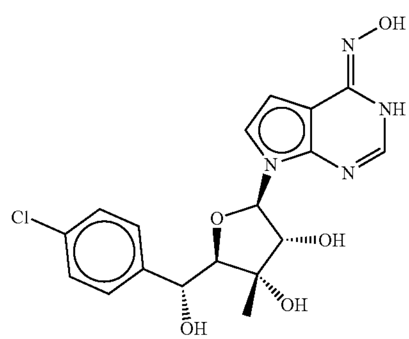 | 406.82 | (Z)-7-((2R,3R,4S,5R)-5-((R)-(4-chloro-phenyl)(hydroxy)-methyl)-3,4-dihydroxy-4-methyl-tetrahydrofuran-2-yl)-3,7-dihydro-4H-pyrrolo[2,3-d]-pyrimidin-4-one oxime |
| 47 | 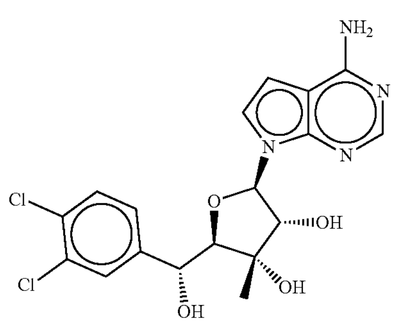 | 425.27 | (2R,3S,4R,5R)-5-(4-amino-7H-pyrrolo-[2,3-d]pyrimidin-7-yl)-2-((R)-(3,4-dichlorophenyl)-(hydroxy)methyl)-3-methyltetrahydro-furan-3,4-diol |

TABLE A-continued

| Ex. # | Structures | MW | Name |
|---|---|---|---|
| 48 | 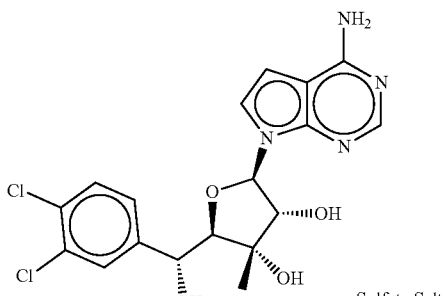 Sulfate Salt | | (2R,3S,4R,5R)-5-(4-amino-7H-pyrrolo-[2,3-d]pyrimidin-7-yl)-2-((R)-(3,4-dichlorophenyl)-(hydroxy)methyl)-3-methyltetrahydro-furan-3,4-diol Sulfate Salt |
| 49 | 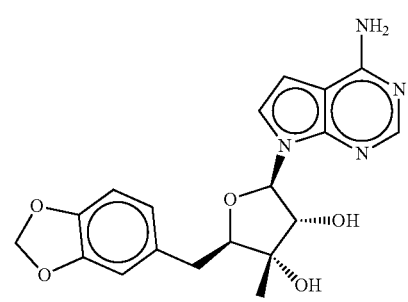 | 384.39 | (2R,3S,4R,5R)-5-(4-amino-7H-pyrrolo-[2,3-d]pyrimidin-7-yl)-2-(benzo[d][1,3]-dioxol-5-ylmethyl)-3-methyltetrahydro-furan-3,4-diol |
| 50 | 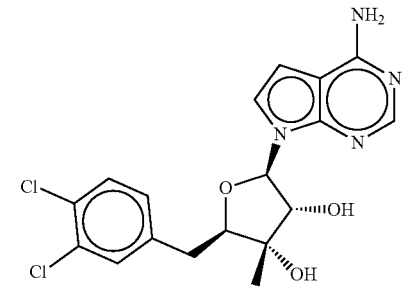 | 409.27 | (2R,3S,4R,5R)-5-(4-amino-7H-pyrrolo-[2,3-d]pyrimidin-7-yl)-2-(3,4-dichloro-benzyl)-3-methyltetra-hydrofuran-3,4-diol |
| 51 | 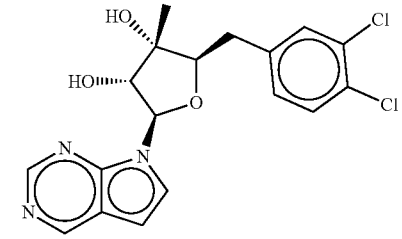 | 394.25 | (2R,3S,4R,5R)-2-(3,4-dichlorobenzyl)-3-methyl-5-(7H-pyrrolo[2,3-d]-pyrimidin-7-yl)tetra-hydrofuran-3,4-diol |
| 52 | 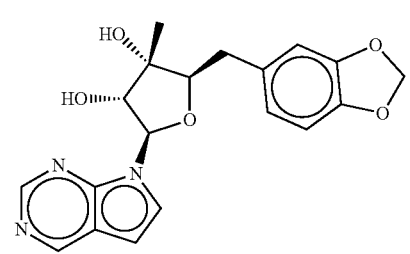 | 369.37 | (2R,3S,4R,5R)-2-(benzo[d][1,3]dioxol-5-ylmethyl)-3-methyl-5-(7H-pyrrolo[2,3-d]pyrimidin-7-yl)-tetrahydrofuran-3,4-diol |

TABLE A-continued

| Ex. # | Structures | MW | Name |
|---|---|---|---|
| 53 | 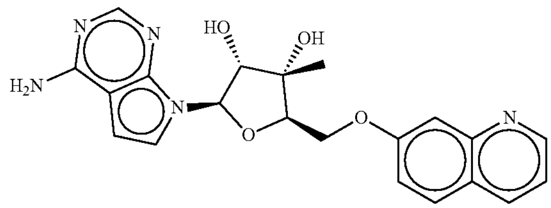 | 407.42 | (2R,3S,4R,5R)-5-(4-amino-7H-pyrrolo-[2,3-d]pyrimidin-7-yl)-3-methyl-2-((quinolin-7-yloxy)-methyl)tetrahydro-furan-3,4-diol |
| 54 | 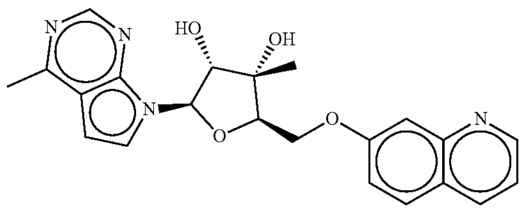 | 406.43 | (2R,3S,4R,5R)-3-methyl-5-(4-methyl-7H-pyrrolo[2,3-d]-pyrimidin-7-yl)-2-((quinolin-7-yloxy)-methyl)tetrahydro-furan-3,4-diol |
| 55 | 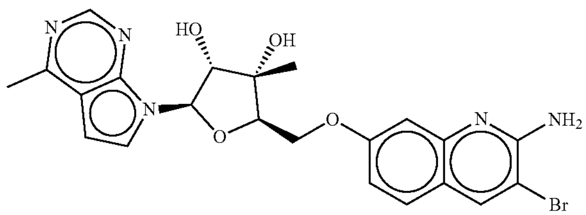 | 500.35 | (2R,3S,4R,5R)-2-(((2-amino-3-bromoquinolin-7-yl)oxy)methyl)-3-methyl-5-(4-methyl-7H-pyrrolo[2,3-d]-pyrimidin-7-yl)tetra-hydrofuran-3,4-diol |
| 56 | 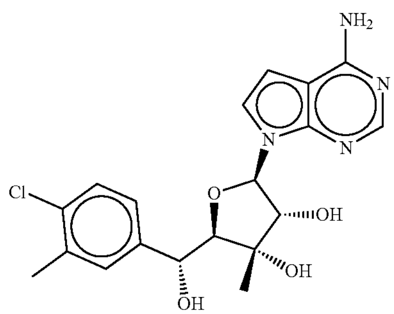 | 404.85 | (2R,3S,4R,5R)-5-(4-amino-7H-pyrrolo-[2,3-d]-pyrimidin-7-yl)-2-((R)-(4-chloro-3-methylphenyl)-(hydroxy)methyl)-3-methyltetrahydro-furan-3,4-diol |
| 57 | 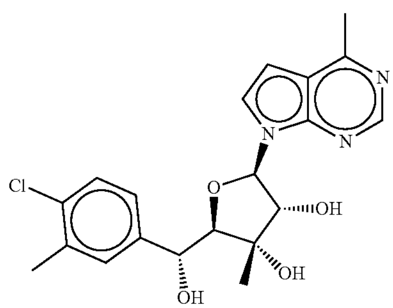 | 403.86 | (2R,3S,4R,5R)-2-((R)-(4-chloro-3-methyl-phenyl)(hydroxy)-methyl)-3-methyl-5-(4-methyl-7H-pyrrolo[2,3-d]-pyrimidin-7-yl)tetra-hydrofuran-3,4-diol |
| 58 | 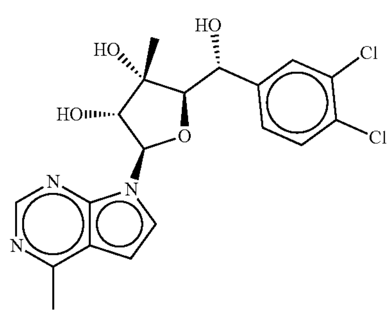 | 424.28 | (2R,3S,4R,5R)-2-((R)-(3,4-dichlorophenyl)-(hydroxy)methyl)-3-methyl-5-(4-methyl-7H-pyrrolo[2,3-d]-pyrimidin-7-yl)tetra-hydrofuran-3,4-diol |

TABLE A-continued

| Ex. # | Structures | MW | Name |
|---|---|---|---|
| 59 | 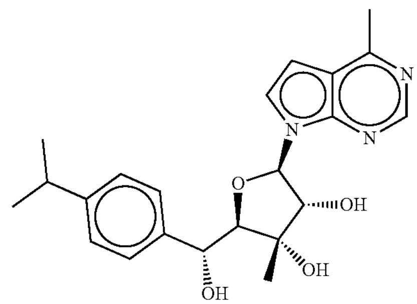 | 397.47 | (2R,3S,4R,5R)-2-((R)-hydroxy(4-isopropylphenyl)methyl)-3-methyl-5-(4-methyl-7H-pyrrolo[2,3-d]pyrimidin-7-yl)tetrahydrofuran-3,4-diol |
| 60 | 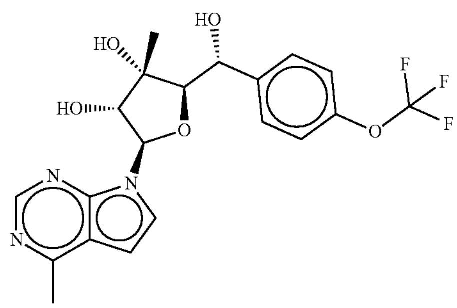 | 439.39 | (2R,3S,4R,5R)-2-((R)-hydroxy(4-(trifluoromethoxy)phenyl)methyl)-3-methyl-5-(4-methyl-7H-pyrrolo[2,3-d]pyrimidin-7-yl)tetrahydrofuran-3,4-diol |
| 61 | 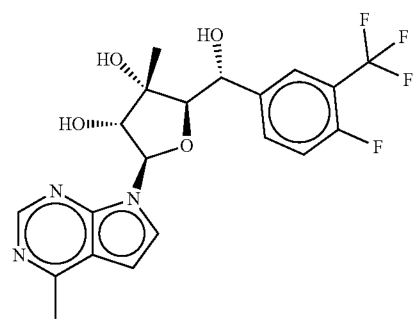 | 441.38 | (2R,3S,4R,5R)-2-((R)-(4-fluoro-3-(trifluoromethyl)phenyl)(hydroxy)methyl)-3-methyl-5-(4-methyl-7H-pyrrolo[2,3-d]pyrimidin-7-yl)tetrahydrofuran-3,4-diol |
| 62 | 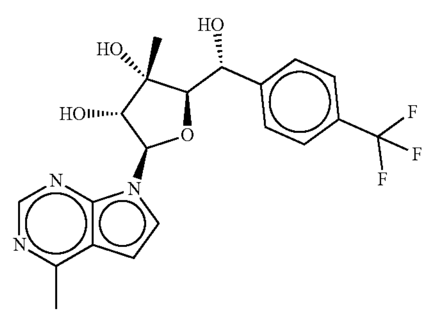 | 423.39 | (2R,3S,4R,5R)-2-((R)-hydroxy(4-(trifluoromethyl)phenyl)methyl)-3-methyl-5-(4-methyl-7H-pyrrolo[2,3-d]pyrimidin-7-yl)tetrahydrofuran-3,4-diol |
| 63 | 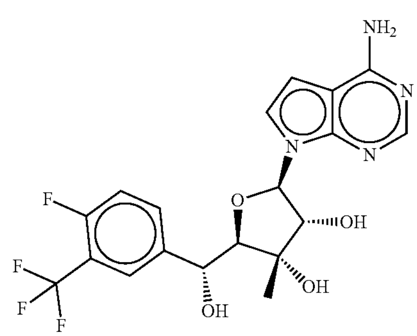 | 442.37 | (2R,3S,4R,5R)-5-(4-amino-7H-pyrrolo[2,3-d]pyrimidin-7-yl)-2-((R)-(4-fluoro-3-(trifluoromethyl)phenyl)(hydroxy)methyl)-3-methyltetrahydrofuran-3,4-diol |

TABLE A-continued

| Ex. # | Structures | MW | Name |
|---|---|---|---|
| 64 | 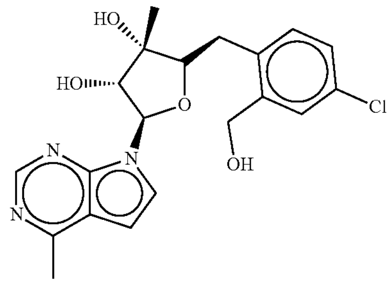 | 403.86 | (2R,3S,4R,5R)-2-(4-chloro-2-(hydroxymethyl)benzyl)-3-methyl-5-(4-methyl-7H-pyrrolo[2,3-d]pyrimidin-7-yl)tetrahydrofuran-3,4-diol |
| 65 | 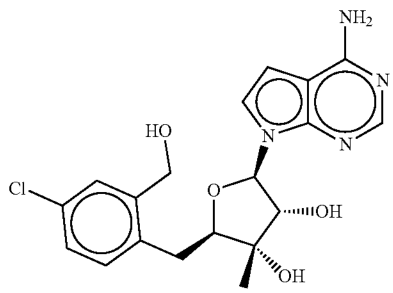 | 404.85 | (2R,3S,4R,5R)-5-(4-amino-7H-pyrrolo-[2,3-d]pyrimidin-7-yl)-2-(4-chloro-2-(hydroxymethyl)benzyl)-3-methyltetrahydrofuran-3,4-diol |
| 66 | 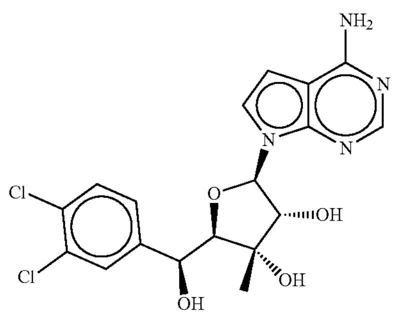 | 425.27 | (2R,3S,4R,5R)-5-(4-amino-7H-pyrrolo-[2,3-d]pyrimidin-7-yl)-2-((S)-(3,4-dichlorophenyl)-(hydroxy)methyl)-3-methyltetrahydrofuran-3,4-diol |
| 67 | 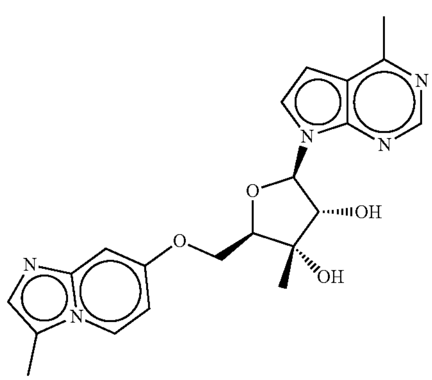 | 409.45 | (2R,3S,4R,5R)-3-methyl-5-(4-methyl-7H-pyrrolo-[2,3-d]pyrimidin-7-yl)-2-(((3-methylimidazo[1,2-a]pyridin-7-yl)oxy)methyl)tetrahydrofuran-3,4-diol |

TABLE A-continued

| Ex. # | Structures | MW | Name |
|---|---|---|---|
| 68 | 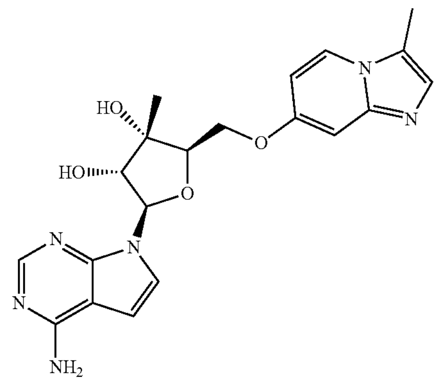 [SMILES: Cc1cnc2cc(OC[C@H]3O[C@@H](n4ccc5c(N)ncnc54)[C@H](O)[C@]3(C)O)ccn12] | 410.43 | (2R,3S,4R,5R)-5-(4-amino-7H-pyrrolo-[2,3-d]pyrimidin-7-yl)-3-methyl-2-(((3-methylimidazo[1,2-a]pyridin-7-yl)oxy)-methyl)tetrahydro-furan-3,4-diol |
| 69 | 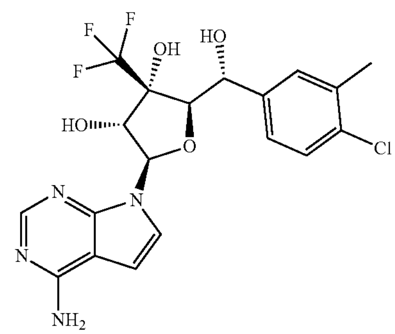 [SMILES: Cc1cc([C@@H](O)[C@H]2O[C@@H](n3ccc4c(N)ncnc43)[C@H](O)[C@@]2(O)C(F)(F)F)ccc1Cl] | 458.82 | (2R,3S,4R,5R)-5-(4-amino-7H-pyrrolo[2,3-d]pyrimidin-7-yl)-2-((R)-(4-chloro-3-methylphenyl)-(hydroxy)methyl)-3-(trifluoromethyl)-tetrahydrofuran-3,4-diol |
| 70 | 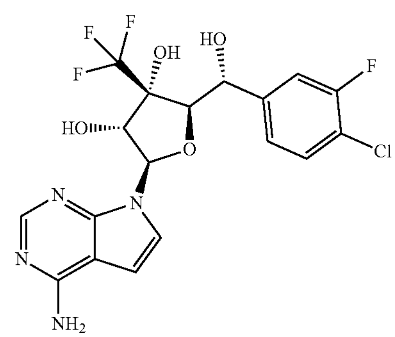 [SMILES: Nc1ncnc2c1ccn2[C@@H]1O[C@H]([C@H](O)c2ccc(Cl)c(F)c2)[C@](O)(C(F)(F)F)[C@H]1O] | 462.79 | (2R,3S,4R,5R)-5-(4-amino-7H-pyrrolo-[2,3-d]pyrimidin-7-yl)-2-((R)-(4-chloro-3-fluorophenyl)-(hydroxy)methyl)-3-(trifluoromethyl)-tetrahydrofuran-3,4-diol |
| 71 | 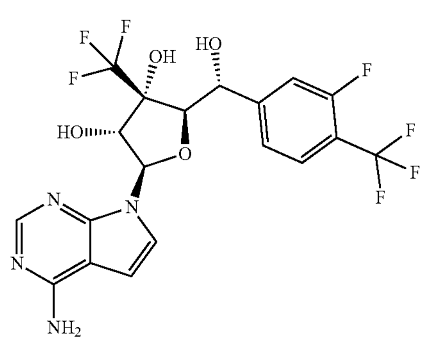 [SMILES: Nc1ncnc2c1ccn2[C@@H]1O[C@H]([C@H](O)c2ccc(C(F)(F)F)c(F)c2)[C@](O)(C(F)(F)F)[C@H]1O] | 496.34 | (2R,3S,4R,5R)-5-(4-amino-7H-pyrrolo-[2,3-d]pyrimidin-7-yl)-2-((R)-(3-fluoro-4-(trifluoromethyl)-phenyl)(hydroxy)-methyl)-3-(trifluoro-methyl)tetrahydro-furan-3,4-diol |

TABLE A-continued

| Ex. # | Structures | MW | Name |
|---|---|---|---|
| 72 | 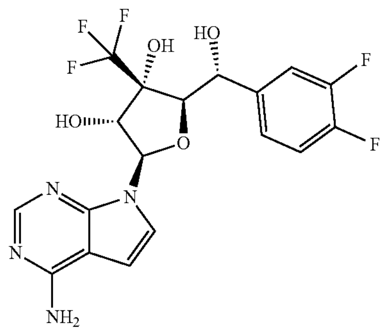 [SMILES: Nc1ncnc2c1ccn2[C@@H]1O[C@H]([C@H](O)c2ccc(F)c(F)c2)[C@](O)(C(F)(F)F)[C@H]1O] | 446.33 | (2R,3S,4R,5R)-5-(4-amino-7H-pyrrolo-[2,3-d]pyrimidin-7-yl)-2-((R)-(3,4-difluorophenyl)-(hydroxy)methyl)-3-(trifluoromethyl)-tetrahydrofuran-3,4-diol |
| 73 | 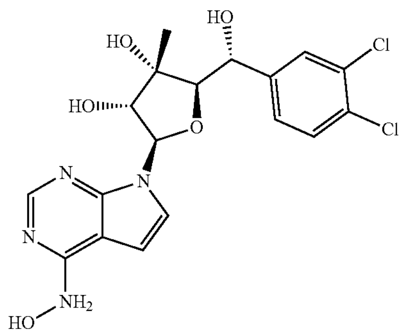 [SMILES: C[C@@]1(O)[C@@H]([C@H](O)c2ccc(Cl)c(Cl)c2)O[C@@H](n2ccc3c(NO)ncnc32)[C@@H]1O] | 441.27 | (2R,3S,4R,5R)-2-((R)-(3,4-dichloro-phenyl)(hydroxy-methyl)-5-(4-(hydroxyamino)-7H-pyrrolo[2,3-d]pyrimidin-7-yl)-3-methyltetra-hydrofuran-3,4-diol |
| 74 | 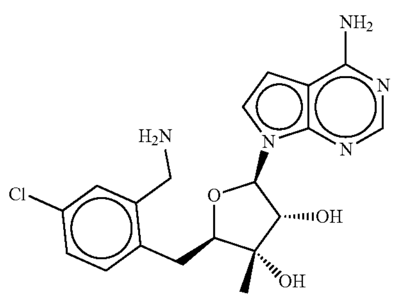 | 403.87 | (2R,3S,4R,5R)-5-(4-amino-7H-pyrrolo[2,3-d]-pyrimidin-7-yl)-2-(2-(aminomethyl)-4-chlorobenzyl)-3-methyltetrahydro-furan-3,4-diol |
| 75 | 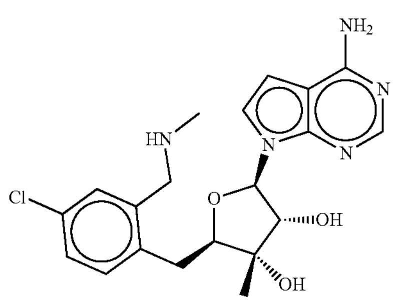 | 417.89 | (2R,3S,4R,5R)-5-(4-amino-7H-pyrrolo-[2,3-d]pyrimidin-7-yl)-2-(4-chloro-2-((methylamino)-methyl)benzyl)-3-methyltetrahydro-furan-3,4-diol |

Experimental Procedures

Synthesis of Intermediates

Synthesis of Int-1

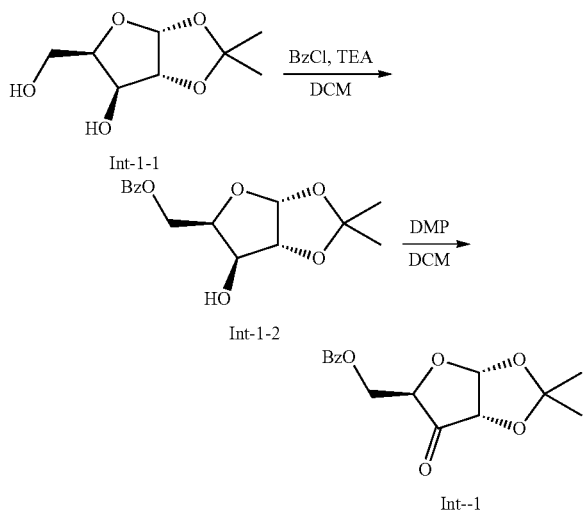

Step 1. Synthesis of ((3aR,5R,6S,6aR)-6-hydroxy-2,2-dimethyltetrahydrofuro[2,3-d][1,3]dioxol-5-yl)methyl benzoate (Int-1-2)

To a mixture of compound Int-1-1 (40.00 g, 210.31 mmol, 1 eq.) in DCM (400 mL) was added dropwise TEA (63.84 g, 630.94 mmol, 87.82 mL, 3 eq.) at 0° C. under $N_2$. BzCl (32.52 g, 231.34 mmol, 26.88 mL, 1.1 eq.) was added dropwise to the mixture at 0° C. under $N_2$. The mixture was stirred at 0° C. for 1 h under $N_2$. The mixture was combined another reaction mixture with 10 g of Int-1-1. The combined mixture was quenched by water (600 mL). The organic layer was separated. The aqueous was extracted with DCM (300 mL×3). The combined organic layers were washed with saturated NaHCO$_3$ solution (400 mL), dried over Na$_2$SO$_4$, filtered and concentrated. The residue was purified by column chromatography (SiO$_2$, Petroleum ether/Ethyl acetate=50/1 to 2/1) to give compound 2 (67.00 g, 227.66 mmol, 86.60% yield) as a yellow solid. $^1$H NMR (400 MHz, CHLOROFORM-d) δ=8.12-7.95 (m, 2H), 7.66-7.53 (m, 1H), 7.51-7.41 (m, 2H), 5.97 (d, J=3.7 Hz, 1H), 4.87-4.75 (m, 1H), 4.60 (d, J=3.5 Hz, 1H), 4.47-4.35 (m, 2H), 4.19 (dd, J=2.2, 4.0 Hz, 1H), 3.27 (d, J=4.0 Hz, 1H), 1.52 (s, 3H), 1.33 (s, 3H).

Step 2. Synthesis of ((3aR,5R,6aS)-2,2-dimethyl-6-oxotetrahydrofuro[2,3-d][1,3]dioxol-5-yl)methyl benzoate (Int-1)

Two batches in parallel: To a mixture of compound Int-1-2 (10.00 g, 33.98 mmol, 1 eq.) in DCM (100 mL) was added DMP (43.24 g, 101.94 mmol, 31.56 mL, 3 eq.) at 0° C. The mixture was stirred at 15° C. for 4 h. The mixture was filtered and the filtrate was concentrated. The residue was diluted with EtOAc (500 mL) and the mixture was filtered. The filtrated was diluted with saturated NaHCO$_3$ (300 mL). The mixture was extracted with EtOAc (200 mL*3). The combined organic layers were washed with brine (300 mL), dried over Na$_2$SO$_4$, filtered and concentrated. The residue was purified by column chromatography (SiO$_2$, Petroleum ether/Ethyl acetate=20/1 to 3/1) to give Int-1 (17.00 g, 58.16 mmol, 85.59% yield) as a white solid. $^1$H NMR (400 MHz, CHLOROFORM-d) δ=8.00-7.91 (m, 2H), 7.65-7.53 (m, 1H), 7.50-7.40 (m, 2H), 6.15 (d, J=4.4 Hz, 1H), 4.78-4.67 (m, 2H), 4.54-4.41 (m, 2H), 1.53 (s, 3H), 1.44 (s, 3H)

Synthesis of 2-chloroquinoline-7-ol (Int-2)

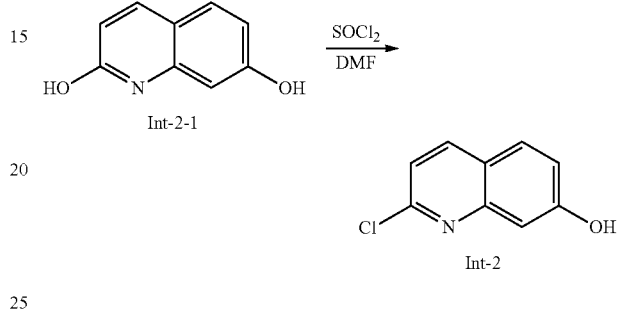

To a mixture of quinoline-2,7-diol (Int-2-1, 5.00 g, 31.03 mmol, 1 eq.) in DMF (50 mL) was added drop wise thionyl chloride (14.76 g, 124.10 mmol, 9.00 mL, 4 eq.) at 0° C. The mixture was stirred at 20° C. for 30 min and then stirred at 70° C. for 2 h. The mixture was concentrated to a residue. The residue was diluted with saturated NaHCO$_3$ solution (100 mL). The mixture was extracted with EtOAc (30 mL×4). The combined organic layers were washed with brine (40 mL), dried over Na$_2$SO$_4$, filtered and concentrated. The residue was purified by column chromatography (SiO$_2$, Petroleum ether/Ethyl acetate=50/1 to 3/1) to give compound Int-2 (5.30 g, 29.51 mmol, 95.11% yield) as a yellow solid. $^1$H NMR (400 MHz, CHLOROFORM-d) δ=8.03 (d, J=8.4 Hz, 1H), 7.73 (d, J=8.8 Hz, 1H), 7.34 (d, J=2.3 Hz, 1H), 7.25 (s, 1H), 7.20 (dd, J=2.5, 8.9 Hz, 1H), 5.45 (s, 1H).

Synthesis of Int-3

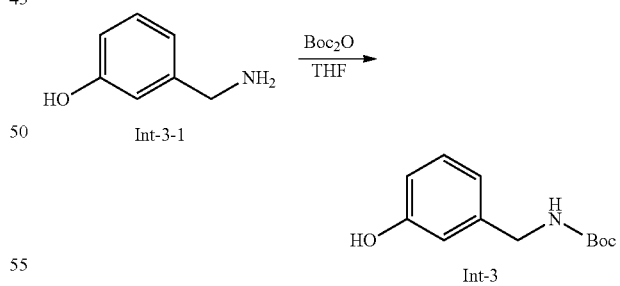

To a mixture of compound Int-3-1 (200 mg, 1.62 mmol, 1 eq.) in THF (6 mL) was added Boc$_2$O (425.32 mg, 1.95 mmol, 447.71 uL, 1.2 eq.) at 25° C. The mixture was stirred at 25° C. for 3 h. LCMS showed compound Int-3-1 was consumed and the desired MS was observed. The reaction was quenched by saturated NaHCO$_3$ solution (10 mL), extracted with EtOAc (5 mL×3). The combined organic layers were dried over Na$_2$SO$_4$, filtered and concentrated. The residue was purified by column chromatography (SiO$_2$, petroleum ether/ethyl acetate=I/O to 1/1) to give compound Int-3 (180 mg, 789.36 umol, 48.61% yield, LCMS purity 97.91%) as colorless oil. $^1$H NMR (400 MHz, CHLOROFORM-d) δ=7.20 (t, J=7.8 Hz, 1H), 6.91-6.69 (m, 3H), 4.81 (s, 1H), 4.28 (br d, J=5.5 Hz, 2H), 1.47 (s, 9H)

Synthesis of Int-4

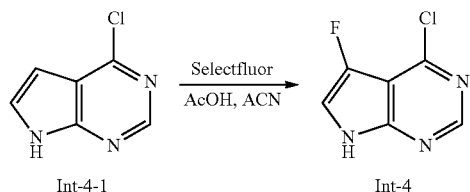 [SMILES: Clc1ncnc2[nH]ccc12 ; Fc1c[nH]c2ncnc(Cl)c12]

A mixture of compound Int-4-1 (14.5 g, 94.42 mmol, 1 eq.) and Selectfluor (50.17 g, 141.63 mmol, 1.5 eq.) was added ACN (725 mL), AcOH (152.25 g, 2.54 mol, 145 mL, 26.85 eq.) and degassed and purged with $N_2$ for 3 times, and then the mixture was stirred at 70° C. for 16 hr under $N_2$ atmosphere. LCMS showed no compound Int-4-1 was remained. Several new peaks were shown on LCMS and ~45% of desired compound was detected. The reaction mixture was concentrated under reduced pressure to remove solvent. The residue was diluted with toluene (200 mL) and concentrated under reduced pressure to remove solvent twice. The residue was purified by column chromatography ($SiO_2$, petroleum ether/ethyl acetate=30/1 to 8/1) to give compound Int-4 (10 g, 54.46 mmol, 57.68% yield, LCMS purity 93.43%) as a yellow solid. $^1$H NMR (400 MHz, DMSO-$d_6$) δ ppm 12.49 (br s, 1H) 8.55-8.67 (m, 1H) 7.71 (t, J=2.63 Hz, 1H); LCMS: (M+H$^+$): 171.9.

Synthesis of Int-5

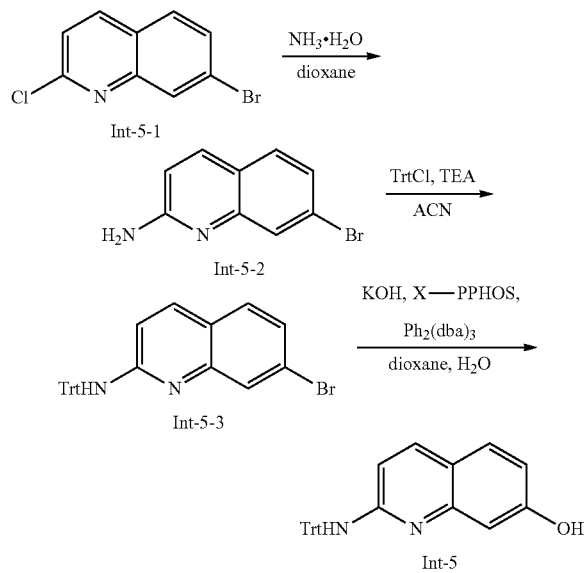

Step 1. Preparation of 7-bromoquinolin-2-amine (Int-5-2)

To a solution of compound Int-5-1 (6 g, 24.74 mmol, 1 eq.) in $NH_3 \cdot H_2O$ (80 mL) and dioxane (80 mL) was stirred at 120° C. for 6 h (50 psi). TLC showed compound Int-1-1 was remained and one new spot formed. The reaction was clean according to TLC (Petroleum ether/Ethyl acetate=5:1, $R_f$=0.08). The reaction mixture was concentrated under reduced pressure to remove solvent. The residue was diluted with $H_2O$ (100 mL) and extracted with EtOAc (50 mL×3). The combined organic layers were dried over $Na_2SO_4$, filtered and concentrated under reduced pressure to give a residue. The residue was purified by column chromatography ($SiO_2$, Petroleum ether/Ethyl acetate=50:1 to 1:1). Compound Int-5-2 (3.25 g, 14.29 mmol, 57.77% yield, 98.11% purity) was obtained as a yellow solid. LCMS: (M+H$^+$): 223.0; TLC (Petroleum ether:Ethyl acetate=5:1) $R_f$=0.08.

Step 2. Preparation of 7-bromo-N-tritylquinolin-2-amine (Int-5-3)

To a solution of compound Int-5-2 (0.2 g, 896.58 umol, 1 eq.) in ACN (10 mL) was added TEA (181.45 mg, 1.79 mmol, 249.59 uL, 2 eq.) and TrtCl (299.93 mg, 1.08 mmol, 1.2 eq.) at 25° C. The mixture was stirred at 80° C. for 0.5 h. TLC showed Compound Int-5-2 was remained and one new point formed (Petroleum ether:Ethyl acetate=3:1, $R_f$=0.68). The reaction mixture was concentrated under reduced pressure to remove solvent. The residue was diluted with $H_2O$ 15 mL and extracted with DCM (10 mL×3). The combined organic layers were washed with brine (20 mL×2), dried over $Na_2SO_4$, filtered and concentrated under reduced pressure to give a residue. The residue was purified by column chromatography ($SiO_2$, Petroleum ether/Ethyl acetate=1:0 to 5:1) and based on TLC (Petroleum ether: Ethyl acetate=3:1, $R_f$=0.68). Compound Int-5-3 (2 g, 3.45 mmol, 76.90% yield, 80.22% purity) was obtained as a white solid. TLC (Petroleum ether:Ethyl acetate=3:1) $R_f$=0.68; LCMS: (M+H$^+$): 467.0. LCMS purity 80.22%; $^1$H NMR (400 MHz, CHLOROFORM-d) δ=7.69 (s, 1H), 7.39 (d, J=9.04 Hz, 1H), 7.13-7.35 (m, 15H), 6.46 (s, 1H), 6.15 (d, J=9.04 Hz, 1H).

Step 3. Preparation of 2-(tritylamino) quinolin-7-ol (Int-5)

To a solution of compound Int-5-3 (0.6 g, 1.29 mmol, 1 eq.) in dioxane (3 mL) and $H_2O$ (3 mL) was added KOH (289.36 mg, 5.16 mmol, 4 eq.), X-PPHOS (95.48 mg, 193.39 umol, 0.15 eq.) and $Pd_2(dba)_3$ (118.06 mg, 128.93 umol, 0.1 eq.) under $N_2$ at 25° C. The mixture was stirred at 80° C. for 16 hr. LC-MS showed no compound Int-5-3 was remained. One main peak was shown on LC-MS and desired compound was detected. The reaction mixture was filtered, and the solution was concentrated under reduced pressure to remove solvent. The residue was diluted with $H_2O$ 10 mL and extracted with DCM (15 mL×2). The combined organic layers were washed with brine (10 mL×2), dried over $Na_2SO_4$, filtered and concentrated under reduced pressure to give a residue. The residue was purified by prep-TLC ($SiO_2$, Petroleum ether/Ethyl acetate=1:1, 5% TEA) and based on TLC (Petroleum ether/Ethyl acetate=1:1, $R_f$=0.21, 5% TEA). Compound Int-5 (0.23 g, crude) was obtained as a yellow solid. TLC (Petroleum ether:Ethyl acetate=1:1, 5% TEA) $R_f$=0.21; LCMS: (M+H$^+$): 403.1.

Synthesis of Int-6

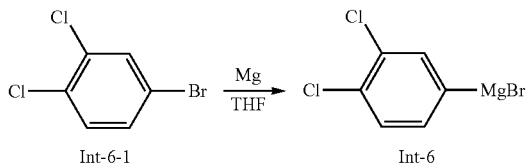

To a solution of Mg (979.09 mg, 40.28 mmol, 1.3 eq.) was added compound Int-6-1 (7 g, 30.99 mmol, 1 eq.) in THF (26 mL) at 40° C. under $N_2$. The mixture was stirred at 40° C. for 0.5 h. Mg was consumed. Compound Int-6 (7.75 g, crude) in THF (26 mL) was used into the next step without further purification as a yellow liquid.

Synthesis of Int-7

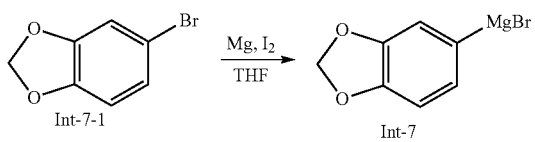

To a mixture of Mg (362.73 mg, 14.92 mmol, 1.5 eq.) and 12 (252.52 mg, 994.94 umol, 200.42 uL, 0.1 eq.) was added compound Int-7-1 (2 g, 9.95 mmol, 1.19 mL, 1 eq.) in THF (20 mL) at 25° C. under $N_2$. The mixture was stirred at 25° C. for 0.5 h. Mg was consumed. Compound Int-7 (2.24 g, crude) in THF (20 mL) was obtained as brown oil which was used for next step.

Synthesis of Int-8

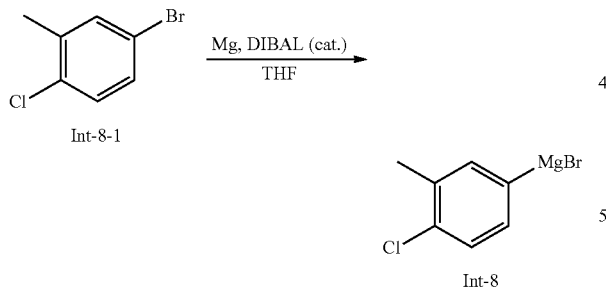

A 50 mL RBF with septum containing Mg (34.01 mg, 1.42 mmol) was dried under high vacuum with a heat gun and cooled under Ar. The flask was charged with THF (0.40 mL), 2/5 portion of 4-Bromo-1-chloro-2-methylbenzene (0.19 mL, 1.34 mmol), and one drop of DIBAL (1M, toluene). The reaction was stirred at rt but no exotherm was observed, which might mean that the magnesium was not initiating. Another drop of DIBAL was added and this time some exotherm took place. After stirring for 10 min, the remaining 4-bromo-1-chloro-2-methylbenzene and another THF (0.30 mL) were added and stirring was continued for 1 h. As all the magnesium dissolved, the Grignard reagent Int-8 was used as it was.

Synthesis of Int-9

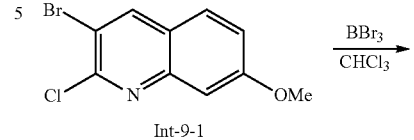

To a solution of 3-bromo-2-chloro-7-methoxy-quinoline (Int-9-1, WO2017/032840 A1) (640 mg, 2.35 mmol) in Chloroform (70 mL) was added Boron tribromide (4.4 mL, 46.97 mmol) at 0° C., the reaction mixture was stirred at 80° C. overnight. TLC (PE:EA=1:1, Rf=0.5) and LCMS showed 12% of SM left. The reaction was quenched with MeOH slowly at 0° C., EA was added and adjusted to pH 8 with aqueous $NaHCO_3$. The organic phase was separated and wash with brine. The organic phase was concentrated under vacuum to give the crude product which was purified by silica gel column chromatography (PE:EA=2:1 to PE:EA=1:1) to give 3-bromo-2-chloro-quinolin-7-ol (Int-9) (339 mg, 1.2852 mmol, 54.727% yield) as a white solid. LCMS $M+H^+$: 258/260.1/262

Example 1. (2R,3S,4R,5R)-5-(4-amino-7H-pyrrolo [2,3-d]pyrimidin-7-yl)-2-(((2-aminoquinolin-7-yl) oxy)methyl)-3-methyltetrahydrofuran-3,4-diol (1)

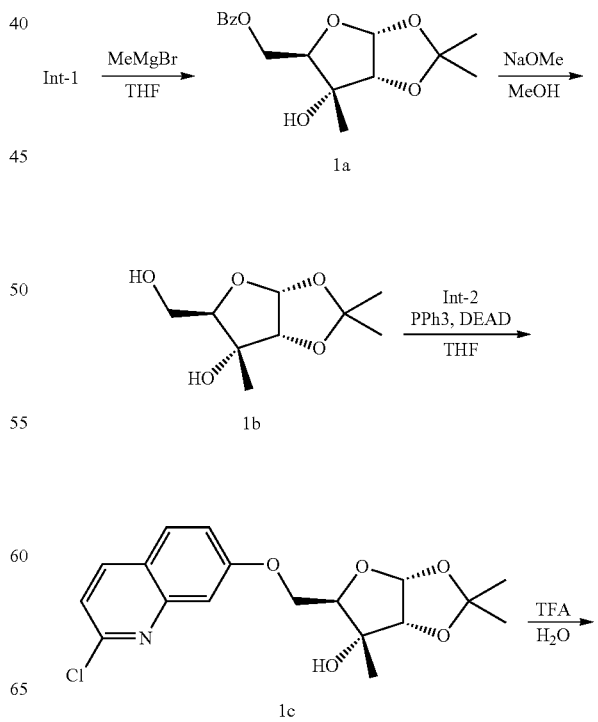

-continued

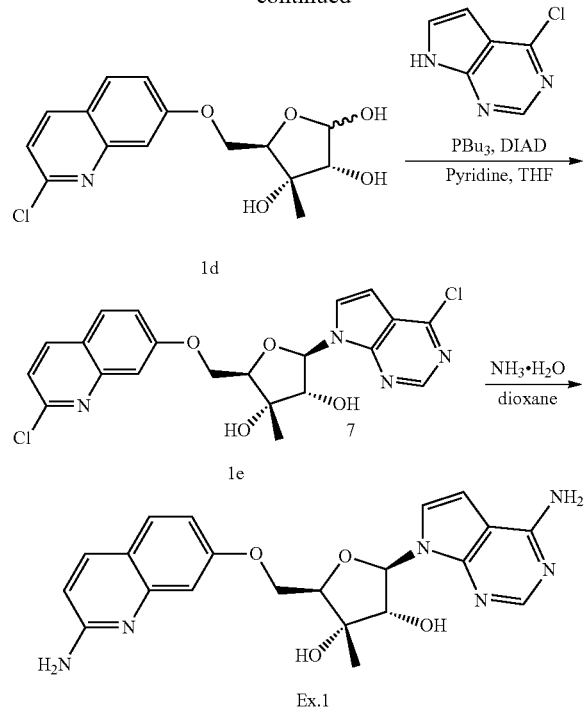

Step 1. Preparation of ((3aR,5R,6R,6aR)-6-hydroxy-2,2,6-trimethyltetrahydrofuro[2,3-d][1,3]dioxol-5-yl)methyl benzoate (1a)

To a mixture of Int-1 (17.00 g, 58.16 mmol, 1 eq.) in THF (200 mL) was added dropwise MeMgBr (3 M, 58.16 mL, 3 eq.) at −78° C. under $N_2$. The mixture was stirred at −78° C. for 1 h under $N_2$. The combined mixture was quenched by saturated $NH_4Cl$ (200 mL), extracted with EtOAc (50 mL*3). The combined organic layers were washed with brine (100 mL), dried over $Na_2SO_4$, filtered and concentrated. The crude product was purified by column chromatography ($SiO_2$, Petroleum ether/Ethyl acetate=15/1 to 5/1) to compound 1a as a white solid. $^1H$ NMR (400 MHz, CHLOROFORM-d) δ=8.13-8.01 (m, 2H), 7.64-7.51 (m, 1H), 7.48-7.38 (m, 2H), 5.83 (d, J=4.0 Hz, 1H), 4.57 (dd, J=3.1, 11.9 Hz, 1H), 4.38 (dd, J=8.2, 11.9 Hz, 1H), 4.21-4.06 (m, 2H), 2.71 (s, 1H), 1.60 (s, 3H), 1.37 (s, 3H), 1.26 (s, 3H).

Step 2. Preparation of (3aR,5R,6R,6aR)-5-(hydroxymethyl)-2,2,6-trimethyltetrahydrofuro[2,3-d][1,3]dioxol-6-ol (1b)

A mixture of compound 1a (2.30 g, 7.46 mmol, 1 eq.) and MeONa (806.00 mg, 14.92 mmol, 2 eq.) in MeOH (20 mL) was stirred at 15° C. for 0.5 h. The mixture was quenched by solid $NH_4Cl$ (4 g) and filtered. The filtrate was concentrated. The crude product was purified by column chromatography ($SiO_2$, Petroleum ether/Ethyl acetate=5/1 to 1/3) to give compound 1b (1.30 g, 6.37 mmol, 85.34% yield) as a white solid. $^1H$ NMR (400 MHz, CHLOROFORM-d) δ=5.80 (d, J=4.0 Hz, 1H), 4.13 (d, J=3.7 Hz, 1H), 3.96-3.71 (m, 3H), 2.67 (s, 1H), 1.81-1.69 (m, 1H), 1.60 (s, 3H), 1.37 (s, 3H), 1.18 (s, 3H)

Step 3. Preparation of (3aR,5R,6R,6aR)-5-(((2-chloroquinolin-7-yl)oxy)methyl)-2,2,6-trimethyltetrahydrofuro[2,3-d][1,3]dioxol-6-ol (1c)

To a mixture of $PPh_3$ (3.50 g, 13.35 mmol, 3 eq.) and DEAD (1.55 g, 8.90 mmol, 1.62 mL, 2 eq.) in THF (15 mL) was stirred at 20° C. for 30 min under $N_2$. 2-chloroquinolin-7-ol (Int-2, 799.51 mg, 4.45 mmol, 1 eq.) was added to the mixture followed by compound 1b (1.00 g, 4.90 mmol, 1.1 eq.) at 20° C. The mixture was stirred at 20° C. for 12 h. The mixture was quenched by water (20 mL), extracted with EtOAc (10 mL×2). The combined organic layers were washed with brine (20 mL), dried over $Na_2SO_4$, filtered and concentrated. The residue was purified by column chromatography ($SiO_2$, Petroleum ether/Ethyl acetate=I/O to 3:1) to give compound 1c (1.4 g, crude) as a white solid. LCMS: (M+H$^+$): 366.1.

Step 4. Preparation of (3R,4S,5R)-5-(((2-chloroquinolin-7-yl)oxy)methyl)-4-methyltetrahydrofuran-2,3,4-triol (1d)

A mixture of compound 1c (900 mg, 2.46 mmol, 1 eq.) in TFA (10 mL) and $H_2O$ (1 mL) was stirred at 20° C. for 0.5 h. The mixture was concentrated and the residue was dissolved into EtOAc (15 mL). Saturated $NaHCO_3$ solution (30 mL) was added to the mixture, and the organic layer was separated. The mixture was extracted with EtOAc (15 mL×4). The combined organic layers were dried over $Na_2SO_4$, filtered and concentrated. The residue was purified by column chromatography ($SiO_2$, Petroleum ether/Ethyl acetate=3/1 to 0/1) to give compound 1d (280 mg, 845.67 umol, 34.37% yield, 98.38% purity) as a white solid. H NMR (400 MHz, METHANOL-$d_4$) δ=8.26 (d, J=8.6 Hz, 1H), 7.88 (d, J=9.3 Hz, 1H), 7.45-7.25 (m, 3H), 5.39-5.20 (m, 1H), 4.59 (s, 1H), 4.40 (dd, J=3.4, 5.6 Hz, 1H), 4.35-4.07 (m, 3H), 3.86 (d, J=4.4 Hz, 1H), 3.68 (d, J=3.5 Hz, 1H), 1.37 (d, J=17.5 Hz, 3H).

Step 5. Preparation of (2R,3S,4R,5R)-5-(4-chloro-7H-pyrrolo[2,3-d]pyrimidin-7-yl)-2-(((2-chloroquinolin-7-yl)oxy)methyl)-3-methyltetrahydrofuran-3,4-diol (1e)

To a mixture of 4-chloro-7H-pyrrolo[2,3-d]pyrimidine (127.29 mg, 828.87 umol, 1 eq.) in THF (10 mL) was added pyridine (65.56 mg, 828.87 umol, 66.90 uL, 1 eq.) at 25° C. DIAD (335.21 mg, 1.66 mmol, 322.32 uL, 2 eq.) was added followed by tributylphosphane (335.39 mg, 1.66 mmol, 409.01 uL, 2 eq.) at 25° C. under $N_2$. Compound 1d was added at 25° C. under $N_2$. The mixture was stirred at 25° C. for 12 h under $N_2$. The mixture was concentrated. The residue was dissolved in EtOAc (50 mL). Water (100 mL) was added to the mixture. The organic layer was separated. The mixture was extracted with EtOAc (50 mL×2). The combined organic layers were washed with brine (100 mL), dried over $Na_2SO_4$, and concentrated. The residue was purified by prep-TLC ($SiO_2$, Petroleum ether/Ethyl acetate=1/3) to give compound 1e (130 mg, crude) as a white solid. LCMS: (M+H$^+$): 462.9.

Step 6. Preparation of (2R,3S,4R,5R)-5-(4-amino-7H-pyrrolo[2,3-d]pyrimidin-7-yl)-2-(((2-aminoquinolin-7-yl)oxy)methyl)-3-methyltetrahydrofuran-3,4-diol (1)

A mixture of compound 1e (80 mg, 173.42 umol, 1 eq.) and $NH_3 \cdot H_2O$ (36.40 g, 259.66 mmol, 40.00 mL, 1497.27 eq.) in dioxane (2 mL) was stirred at 145° C. for 48 h. The mixture was concentrated. The residue was purified by prep-HPLC ([water (10 mM NH$_4$HCO$_3$)–ACN]; B %: 20%-50%) to give compound 1 (9.13 mg, 21.33 umol, 12.30% yield, 98.71% purity) as a light yellow solid. $^1$H NMR (400 MHz, DMSO-d$_6$) δ=8.07 (s, 1H), 7.80 (d, J=8.8 Hz, 1H), 7.55 (d, J=8.8 Hz, 1H), 7.41 (d, J=3.7 Hz, 1H), 7.04-6.92 (m, 3H), 6.87 (dd, J=2.4, 8.7 Hz, 1H), 6.64-6.57 (m, 2H), 6.33 (s, 2H), 6.17 (d, J=7.9 Hz, 1H), 5.37 (d, J=7.2 Hz, 1H), 5.00 (s, 1H), 4.42 (t, J=7.5 Hz, 1H), 4.27-4.13 (m, 3H), 1.30 (s, 3H); $^1$H NMR (400 MHz, DMSO-d$_6$+D$_2$O) δ=8.07 (s, 1H), 7.81 (d, J=8.8 Hz, 1H), 7.56 (d, J=8.7 Hz, 1H), 7.40 (d, J=3.8 Hz, 1H), 6.99-6.84 (m, 2H), 6.67-6.57 (m, 2H), 6.17 (d, J=7.9 Hz, 1H), 4.24-4.12 (m, 3H), 1.30 (s, 3H) LCMS: (M+H$^+$): 423.1.

Example 2. (2R,3S,4R,5R)-5-(4-amino-7H-pyrrolo[2,3-d]pyrimidin-7-yl)-2-(((2-amino quinolin-7-yl)oxy)methyl)-3-(trifluoromethyl)tetrahydrofuran-3,4-diol (2)

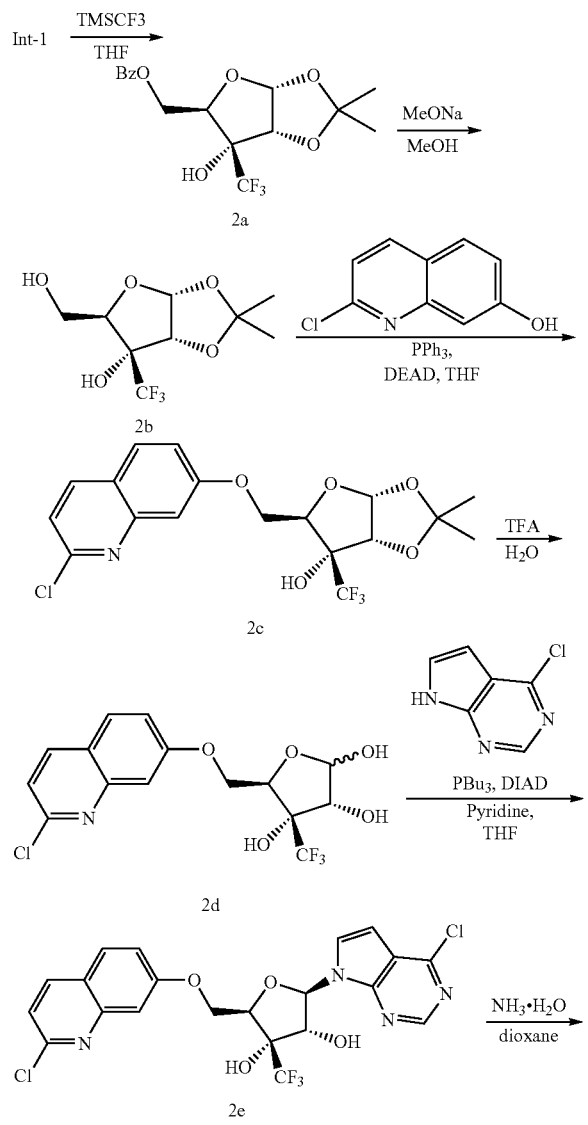

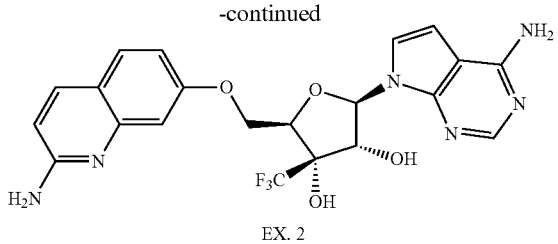

EX. 2

Step 1. Preparation of ((3aR,5R,6R,6aR)-6-hydroxy-2,2-dimethyl-6-(trifluoromethyl) tetrahydrofuro[2,3-d][1,3]dioxol-5-yl)methyl benzoate (2a)

A mixture of compound Int-1 (4.00 g, 13.69 mmol, 1 eq.) in THF (40 mL) was degassed and purged with N$_2$ for 3 times, and then the mixture was cooled to 0° C., and then the mixture was added TMSCF$_3$ (4.09 g, 28.74 mmol, 2.1 eq.), TBAF (1 M, 13.69 mL, 1 eq.), then the mixture was stirred at 0° C. for 1 h under N$_2$ atmosphere. TLC indicated compound Int-1 was consumed completely and new spots formed. The reaction was clean according to TLC. The reaction was quenched by sat. aq. NH$_4$Cl (10 mL), and extracted with EtOAc (10 mL×2), and then the organic phase was concentrated in vacuo. Compound 2a (4 g, crude) was obtained as a yellow oil. TLC (Petroleum ether:Ethyl acetate=3:1) R$_f$=0.29.

Step 2. Preparation of (3aR,5R,6R,6aR)-5-(hydroxymethyl)-2,2-dimethyl-6-(trifluoromethyl)tetrahydrofuro[2,3-d][1,3]dioxol-6-ol (2b)

To a solution of compound 2a (4.00 g, 11.04 mmol, 1 eq.) in MeOH (20 mL) was added NaOMe (1.19 g, 22.08 mmol, 2 eq.). The mixture was stirred at 25° C. for 0.5 h. TLC indicated compound 2a was consumed completely and new spots formed. The reaction was clean according to TLC. The reaction was quenched by NH$_4$Cl (20 g), and filtered, the filtrate was concentrated in vacuo. The residue was purified by column chromatography (SiO$_2$, Petroleum ether/Ethyl acetate=4/1 to 0:1). Compound 2b (2.6 g, crude) was obtained as a white solid. TLC (Petroleum ether:Ethyl acetate=3:1) R$_f$=0.07.

Step 3. Preparation of (3aR,5R,6R,6aR)-5-(((2-chloroquinolin-7-yl)oxy)methyl)-2,2-dimethyl-6-(trifluoromethyl)tetrahydrofuro[2,3-d][1,3]dioxol-6-ol (2c)

A mixture of PPh$_3$ (5.28 g, 20.14 mmol, 2 eq.) in THF (20 mL) was degassed and purged with N$_2$ for 3 times, and then the mixture was cooled to 0° C., then the mixture was added DEAD (3.51 g, 20.14 mmol, 3.66 mL, 2 eq.) stirred at 0° C. for 30 min, then compound 2b (2.6 g, 10.07 mmol, 1 eq.) and 2-chloroquinolin-7-ol (2.17 g, 12.08 mmol, 1.2 eq.) was added at 0° C., the mixture was stirred at 25° C. for 12 h under N$_2$ atmosphere. LC-MS showed compound 2b was consumed completely and one main peak with desired mass was detected. TLC indicated compound 2b was consumed completely and new spots formed. The reaction was clean according to TLC. The mixture was concentrated in vacuo. The residue was purified by column chromatography (SiO$_2$, Petroleum ether/Ethyl acetate=4/1 to 1:1). Compound 2c (1.5 g, crude) was obtained as a yellow oil. LCMS: (M+H$^+$): 420.0; TLC (Petroleum ether:Ethyl acetate=3:1) R$_f$=0.36.

Step 4. Preparation of (3R,4S,5R)-5-(((2-chloroquinolin-7-yl)oxy)methyl)-4-(trifluoromethyl)tetrahydrofuran-2,3,4-triol (2d)

To compound 2c (1.50 g, 3.57 mmol, 1 eq.) was added TFA (452.71 mg, 3.57 mmol, 293.97 uL, 90% purity, 1 eq.), the mixture was stirred at 25° C. for 20 min. TLC indicated compound 2c was consumed completely and new spots formed. The reaction was clean according to TLC. The reaction was quenched by sat. NaHCO₃ (30 mL) and then extracted with EtOAc (10 mL×2). The combined organic phase was washed with brine (10 mL), dried over anhydrous Na₂SO₄, filtered and concentrated in vacuo. The crude product compound 2d (1 g, crude) was used into the next step without further purification as a yellow oil. TLC (Petroleum ether:Ethyl acetate=1:1) $R_f$=0.24.

Step 5. Preparation of (2R,3S,4R,5R)-5-(4-chloro-7H-pyrrolo[2,3-d]pyrimidin-7-yl)-2-(((2-chloroquinolin-7-yl)oxy)methyl)-3-(trifluoromethyl)tetrahydrofuran-3,4-diol (2e)

A solution of 4-chloro-7H-pyrrolo[2,3-d]pyrimidine (161.77 mg, 1.05 mmol, 1 eq.) in THF (10 mL) was added pyridine (83.33 mg, 1.05 mmol, 85.03 uL, 1 eq.), DIAD (426.02 mg, 2.11 mmol, 409.64 uL, 2 eq.), tributylphosphane (426.26 mg, 2.11 mmol, 519.83 uL, 2 eq.), compound 2d (400 mg, 1.05 mmol, 1 eq.) all at once, the mixture was stirred at 25° C. for 12 h under N₂. LC-MS showed compound 2d was consumed completely and one main peak with desired mass was detected. The mixture was concentrated in vacuo. The residue was dissolved in H₂O (10 mL), and then extracted with EtOAc (10 mL×3), the organic phase was concentrated in vacuo. The residue was purified by column chromatography (SiO₂, Petroleum ether/Ethyl acetate=10/1 to 4:1). Compound 2e (300 mg, crude) was obtained as a white solid. TLC (Petroleum ether:Ethyl acetate=1:1) $R_f$=0.58.

Step 6. Preparation of (2R,3S,4R,5R)-5-(4-amino-7H-pyrrolo[2,3-d]pyrimidin-7-yl)-2-(((2-aminoquinolin-7-yl)oxy)methyl)-3-(trifluoromethyl)tetrahydrofuran-3,4-diol (2)

To a solution of compound 2e (300 mg, 582.22 umol, 1 eq.) in dioxane (3 mL) was added NH₃.H₂O (19.98 g, 142.50 mmol, 21.95 mL, 25% purity, 244.75 eq.), the mixture was stirred at 145° C. for 12 h. LC-MS showed compound 2e was consumed completely and one main peak with desired MS was detected. The mixture was concentrated in vacuo. The residue was purified by prep-HPLC (basic condition, HPLC: column: Waters Xbridge Prep OBD C18 150*30 10 u; mobile phase: [water (0.04% NH₃H₂O)–ACN]; B %: 10%-40%, 10 min). Compound 3 (15.73 mg, 32.58 umol, 5.60% yield, and 98.67% LCMS purity) was obtained as a white solid. ¹H NMR (400 MHz, DMSO-d₆) δ=8.08 (s, 1H), 7.78 (d, J=8.6 Hz, 1H), 7.52 (d, J=8.8 Hz, 1H), 7.44 (d, J=3.5 Hz, 1H), 7.08 (br s, 2H), 6.86 (d, J=2.4 Hz, 1H), 6.82-6.76 (m, 2H), 6.65 (d, J=3.5 Hz, 1H), 6.59 (d, J=8.8 Hz, 1H), 6.35 (s, 2H), 6.21 (d, J=7.3 Hz, 1H), 6.15 (d, J=7.7 Hz, 1H), 4.99 (t, J=7.5 Hz, 1H), 4.41-4.25 (m, 3H); ¹H NMR (400 MHz, DMSO-d₆+D₂O) δ=8.05 (s, 1H), 7.77 (d, J=8.8 Hz, 1H), 7.51 (d, J=8.8 Hz, 1H), 7.41 (d, J=3.5 Hz, 1H), 6.84 (d, J=2.2 Hz, 1H), 6.78 (d, J=2.5, 8.7 Hz, 1H), 6.63 (d, J=3.7 Hz, 1H), 6.58 (d, J=8.8 Hz, 1H), 6.12 (d, J=7.9 Hz, 1H), 4.97 (d, J=7.7 Hz, 1H), 4.39-4.22 (m, 3H); LCMS: (M+H⁺): 477.1; HPLC purity: 100.0%.

Example 3. (2R,3S,4R,5R)-5-(4-amino-7H-pyrrolo[2,3-d]pyrimidin-7-yl)-2-(((2-amino quinolin-7-yl)oxy)methyl)-3-ethynyltetrahydrofuran-3,4-diol (3)

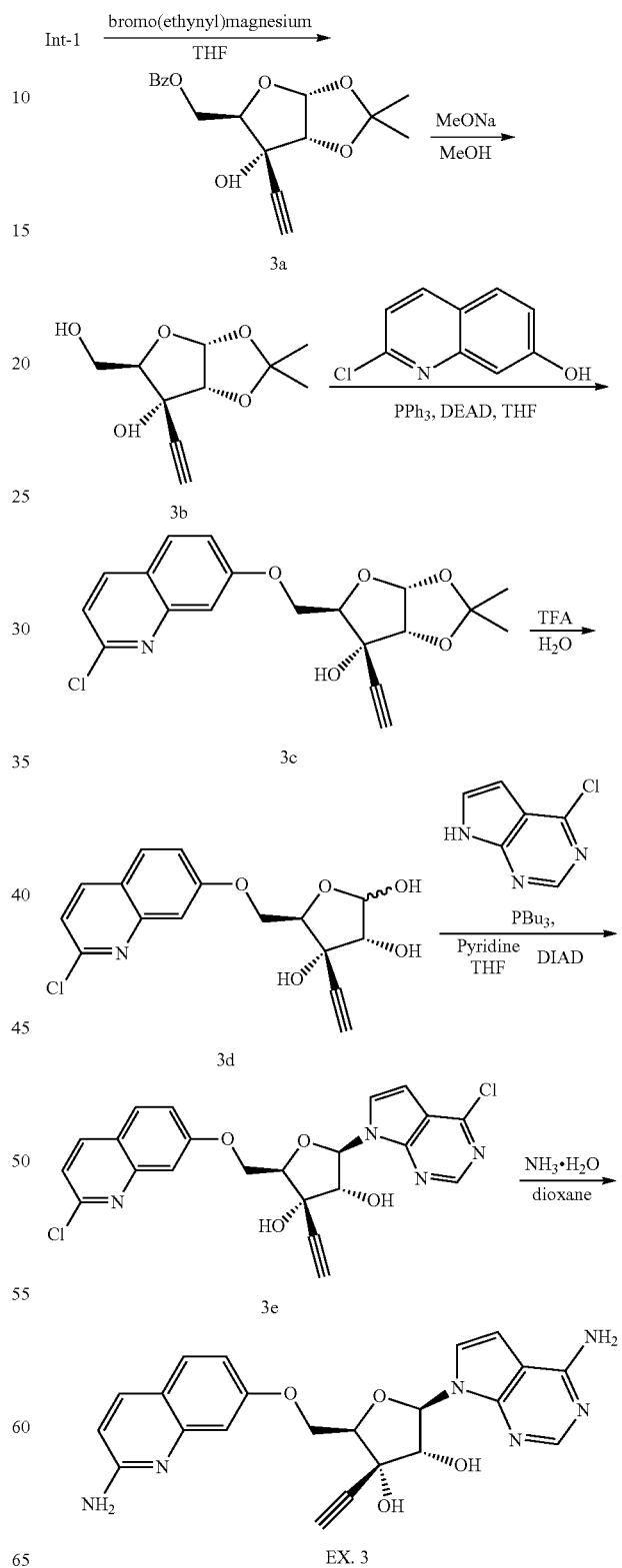

Step 1. Preparation of ((3aR,5R,6R,6aR)-6-ethynyl-6-hydroxy-2,2-dimethyltetrahydrofuro [2,3-d][1,3]dioxol-5-yl)methyl benzoate (3a)

A mixture of compound Int-1 (4.00 g, 13.69 mmol, 1 eq.) in THF (40 mL) was degassed and purged with $N_2$ for 3 times, and then the mixture was cooled to 0° C., and then the mixture was added bromo(ethynyl)magnesium (0.5 M, 41.06 mL, 1.5 eq.), the mixture was stirred at 0° C. for 3 h under $N_2$ atmosphere. TLC indicated compound Int-1 was consumed completely and one new spot formed. The reaction was clean according to TLC. The reaction was quenched by sat. aq. $NH_4Cl$ (4 mL) and extracted with EtOAc (5 mL×3). The organic phase was concentrated in vacuo. Compound 3a (4 g, crude) was obtained as a yellow oil. TLC (Petroleum ether: Ethyl acetate=2:1) $R_f$=0.43.

Step 2. Preparation of (3aR,5R,6R,6aR)-6-ethynyl-5-(hydroxymethyl)-2,2-dimethyl tetrahydrofuro [2,3-d][1,3]dioxol-6-ol (3b)

To a solution of compound 3a (4.00 g, 12.57 mmol, 1 eq.) in MeOH (30 mL) was added NaOMe (1.36 g, 25.13 mmol, 2 eq.). The mixture was stirred at 25° C. for 0.5 h. TLC indicated compound 3a was consumed completely and new spots formed. The reaction was clean according to TLC. The reaction was quenched by $NH_4Cl$ (20 g), and then filtered, and the filtrate was concentrated in vacuo at 25° C. The residue was purified by column chromatography ($SiO_2$, Petroleum ether/Ethyl acetate=4/1 to 1:1). Compound 3b (2.6 g, crude) was obtained as a white solid. TLC (Petroleum ether:Ethyl acetate=1:1) $R_f$=0.24.

Step 3. Preparation of (3aR,5R,6R,6aR)-5-(((2-chloroquinolin-7-yl)oxy)methyl)-6-ethynyl-2,2-dimethyltetrahydrofuro[2,3-d][1,3]dioxol-6-ol (3c)

A mixture of $PPh_3$ (6.37 g, 24.27 mmol, 2 eq.) in THF (20 mL) was degassed and purged with $N_2$ for 3 times, and then the mixture was cooled to 0° C., and then the mixture was added DEAD (4.23 g, 24.27 mmol, 4.41 mL, 2 eq.), the mixture was stirred at 0° C. for 30 min, then the mixture was added 2-chloroquinolin-7-ol (2.62 g, 14.56 mmol, 1.2 eq.), then the mixture was added compound 3b (2.60 g, 12.14 mmol, 1 eq.) at 0° C., then the mixture was stirred at 25° C. for 12 h under $N_2$ atmosphere. TLC indicated compound 3b was consumed completely and new spots formed. The reaction was clean according to TLC. The reaction was concentrated in vacuo at 25° C. The residue was purified by column chromatography ($SiO_2$, Petroleum ether/Ethyl acetate=4/1 to 4:1). Compound 3c (2.4 g, crude) was obtained as a white solid. TLC (Petroleum ether: Ethyl acetate=3:1) $R_f$=0.62.

Step 4. Preparation of (3R,4S,5R)-5-(((2-chloroquinolin-7-yl)oxy)methyl)-4-ethynyltetra hydrofuran-2,3,4-triol (3d)

To a solution of compound 3c (2.40 g, 6.39 mmol, 1 eq.) was added TFA (809.08 mg, 6.39 mmol, 525.38 uL, 90% purity, 1 eq.), the mixture was stirred at 25° C. for 20 min. TLC indicated compound 3c was consumed completely and new spots formed. The reaction was clean according to TLC. The reaction was quenched by sat. $NaHCO_3$ (30 mL) and then extracted with EtOAc (10 mL×2). The combined organic phase was washed with brine (10 mL), dried over anhydrous $Na_2SO_4$, filtered and concentrated in vacuo. The crude product compound 3d (1.9 g, crude) was used into the next step without further purification as a yellow oil. TLC (Petroleum ether: Ethyl acetate=1:1) $R_f$=0.24.

Step 5. Preparation of (2R,3S,4R,5R)-5-(4-chloro-7H-pyrrolo[2,3-d]pyrimidin-7-yl)-2-(((2-chloroquinolin-7-yl)oxy)methyl)-3-ethynyltetrahydrofuran-3,4-diol (3e)

A solution of 4-chloro-7H-pyrrolo[2,3-d]pyrimidine (182.96 mg, 1.19 mmol, 1 eq.) in THF (10 mL) was added pyridine (94.24 mg, 1.19 mmol, 96.16 uL, 1 eq.), DIAD (481.83 mg, 2.38 mmol, 463.29 uL, 2 eq.), tributylphosphane (482.09 mg, 2.38 mmol, 587.91 uL, 2 eq.), compound 3d (400 mg, 1.19 mmol, 1 eq.) all at once, the mixture was stirred at 25° C. for 12 h under $N_2$. LC-MS showed compound 3d was consumed completely and one main peak with desired MS was detected. The mixture was concentrated in vacuo. The residue was dissolved in $H_2O$ (10 mL), and then extracted with EtOAc (10 mL*3), the organic phase was concentrated in vacuo. The residue was purified by column chromatography ($SiO_2$, Petroleum ether/Ethyl acetate=10/1 to 4:1). Compound 3e (300 mg, crude) was obtained as a white solid. TLC (Petroleum ether:Ethyl acetate=2:1) $R_f$=0.12; LCMS: (M+H$^+$): 473.0.

Step 6. Preparation of (2R,3S,4R,5R)-5-(4-amino-7H-pyrrolo[2,3-d]pyrimidin-7-yl)-2-(((2-aminoquinolin-7-yl)oxy)methyl)-3-ethynyltetrahydrofuran-3,4-diol (3)

To a solution of compound 3e (300 mg, 636.55 umol, 1 eq.) in dioxane (3 mL) was added $NH_3·H_2O$ (5.46 g, 155.80 mmol, 6 mL, 244.75 eq.). The mixture was stirred at 145° C. for 12 h. LC-MS showed compound 3e was consumed completely and one main peak with desired MS was detected. The mixture was concentrated in vacuo. The residue was purified by prep-HPLC (HCl condition, column: Luna C18 100*30 5u; mobile phase: [water (0.05% HCl)–ACN]; B %: 1%-20%, 10 min). Compound 3 (3.32 mg, 6.30 umol, 0.99% yield, 95.96% LCMS purity, 2HCl) was obtained as a white gum. $^1$H NMR (400 MHz, DMSO-d$_6$) δ=8.42 (s, 1H), 8.28 (d, J 9.3 Hz, 1H), 7.86 (d, J 8.6 Hz, 1H), 7.70 (d, J 3.5 Hz, 1H), 7.34 (s, 1H), 7.23-7.16 (m, 2H), 7.09 (s, 1H), 7.03 (d, J 3.5 Hz, 1H), 6.92 (d, J 9.5 Hz, 1H), 6.36 (s, 1H), 6.15 (d, J 7.7 Hz, 1H), 4.72 (d, J 7.3 Hz, 1H), 4.42-4.35 (m, 2H), 3.61 (s, 1H); $^1$H NMR (400 MHz, DMSO-d$_6$+D$_2$O) δ=8.37 (s, 1H), 8.28 (d, J 9.3 Hz, 1H), 7.85 (d, J 9.5 Hz, 1H), 7.67 (d, J 3.5 Hz, 1H), 7.21-7.16 (m, 2H), 6.98 (d, J 3.7 Hz, 1H), 6.89 (d, J 9.0 Hz, 1H), 6.15 (d, J 7.7 Hz, 1H), 4.70 (d, J 7.7 Hz, 1H), 4.41-4.35 (m, 3H); LCMS: (M+H$^+$): 433.0; HPLC purity: 100.0%.

Example 4. (2R,3S,4R,5R)-5-(4-amino-7H-pyrrolo[2,3-d]pyrimidin-7-yl)-2-(((2-amino quinolin-7-yl)oxy)methyl)-3-vinyltetrahydrofuran-3,4-diol (4)

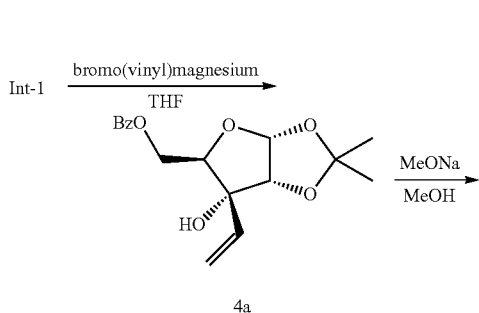

4a

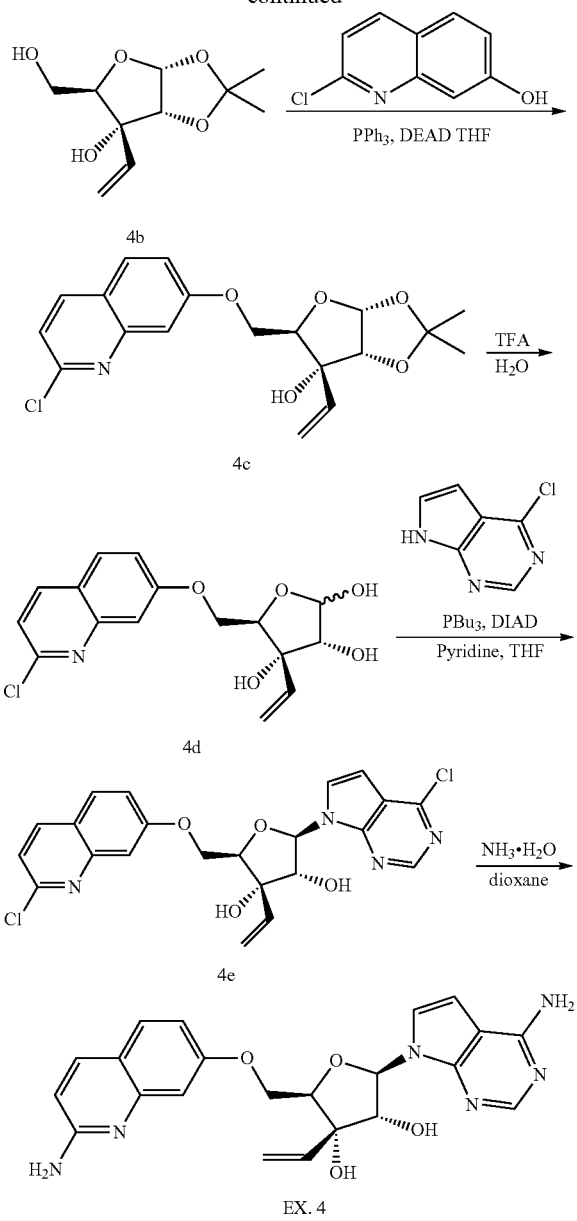

Step 1. Preparation of ((3aR,5R,6R,6aR)-6-hydroxy-2,2-dimethyl-6-vinyltetrahydrofuro [2,3-d][1,3]dioxol-5-yl)methyl benzoate (4a)

A mixture of compound Int-1 (3.00 g, 10.26 mmol, 1 eq.) in THF (20 mL) was degassed and purged with $N_2$ for 3 times, and then the mixture was cooled to –78° C., and then the mixture was added bromo(vinyl)magnesium (1 M, 20.53 mL, 2 eq.), then the mixture was stirred at –78° C. for 3 h under $N_2$ atmosphere. LC-MS showed compound Int-1 was consumed completely and one main peak with desired mass was detected. The reaction was quenched by sat. aq. $NH_4Cl$ (10 mL), and then extracted with EtOAc (10 mL×3), and the organic phase was concentrated in vacuo. No purification. Compound 4a (3.29 g, crude) was obtained as a yellow solid. LCMS: (M+H+): 319.1.

Step 2. Preparation of (3aR,5R,6R,6aR)-5-(hydroxymethyl)-2,2-dimethyl-6-vinyltetrahydrofuro[2,3-d][1,3]dioxol-6-ol (4b)

To a solution of compound 4a (3.29 g, 10.27 mmol, 1 eq.) in MeOH (30 mL) was added NaOMe (1.11 g, 20.54 mmol, 2 eq.). The mixture was stirred at 25° C. for 0.5 h. TLC indicated compound 4a was consumed completely and new spots formed. The reaction was clean according to TLC. The reaction was quenched by $NH_4Cl$ (20 g), and filtered, the filtrate was concentrated in vacuo. The residue was purified by column chromatography ($SiO_2$, Petroleum ether: Ethyl acetate=5/1 to 1:1). Compound 4b (1.9 g, crude) was obtained as a white solid. $^1H$ NMR (400 MHz, CHLOROFORM-d) δ=5.85 (d, J 3.7 Hz, 1H), 5.81-5.71 (m, 1H), 5.53 (dd, J 1.2, 17.2 Hz, 1H), 5.30 (dd, J 1.1, 11.0 Hz, 1H), 4.23 (d, J 3.8 Hz, 1H), 4.00 (t, J 5.6 Hz, 1H), 3.69 (d, J 5.7 Hz, 2H), 1.61 (s, 3H), 1.37 (s, 2H), 1.40-1.33 (m, 1H).

Step 3. Preparation of (3aR,5R,6R,6aR)-5-(((2-chloroquinolin-7-yl)oxy)methyl)-2,2-dimethyl-6-vinyltetrahydrofuro[2,3-d][1,3]dioxol-6-ol (4c)

A mixture of $PPh_3$ (4.65 g, 17.74 mmol, 2 eq.) in THF (20 mL) was degassed and purged with $N_2$ for 3 times, and then the mixture was cooled to 0° C., and then the mixture was added DEAD (3.09 g, 17.74 mmol, 3.22 mL, 2 eq.), the mixture was stirred at 0° C. for 30 min, then the mixture was added 2-chloroquinolin-7-ol (1.91 g, 10.64 mmol, 1.2 eq.), then the mixture was added compound 4b (1.92 g, 8.87 mmol, 1 eq.) at 0° C., then the mixture was stirred at 25° C. for 12 h under $N_2$ atmosphere. LC-MS showed compound 4b was consumed completely and one main peak with desired MS was detected. The reaction was concentrated in vacuo at 25° C. The residue was purified by column chromatography ($SiO_2$, Petroleum ether/Ethyl acetate=4/1 to 4:1). Compound 4c (1.2 g, crude) was obtained as a white solid. $^1H$ NMR (400 MHz, CHLOROFORM-d) δ=8.01 (d, J 8.6 Hz, 1H), 7.73-7.64 (m, 1H), 7.33 (d, J 2.4 Hz, 1H), 7.27 (d, J 2.6 Hz, 1H), 7.26-7.23 (m, 1H), 5.95 (d, J 3.7 Hz, 1H), 5.87-5.76 (m, 1H), 5.70-5.58 (m, 1H), 5.38 (dd, J 1.4, 10.9 Hz, 1H), 4.36-4.31 (m, 1H), 4.29 (d, J 4.0 Hz, 1H), 4.17 (dd, J 1.9, 10.7 Hz, 1H), 4.10-4.06 (m, 1H), 1.66 (s, 3H), 1.40 (s, 3H); LCMS: (M+H+): 378.1.

Step 4. Preparation of (3R,4S,5R)-5-(((2-chloroquinolin-7-yl)oxy)methyl)-4-vinyltetrahydrofuran-2,3,4-triol (4d)

A solution compound 4c of (400 mg, 1.06 mmol, 1 eq.) in TFA (120.72 mg, 1.06 mmol, 78.39 uL, 1 eq.), the mixture was stirred at 25° C. for 1 h. LC-MS showed compound 4c was consumed completely and one main peak with desired mass was detected. The mixture was concentrated in vacuo, and then dissolved in toluene (10 mL), and then concentrated in vacuo, and repeated this three times. The crude product compound 4d (400 mg, crude, TFA) was as a yellow oil and used into the next step without further purification. LCMS: (M+H+): 338.2.

Step 5. Preparation of (2R,3S,4R,5R)-5-(4-chloro-7H-pyrrolo[2,3-d]pyrimidin-7-yl)-2-(((2-chloroquinolin-7-yl)oxy)methyl)-3-vinyltetrahydrofuran-3,4-diol (4e)

A solution of 4-chloro-7H-pyrrolo[2,3-d]pyrimidine (136.40 mg, 888.22 umol, 1 eq.) in THF (10 mL) was added pyridine (70.26 mg, 888.22 umol, 71.69 uL, 1 eq.), DIAD (359.21 mg, 1.78 mmol, 345.39 uL, 2 eq.), tributylphosphane (359.40 mg, 1.78 mmol, 438.30 uL, 2 eq.), compound 4d (300 mg, 888.22 umol, 1 eq.) all at once, the mixture was stirred at 25° C. for 12 h under N₂. LC-MS showed compound 4d was consumed completely and one main peak with desired MS was detected. The mixture was concentrated in vacuo. The residue was dissolved in H₂O (10 mL), and then extracted with EtOAc (10 mL×3), the organic phase was concentrated in vacuo. The residue was purified by prep-TLC (SiO₂, Petroleum ether: Ethyl acetate=3:1). Compound 4e (400 mg, crude) was obtained as a yellow oil. TLC (Petroleum ether:Ethyl acetate=3:1) R$_f$=0.37; LCMS: (M+H⁺): 473.0.

Step 6. Preparation of (2R,3S,4R,5R)-5-(4-amino-7H-pyrrolo[2,3-d]pyrimidin-7-yl)-2-(((2-aminoquinolin-7-yl)oxy)methyl)-3-vinyltetrahydrofuran-3,4-diol (4)

To a solution of compound 4e (20 mg, 42.26 umol, 1 eq.) in dioxane (3 mL) was added NH₃·H₂O (5.46 g, 38.95 mmol, 6 mL, 25%, 921.74 eq.). The mixture was stirred at 145° C. for 12 h. LC-MS showed compound 4e was consumed completely and one main peak with desired MS was detected. The mixture was concentrated in vacuo. The residue was purified by prep-HPLC (basic condition; column: YMC-Actus Triart C18 100*30 mm*5 um; mobile phase: [water (10 mM NH₄HCO₃)–ACN]; B %: 15%-35%, 12 min.). Compound 4 was got batch 1 (2.7 mg, 98.93%) and batch 2 (9.29 mg, 95%) as a white solid. (Batch 1) 1H NMR (400 MHz, DMSO-d₆) δ=8.07 (s, 1H), 7.80 (br d, J 8.7 Hz, 1H), 7.55 (br d, J 8.6 Hz, 1H), 7.44 (br d, J 3.4 Hz, 1H), 7.01 (br s, 2H), 6.93-6.82 (m, 2H), 6.64-6.55 (m, 2H), 6.34 (br s, 2H), 6.25 (br d, J 8.1 Hz, 1H), 6.01 (br dd, J 10.6, 17.0 Hz, 1H), 5.61-5.46 (m, 2H), 5.28 (br d, J 11.1 Hz, 1H), 5.19 (s, 1H), 4.70 (br t, J 7.5 Hz, 1H), 4.20-4.09 (m, 3H); (Batch 1) ¹H NMR (400 MHz, DMSO-d₆+D₂O) δ=8.06 (s, 1H), 7.81 (d, J 8.8 Hz, 1H), 7.57 (d, J 8.6 Hz, 1H), 7.42 (d, J 3.5 Hz, 1H), 6.91-6.86 (m, 2H), 6.63-6.58 (m, 2H), 6.24 (d, J 7.9 Hz, 1H), 5.99 (dd, J 10.9, 17.1 Hz, 1H), 5.54 (dd, J 1.7, 17.1 Hz, 1H), 5.30-5.25 (m, 1H), 4.70 (d, J 7.9 Hz, 1H), 4.18-4.16 (m, 1H), 4.14-4.08 (m, 1H); (Batch 1) LCMS: (M+H⁺): 435.1; (Batch 1) HPLC purity: 100.0%; (Batch 2)₁H NMR (400 MHz, DMSO-d₆) δ=8.07 (s, 1H), 7.80 (d, J=8.9 Hz, 1H), 7.55 (d, J=8.7 Hz, 1H), 7.44 (d, J=3.4 Hz, 1H), 7.01 (br s, 2H), 6.94-6.82 (m, 2H), 6.66-6.55 (m, 2H), 6.33 (s, 2H), 6.25 (d, J=7.8 Hz, 1H), 6.01 (dd, J=10.7, 17.3 Hz, 1H), 5.60-5.46 (m, 2H), 5.28 (br d, J=12.2 Hz, 1H), 5.18 (s, 1H), 4.70 (t, J=7.5 Hz, 1H), 4.21-4.13 (m, 3H), 4.13-4.08 (m, 1H); (Batch 2)₁H NMR (400 MHz, DMSO-d₆+D₂O) δ=8.06 (s, 1H), 7.81 (d, J 8.7 Hz, 1H), 7.57 (d, J 8.3 Hz, 1H), 7.43 (d, J 3.7 Hz, 1H), 6.93-6.83 (m, 2H), 6.64-6.56 (m, 2H), 6.24 (d, J 7.9 Hz, 1H), 5.99 (dd, J 10.8, 17.1 Hz, 1H), 5.57-5.49 (m, 1H), 5.28 (br d, J 11.6 Hz, 1H), 4.70 (d, J 8.1 Hz, 1H), 4.20-4.03 (m, 3H); (Batch 2) LCMS: (M+H⁺): 435.1; (Batch 2) HPLC purity: 100.0%.

Example 6. (2R,3S,4R,5R)-5-(4-amino-5-fluoro-7H-pyrrolo[2,3-d]pyrimidin-7-yl)-2-(((2-aminoquinolin-7-yl)oxy)methyl)-3-methyltetrahydrofuran-3,4-diol (6)

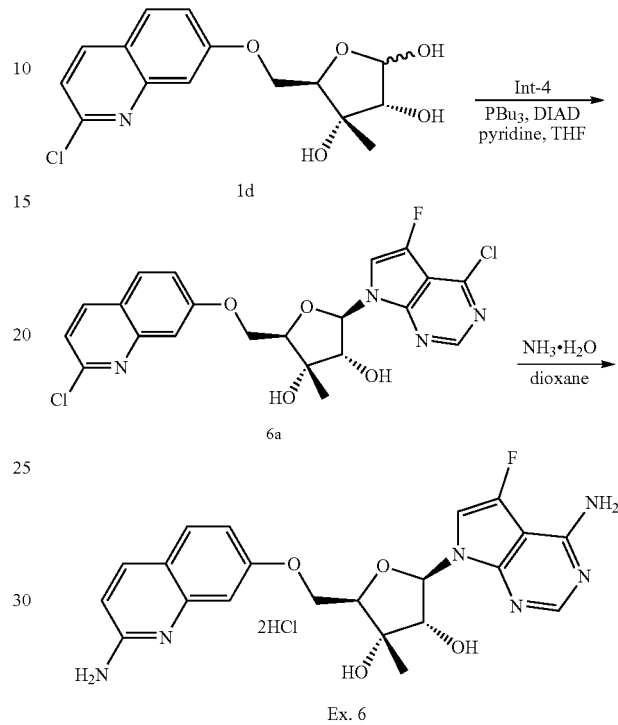

Step 1. Preparation of ((3aR,5R,6R,6aR)-6-hydroxy-2,2,6-trimethyltetrahydrofuro[2,3-d][1,3]dioxol-5-yl)methyl benzoate (6a)

To a mixture of compound Int-4 (94.80 mg, 552.58 umol, 1.2 eq.) in THF (4 mL) was added pyridine (36.42 mg, 460.48 umol, 37.17 uL, 1 eq.) at 25° C. DIAD (186.23 mg, 920.97 umol, 179.07 uL, 2 eq.) was added followed by tributylphosphane (186.33 mg, 920.97 umol, 227.23 uL, 2 eq.) at 25° C. under N₂. Compound 1d (150.00 mg, 460.48 umol, 1 eq.) was added at 25° C. under N₂. The mixture was stirred at 25° C. for 12 h under N₂. LCMS showed compound 1d were consumed and the desired MS was observed. The mixture was concentrated. The residue was dissolved in EtOAc (50 mL). Water (20 mL) was added to the mixture. The organic layer was separated. The mixture was extracted with EtOAc (10 mL×3). The combined organic layers were washed with brine (20 mL), dried over Na₂SO₄, filtered and concentrated. The residue was purified by prep-TLC (SiO₂, petroleum ether/ethyl acetate=1/3) to give compound 6a (100 mg, 140.99 umol, 30.62% yield, LCMS purity 67.6%) as a yellow solid. LCMS: (M+H⁺): 479.0.

Step 2. Preparation of (2R,3S,4R,5R)-5-(4-amino-5-fluoro-7H-pyrrolo[2,3-d]pyrimidin-7-yl)-2-(((2-aminoquinolin-7-yl)oxy)methyl)-3-methyltetrahydrofuran-3,4-diol (6)

A mixture of compound 6a (50 mg, 104.32 umol, 1 eq.) and NH₃·H₂O (3.64 g, 25.97 mmol, 4 mL, 248.91 eq.) in dioxane (3 mL) was stirred at 145° C. for 24 h. LCMS showed compound 6a was consumed. The mixture was concentrated. The residue was purified by prep-HPLC (column: UniSil 120*30*10 um; mobile phase: [water (0.05% HCl)–ACN]; B %: 1%-20%, 11 min). Compound 6 (7.24 mg, 15.27 umol, 14.64% yield, LCMS purity 92.88%) was obtained as a brown solid. 1H NMR (400 MHz, DMSO-$d_6$) δ=13.95 (br s, 1H), 8.49-8.17 (m, 4H), 7.89 (d, J=8.9 Hz, 1H), 7.60 (s, 1H), 7.27-7.16 (m, 2H), 6.93 (d, J=9.3 Hz, 1H), 6.24-6.17 (m, 1H), 4.44-4.11 (m, 5H), 1.31 (s, 3H); $^1$H NMR (400 MHz, DMSO-$d_6$+$D_2$O) δ=8.37-8.27 (m, 2H), 7.89 (d, J=8.8 Hz, 1H), 7.59 (s, 1H), 7.29-7.16 (m, 2H), 6.92 (d, J=9.2 Hz, 1H), 6.21 (dd, J=1.8, 8.0 Hz, 1H), 4.39-4.21 (m, 4H), 1.30 (s, 3H); LCMS: (M+H$^+$): 441.2.

Example 10. (2R,3S,4R,5R)-2-(((2-aminoquinolin-7-yl)oxy)methyl)-3-methyl-5-(4-methyl-7H-pyrrolo[2,3-d]pyrimidin-7-yl)tetrahydrofuran-3,4-diol (10)

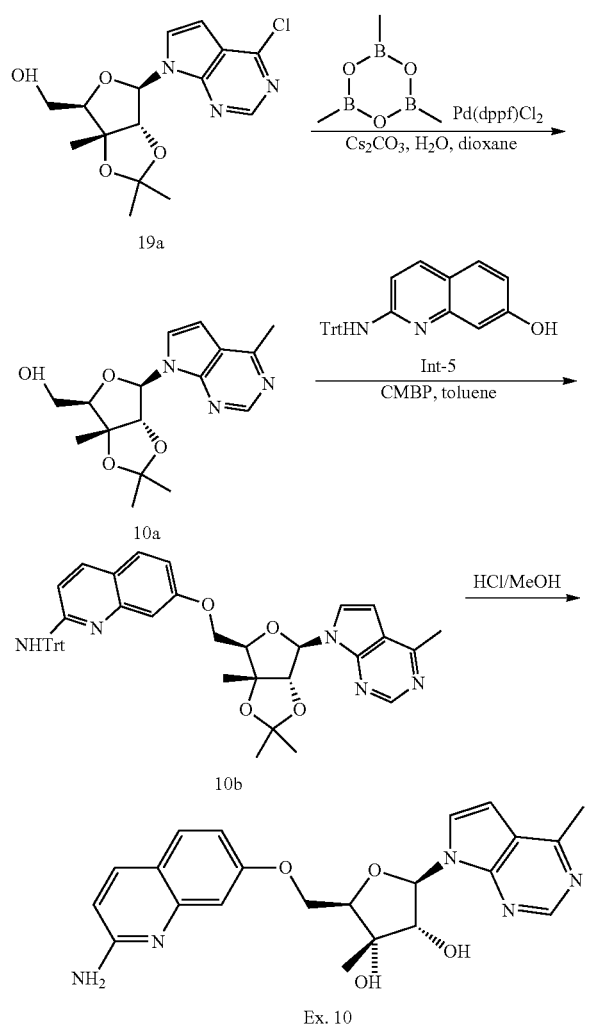

Step 1. Preparation of ((3aR,4R,6R,6aR)-2,2,3a-trimethyl-6-(4-methyl-7H-pyrrolo[2,3-d]pyrimidin-7-yl)tetrahydrofuro[3,4-d][1,3]dioxol-4-yl)methanol (10a)

To a solution of compound 19a (150 mg, 441.47 umol, 1 eq.) in H$_2$O (0.3 mL) and dioxane (30 mL) was added Cs$_2$CO$_3$ (431.52 mg, 1.32 mmol, 3 eq.) and 2,4,6-trimethyl-1,3,5,2,4,6-trioxatriborinane (2.69 g, 10.73 mmol, 3.00 mL, 24.31 eq.) and Pd(dppf)Cl$_2$ (32.30 mg, 44.15 umol, 0.1 eq.) under N$_2$. The mixture was stirred at 80° C. for 16 h under N$_2$. LC-MS showed no compound 19a was remained. Several new peaks were shown on LC-MS and ~58% of desired compound 10a was detected. The reaction mixture was concentrated under reduced pressure to remove solvent. The residue was diluted with water 30 mL and extracted with DCM (30 mL×3). The combined organic layers were washed with brine (30 mL×2), dried over Na$_2$SO$_4$, filtered and concentrated under reduced pressure to give a residue. The residue was purified by prep-TLC (SiO$_2$, Petroleum ether/Ethyl acetate=0:1). Compound 10a (70 mg, 219.19 umol, 49.65% yield) was obtained as a yellow oil. $^1$H NMR (400 MHz, CHLOROFORM-d) δ=8.69 (s, 1H), 7.21-7.15 (m, 3H), 7.13-7.06 (m, 1H), 6.52 (d, J=3.7 Hz, 1H), 6.13 (d, J=3.4 Hz, 1H), 4.78 (d, J=3.4 Hz, 1H), 4.21 (dd, J=3.4, 4.8 Hz, 1H), 3.92-3.81 (m, 1H), 3.79-3.69 (m, 1H), 3.47 (br s, 1H), 2.66 (s, 3H), 2.28 (s, 1H), 1.64 (s, 3H), 1.57 (s, 3H), 1.38 (s, 3H); TLC (SiO$_2$, Petroleum ether/Ethyl acetate=0:1): R$_f$=0.45; LCMS: (M+H$^+$): 320.1.

Step 2. Preparation of 7-(((3aR,4R,6R,6aR)-2,2,3a-trimethyl-6-(4-methyl-7H-pyrrolo[2,3-d]pyrimidin-7-yl)tetrahydrofuro[3,4-d][1,3]dioxol-4-yl)methoxy)-N-tritylquinolin-2-amine (10b)

To a mixture of compound 10a (120 mg, 375.76 umol, 1 eq.) and compound Int-5 (196.61 mg, 488.48 umol, 1.3 eq.) in toluene (3 mL) was added 2-(tributyl-phosphanylidene)acetonitrile (181.38 mg, 751.52 umol, 2 eq.) in one portion at 25° C. under N$_2$. The mixture was stirred at 80° C. for 12 h. LC-MS showed no compound 10a was remained. Several new peaks were shown on LC-MS and 55% of desired compound 10b was detected. The reaction mixture was concentrated under reduced pressure to remove solvent. The residue was diluted with water 10 mL and extracted with EtOAc 20 mL (10 mL×2). The combined organic layers were washed with brine 10 mL, dried over Na$_2$CO$_3$, filtered and concentrated under reduced pressure to give a residue. The residue was purified by prep-TLC (SiO$_2$, Petroleum ether/Ethyl acetate=5:1). Compound 10b (100 mg, 133.56 umol, 35.54% yield, 94% purity) was obtained as a yellow solid. 1H NMR (400 MHz, CHLOROFORM-d) δ=8.80 (s, 1H), 7.39-7.34 (m, 7H), 7.30-7.22 (m, 10H), 6.98 (s, 1H), 6.84 (dd, J=2.2, 8.8 Hz, 1H), 6.58 (d, J=3.5 Hz, 1H), 6.44 (br s, 1H), 6.41 (d, J=2.2 Hz, 1H), 6.02 (d, J=8.8 Hz, 1H), 4.87 (d, J=2.2 Hz, 1H), 4.54 (dd, J=3.5, 7.0 Hz, 1H), 4.34-4.27 (m, 1H), 4.23-4.16 (m, 1H), 2.71 (s, 3H), 1.66 (d, J=11.0 Hz, 6H), 1.44 (s, 3H); LCMS: (M+H$^+$): 704.5; TLC (SiO$_2$, petroleum ether/ethyl acetate=5/1): R$_f$=0.75.

Step 3. Preparation of (2R,3S,4R,5R)-2-(((2-aminoquinolin-7-yl)oxy)methyl)-3-methyl-5-(4-methyl-7H-pyrrolo[2,3-d]pyrimidin-7-yl)tetrahydrofuran-3,4-diol (10)

To a solution of compound 10b (0.1 g, 142.08 umol, 1 eq.) was added TFA (1.54 g, 12.16 mmol, 1 mL, 90% purity, 85.55 eq.). The mixture was stirred at 25° C. for 5 min. LC-MS showed no compound 10b was remained. Several new peaks were shown on LC-MS and the desired compound 10 was detected. The reaction mixture was concentrated under reduced pressure to remove solvent. The residue was added NH$_3$.H$_2$O to adjusted pH around 8. The residue was purified by prep-HPLC (basic condition: column:

Waters Xbridge 150*25 5u; mobile phase: [water (0.04% NH$_3$.H$_2$O+10 mM NH$_4$HCO$_3$)–ACN]; B %: 5%-35%, 10 min). Compound 10 (27.28 mg, 64.54 umol, 45.42% yield, 99.70% purity) was obtained as a white solid. 1H NMR (400 MHz, DMSO-d$_6$) δ=8.66 (s, 1H), 7.80 (dd, J=2.4, 6.4 Hz, 2H), 7.55 (d, J=8.8 Hz, 1H), 6.95 (d, J=2.2 Hz, 1H), 6.87 (dd, J=2.6, 8.8 Hz, 1H), 6.78 (d, J=3.9 Hz, 1H), 6.59 (d, J=9.2 Hz, 1H), 6.33 (s, 2H), 6.30 (d, J=8.3 Hz, 1H), 5.46 (br d, J=6.6 Hz, 1H), 5.11 (s, 1H), 4.48 (t, J=7.0 Hz, 1H), 4.27-4.16 (m, 2H), 2.64 (s, 3H), 1.31 (s, 3H); $^1$H NMR (400 MHz, DMSO-d$_6$+D$_2$O) δ=8.64 (s, 1H), 7.82 (d, J=8.8 Hz, 1H), 7.75 (d, J=3.5 Hz, 1H), 7.57 (d, J=8.8 Hz, 1H), 6.96-6.86 (m, 2H), 6.77 (d, J=3.9 Hz, 1H), 6.61 (d, J=8.8 Hz, 1H), 6.28 (d, J=7.9 Hz, 1H), 4.47 (d, J=7.9 Hz, 1H), 4.24-4.17 (m, 3H), 2.63 (s, 3H), 1.30 (s, 3H); LCMS: (M+H$^+$): 422.2; LCMS purity 99.69%; HPLC purity: 100.00%.

Example 12. (2R,3S,4R,5R)-2-(((2-amino-3-bromo-quinolin-7-yl)oxy)methyl)-5-(4-amino-7H-pyrrolo[2,3-d]pyrimidin-7-yl)-3-methyltetrahydrofuran-3,4-diol (12)

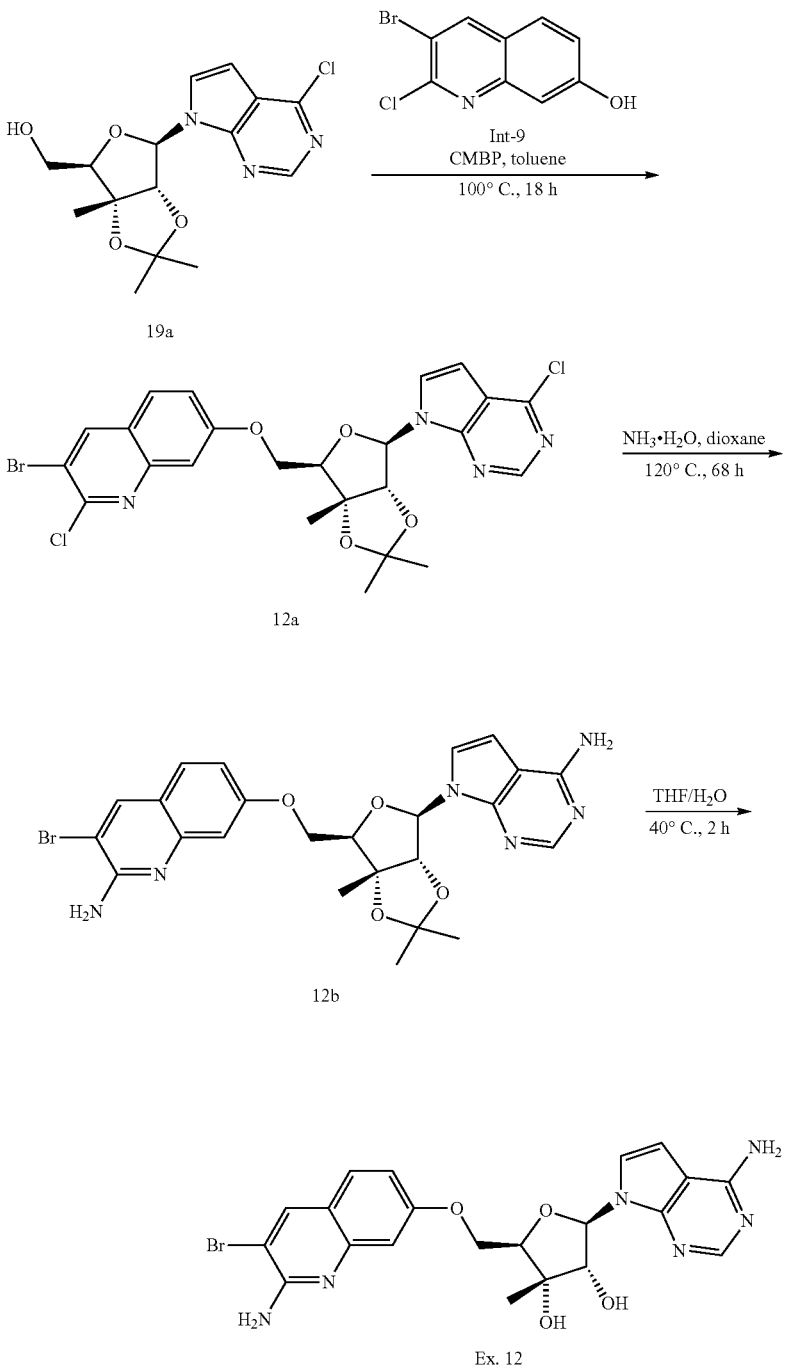

Step 1. Preparation of 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]-3-bromo-2-chloro-quinoline (12a)

To a solution of [(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methanol (19a) (137.5 mg, 0.40 mmol) and 3-bromo-2-chloro-quinolin-7-ol (Int-9) (95.0 mg, 0.37 mmol) in Toluene (5.0 mL), Cyanomethylenetributylphosphorane (0.14 mL, 0.55 mmol) was added at rt. The mixture was stirred at 100° C. for 18 h under N$_2$. The mixture was diluted with DCM (50.0 mL) and washed with brine (20.0 mL×3), dried over Na$_2$SO$_4$, filtered and concentrated in vacuum to give crude product which was purified by silica gel column chromatography (EA:PE=2:1) to obtain 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]-3-bromo-2-chloro-quinoline (19a) (38.0 mg, 0.06 mmol, 17.5% yield) as a white solid. LCMS [M+H]: 579.0.

Step 2. Preparation of Compound 12b

A solution of 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]-3-bromo-2-chloro-quinoline (12a) (38.0 mg, 0.07 mmol) in 1,4-Dioxane (1.0 mL) and Ammonium hydroxide (1.5 mL, 39.69 mmol) was stirred at 140° C. for 68 h in a autoclave. LCMS showed the reaction was done and 16.0% of SM was left. The mixture was concentrated in vacuum to give crude product 12b (37.0 mg) which was used in the next step directly. LCMS [M+H]: 541.1.

Step 3. Preparation of (2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol (12)

A solution of 7-[[(3aR,4R,6R,6aR)-6-(4-aminopyrrolo[2,3-d]pyrimidin-7-yl)-2,2,3a-trimethyl-6,6a-dihydro-4H-furo[3,4-d][1,3]dioxol-4-yl]methoxy]-3-bromo-quinolin-2-amine (12b) (37.0 mg, 0.07 mmol) in Water (1.0 mL) and TFA (1.5 mL, 20.19 mmol) was stirred at 40° C. for 2 h. LCMS showed the reaction was completed, the reaction mixture was purified by prep-HPLC, eluted with MeCN in H$_2$O (0.1% NH$_3$.H$_2$O) from 10.0% to 95.0% to give (2R,3S,4R,5R)-2-[(2-amino-3-bromo-7-quinolyl)oxymethyl]-5-(4-aminopyrrolo[2,3-d]pyrimidin-7-yl)-3-methyl-tetrahydrofuran-3,4-diol (Ex. 12) (3.1 mg, 0.0061 mmol, 8.9% yield) as a white solid. LCMS [M+H]: 501.1. $^1$H NMR (400 MHz, DMSO-d$_6$) δ 8.29 (s, 1H), 8.06 (s, 1H), 7.60 (d, J=8.8 Hz, 1H), 7.39 (d, J=3.6 Hz, 1H), 6.93-6.99 (m, 4H), 6.55-6.60 (m, 3H), 6.16 (d, J=8.0 Hz, 1H), 5.11-5.33 (m, 2H), 4.41 (d, J=7.6 Hz, 1H), 4.17-4.25 (m, 3H), 1.30 (s, 3H). $^1$H NMR (400 MHz, DMSO-d$_6$+D$_2$O) 8.30 (s, 1H), 8.07 (s, 1H), 7.62 (d, J=8.4 Hz 1H), 7.39 (d, J=3.6 Hz, 1H), 6.95-6.98 (m, 2H), 6.61 (d, J=3.6 Hz, 1H), 6.17 (d, J=8.0 Hz, 1H), 4.42 (d, J=8.0 Hz, 1H), 4.19-4.25 (m, 3H), 1.30 (s, 3H).

Example 17. (2S,3S,4R,5R)-5-(4-amino-7H-pyrrolo[2,3-d]pyrimidin-7-yl)-3-methyl-2-((methylthio)methyl)tetrahydrofuran-3,4-diol (17)

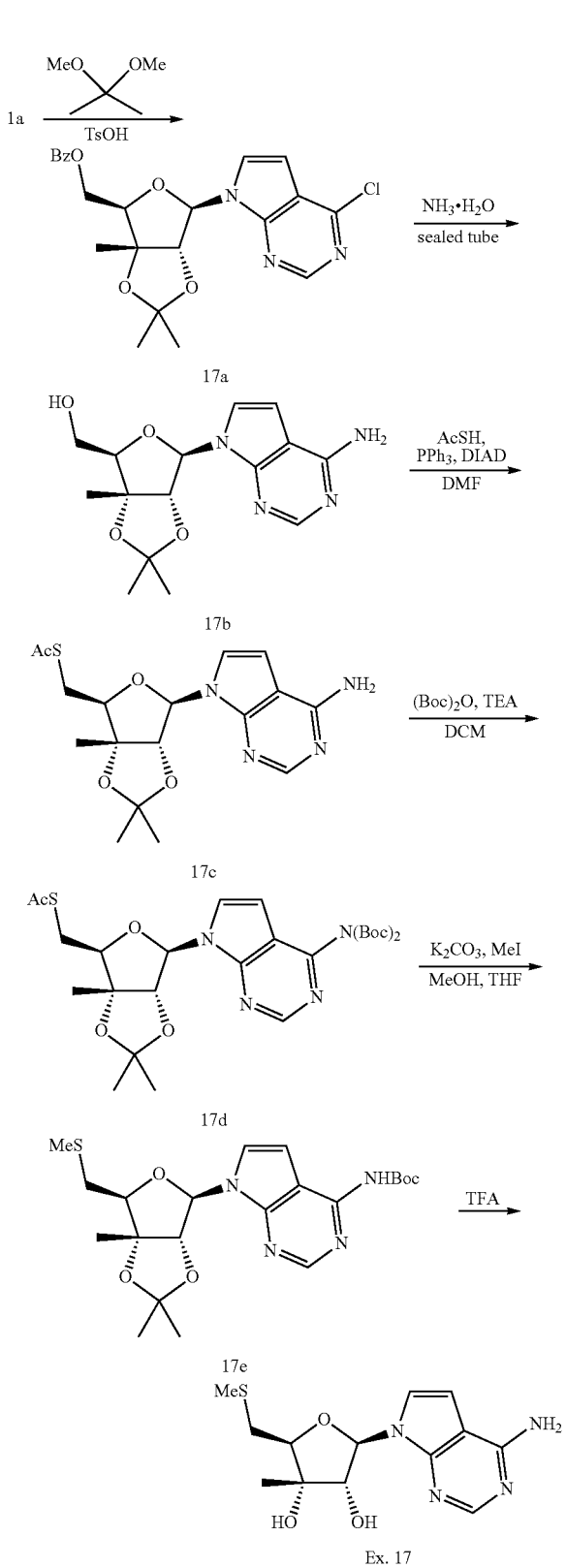

Step 1. Preparation of ((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl) methyl benzoate (17a)

To a solution of compound 1a (1 g, 2.48 mmol, 1 eq.) in 2,2-dimethoxypropane (12.75 g, 122.42 mmol, 15 mL, 49.44 eq.) was added TsOH.H₂O (141.31 mg, 742.91 umol, 0.3 eq.). The mixture was stirred at 25° C. for 12 hr. LC-MS showed compound 1a was remained. Several new peaks were shown on LC-MS and desired compound was detected. The reaction was stirred at 60° C. for 2 hr. TLC indicated compound 1a was consumed completely and new spots formed. The reaction was clean according to TLC. The reaction was quenched by NaHCO₃ (20 mL), and extracted with EtOAc (10 mL*3). The organic was concentrated in vacuo. The residue was purified by column chromatography (SiO₂, Petroleum ether/Ethyl acetate=5/1 to 4:1). Compound 17a (730 mg, crude) was obtained as a yellow oil. TLC (Petroleum ether:Ethyl acetate=1:1) $R_f$=0.79.

Step 2. Preparation of ((3aR,4R,6R,6aR)-6-(4-amino-7H-pyrrolo[2,3-d]pyrimidin-7-yl)-2,2,3a-trimethyltetrahydrofuro[3,4-d][1,3]dioxol-4-yl) methanol (17b)

To a solution of compound 17a (200 mg, 450.57 umol, 1 eq.) in THF (2 mL) was added NH₃.H₂O (7.28 g, 51.93 mmol, 8.00 mL, 25% purity, 115.26 eq.). The mixture was stirred at 100° C. for 12 hr in a sealed tube. TLC indicated compound 17a was consumed completely and new spots formed. The reaction was clean according to TLC. The mixture was concentrated in vacuo. The residue was purified by prep-TLC (SiO₂, Petroleum ether: Ethyl acetate=0:1). Compound 17b (140 mg, crude) was obtained as a white solid. TLC (Petroleum ether:Ethyl acetate=0:1) $R_f$=0.14.

Step 3. Preparation of S-(((3aS,4S,6R,6aR)-6-(4-amino-7H-pyrrolo[2,3-d]pyrimidin-7-yl)-2,2,3a-trimethyltetrahydrofuro[3,4-d][1,3]dioxol-4-yl) methyl) ethanethioate (17c)

A solution of PPh₃ (229.26 mg, 874.06 umol, 2 eq.) in THF (4 mL) was added DIAD (176.74 mg, 874.06 umol, 169.95 uL, 2 eq.) at 0° C., the solution was stirred for 10 min at 0° C., then added ethanethioic S-acid (66.53 mg, 874.06 umol, 62.18 uL, 2 eq.), and then added compound 17b (140 mg, 437.03 umol, 1 eq.) after the solution was stirred for 10 min at 0° C., then the mixture was stirred at 25° C. for 1 hr. LC-MS showed compound 17b was consumed completely and one main peak with desired MS was detected. The mixture was concentrated in vacuo. The residue was purified by prep-TLC (SiO₂, Petroleum ether: Ethyl acetate=1:1). Compound 17c (165 mg, crude) was obtained as a yellow solid. TLC (Petroleum ether:Ethyl acetate=1:1) $R_f$=0.05.

Step 4. Preparation of S-(((3aS,4S,6R,6aR)-6-(4-(N,N-di(tert-butoxycarbonyl))amino-7H-pyrrolo[2,3-d]pyrimidin-7-yl)-2,2,3a-trimethyltetrahydrofuro[3,4-d][1,3]dioxol-4-yl)methyl) ethanethioate (17d)

To a solution of compound 17c (165 mg, 435.99 umol, 1 eq.) in DCM (5 mL) was added TEA (352.95 mg, 3.49 mmol, 485.48 uL, 8 eq.) and Boc₂O (380.62 mg, 1.74 mmol, 400.66 uL, 4 eq.). The mixture was stirred at 25° C. for 12 hr. LC-MS showed one main peak with desired MS was detected. The reaction was quenched by H₂O (5 mL), and then extracted with TBME (5 mL*3), the organic phase was concentrated in vacuo. The crude product compound 17d (252 mg, crude) was used into the next step without further purification as a yellow oil. LCMS: (M+H⁺): 579.2.

Step 5. Preparation of tert-butyl (7-((3aR,4R,6S,6aS)-2,2,6a-trimethyl-6-((methylthio)methyl)tetrahydrofuro[3,4-d][1,3]dioxol-4-yl)-7H-pyrrolo[2,3-d]pyrimidin-4-yl)carbamate (17e)

To a solution of compound 17d (252 mg, 435.48 umol, 1 eq.) in MeOH (2 mL) and THF (2 mL) was added K₂CO₃ (120.37 mg, 870.95 umol, 2 eq.) and MeI (309.06 mg, 2.18 mmol, 135.55 uL, 5 eq.). The mixture was stirred at 25° C. for 2 hr. LC-MS showed compound 17d was consumed completely and one main peak with desired MS was detected. The reaction was filtered and the filtrate was concentrated in cacuo. The residue was purified by prep-TLC (SiO₂, Petroleum ether: Ethyl acetate=3:1). The crude product compound 17e (100 mg, crude) was used into the next step without further purification as a yellow oil. TLC (Petroleum ether:Ethyl acetate=3:1) $R_f$=0.24.

Step 6. Preparation of (2S,3S,4R,5R)-5-(4-amino-7H-pyrrolo[2,3-d]pyrimidin-7-yl)-3-methyl-2-((methylthio)methyl)tetrahydrofuran-3,4-diol (17)

A solution of compound 17e (100 mg, 221.95 umol, 1 eq.) in TFA (3.08 g, 24.31 mmol, 2 mL, 90% purity, 109.53 eq.), The mixture was stirred at 25° C. for 3 hr. LC-MS showed compound 17e was consumed completely and one main peak with desired MS was detected. The reaction was concentrated in vacuo at 25° C. The residue was purified by prep-HPLC. Compound 17 (46.96 mg, 135.40 umol, 61.00% yield, 100% purity, HCl salt) was obtained as a white solid. ¹H NMR (400 MHz, DMSO-d₆) δ=9.41 (br s, 1H), 8.80-8.48 (m, 1H), 8.41 (s, 1H), 7.74 (d, J=3.7 Hz, 1H), 7.06 (d, J=3.5 Hz, 1H), 6.08 (d, J=7.9 Hz, 1H), 5.49 (br s, 1H), 4.28 (d, J=7.7 Hz, 1H), 3.99 (dd, J=4.3, 8.9 Hz, 1H), 2.85-2.71 (m, 2H), 2.03 (s, 3H), 1.23 (s, 3H); ¹H NMR (400 MHz, DMSO-d₆+D₂O) δ=8.38 (s, 1H), 7.73 (d, J=3.7 Hz, 1H), 7.02 (d, J=3.7 Hz, 1H), 6.08 (d, J=7.7 Hz, 1H), 4.27 (d, J=7.9 Hz, 1H), 3.99 (dd, J=4.3, 8.9 Hz, 1H), 2.83-2.69 (m, 2H), 2.02 (s, 3H), 1.22 (s, 3H); LCMS: (M+H⁺): 311.1.

Example 19. (2R,3S,4R,5R)-5-(4-amino-7H-pyrrolo[2,3-d]pyrimidin-7-yl)-2-(methoxymethyl)-3-methyltetrahydrofuran-3,4-diol (19)

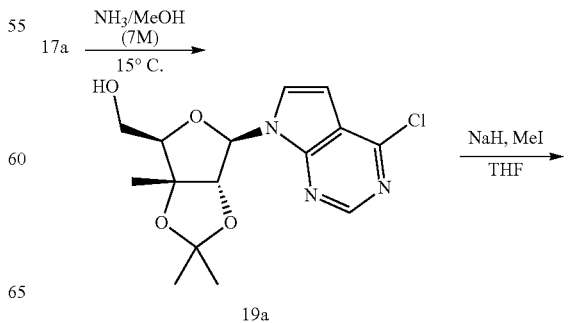

19a

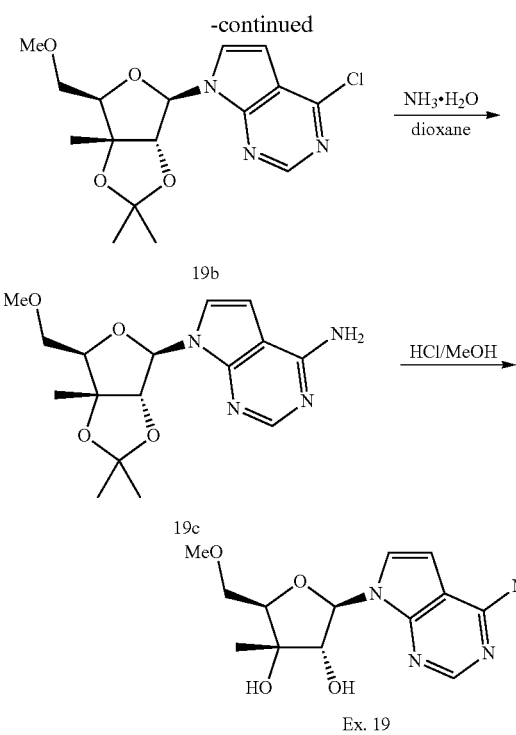

Ex. 19

Step 1. Preparation of ((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methanol (19a)

A mixture of compound 17a (600 mg, 1.35 mmol, 1 eq.) and NH₃ in MeOH (7 M, 10 mL, 51.79 eq.) was stirred at 25° C. for 12 h. LCMS showed the desired MS was observed. The mixture was concentrated. The residue was purified by column chromatography (SiO₂, Petroleum ether/Ethyl acetate=1/0 to 3:1). Compound 19a (450 mg, 1.32 mmol, 97.98% yield) was obtained as white solid. ¹H NMR (400 MHz, CHLOROFORM-d) δ=8.60 (s, 1H), 7.29 (d, J=3.7 Hz, 1H), 6.60 (d, J=3.7 Hz, 1H), 6.17 (d, J=3.2 Hz, 1H), 4.74 (d, J=3.1 Hz, 1H), 4.20 (dd, J=3.5, 5.6 Hz, 1H), 3.89-3.71 (m, 2H), 1.61 (s, 3H), 1.57 (s, 3H), 1.38 (s, 3H); LCMS: (M+H⁺): 340.1.

Step 2. Preparation of 4-chloro-7-((3aR,4R,6R,6aR)-6-(methoxymethyl)-2,2,6a-trimethyltetrahydrofuro[3,4-d][1,3]dioxol-4-yl)-7H-pyrrolo[2,3-d]pyrimidine (19b)

To a mixture of compound 19a (150 mg, 441.47 umol, 1 eq.) and MeI (4.56 g, 32.13 mmol, 2 mL, 72.77 eq.) in THF (1 mL) was added NaH (26.49 mg, 662.21 umol, 60% purity, 1.5 eq.) at 0° C. The mixture was stirred at 25° C. for 1 h. TLC showed compound 19a was consumed and a new major spot formed. The mixture was quenched by saturated NH₄Cl solution (10 mL), extracted with EtOAc (5 mL×3). The combined organic layers were dried over Na₂SO₄, filtered and concentrated. The residue was purified by Prep-TLC (SiO₂, Petroleum ether/Ethyl acetate=2:1). Compound 19b (140 mg, 395.70 umol, 89.63% yield) was obtained as a white solid. ¹H NMR (400 MHz, CHLOROFORM-d) δ=8.67 (s, 1H), 7.42 (d, J=3.7 Hz, 1H), 6.65 (d, J=3.7 Hz, 1H), 6.35-6.31 (m, 1H), 4.75 (d, J=2.4 Hz, 1H), 4.26 (dd, J=4.0, 7.1 Hz, 1H), 3.67-3.53 (m, 2H), 3.42-3.37 (m, 3H), 1.63 (s, 3H), 1.61 (s, 3H), 1.42 (s, 3H); LCMS: (M+H⁺): 354.0; TLC (Petroleum ether/Ethyl acetate=2:1) R_f=0.50.

Step 3. Preparation of 7-((3aR,4R,6R,6aR)-6-(methoxymethyl)-2,2,6a-trimethyltetrahydrofuro[3,4-d][1,3]dioxol-4-yl)-7H-pyrrolo[2,3-d]pyrimidin-4-amine (19c)

A mixture of compound 19b (119.10 mg, 336.64 umol, 1 eq.) and NH₃.H₂O (47.19 mg, 336.64 umol, 51.86 uL, 25% purity, 1 eq.) in dioxane (5 mL) was stirred at 120° C. for 12 h. LCMS showed compound 19b was consumed and the desired MS was observed. The mixture was concentrated. No further purification. Compound 19c (120 mg, crude) was obtained as a white solid, which was used for next step with purification. H NMR (400 MHz, CHLOROFORM-d) δ=8.26 (s, 1H), 7.08 (d, J=3.7 Hz, 1H), 6.36 (d, J=3.5 Hz, 1H), 6.23 (d, J=2.2 Hz, 1H), 5.30 (br s, 2H), 4.65 (d, J=2.4 Hz, 1H), 4.16 (dd, J=4.3, 7.2 Hz, 1H), 3.59-3.46 (m, 2H), 3.33 (s, 3H), 1.55 (s, 3H), 1.53 (s, 3H), 1.34 (s, 3H); LCMS: (M+H⁺): 335.1.

Step 4. Preparation of (2R,3S,4R,5R)-5-(4-amino-7H-pyrrolo[2,3-d]pyrimidin-7-yl)-2-(methoxymethyl)-3-methyltetrahydrofuran-3,4-diol (19)

A mixture of compound 19c (120 mg, 358.88 umol, 1 eq.) and HCl/MeOH (7 M, 1 mL, 19.50 eq.) was stirred at 25° C. for 10 min. LCMS showed compound 19c was consumed and the desired MS was observed. The mixture was concentrated. The residue was purified by prep-HPLC (HCl condition). Compound 19 (50.11 mg, 150.54 umol, 41.95% yield, 99.37% purity, HCl salt) was obtained as a white solid. ¹H NMR (400 MHz, DMSO-d₆) δ=13.66 (br s, 1H), 9.12 (br s, 1H), 8.39 (s, 1H), 7.66 (d, J=3.8 Hz, 1H), 7.01 (d, J=3.7 Hz, 1H), 6.12 (d, J=7.8 Hz, 1H), 5.40 (br s, 1H), 5.01 (br s, 1H), 4.19 (d, J=7.8 Hz, 1H), 3.95 (t, J=3.5 Hz, 1H), 3.57-3.42 (m, 2H), 3.34 (s, 3H), 1.24 (s, 3H); (¹H NMR 400 MHz, DMSO-d₆+D₂O) δ=8.36 (s, 1H), 7.65 (d, J=3.7 Hz, 1H), 6.98 (d, J=3.7 Hz, 1H), 6.12 (d, J=7.8 Hz, 1H), 4.18 (d, J=7.8 Hz, 1H), 3.94 (t, J=3.4 Hz, 1H), 3.57-3.39 (m, 2H), 3.33 (s, 3H), 1.23 (s, 3H); LCMS: (M+H⁺): 295.2.

Example 20. (2R,3S,4R,5R)-5-(4-amino-7H-pyrrolo[2,3-d]pyrimidin-7-yl)-3-methyl-2-(phenoxymethyl)tetrahydrofuran-3,4-diol (20)

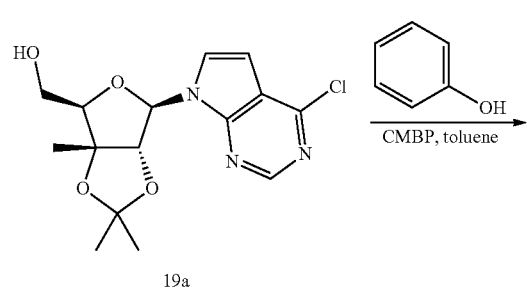

19a

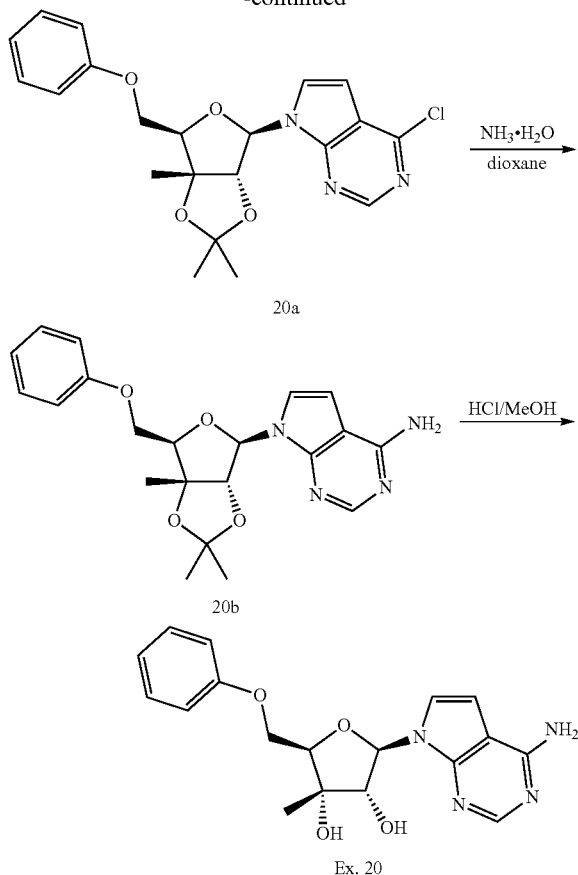

20a

20b

Ex. 20

Step 1. Preparation of 4-chloro-7-((3aR,4R,6R,6aR)-2,2,6a-trimethyl-6-(phenoxymethyl)tetrahydrofuro[3,4-d][1,3]dioxol-4-yl)-7H-pyrrolo[2,3-d]pyrimidine (20a)

A mixture of compound 19a (200 mg, 588.63 umol, 1 eq.) and phenol (60.94 mg, 647.49 umol, 56.95 uL, 1.1 eq.) in toluene (1 mL) was added CMBP (213.10 mg, 882.94 umol, 1.5 eq) at 25° C. under $N_2$. The mixture was stirred at 80° C. for 12 h under $N_2$. LCMS showed compound 19a was consumed and the desired MS was observed. The mixture was concentrated. The residue was dissolved into water (5 mL). The mixture was extracted with EtOAc (3 mL×3). The combined organic layers were dried over $Na_2SO_4$, filtered and concentrated. The residue was purified by prep-TLC ($SiO_2$, petroleum ether/ethyl acetate=3/1). Compound 20a (130 mg, crude) was obtained as brown oil. LCMS: (M+H$^+$): 416.2; $^1$H NMR (400 MHz, CHLOROFORM-d) δ=8.70 (s, 1H), 7.46 (d, J=3.7 Hz, 1H), 7.32-7.29 (m, 1H), 6.99 (t, J=7.2 Hz, 1H), 6.94-6.88 (m, 2H), 6.84 (d, J=7.5 Hz, 1H), 6.65 (d, J=3.7 Hz, 1H), 6.39 (d, J=2.2 Hz, 1H), 4.86 (d, J=2.0 Hz, 1H), 4.52 (dd, J=3.7, 6.8 Hz, 1H), 4.30-4.23 (m, 1H), 4.15-4.11 (m, 1H), 1.69 (s, 3H), 1.66 (s, 3H), 1.47 (s, 3H).

Step 2. Preparation of 7-((3aR,4R,6R,6aR)-2,2,6a-trimethyl-6-(phenoxymethyl)tetrahydrofuro[3,4-d][1,3]dioxol-4-yl)-7H-pyrrolo[2,3-d]pyrimidin-4-amine (20b)

A mixture of compound 20a (130 mg, 312.60 umol, 1 eq.) and $NH_3 \cdot H_2O$ (2.73 g, 19.47 mmol, 3 mL, 62.30 eq.) in dioxane (3 mL) was stirred at 120° C. for 12 h. LCMS showed compound 20a was consumed and the desired MS was observed. The mixture was concentrated. The crude product was used for next step without further purification. Compound 20b (123 mg, crude) was obtained as brown oil. LCMS: (M+H$^+$): 397.2.

Step 3. Preparation of (2R,3S,4R,5R)-5-(4-amino-7H-pyrrolo[2,3-d]pyrimidin-7-yl)-3-methyl-2-(phenoxymethyl)tetrahydrofuran-3,4-diol (20)

A mixture of compound 20b (123 mg, 310.26 umol, 1 eq.) in HCl/MeOH (4 M, 4 mL, 51.57 eq.) was stirred at 25° C. for 0.5 h. LCMS showed compound 20b was consumed and the desired MS was observed. The mixture was concentrated. The residue was purified by prep-HPLC (column: UniSil 120*30*10 um; mobile phase: [water (0.05% HCl)–ACN]; B %: 5%-35%, 11 min). Compound 20 (4.49 mg, 11.26 umol, 3.63% yield, 98.518% LCMS purity, HCl salt) was obtained as a white solid. $^1$H NMR (400 MHz, DMSO-$d_6$) δ=8.39 (s, 1H), 7.68 (d, J=3.7 Hz, 1H), 7.37-7.25 (m, 2H), 7.07-6.91 (m, 4H), 6.18 (d, J=7.9 Hz, 1H), 4.38 (d, J=7.9 Hz, 1H), 4.24-4.04 (m, 3H), 1.28 (s, 3H); $^1$H NMR (400 MHz, DMSO-$d_6$+$D_2O$) δ=8.38 (s, 1H), 7.67 (d, J=3.7 Hz, 1H), 7.40-7.24 (m, 2H), 7.08-6.90 (m, 4H), 6.19 (d, J=7.9 Hz, 1H), 4.38 (d, J=8.2 Hz, 1H), 4.23-4.03 (m, 3H), 1.28 (s, 3H); LCMS: (M+H$^+$): 357.1; LCMS purity 98.52%; HPLC purity: 100.00%.

Example 21. 1-(3-(((2R,3S,4R,5R)-5-(4-amino-7H-pyrrolo[2,3-d]pyrimidin-7-yl)-3,4-dihydroxy-3-methyltetrahydrofuran-2-yl)methoxy)phenyl)urea hydrochloride (21)

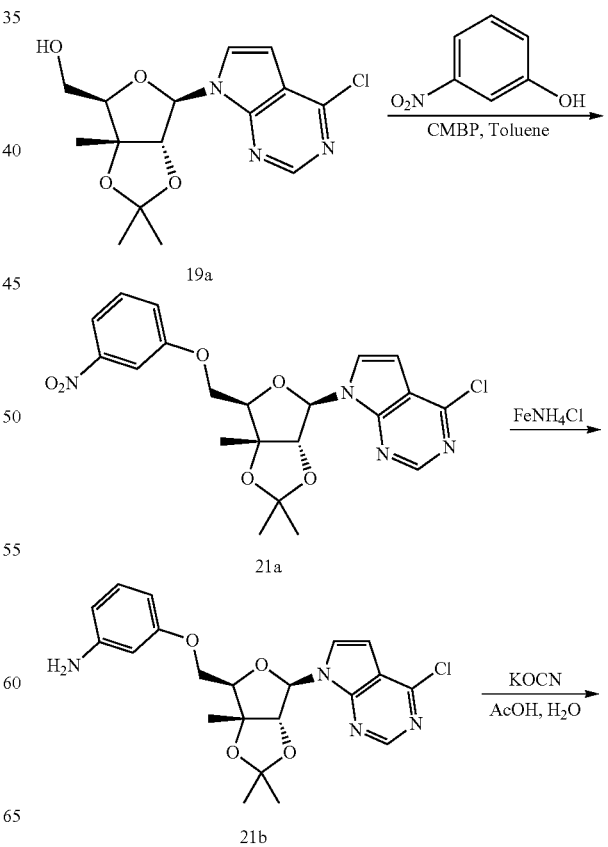

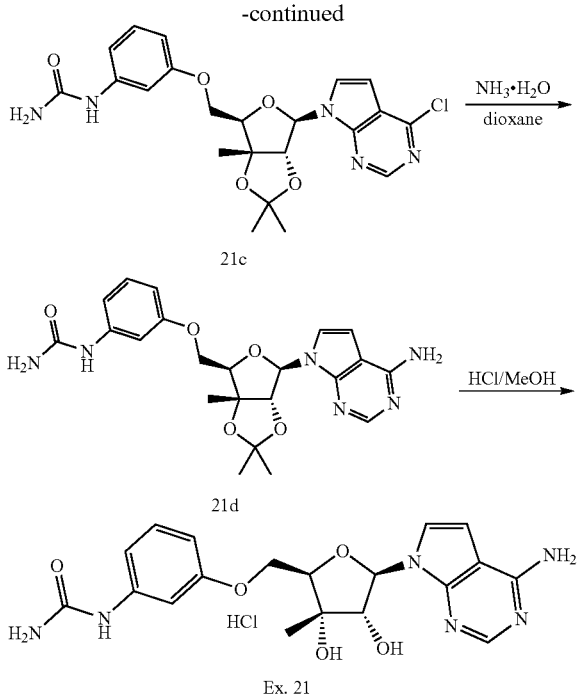

Step 1. Preparation of 4-chloro-7-((3aR,4R,6R, 6aR)-2,2,6a-trimethyl-6-((3-nitrophenoxy)methyl) tetrahydrofuro[3,4-d][1,3]dioxol-4-yl)-7H-pyrrolo[2, 3-d]pyrimidine (21a)

A mixture of compound 19a (300 mg, 882.94 umol, 1 eq.) and 3-nitrophenol (122.82 mg, 882.94 umol, 175.46 uL, 1 eq.) in toluene (3 mL) was added CMBP (426.20 mg, 1.77 mmol, 2 eq.) at 25° C. under $N_2$. The mixture was stirred at 80° C. for 12 h under $N_2$. TLC showed the compound 19a was consumed and a major new spot was observed. The reaction solution was concentrated. The residue was dissolved in water (15 mL) and the mixture was extracted with EtOAc (10 mL×3). The combined organic layers were dried over $Na_2SO_4$, filtered and concentrated. The residue was purified by prep-TLC (SiO$_2$, petroleum ether/ethyl acetate=3/1). Compound 21a (410 mg, crude) was obtained as brown oil. TLC (Petroleum ether:Ethyl acetate=3:1) $R_f$=0.6.

Step 2. Preparation of 3-(((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl) methoxy)aniline (21b)

A mixture of compound 21a (410 mg, 889.63 umol, 1 eq.), Fe (248.41 mg, 4.45 mmol, 5 eq.) and NH$_4$Cl (475.88 mg, 8.90 mmol, 311.03 uL, 10 eq.) in EtOH (5 mL) and H$_2$O (1 mL) was stirred at 75° C. for 1 h. LCMS showed the compound 21a was consumed and the desired MS was observed. The mixture was filtered and concentrated. The residue was dissolved into water (10 mL). The mixture was extracted with EtOAc (5 mL×4). The combined organic layers were dried over Na$_2$SO$_4$, filtered and concentrated. The residue was purified by prep-TLC (SiO$_2$, petroleum ether/ethyl acetate=1/3). Compound 21b (100 mg, 168.91 umol, 26.09% yield) was obtained as brown oil. $^1$H NMR (400 MHz, CHLOROFORM-d) δ=8.69 (s, 1H), 7.46 (d, J=3.8 Hz, 1H), 7.06 (t, J=8.1 Hz, 1H), 6.65 (d, J=3.7 Hz, 1H), 6.39 (d, J=2.2 Hz, 1H), 6.32 (ddd, J=2.4, 5.0, 7.5 Hz, 2H), 6.24-6.20 (m, 1H), 4.86 (d, J=2.3 Hz, 1H), 4.50 (dd, J=3.9, 6.5 Hz, 1H), 4.22 (dd, J=3.8, 10.5 Hz, 1H), 4.10-4.05 (m, 1H), 1.66 (d, J=3.3 Hz, 6H), 1.46 (s, 3H); LCMS: (M+H$^+$): 431.1; TLC (Petroleum ether:Ethyl acetate=1:3) $R_f$=0.8.

Step 3. Preparation of 1-(3-(((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl) methoxy)phenyl)urea (21c)

To a mixture of compound 21b (100 mg, 232.08 umol, 1 eq.) in AcOH (1.6 mL) and H$_2$O (0.2 mL) was added the mixture of potassium cyanate (28.24 mg, 348.12 umol, 13.71 uL, 1.5 eq.) in H$_2$O (0.3 mL) at 0° C. The mixture was stirred at 25° C. for 12 h. LCMS showed the compound 1c was consumed and the desired MS was observed. The mixture was quenched by saturated NaHCO$_3$ solution to pH=8-9. The mixture was extracted with EtOAc (10 mL×4). The combined organic layers were dried over Na$_2$SO$_4$, filtered and concentrated. The residue was purified by prep-TLC (SiO$_2$, petroleum ether/ethyl acetate=1/3). Compound 21c (80 mg, 168.81 umol, 72.74% yield) was obtained as a white solid. 1H NMR (400 MHz, CHLOROFORM-d) δ=8.70 (s, 1H), 7.44 (d, J=3.7 Hz, 1H), 7.25-7.20 (m, 1H), 7.00 (s, 1H), 6.85 (d, J=8.2 Hz, 1H), 6.69-6.65 (m, 2H), 6.38 (d, J=2.2 Hz, 1H), 6.27 (s, 1H), 4.87 (d, J=2.2 Hz, 1H), 4.60 (br s, 2H), 4.53-4.46 (m, 2H), 4.30-4.23 (m, 1H), 1.69 (s, 3H), 1.66 (s, 3H), 1.46 (s, 3H); LCMS: (M+H$^+$): 474.2; TLC (Petroleum ether:Ethyl acetate=1:3) $R_f$=0.5.

Step 4. Preparation of 1-(3-(((3aR,4R,6R,6aR)-6-(4-amino-7H-pyrrolo[2,3-d]pyrimidin-7-yl)-2,2,3a-trimethyltetrahydrofuro[3,4-d][1,3]dioxol-4-yl) methoxy)phenyl)urea (21d)

A mixture of compound 21c (75 mg, 158.26 umol, 1 eq.) in NH$_3$·H$_2$O (910.00 mg, 6.49 mmol, 1 mL, 25% purity, 41.02 eq.) and dioxane (1 mL) was stirred at 60° C. for 12 h. LCMS showed the compound 21c was remained and the mixture was stirred at 80° C. for 2 h. TLC showed the compound 21c was consumed. The crude product was used for next step without purification. Compound 21d (70 mg, crude) was obtained as a brown solid which was used for next step without purification. LCMS: (M+H$^+$): 455.2; TLC (Petroleum ether:Ethyl acetate=1:3) $R_f$=0.4.

Step 5. Preparation of 1-(3-(((2R,3S,4R,5R)-5-(4-amino-7H-pyrrolo[2,3-d]pyrimidin-7-yl)-3,4-dihydroxy-3-methyltetrahydrofuran-2-yl)methoxy)phenyl)urea (21)

A mixture of compound 21d (70 mg, 154.02 umol, 1 eq.) in HCl/MeOH (4 M, 2 mL, 51.94 eq.) was stirred at 25° C. for 1 h. LCMS showed the compound 21d was consumed and the desired MS was observed. The mixture was concentrated. The residue was purified by prep-HPLC (column: UniSil 120*30*10 um; mobile phase: [water (0.05% HCl)–ACN]; B %: 1%-30%, 11 min). Compound 21 (33.54 mg, 74.39 umol, 48.30% yield, LCMS 100% purity, HCl) was obtained as a white solid. $^1$H NMR (400 MHz, DMSO-d$_6$) δ=8.61 (br s, 1H), 8.41 (s, 1H), 7.72-7.65 (m, 1H), 7.28 (s, 1H), 7.17-7.11 (m, 1H), 7.01 (br s, 1H), 6.86 (br d, J=7.9 Hz, 1H), 6.55 (br d, J=7.3 Hz, 1H), 6.18 (d, J=7.7 Hz, 1H), 5.84 (br s, 2H), 4.37 (d, J=7.7 Hz, 1H), 4.18 (s, 1H), 4.15-4.02 (m, 2H), 1.28 (s, 3H); $^1$H NMR (400 MHz, DMSO-d$_6$+D$_2$O) δ=8.39 (s, 1H), 7.67 (d, J=3.7 Hz, 1H), 7.26 (s, 1H), 7.15 (t, J=8.2 Hz, 1H), 6.98 (d, J=3.7 Hz, 1H), 6.84 (d, J=7.9 Hz, 1H), 6.57 (br d, J=8.2 Hz, 1H), 6.18 (d, J=7.9 Hz, 1H), 4.36 (d, J=7.9 Hz, 1H), 4.20-4.16 (m, 1H), 4.12-4.01 (m, 2H), 1.27 (s, 3H); LCMS: (M+H$^+$): 415.1; LCMS purity 100.00%; HPLC purity: 100.00%.

Example 22. (2R,3S,4R,5R)-5-(4-amino-7H-pyrrolo[2,3-d]pyrimidin-7-yl)-2-((3-(aminomethyl)phenoxy)methyl)-3-methyltetrahydrofuran-3,4-diol (22)

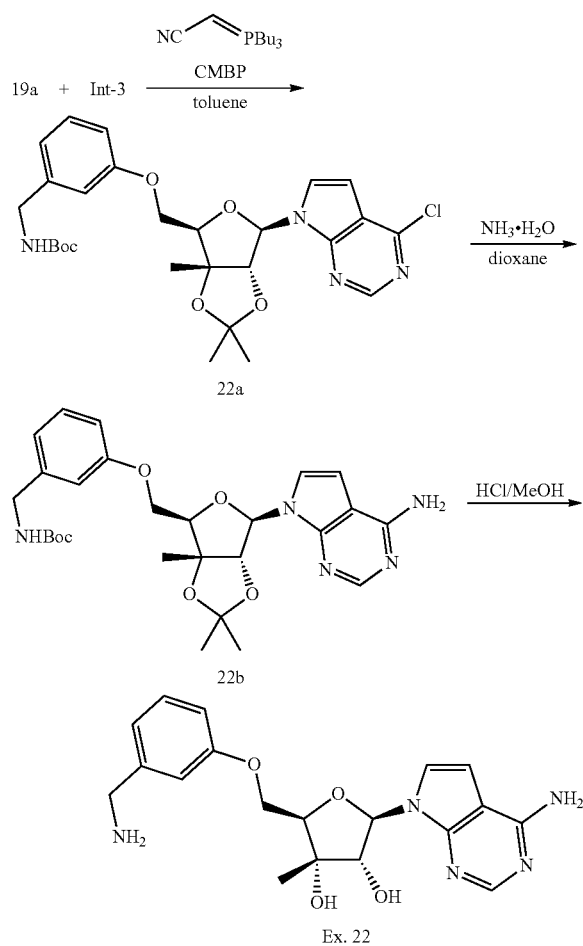

Step 1. Preparation of tert-butyl 3-(((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methoxy) benzylcarbamate (22a)

To a mixture of compound 19a (80 mg, 235.45 umol, 1 eq.) and compound Int-3 (57.83 mg, 259.00 umol, 1.1 eq.) in toluene (2 mL) was added CMBP (85.24 mg, 353.18 umol, 1.5 eq.) at 25° C. under N$_2$. LCMS showed the compound 19a was consumed and the desired MS was observed. The mixture was stirred at 80° C. for 12 h under N$_2$. The mixture was concentrated, and the residue was dissolved into water (10 mL). The mixture was extracted with EtOAc (5 mL×3). The combined organic layers were dried over Na$_2$SO$_4$, filtered and concentrated. The residue was purified by prep-TLC (SiO$_2$, petroleum ether/ethyl acetate=3/1) to give compound 22a (90 mg, 165.13 umol, 70.13% yield) as brown oil. $^1$H NMR (400 MHz, CHLOROFORM-d) δ=8.70 (s, 1H), 7.45 (d, J=3.7 Hz, 1H), 7.26-7.20 (m, 1H), 6.93-6.73 (m, 4H), 6.66 (d, J=3.7 Hz, 1H), 6.39 (d, J=2.2 Hz, 1H), 4.85 (d, J=2.2 Hz, 1H), 4.50 (dd, J=3.6, 6.7 Hz, 1H), 4.34-4.19 (m, 4H), 1.69 (s, 3H), 1.66 (s, 3H), 1.48-1.46 (m, 12H); LCMS: (M+H$^+$): 545.1;

Step 2. Preparation of tert-butyl 3-(((3aR,4R,6R,6aR)-6-(4-amino-7H-pyrrolo[2,3-d]pyrimidin-7-yl)-2,2,3a-trimethyltetrahydrofuro[3,4-d][1,3]dioxol-4-yl)methoxy) benzylcarbamate (22b)

A mixture of compound 22a (90 mg, 165.13 umol, 1 eq.) and NH$_3$.H$_2$O (2.73 g, 19.47 mmol, 3 mL, 117.94 eq.) in dioxane (3 mL) was stirred at 120° C. for 12 h. LCMS showed compound 22a was consumed and the desired MS was observed. The mixture was concentrated to give compound 22b (86 mg, crude) as yellow oil which was used for next step without further purification. LCMS: (M+H$^+$): 526.2

Step 3. Preparation of (2R,3S,4R,5R)-5-(4-amino-7H-pyrrolo[2,3-d]pyrimidin-7-yl)-2-((3-(aminomethyl)phenoxy)methyl)-3-methyltetrahydrofuran-3,4-diol (22)

A mixture of compound 22b (80 mg, 152.21 umol, 1 eq.) in HCl/MeOH (4 M, 4 mL, 105.12 eq.) was stirred at 25° C. for 0.5 h. LCMS showed compound 22b was consumed and the desired MS was observed. The mixture was concentrated. The residue was purified by prep-HPLC (part by column: UniSil 120*30*10 um; mobile phase: [water (0.05% HCl)–ACN]; B %: 1%-15%, 11 min, to give the HCl salt, and the other part by column: Agela Durashell C18 150*25 5 u; mobile phase: [water (0.04% NH$_3$H$_2$O)–ACN]; B %: 5%-35%, 10 min) to give the free base.

Compound 22 (HCl salt) (7.85 mg, 18.61 umol, 12.22% yield, HCl salt, LCMS purity 100.0%) was obtained as a gray solid. $^1$H NMR (400 MHz, DMSO-d$_6$) δ=8.39 (s, 1H), 8.33 (br s, 3H), 7.69 (d, J=3.7 Hz, 1H), 7.37 (t, J=7.9 Hz, 1H), 7.22 (s, 1H), 7.10-7.00 (m, 3H), 6.19 (d, J=7.9 Hz, 1H), 5.53 (br s, 1H), 5.21 (s, 1H), 4.39 (d, J=8.1 Hz, 1H), 4.24-4.09 (m, 3H), 4.02 (br d, J=5.7 Hz, 2H), 1.30 (s, 3H); $^1$H NMR (400 MHz, DMSO-d$_6$+D$_2$O) δ=8.38 (s, 1H), 7.66 (d, J=3.8 Hz, 1H), 7.38 (t, J=7.9 Hz, 1H), 7.17 (s, 1H), 7.10-7.03 (m, 2H), 6.98 (d, J=3.4 Hz, 1H), 6.19 (d, J=7.9 Hz, 1H), 4.38 (d, J=8.1 Hz, 1H), 4.24-4.08 (m, 3H), 4.05-3.98 (m, 2H), 1.29 (s, 3H); LCMS: (M+H$^+$): 386.2.

Compound 22 (free base) (21.67 mg, 55.74 umol, 36.62% yield, LCMS purity 99.13%) was obtained as a white solid. $^1$H NMR (400 MHz, DMSO-d$_6$) δ=8.06 (s, 1H), 7.37 (d, J=3.7 Hz, 1H), 7.22 (t, J=7.9 Hz, 1H), 6.99 (br s, 3H), 6.91 (d, J=7.5 Hz, 1H), 6.82 (dd, J=2.3, 8.1 Hz, 1H), 6.60 (d, J=3.7 Hz, 1H), 6.15 (d, J=7.9 Hz, 1H), 5.38 (br s, 1H), 5.01 (br s, 1H), 4.38 (br d, J=7.6 Hz, 1H), 4.17-4.02 (m, 3H), 3.69 (s, 2H), 1.28 (s, 3H); $^1$H NMR (400 MHz, DMSO-d$_6$+D$_2$O) δ=8.05 (s, 1H), 7.35 (d, J=3.8 Hz, 1H), 7.21 (t, J=7.8 Hz, 1H), 6.98 (s, 1H), 6.90 (d, J=7.7 Hz, 1H), 6.81 (dd, J=2.1, 7.9 Hz, 1H), 6.59 (d, J=3.7 Hz, 1H), 6.14 (d, J=8.1 Hz, 1H), 4.37 (d, J=8.1 Hz, 1H), 4.16-4.01 (m, 3H), 3.65 (s, 2H), 1.26 (s, 3H); LCMS: (M+H$^+$): 386.3

Example 26. (2R,3S,4R,5R)-5-(4-amino-7H-pyrrolo[2,3-d]pyrimidin-7-yl)-2-((R)-(4-chlorophenyl)(hydroxy)methyl)-3-methyltetrahydrofuran-3,4-diol (26)

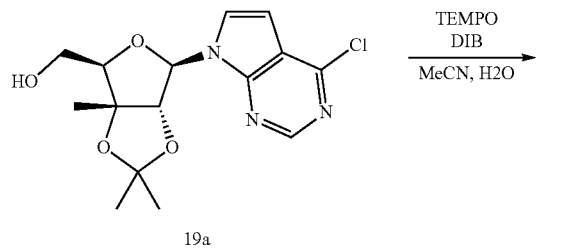
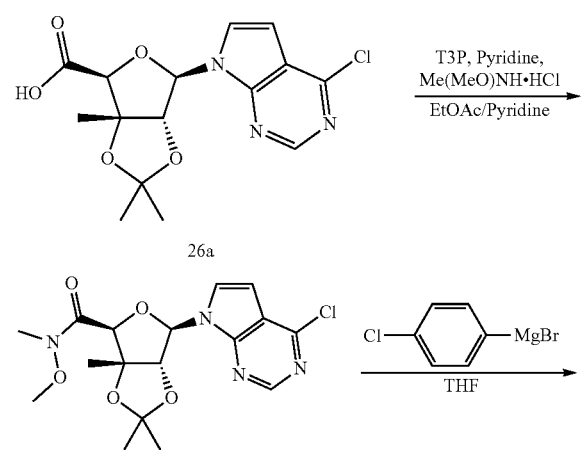
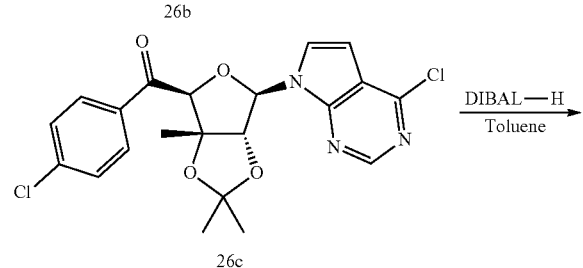
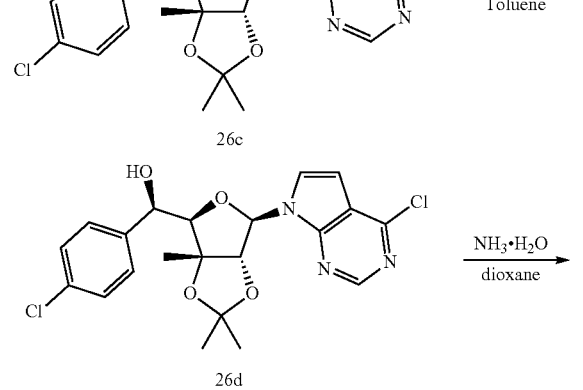
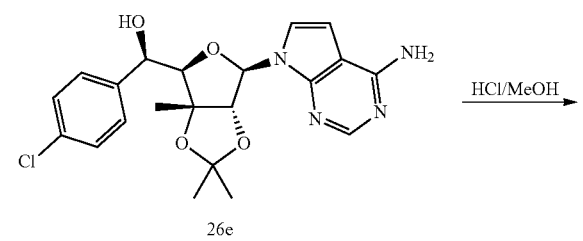

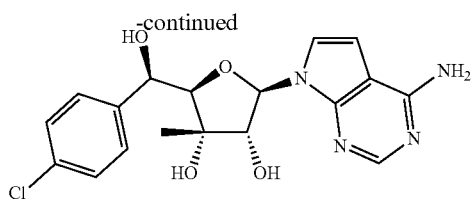

Ex. 26

Step 1. Preparation of (3aS,4S,6R,6aR)-6-(4-chloro-7H-pyrrolo[2,3-d]pyrimidin-7-yl)-2,2,3a-trimethyltetrahydrofuro[3,4-d][1,3]dioxole-4-carboxylic acid (26a)

To a mixture of compound 19a (500 mg, 1.47 mmol, 1 eq.), diacetoxyiodobenzene (DAIB) (1.04 g, 3.24 mmol, 2.2 eq.) in MeCN (2 mL) and H₂O (2 mL) was added TEMPO (46.28 mg, 294.31 umol, 0.2 eq.) at 0° C. The mixture was stirred at 25° C. for 1 h. TLC showed the compound 19a was consumed. The mixture was concentrated. The residue was dissolved in toluene (10 mL). The mixture was concentrated. The crude product was used for next step without further purification. Compound 26a (520 mg, crude) was obtained as brown oil. TLC (SiO₂, ethyl acetate/ethanol=1/1): $R_f$=0.5.

Step 2. Preparation of (3aS,4S,6R,6aR)-6-(4-chloro-7H-pyrrolo[2,3-d]pyrimidin-7-yl)-N-methoxy-N,2,2,3a-tetramethyltetrahydrofuro[3,4-d][1,3]dioxole-4-carboxamide (26b)

To a mixture of compound 26a (520 mg, 1.47 mmol, 1 eq.), N-methoxymethanamine (215.07 mg, 2.20 mmol, 1.5 eq., HCl), pyridine (348.82 mg, 4.41 mmol, 355.93 uL, 3 eq.) in EtOAc (5 mL) was added T3P (1.87 g, 2.94 mmol, 1.75 mL, 50% purity, 2 eq.) at 25° C. The mixture was stirred at 25° C. for 12 h. TLC showed the compound 26a was consumed. The mixture was quenched by water (50 mL) and extracted with EtOAc (25 mL×3). The combined organic layers were dried over Na₂SO₄, filtered and concentrated. The residue was purified by prep-TLC (SiO₂, Petroleum ether/Ethyl acetate=1/1). Compound 26b (450 mg, 1.13 mmol, 77.15% yield) was obtained as colorless oil. ¹H NMR (400 MHz, CHLOROFORM-d) δ=8.67 (s, 1H), 8.21 (d, J=3.7 Hz, 1H), 6.69-6.63 (m, 2H), 5.26 (s, 1H), 4.60 (d, J=1.3 Hz, 1H), 3.79 (s, 3H), 3.28 (s, 3H), 1.70 (s, 3H), 1.46 (d, J=3.5 Hz, 6H); LCMS: (M+H⁺): 397.2; TLC (SiO₂, petroleum ether/ethyl acetate=1/1): $R_f$=0.6.

Step 3. Preparation of ((3aS,4S,6R,6aR)-6-(4-chloro-7H-pyrrolo[2,3-d]pyrimidin-7-yl)-2,2,3a-trimethyltetrahydrofuro[3,4-d][1,3]dioxol-4-yl)(4-chlorophenyl)methanone (26c)

To a mixture of compound 26b (200 mg, 504.00 umol, 1 eq.) in THF (2 mL) was added bromo-(4-chlorophenyl)magnesium (1 M, 1.01 mL, 2 eq.) at −10° C. under N₂. The mixture was stirred at 0° C. for 1 h under N₂. TLC showed the compound 26b was consumed. The mixture was quenched by saturated NH₄Cl solution (10 mL), extracted with EtOAc (5 mL×3). The combined organic layers were dried over Na₂SO₄, filtered and concentrated. The residue was purified by prep-TLC (SiO₂, Petroleum ether/Ethyl acetate=3/1). Compound 26c (200 mg, 446.13 umol, 88.52% yield) was obtained as colorless oil. LCMS: (M+H⁺): 448.1; TLC (SiO₂, Petroleum ether/Ethyl acetate=3/1): R_f=0.6.

Step 4. Preparation of (R)-((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)(4-chlorophenyl)methanol (26d)

To a mixture of compound 26c (200 mg, 446.13 umol, 1 eq.) in toluene (2 mL) was added DIBAL-H (1 M, 892.26 uL, 2 eq.) at −70° C. under N₂. The mixture was stirred at −70° C. for 0.5 h under N₂. TLC showed the compound 26c was consumed. The mixture was quenched by water (0.5 mL), 15% NaOH solution (0.5 mL), water (0.5 mL) and the mixture was stirred for 10 min. The mixture was dried over MgSO₄, filtered and concentrated. The residue was purified by prep-TLC (SiO₂, Petroleum ether/Ethyl acetate=3/1). Compound 26d (190 mg, 421.93 umol, 94.57% yield) was obtained as colorless oil. ¹H NMR (400 MHz, CHLORO-FORM-d) δ=8.68 (s, 1H), 7.39-7.30 (m, 5H), 6.68 (d, J=3.7 Hz, 1H), 6.19 (d, J=2.6 Hz, 1H), 4.84 (d, J=8.4 Hz, 1H), 4.72 (d, J=2.6 Hz, 1H), 4.14 (d, J=8.4 Hz, 1H), 2.64 (br d, J=0.7 Hz, 1H), 1.85 (s, 3H), 1.67 (s, 3H), 1.43 (s, 3H); TLC (SiO₂, petroleum ether/ethyl acetate=1/1): R_f=0.4.

Step 5. Preparation of (R)-((3aR,4R,6R,6aR)-6-(4-amino-7H-pyrrolo[2,3-d]pyrimidin-7-yl)-2,2,3a-trimethyltetrahydrofuro[3,4-d][1,3]dioxol-4-yl)(4-chlorophenyl)methanol (26e)

A mixture of compound 26d (140 mg, 310.89 umol, 1 eq.) in NH₃.H₂O (1.59 g, 11.36 mmol, 1.75 mL, 25% purity, 36.54 eq.) and dioxane (2 mL) was stirred at 100° C. for 12 h. LCMS showed the compound 26d was consumed and the desired MS was observed. The mixture was concentrated. The crude product was used for next step without further purification. Compound 26e (133 mg, crude) was obtained as a light yellow oil which was used for next step without further purification. LCMS: (M+H⁺): 431.1.

Step 6. Preparation of (2R,3S,4R,5R)-5-(4-amino-7H-pyrrolo[2,3-d]pyrimidin-7-yl)-2-((R)-(4-chlorophenyl)(hydroxy)methyl)-3-methyltetrahydrofuran-3,4-diol (26)

A mixture of compound 26e (133 mg, 308.67 umol, 1 eq.) in HCl/MeOH (4 M, 1.77 mL, 22.98 eq.) was stirred at 25° C. for 1 h. LCMS showed the compound 26e was consumed and the desired MS was observed. The mixture was concentrated. The residue was purified by prep-HPLC (column: Waters Xbridge 150*25 5 u; mobile phase: [water (0.04% NH₃H₂O+10 Mm, NH₄HCO₃)–ACN]; B %: 10%-40%, 10 min). Compound 26 (56.96 mg, 145.24 umol, 47.05% yield, LCMS 99.65% purity) was obtained as a white solid. ¹H NMR (400 MHz, DMSO-d₆) δ=8.04 (s, 1H), 7.45-7.37 (m, 3H), 7.31 (d, J=8.4 Hz, 2H), 7.08 (br s, 2H), 6.63-6.55 (m, 2H), 5.84 (d, J=8.1 Hz, 1H), 5.24 (d, J=7.1 Hz, 1H), 4.87-4.79 (m, 1H), 4.74 (s, 1H), 4.43 (br t, J=7.5 Hz, 1H), 4.06 (d, J=5.7 Hz, 1H), 1.15 (s, 3H); ¹H NMR (400 MHz, DMSO-d₆+D₂O) δ=8.02 (s, 1H), 7.43-7.26 (m, 5H), 6.58 (d, J=3.5 Hz, 1H), 5.82 (d, J=8.1 Hz, 1H), 4.79 (d, J=5.7 Hz, 1H), 4.39 (d, J=8.2 Hz, 1H), 4.06 (d, J=5.7 Hz, 1H), 1.13 (s, 3H); LCMS: (M+H⁺): 391.0; LCMS purity 99.65%; HPLC purity: 100.00%.

Example 32. 7-((2R,3R,4S,5R)-5-(((2-aminoquinolin-7-yl)oxy)methyl)-3,4-dihydroxy-4-methyltetrahydrofuran-2-yl)-1H-pyrrolo[2,3-d]pyrimidin-4(7H)-one O-methyloxime (32)

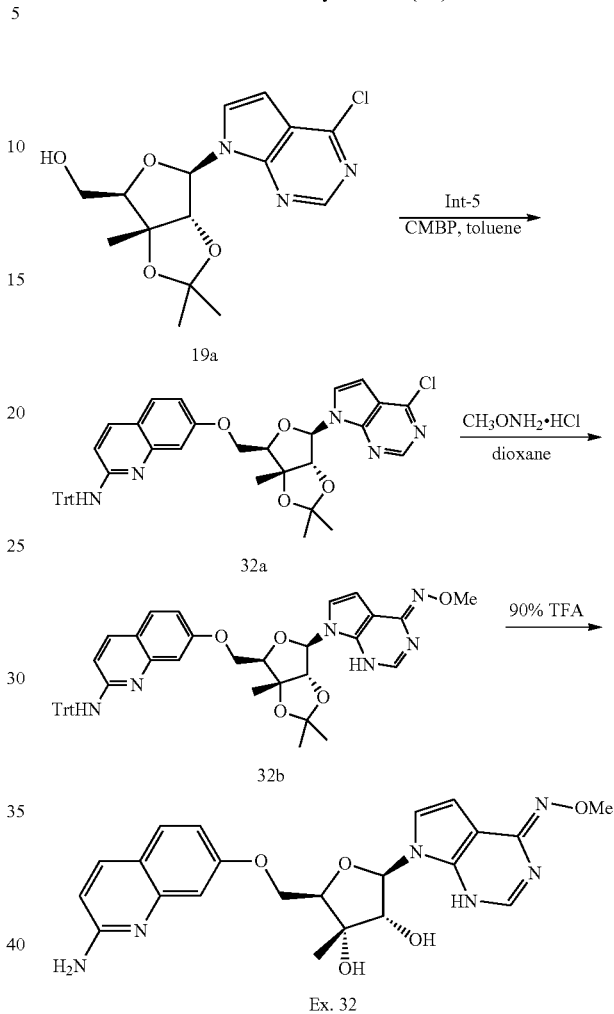

Step 1. Preparation of 7-(((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methoxy)-N-tritylquinolin-2-amine (32a)

To a solution of compound 19a (150 mg, 441.47 umol, 1 eq.) and compound Int-5 (230 mg, 571.45 umol, 1.29 eq.) in toluene (3 mL) was added 2-(tributyl-phosphanylidene)acetonitrile (213.10 mg, 882.94 umol, 2 eq.) under N₂ at 25° C. The mixture was stirred at 80° C. for 12 h. LC-MS showed compound 19a was remained. Several new peaks were shown on LC-MS and desired compound 32a was detected. The reaction mixture was concentrated under reduced pressure to remove solvent. The residue was purified by prep-TLC (SiO₂, Petroleum ether/Ethyl acetate=3:1) and based on TLC (Petroleum ether/Ethyl acetate=3:1, R_f=0.37). Compound 32a (0.13 g, crude) was obtained as a yellow solid. TLC (Petroleum ether:Ethyl acetate=3:1) R_f=0.37; LCMS: (M+H⁺): 724.2.

Step 2. Preparation of 7-((3aR,4R,6R,6aR)-2,2,6a-trimethyl-6-(((2-(tritylamino)quinolin-7-yl)oxy)methyl)tetrahydrofuro[3,4-d][1,3]dioxol-4-yl)-1H-pyrrolo[2,3-d]pyrimidin-4(7H)-one O-methyl oxime (32b)

To a solution of compound 32a (120 mg, 165.69 umol, 1 eq.) in t-BuOH (2 mL) was added O-methylhydroxylamine hydrochloride (110.70 mg, 1.33 mmol, 100.64 uL, 8 eq.) under $N_2$. The mixture was stirred at 80° C. for 16 h. LC-MS showed compound 32a was almost consumed. Several new peaks were shown on LC-MS and desired compound 32b was detected. The reaction mixture was concentrated under reduced pressure to remove solvent. The residue was added aq. $NaHCO_3$ and extracted with DCM (5 mL×2) and EtOAc (5 mL×2), the organic layer was washed with brine (10 mL×2), dried over $Na_2SO_4$, filtered and concentrated under reduced pressure to give a residue. The residue was purified by prep-TLC ($SiO_2$, Petroleum ether/Ethyl acetate=2:3, $R_f$=0.57) and based on TLC (Petroleum ether:Ethyl acetate=2:3 $R_f$=0.57). Compound 32b (0.1 g, 134.67 umol, 81.28% yield, 98.96% purity) was obtained as a yellow solid. LCMS1: (M+H$^+$): 735.2; TLC (Petroleum ether:Ethyl acetate=2:3) $R_f$=0.57; LCMS2: (M+H$^+$): 735.5. LCMS purity 98.96%. $^1$H NMR (400 MHz, CHLOROFORM-d) δ=7.35-7.44 (m, 6.6H), 7.28-7.33 (m, 3.6H), 7.19-7.26 (m, 3H), 7.01 (br s, 0.7H), 6.83-6.91 (m, 1H), 6.66 (br d, J=3.67 Hz, 0.4H), 6.39-6.52 (m, 1.5H), 6.25 (s, 0.4H), 6.04 (d, J=8.93 Hz, 0.7H), 4.81 (s, 0.4H), 4.66 (s, 0.4H), 4.42-4.58 (m, 0.9H), 4.18-4.39 (m, 1.8H), 3.88 (d, J=5.62 Hz, 2.4H), 1.52-1.73 (m, 4.7H), 1.44 (br d, J=5.75 Hz, 3H), 0.80-0.93 (m, 1H).

Step 3. Preparation of 7-((2R,3R,4S,5R)-5-(((2-aminoquinolin-7-yl)oxy)methyl)-3,4-dihydroxy-4-methyltetrahydrofuran-2-yl)-1H-pyrrolo[2,3-d]pyrimidin-4(7H)-one O-methyl oxime (32)

To a solution of compound 32b (0.1 g, 136.08 umol, 1 eq.) was added TFA (1.54 g, 12.16 mmol, 1 mL, 90% purity, 89.32 eq.). The mixture was stirred at 25° C. for 2 h. LC-MS showed compound 32b was consumed completely and one main peak with desired product compound 32 was detected. The reaction mixture was added $NH_3.H_2O$ adjusted pH around 8 and concentrated under reduced pressure to remove solvent. The residue was purified by prep-HPLC (basic condition column: Waters Xbridge 150*25 5u; mobile phase: [water (0.04% $NH_3H_2O$+10 mM $NH_4HCO_3$)–ACN]; B %: 5%-35%, 10 min). Compound 32 (8.59 mg, 18.25 umol, 13.41% yield, 96.15% LCMS purity) was obtained as a white solid. $^1$H NMR (400 MHz, DMSO-d$_6$) δ=7.79 (d, J=8.77 Hz, 0.6H), 7.54 (d, J=9.21 Hz, 0.7H), 7.48 (s, 0.4H), 7.21 (d, J=3.51 Hz, 0.4H), 6.92 (br d, J=7.45 Hz, 0.6H), 6.81-6.89 (m, 0.6H), 6.56-6.62 (m, 0.9H), 6.33 (s, 1.5H), 6.25 (d, J=3.07 Hz, 0.6H), 6.00 (d, J=8.33 Hz, 0.4H), 5.41 (br d, J=6.58 Hz, 0.6H), 4.99-5.06 (m, 0.5H), 4.33 (t, J=7.89 Hz, 0.4H), 4.10-4.24 (m, 2.2H), 3.71 (s, 2.2H), 3.32 (br s, 1.1H), 1.23-1.34 (m, 3H); $^1$H NMR (400 MHz, DMSO-d$_6$+ D$_2$O) δ=7.82 (s, 0.3H), 7.80 (s, 0.3H), 7.56 (d, J=9.21 Hz, 0.7H), 7.51 (s, 0.4H), 7.19 (d, J=3.07 Hz, 0.4H), 6.90-6.94 (m, 0.7H), 6.84-6.90 (m, 0.7H), 6.62 (s, 0.3H), 6.57-6.60 (m, 0.6H), 6.27 (d, J=3.07 Hz, 0.5H), 5.99 (d, J=7.89 Hz, 0.4H), 4.33 (d, J=7.89 Hz, 0.5H), 4.18 (br s, 0.8H), 4.14 (br s, 1.1H), 4.09-4.13 (m, 0.5H), 1.24-1.30 (m, 3H); LCMS1: (M+H$^+$): 453.2; LCMS: (M+H$^+$): 453.3; LCMS purity 96.15%; HPLC purity: 100.00%.

Example 37. 7-((2R,3R,4S,5R)-5-((R)-(3,4-dichlorophenyl)(hydroxy)methyl)-3,4-dihydroxy-4-methyl-tetrahydrofuran-2-yl)-1H-pyrrolo[2,3-d]pyrimidin-4(7H)-one O-methyl oxime (37)

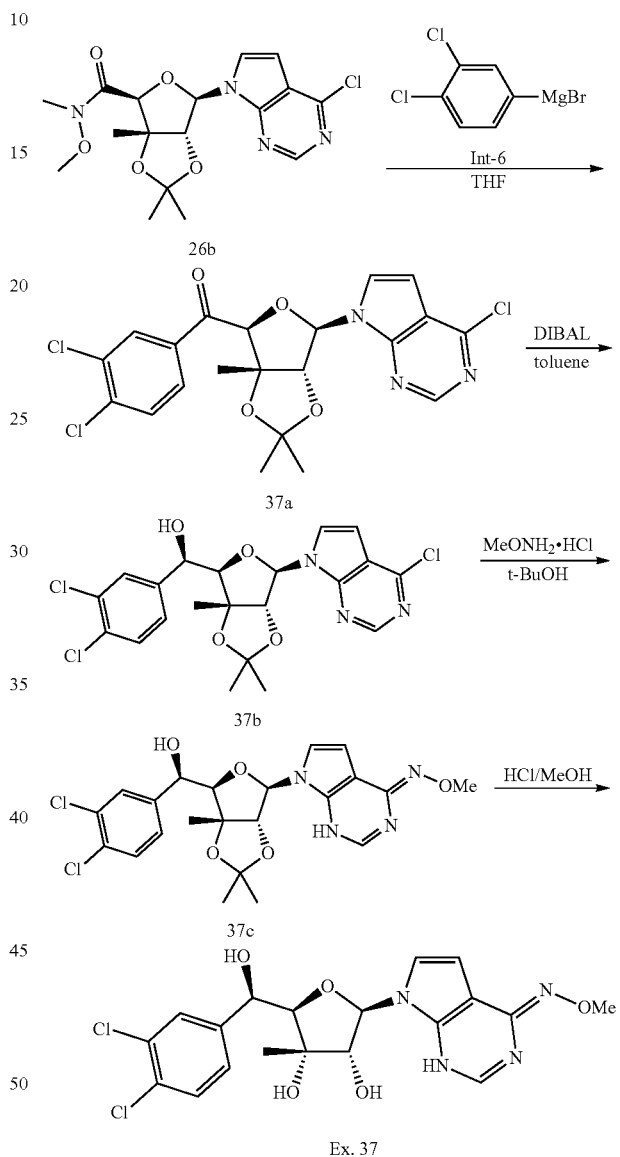

Step 1. Preparation of ((3aS,4S,6R,6aR)-6-(4-chloro-7H-pyrrolo[2,3-d]pyrimidin-7-yl)-2,2,3a-trimethyltetrahydrofuro[3,4-d][1,3]dioxol-4-yl)(3,4-dichlorophenyl)methanone (37a)

To a solution of compound 26b (1 g, 2.52 mmol, 1 eq.) in THF (15 mL) was added compound Int-6 (1 M, 10.08 mL, 4 eq.) at −10° C. under $N_2$. The mixture was stirred at 0° C. for 5 min. TLC indicated compound 26b was consumed completely and many new spots formed. The reaction was clean according to TLC (Petroleum ether:Ethyl acetate=3:1 $R_f$=0.48). The solution was added aq. sat. $NH_4Cl$ (15 mL)

and extracted with DCM (10 mL×2). The combined organic layers were washed with brine (20 mL×2), dried over Na₂SO₄, filtered and concentrated under reduced pressure to give a residue. The residue was purified by column chromatography (SiO₂, Petroleum ether/Ethyl acetate=1/0 to 15/1) and based on TLC (Petroleum ether:Ethyl acetate=3:1 $R_f$=0.48). Compound 37a (660 mg, 1.27 mmol, 50.42% yield, LCMS purity 92.94%) was obtained as a white solid. 1H NMR (400 MHz, CHLOROFORM-d) δ=8.64-8.73 (m, 1H), 8.28 (d, J=2.19 Hz, 1H), 7.99 (dd, J=8.33, 2.19 Hz, 1H), 7.89 (d, J=3.95 Hz, 1H), 7.63 (d, J=8.33 Hz, 1H), 6.72 (d, J=3.95 Hz, 1H), 6.59 (d, J=1.32 Hz, 1H), 5.54 (s, 1H), 4.70 (d, J=1.32 Hz, 1H), 1.83 (s, 3H), 1.47 (s, 3H), 1.36 (s, 3H); LCMS: (M+H⁺): 483.9, LCMS purity 92.94%; TLC (Petroleum ether:Ethyl acetate=3:1) $R_f$=0.48.

Step 2. Preparation of (R)-((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)(3,4-dichlorophenyl)methanol (37b)

To a solution of compound 37a (660 mg, 1.37 mmol, 1 eq.) in toluene (10 mL) was added DIBAL-H (1 M, 2.73 mL, 2 eq.) at −70° C. under N₂. The mixture was stirred at −70° C. for 5 min. TLC indicated compound 37a was consumed completely and one new spot formed. The reaction was clean according to TLC (Petroleum ether:Ethyl acetate=3:1 $R_f$=0.30). The reaction solution was added aq. sat. seignette salt (30 mL) and MTBE (20 mL) stirred at 25° C. for 0.5 h and extracted with MTBE (10 mL×4), washed with brine (10 mL×2), dried Na₂SO₄, filtered and concentrated under reduced pressure to give a residue. The residue was purified by column chromatography (SiO₂, Petroleum ether/Ethyl acetate=1/0 to 1/1) and based on TLC (Petroleum ether:Ethyl acetate=3:1 $R_f$=0.30). Compound 37b (310 mg, 513.06 umol, 37.53% yield, LCMS purity 80.23%) was obtained as a white solid. ¹H NMR (400 MHz, CHLOROFORM-d) δ=8.67 (s, 1H), 7.52 (d, J=1.75 Hz, 1H), 7.40 (d, J=8.33 Hz, 1H), 7.31 (d, J=3.51 Hz, 1H), 7.22 (dd, J=8.33, 1.75 Hz, 1H), 6.69 (d, J=3.95 Hz, 1H), 6.17 (d, J=2.63 Hz, 1H), 4.83 (d, J=8.33 Hz, 1H), 4.76 (d, J=2.63 Hz, 1H), 4.05-4.18 (m, 1H), 2.94 (br s, 1H), 1.84 (s, 3H), 1.67 (s, 3H), 1.43 (s, 3H); LCMS: (M+H⁺): 484.3. LCMS purity 80.23%; TLC (Petroleum ether:Ethyl acetate=3:1) $R_f$=0.30.

Step 3. Preparation of 7-((3aR,4R,6R,6aR)-6-((R)-(3,4-dichlorophenyl) (hydroxy) methyl)-2,2,6a-trimethyltetrahydrofuro[3,4-d][1,3]dioxol-4-yl)-1H-pyrrolo[2,3-d]pyrimidin-4(7H)-one O-methyl oxime (37c)

To a solution of compound 37b (0.1 g, 206.29 umol, 1 eq.) in t-BuOH (1 mL) was added O-methylhydroxylamine hydrochloride (137.83 mg, 1.65 mmol, 125.30 uL, 8 eq.) under N₂ at 25° C. The mixture was stirred at 80° C. for 16 h. LC-MS showed no compound 37b was remained. Several new peaks were shown on LC-MS and desired compound was detected. The reaction mixture was concentrated under reduced pressure to remove solvent. Compound 37c (100 mg, crude) was used into the next step without further purification as a pink solid. LCMS: (M+H⁺): 495.4.

Step 4. Preparation of 7-((2R,3R,4S,5R)-5-((R)-(3,4-dichlorophenyl)(hydroxy)methyl)-3,4-dihydroxy-4-methyltetrahydrofuran-2-yl)-1H-pyrrolo[2,3-d]pyrimidin-4(7H)-one O-methyl oxime (37)

To a solution of compound 37c (100.00 mg, 201.88 umol, 1 eq.) was added HCl/MeOH (4 M, 5 mL, 99.07 eq.) at 0° C. The mixture was stirred at 25° C. for 10 min. LC-MS showed compound 1b was consumed completely and one main peak with desired MS was detected. The reaction mixture was concentrated under reduced pressure to remove solvent at 25° C. The residue was added NH₃.H₂O to adjusted pH around 8. The residue was purified by prep-HPLC (basic condition, column: Waters Xbridge 150*25 5u; mobile phase: [water (0.04% NH₃H₂O+10 mM NH₄HCO₃)−ACN]; B %: 10%-40%, 10 min). Compound 37 (18.03 mg, 39.00 umol, 19.32% yield, 98.48% LCMS purity) was obtained as a white solid. ¹H NMR (400 MHz, DMSO-d₆) δ=10.93 (br s, 0.6H), 10.64 (br s, 0.4H), 7.43-7.63 (m, 3H), 7.31-7.40 (m, 1H), 7.28 (br s, 0.6H), 6.57 (br s, 0.3H), 6.24 (br s, 1H), 5.97 (br s, 1H), 5.78 (br d, J=8.33 Hz, 0.6H), 5.30 (br s, 1H), 4.78-4.88 (m, 1.3H), 4.74 (br s, 0.6H), 4.40 (br s, 0.4H), 4.27 (br s, 0.6H), 3.97 (br d, J=6.58 Hz, 0.3H), 3.89 (br d, J=7.02 Hz, 0.5H), 3.65-3.79 (m, 3H), 1.24 (br s, 3H); ¹H NMR (400 MHz, DMSO-d₆+D₂O) δ=7.51 (br d, J=19.73 Hz, 2.5H), 7.28-7.39 (m, 1H), 7.23 (br s, 0.6H), 6.57 (br s, 0.3H), 6.26 (br s, 0.5H), 5.92 (br s, 0.2H), 5.75 (br d, J=8.33 Hz, 0.5H), 4.67-4.81 (m, 0.8H), 4.39 (br s, 0.3H), 4.25-4.26 (m, 0.5H), 3.96 (br s, 0.5H), 3.89 (br d, J=7.45 Hz, 0.8H), 1.22 (br s, 3H); LCMS: (M+H⁺): 455.1. LCMS purity 98.48%; HPLC purity: 98.50%.

Example 40. (2S,3S,4R,5R)-3-methyl-5-(4-(methylamino)-7H-pyrrolo[2,3-d]pyrimidin-7-yl)-2-((methylthio)methyl)tetrahydrofuran-3,4-diol (40)

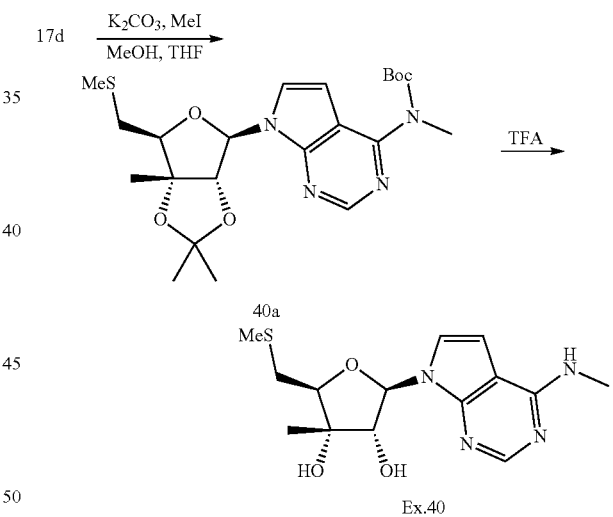

Step 1. Preparation of tert-butyl methyl(7-((3aR,4R,6S,6aS)-2,2,6a-trimethyl-6-((methylthio)methyl)tetrahydrofuro[3,4-d][1,3]dioxol-4-yl)-7H-pyrrolo[2,3-d]pyrimidin-4-yl)carbamate (40a)

To a solution of compound 17d in MeOH (1 mL) and THF (1 mL) was added K₂CO₃ (95.53 mg, 691.23 umol, 2 eq.) and MeI (245.28 mg, 1.73 mmol, 107.58 uL, 5 eq.). The mixture was stirred at 25° C. for 2 hr. LC-MS showed compound 17d was consumed completely and one main peak with desired MS was detected. The reaction was filtered, and the filtrate was concentrated in vacuo. The residue was purified by prep-TLC (SiO₂, Petroleum ether: Ethyl acetate=3:1). The crude product compound 40a (60 mg, crude) was used into the next step without further purification as a yellow oil. TLC (Petroleum ether:Ethyl acetate=3:1) $R_f$=0.24.

Step 2. Preparation of (2S,3S,4R,5R)-3-methyl-5-(4-(methylamino)-7H-pyrrolo[2,3-d]pyrimidin-7-yl)-2-((methylthio)methyl)tetrahydrofuran-3,4-diol (40)

A solution of compound 40a (103.11 mg, 221.95 umol, 1 eq.) in TFA (3.08 g, 24.31 mmol, 2.00 mL, 90% purity, 109.53 eq.), the mixture was stirred at 25° C. for 3 hr. LC-MS showed compound 40a was consumed completely and one main peak with desired MS was detected. The reaction was concentrated in vacuo at 25° C. The residue was purified by prep-HPLC. Compound 40 (6.78 mg, 19.77 umol, 8.91% yield, 94.59% purity) was obtained as a white solid. $^1$H NMR (400 MHz, DMSO-d$_6$) δ=8.15 (s, 1H), 7.47 (br s, 1H), 7.35 (br s, 1H), 6.60 (br s, 1H), 6.02 (br d, J=7.7 Hz, 1H), 5.32 (br d, J=6.6 Hz, 1H), 4.90 (s, 1H), 4.30 (br t, J=6.6 Hz, 1H), 3.93 (br s, 1H), 2.95 (br s, 3H), 2.83-2.70 (m, 2H), 2.01 (s, 3H), 1.22 (s, 3H); $^1$H NMR (400 MHz, DMSO-d$_6$+D$_2$O) δ=8.13 (s, 1H), 7.33 (d, J=3.7 Hz, 1H), 6.59 (d, J=3.7 Hz, 1H), 6.01 (d, J=7.7 Hz, 1H), 4.28 (d, J=7.9 Hz, 1H), 3.92 (dd, J=4.2, 8.8 Hz, 1H), 2.93 (s, 3H), 2.80-2.67 (m, 2H), 2.00 (s, 3H), 1.21 (s, 3H); LCMS: (M+H$^+$): 325.1.

Example 41. 1-(3-(((2R,3S,4R,5R)-5-(4-chloro-7H-pyrrolo[2,3-d]pyrimidin-7-yl)-3,4-dihydroxy-3-methyltetrahydrofuran-2-yl)methoxy)phenyl)urea (41)

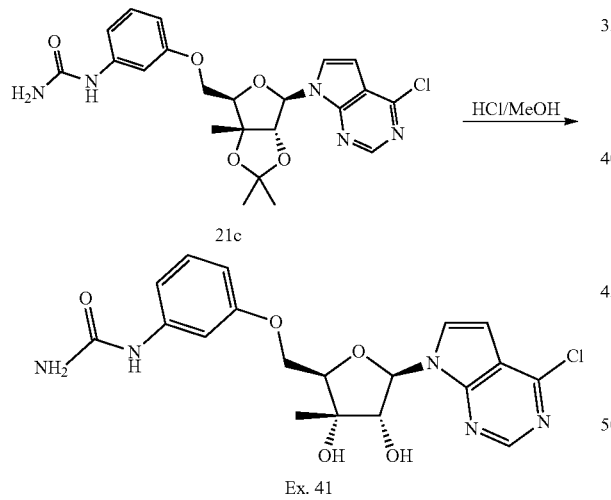

A mixture of compound 21c (50 mg, 105.51 umol, 1 eq.) in TFA (1 mL) and H$_2$O (0.2 mL) was stirred at 25° C. for 0.5 h. LCMS showed the compound 21c was consumed and the desired MS was observed. The mixture was concentrated. The residue was dissolved in aq. saturated NaHCO$_3$ (10 mL) and the mixture was extracted with EtOAc (5 mL×3). The combined organic layers were dried over Na$_2$SO$_4$, filtered and concentrated. The residue was purified by prep-HPLC (column: Waters Xbridge 150*25 5 u; mobile phase: [water (0.05% ammonia hydroxide v/v)–ACN]; B %: 5%-30%, 11 min). Compound 41 (11.81 mg, 27.22 umol, 25.80% yield, LCMS 100% purity, free base) was obtained as a white solid. $^1$H NMR (400 MHz, DMSO-d$_6$) δ=8.69 (s, 1H), 8.55 (s, 1H), 7.95 (d, J=3.8 Hz, 1H), 7.25 (s, 1H), 7.14 (t, J=8.1 Hz, 1H), 6.88 (d, J=8.8 Hz, 1H), 6.77 (d, J=3.8 Hz, 1H), 6.56 (dd, J=2.1, 8.2 Hz, 1H), 6.28 (d, J=7.8 Hz, 1H), 5.85 (s, 2H), 5.54 (br s, 1H), 5.13 (br s, 1H), 4.45 (br d, J=7.9 Hz, 1H), 4.24-4.02 (m, 3H), 1.29 (s, 3H); $^1$H NMR (400 MHz, DMSO-d$_6$) δ=8.66 (s, 1H), 7.89 (d, J=3.9 Hz, 1H), 7.22 (s, 1H), 7.15 (t, J=8.1 Hz, 1H), 6.85 (d, J=8.2 Hz, 1H), 6.76 (d, J=3.8 Hz, 1H), 6.57 (dd, J=2.2, 8.2 Hz, 1H), 6.26 (d, J=7.9 Hz, 1H), 4.43 (d, J=8.1 Hz, 1H), 4.21-4.16 (m, 1H), 4.14-4.02 (m, 2H), 1.27 (s, 3H); LCMS: (M+H$^+$): 434.2; LCMS purity 100.00%; HPLC purity: 100.00%.

Example 42. (2S,3S,4R,5R)—N-(3-(aminomethyl)phenyl)-5-(4-chloro-7H-pyrrolo[2,3-d]pyrimidin-7-yl)-3,4-dihydroxy-3-methyltetrahydrofuran-2-carboxamide (42)

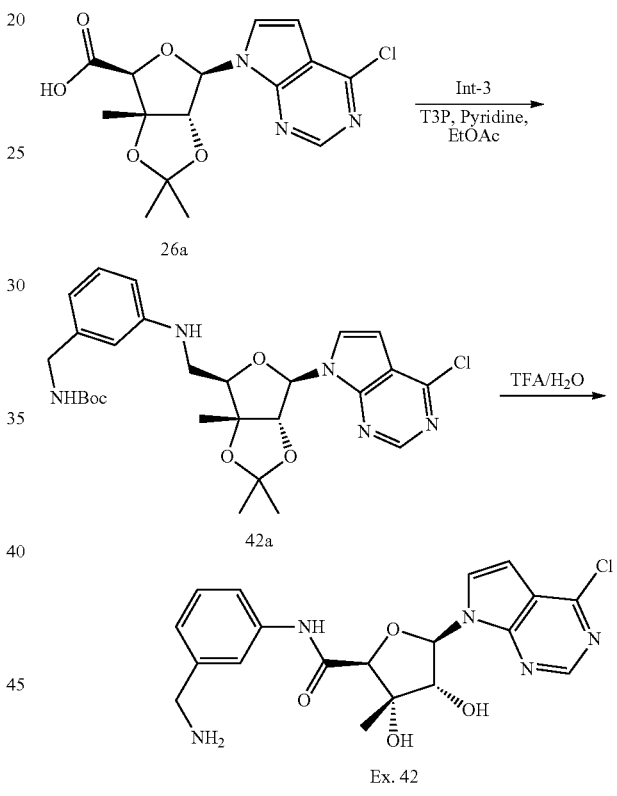

Step 1. Preparation of tert-butyl 3-((3aS,4S,6R,6aR)-6-(4-chloro-7H-pyrrolo[2,3-d]pyrimidin-7-yl)-2,2,3a-trimethyltetrahydrofuro[3,4-d][1,3]dioxole-4-carboxamido)benzylcarbamate (42a)

To a mixture of compound 26a (300 mg, 848.04 umol, 1 eq.), compound Int-3 (282.76 mg, 1.27 mmol, 1.5 eq.) and pyridine (201.24 mg, 2.54 mmol, 205.35 uL, 3 eq.) in EtOAc (3 mL) was added T3P (2.16 g, 3.39 mmol, 2.02 mL, 50% purity, 4 eq.) at 0° C. under N$_2$. The mixture was stirred at 25° C. for 12 h. TLC showed the compound 26a was consumed. The mixture was quenched by water (10 mL) and extracted with EtOAc (5 mL×3). The combined organic layers were dried over Na$_2$SO$_4$, filtered and concentrated. The residue was purified by prep-TLC (SiO$_2$, petroleum ether/ethyl acetate=1/1). Compound 42a (360 mg, 645.13 umol, 76.07% yield) was obtained as a brown solid. TLC (SiO₂, petroleum ether/ethyl acetate=1/1): $R_f$=0.6; ¹H NMR (400 MHz, CHLOROFORM-d) δ=8.70 (s, 1H), 8.50-8.37 (m, 1H), 7.47 (s, 1H), 7.42-7.34 (m, 2H), 7.31-7.28 (m, 1H), 7.07 (br d, J=7.6 Hz, 1H), 6.76 (d, J=3.7 Hz, 1H), 6.28 (d, J=2.9 Hz, 1H), 4.88 (br d, J=2.8 Hz, 2H), 4.71 (s, 1H), 4.29 (br d, J=5.5 Hz, 2H), 1.81 (s, 3H), 1.69 (s, 3H), 1.45 (s, 12H).

Step 2. Preparation of (2S,3S,4R,5R)—N-(3-(aminomethyl)phenyl)-5-(4-chloro-7H-pyrrolo[2,3-d]pyrimidin-7-yl)-3,4-dihydroxy-3-methyltetrahydrofuran-2-carboxamide (42)

A mixture of compound 42a (100 mg, 179.20 umol, 1 eq.) in TFA (2 mL) and H₂O (0.2 mL) was stirred at 25° C. for 12 h. LCMS showed the compound 42a was consumed and the desired MS was observed. The mixture was quenched by saturated NaHCO₃ solution to pH=8-9. The mixture was filtered and concentrated. The residue was purified by prep-HPLC (column: Waters Xbridge 150*25 5 u; mobile phase: [water (0.04% NH₃.H₂O)–ACN]; B %: 1%-30%, 10 min). Compound 42 (22.04 mg, 58.56 umol, 32.68% yield, LCMS 97.87% purity) was obtained as a white solid. ¹H NMR (400 MHz, DMSO-d₆) δ=10.41 (s, 1H), 8.71-8.66 (m, 1H), 8.44 (d, J=3.7 Hz, 1H), 7.62 (s, 1H), 7.58-7.45 (m, 1H), 7.28 (t, J=7.7 Hz, 1H), 7.09 (d, J=7.7 Hz, 1H), 6.84 (d, J=3.5 Hz, 1H), 6.41 (d, J=7.9 Hz, 1H), 5.73-5.44 (m, 2H), 4.56 (s, 1H), 4.40 (br d, J=7.5 Hz, 1H), 3.72 (s, 2H), 1.24 (s, 3H); ¹H NMR (400 MHz, DMSO-d₆) δ=8.66 (s, 1H), 8.37 (d, J=3.7 Hz, 1H), 7.56 (s, 1H), 7.47 (br d, J=8.2 Hz, 1H), 7.29 (t, J=7.8 Hz, 1H), 7.10 (d, J=8.2 Hz, 1H), 7.03 (s, 1H), 6.82 (d, J=3.7 Hz, 1H), 6.38 (d, J=7.9 Hz, 1H), 4.52 (s, 1H), 4.40 (d, J=7.9 Hz, 1H), 1.22 (s, 3H); LCMS: (M+H⁺): 418.0; LCMS purity: 97.87%; HPLC purity: 99.08%.

Example 43. (2S,3S,4R,5R)—N-(3-(aminomethyl)phenyl)-5-(4-chloro-7H-pyrrolo[2,3-d]pyrimidin-7-yl)-3,4-dihydroxy-3-methyltetrahydrofuran-2-carboxamide (43)

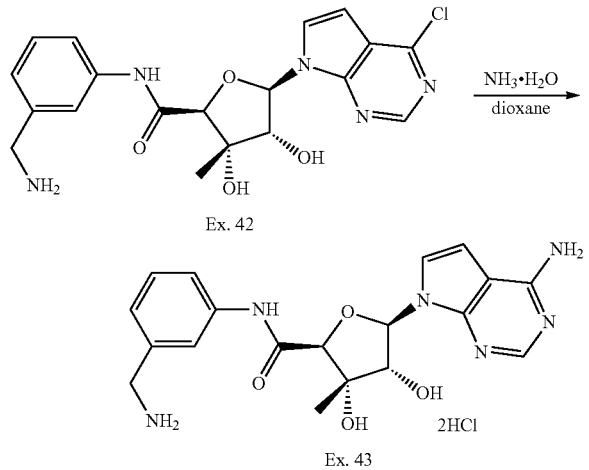

To mixture of compound 42 (89 mg, 213.00 umol, 1 eq.) in saturated NaHCO₃ solution (5 mL) and dioxane (2 mL) was added NH₃·H₂O (1.82 g, 12.98 mmol, 2 mL, 25% purity, 60.95 eq.) at 25° C. The mixture was stirred at 67° C. for 12 h. LCMS showed the compound 42 was consumed and the desired MS was observed. The mixture was concentrated. The residue was dissolved in MeCN (10 mL), filtered and concentrated. The residue was purified by prep-HPLC (column: UniSil 120*30*10 um; mobile phase: [water (0.05% HCl)–ACN]; B %: 1%-15%, 11 min). Compound 43 (12.61 mg, 26.21 umol, 12.31% yield, LCMS 97.98% purity, 2HCl) was obtained as a white solid. ¹H NMR (400 MHz, DMSO-d₆) δ=10.66 (s, 1H), 8.49-8.32 (m, 5H), 8.16 (d, J=3.7 Hz, 1H), 7.82 (s, 1H), 7.58 (br d, J=8.2 Hz, 1H), 7.41 (t, J=7.8 Hz, 1H), 7.29-7.23 (m, 1H), 7.09 (d, J=3.7 Hz, 1H), 6.29 (d, J=7.9 Hz, 1H), 5.92-5.28 (m, 2H), 4.60 (s, 1H), 4.36 (d, J=7.9 Hz, 1H), 4.05-3.98 (m, 2H), 3.85 (s, 1H), 1.23 (s, 3H); ¹H NMR (400 MHz, DMSO-d₆+D₂O) δ=10.65 (s, 1H), 8.36 (s, 1H), 8.13 (d, J=3.8 Hz, 1H), 7.77 (d, J=1.7 Hz, 1H), 7.57 (br d, J=8.1 Hz, 1H), 7.41 (t, J=7.9 Hz, 1H), 7.22 (d, J=7.8 Hz, 1H), 7.02 (d, J=3.7 Hz, 1H), 6.28 (d, J=7.9 Hz, 1H), 4.56 (s, 1H), 4.35 (d, J=7.9 Hz, 1H), 4.01 (s, 2H), 1.23 (s, 3H); LCMS: (M+H⁺): 399.1; LCMS purity 97.98%; HPLC purity: 98.57%.

Example 44. 7-((2R,3R,4S,5R)-5-((R)-(4-chlorophenyl)(hydroxy)methyl)-3,4-dihydroxy-4-methyltetrahydrofuran-2-yl)-1H-pyrrolo[2,3-d]pyrimidin-4(7H)-one O-methyl oxime (44)

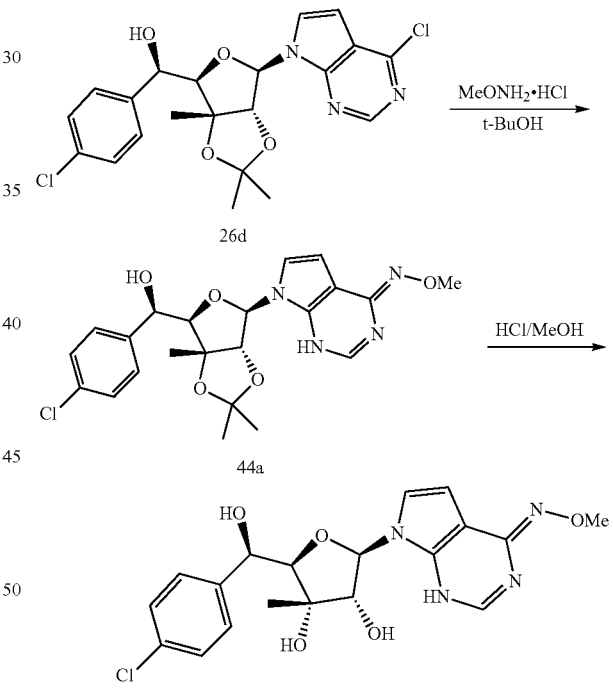

Step 1. Preparation of 7-((3aR,4R,6R,6aR)-6-((R)-(4-chlorophenyl)(hydroxy)methyl)-2,2,6a-trimethyl-tetrahydrofuro[3,4-d][1,3]dioxol-4-yl)-1H-pyrrolo[2,3-d]pyrimidin-4(7H)-one O-methyl oxime (44a)

A mixture of compound 26d (130 mg, 288.69 umol, 1 eq.) and 0-methyhydroxylamine hydrochloride (192.88 mg, 2.31 mmol, 175.35 uL, 8 eq.) in t-BuOH (3 mL) was stirred at 80° C. for 12 h. LCMS showed the compound 6d was consumed and the desired MS was observed. The mixture was concentrated. Compound 44a (133 mg, 288.56 umol, 99.96% yield) was obtained as a white solid which was used for the next step without further purification. LCMS: (M+H$^+$): 461.1.

Step 2. Preparation of 7-((2R,3R,4S,5R)-5-((R)-(4-chlorophenyl)(hydroxy)methyl)-3,4-dihydroxy-4-methyltetrahydrofuran-2-yl)-1H-pyrrolo[2,3-d]pyrimidin-4(7H)-one O-methyl oxime (44)

A mixture of compound 44a (133.00 mg, 288.56 umol, 1 eq.) in HCl/MeOH (4 M, 2.00 mL, 27.72 eq.) was stirred at 25° C. for 1 h. LCMS showed the compound 44a was consumed. The mixture was concentrated. The residue was purified by prep-HPLC (column: Waters Xbridge 150*25 5 u; mobile phase: [water (0.04% NH$_3$H$_2$O+10 mM NH$_4$HCO$_3$)–ACN]; B %: 10%-40%, 10 min). Compound 44 (28.44 mg, 65.98 umol, 22.87% yield, LCMS 97.6% purity) was obtained as an off-white solid. $^1$H NMR (400 MHz, DMSO-d$_6$) δ=11.13-10.34 (m, 1H), 8.12 (br s, 0.2H), 7.59-7.20 (m, 5H), 6.58 (br d, J=3.1 Hz, 0.3H), 6.31-6.10 (m, 0.8H), 6.03-5.70 (m, 1H), 5.34-5.17 (m, 1H), 4.85-4.70 (m, 2H), 4.39 (br s, 0.3H), 4.26 (br t, J=7.5 Hz, 0.5H), 4.02 (br d, J=6.4 Hz, 0.4H), 3.95 (br d, J=6.8 Hz, 0.6H), 3.78-3.70 (m, 3H), 1.30-1.17 (m, 3H); $^1$H NMR (400 MHz, DMSO-d$_6$+D$_2$O) δ=8.08 (br s, 0.2H), 7.54-7.12 (m, 5H), 6.57 (d, J=3.5 Hz, 0.3H), 6.27 (d, J=3.4 Hz, 0.5H), 5.91 (br d, J=8.2 Hz, 0.3H), 5.74 (d, J=8.2 Hz, 0.5H), 4.81-4.63 (m, 1H), 4.35 (br d, J=8.3 Hz, 0.3H), 4.23 (d, J=8.1 Hz, 0.6H), 4.03 (br d, J=6.2 Hz, 0.3H), 3.96 (d, J=7.0 Hz, 0.5H), 3.77-3.64 (m, 3H), 1.19 (s, 3H); LCMS: (M+H$^+$): 421.1; LCMS purity 97.64%; HPLC purity: 98.24%.

Example 45. 7-(((2R,3S,4R,5R)-3,4-dihydroxy-5-(4-(methoxyimino)-3H-pyrrolo[2,3-d]pyrimidin-7(4H)-yl)-3-methyltetrahydrofuran-2-yl)methoxy)quinolin-2(1H)-one O-methyl oxime (45)

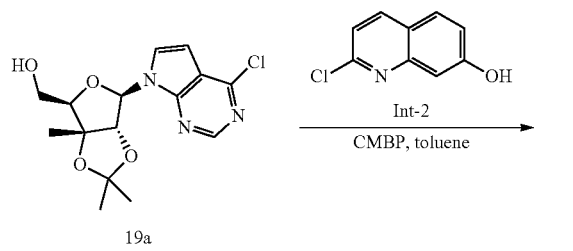

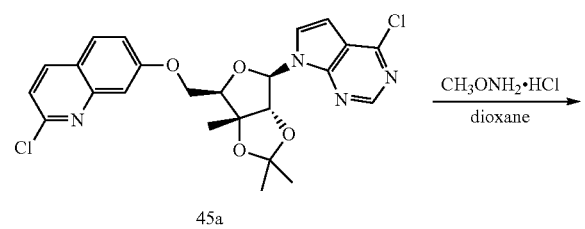

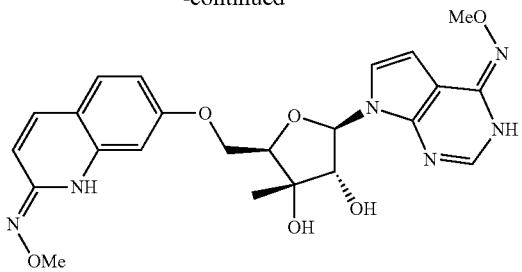

Ex. 45

Step 1. Preparation of 2-chloro-7-(((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methoxy)quinoline (45a)

To a solution of compound 19a (0.2 g, 588.63 umol, 1 eq.) and compound Int-2 (158.58 mg, 882.94 umol, 1.5 eq.) in toluene (4 mL) was added 2-(tributyl-phosphanylidene)acetonitrile (284.13 mg, 1.18 mmol, 2 eq.) under N$_2$ at 25° C. The mixture was stirred at 80° C. for 10 h. LC-MS showed no compound 19a was remained. Several new peaks were shown on LC-MS and desired compound was detected. The reaction mixture was concentrated under reduced pressure to remove solvent. The residue was purified by prep-TLC (SiO$_2$, Petroleum ether/Ethyl acetate=3:1) and based on TLC (Plate 1 Petroleum ether/Ethyl acetate=3:1 R$_f$=0.21). Compound 45a (220 mg, crude) was obtained as a white solid. LCMS: (M+H$^+$): 501.1; TLC (Petroleum ether:Ethyl acetate=3:1) R$_f$=0.21.

Step 2. Preparation of 7-(((2R,3S,4R,5R)-3,4-dihydroxy-5-(4-(methoxyimino)-3H-pyrrolo[2,3-d]pyrimidin-7(4H)-yl)-3-methyltetrahydrofuran-2-yl)methoxy)quinolin-2(1H)-one O-methyl oxime (45)

To a solution of compound 45a (0.22 g, 438.81 umol, 1 eq.) in t-BuOH (1 mL) was added O-methylhydroxylamine hydrochloride (293.18 mg, 3.51 mmol, 266.53 uL, 8 eq.) under N$_2$ at 25° C. The mixture was stirred at 100° C. for 12 h. LC-MS showed compound 1c was consumed completely and one main peak with desired MS was detected. The reaction mixture was concentrated under reduced pressure to remove solvent. The residue was added sat. aq. NaHCO$_3$ and extracted with DCM (5 mL×2) and EtOAc (5 mL×2). The organic layer was washed with brine (10 mL×2), dried over Na$_2$SO$_4$, filtered and concentrated under reduced pressure to give a residue. The residue was purified by prep-HPLC (basic condition column: YMC-Actus Triart C18 100*30 mm*5 um; mobile phase: water (0.04% NH$_3$.H$_2$O 10 mM NH$_4$HCO$_3$)–ACN B %: 20% -40%, 12 min). Compound 45 (57.41 mg, 114.87 umol, 26.18% yield, LCMS purity 96.54%) was obtained as a yellow solid. $^1$H NMR (400 MHz, DMSO-d$_6$) δ=10.91 (br s, 0.6H), 10.55 (s, 0.3H), 9.84 (s, 1H), 7.46 (d, J=3.51 Hz, 0.7H), 7.16-7.26 (m, 0.8H), 7.13 (d, J=3.51 Hz, 0.5H), 6.93-7.05 (m, 1.8H), 6.48-6.62 (m, 1.1H), 6.23 (d, J=3.51 Hz, 0.7H), 5.90-6.11 (m, 1.3H), 5.31-5.46 (m, 1H), 4.92-5.07 (m, 1H), 4.22-4.43 (m, 1H), 3.96-4.16 (m, 2.6H), 3.70 (d, J=10.09 Hz, 5.5H), 3.28 (br s, 1H), 1.17-1.30 (m, 3H); $^1$H NMR (400 MHz, DMSO-d$_6$+D$_2$O) δ=7.51 (s, 0.5H), 7.23-7.25 (m, 0.4H), 7.20-7.23 (m, 0.6H), 7.13 (d, J=3.51 Hz, 0.6H), 7.06 (s, 0.4H), 7.04 (s, 0.5H), 6.93-6.98 (m, 1H), 6.55-6.62 (m, 1.2H), 6.28 (d, J=3.51 Hz, 0.5H), 6.09 (s, 0.4H), 6.07 (s, 0.4H), 5.96 (d, J=7.89 Hz, 0.5H), 4.27 (d, J=7.89 Hz, 0.6H), 3.99-4.17 (m, 2.7H), 3.75 (s, 1.6H), 3.69-3.72 (m, 4H), 3.68 (s, 2H), 1.19-1.29 (m, 3H); LCMS: (M+H$^+$): 483.3. LCMS purity 96.54%; HPLC purity: 100.00%.

Example 46. 7-((2R,3R,4S,5R)-5-((R)-(4-chlorophenyl)(hydroxy)methyl)-3,4-dihydroxy-4-methyltetrahydrofuran-2-yl)-1H-pyrrolo[2,3-d]pyrimidin-4(7H)-one oxime hydrochloride (46)

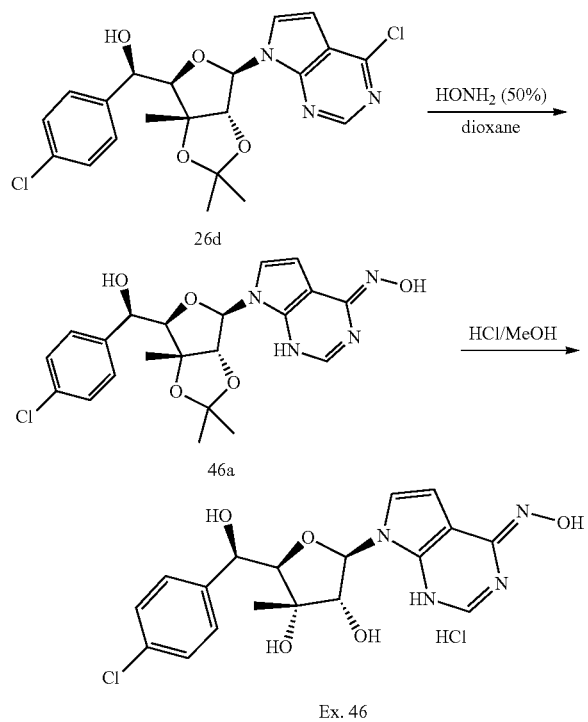

Step 1. Preparation of (Z)-7-((3aR,4R,6R,6aR)-6-((R)-(4-chlorophenyl)(hydroxy)methyl)-2,2,6a-trimethyltetrahydrofuro[3,4-d][1,3]dioxol-4-yl)-1H-pyrrolo[2,3-d]pyrimidin-4(7H)-one oxime (46a)

A mixture of compound 26d (80 mg, 177.65 umol, 1 eq.) and hydroxylamine (11.74 mg, 177.65 umol, 2 mL, 50% purity, 1 eq.) in dioxane (2 mL) was stirred at 100° C. for 12 h. LCMS showed the compound 26d was consumed and the desired MS was observed. The mixture was concentrated. Compound 46a (79 mg, crude) was obtained as brown oil, which was used for next step without further purification. LCMS: (M+H$^+$): 447.1.

Step 2. Preparation of (Z)-7-((2R,3R,4S,5R)-5-((R)-(4-chlorophenyl)(hydroxy)methyl)-3,4-dihydroxy-4-methyltetrahydrofuran-2-yl)-1H-pyrrolo[2,3-d]pyrimidin-4(7H)-one oxime hydrochloride (46)

A mixture of compound 46a (79.00 mg, 176.78 umol, 1 eq.) in HCl/MeOH (4 M, 2 mL, 45.25 eq.) was stirred at 25° C. for 0.5 h. LCMS showed the compound 1f was consumed and the desired MS was observed. The mixture was concentrated. The residue was purified by prep-HPLC (column: UniSil 120*30*10 um; mobile phase: [water (0.05% HCl)–ACN]; B %: 5% -30%, 11 min). Compound 46 (17.12 mg, 38.08 umol, 21.54% yield, LCMS 98.587% purity, HCl) was obtained as a white solid. $^1$H NMR (400 MHz, DMSO-d$_6$) δ=10.99 (br s, 1H), 8.26 (s, 1H), 7.83 (br d, J=3.1 Hz, 1H), 7.42-7.35 (m, 2H), 7.33-7.26 (m, 2H), 6.87 (br s, 1H), 6.01 (d, J=8.1 Hz, 1H), 4.77 (d, J=7.6 Hz, 1H), 4.32 (d, J=8.1 Hz, 1H), 3.98 (d, J=7.6 Hz, 1H), 1.32-1.19 (m, 3H); $^1$H NMR (400 MHz, DMSO-d$_6$+D$_2$O) δ=8.28 (s, 1H), 7.79 (d, J=3.7 Hz, 1H), 7.41-7.25 (m, 4H), 6.82 (d, J=3.7 Hz, 1H), 6.01 (d, J=8.1 Hz, 1H), 4.74 (d, J=7.5 Hz, 1H), 4.30 (d, J=8.1 Hz, 1H), 3.99 (d, J=7.5 Hz, 1H), 1.30-1.19 (m, 3H); LCMS: (M+H$^+$): 407.1; LCMS purity 98.59%; HPLC purity: 99.35%.

Example 47. (2R,3S,4R,5R)-5-(4-amino-7H-pyrrolo[2,3-d]pyrimidin-7-yl)-2-((R)-(3,4-dichlorophenyl)(hydroxy)methyl)-3-methyltetrahydrofuran-3,4-diol (47)

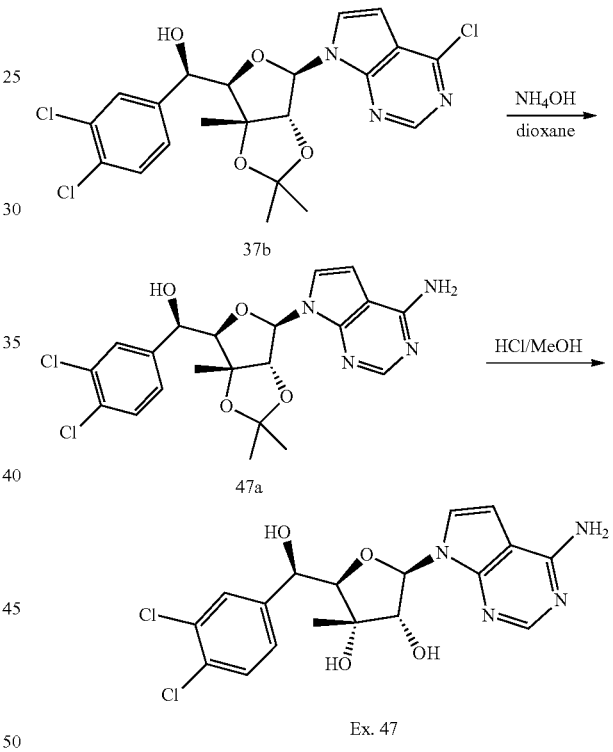

Step 1. Preparation of (R)-((3aR,4R,6R,6aR)-6-(4-amino-7H-pyrrolo[2,3-d]pyrimidin-7-yl)-2,2,3a-trimethyltetrahydrofuro[3,4-d][1,3]dioxol-4-yl)(3,4-dichlorophenyl)methanol (47a)

To a solution of compound 37b (90 mg, 185.66 umol, 1 eq.) in dioxane (5 mL) was added NH$_3$.H$_2$O (26.03 mg, 185.66 umol, 28.60 uL, 25% purity, 1 eq.) at 25° C. The mixture was sealed and stirred at 100° C. for 12 h (30 psi). LC-MS showed compound 37b was consumed completely and one main peak with desired product was detected. The reaction mixture was concentrated under reduced pressure to remove solvent. Compound 47a (80 mg, crude) was used into the next step without further purification as a yellow solid.

Step 2. Preparation of (2R,3S,4R,5R)-5-(4-amino-7H-pyrrolo[2,3-d]pyrimidin-7-yl)-2-((R)-(3,4-dichlorophenyl)(hydroxy)methyl)-3-methyltetrahydrofuran-3,4-diol (47)

To a solution of Compound 47a (80 mg, 171.92 umol, 1 eq.) was added HCl/MeOH (4 M, 4.26 mL, 99.07 eq.) at 0° C. The mixture was stirred at 25° C. for 10 min. LC-MS showed no Compound 47a was remained. Several new peaks were shown on LC-MS and desired compound was detected. The reaction mixture was concentrated under reduced pressure to remove solvent. The residue was added $NH_3 \cdot H_2O$ to adjusted pH around 8. The residue was purified by prep-HPLC (basic condition column: Waters Xbridge 150*25 5u; mobile phase: [water (0.04% $NH_3H_2O$+10 mM $NH_4HCO_3$)–ACN]; B %: 15%-45%, 10 min). Compound 47 (29.83 mg, 69.48 umol, 40.41% yield, LCMS purity 99.05%) was obtained as a white solid. $^1$H NMR (400 MHz, DMSO-$d_6$) δ=8.04 (s, 1H), 7.61 (d, J=1.75 Hz, 1H), 7.51 (d, J=8.77 Hz, 1H), 7.42 (d, J=3.51 Hz, 1H), 7.38 (dd, J=8.33, 1.75 Hz, 1H), 7.07 (br s, 2H), 6.55-6.64 (m, 2H), 5.85 (d, J=8.33 Hz, 1H), 5.27 (d, J=7.45 Hz, 1H), 4.78-4.86 (m, 2H), 4.43 (t, J=7.89 Hz, 1H), 4.01 (d, J=6.14 Hz, 1H), 1.18 (s, 3H); $^1$H NMR (400 MHz, DMSO-$d_6$+$D_2O$) δ=8.03 (s, 1H), 7.58 (d, J=1.54 Hz, 1H), 7.50 (d, J=8.16 Hz, 1H), 7.34-7.41 (m, 2H), 6.58 (d, J=3.53 Hz, 1H), 5.84 (d, J=8.16 Hz, 1H), 4.80 (d, J=6.39 Hz, 1H), 4.41 (d, J=8.16 Hz, 1H), 4.00 (d, J=6.39 Hz, 1H), 1.18 (s, 3H); LCMS: (M+H$^+$): 425.1. LCMS purity 99.05%; HPLC purity: 100.00%.

Example 48. (2R,3S,4R,5R)-5-(4-amino-7H-pyrrolo[2,3-d]pyrimidin-7-yl)-2-((R)-(3,4-dichlorophenyl)(hydroxy)methyl)-3-methyltetrahydrofuran-3,4-diol, bisulfate (48)

To (2R,3S,4R,5R)-5-(4-aminopyrrolo[2,3-d]pyrimidin-7-yl)-2-[(R)-(3,4-dichlorophenyl)-hydroxy-methyl]-3-methyl-tetrahydrofuran-3,4-diol (100 mg, 0.24 mmol) in IPA (5 mL) was sonicated at 50° C. to get a clear solution and then was added the sulfuric acid (2.14 mL, 0.24 mmol) and again sonicated at 50° C. for 5 mins. The mixture was allowed to cool slowly and solid obtained was centrifuged, washed with minimal amount of water and dried under high vacuum to give 95 mg of needle like crystals; m.p. 216-219° C. $^1$H NMR (500 MHz, DMSO-$d_6$) δ 8.21 (s, 1H), 7.65 (d, J=3.7 Hz, 1H), 7.60 (d, J=1.9 Hz, 1H), 7.51 (d, J=8.3 Hz, 1H), 7.37 (dd, J=1.9, 8.3 Hz, 1H), 6.79 (d, J=3.6 Hz, 1H), 6.24 (br s, 1H), 5.94 (d, J=8.2 Hz, 1H), 5.33 (br s, 1H), 4.90 (br s, 1H), 4.80 (d, J=7.2 Hz, 1H), 4.44-4.33 (m, 1H), 3.98 (d, J=7.2 Hz, 1H), 1.25 (s, 3H).

Example 49. (2R,3S,4R,5R)-5-(4-amino-7H-pyrrolo[2,3-d]pyrimidin-7-yl)-2-(benzo[d][1,3]dioxol-5-ylmethyl)-3-methyltetrahydrofuran-3,4-diol (49)

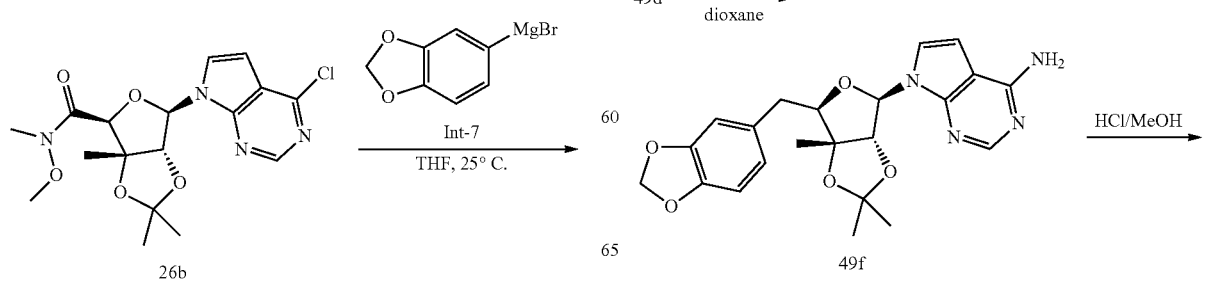

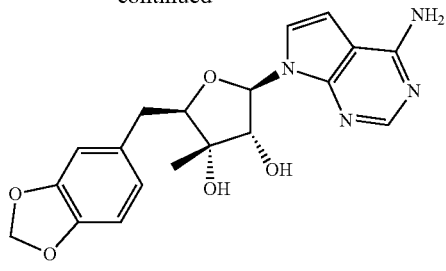

Ex. 49

Step 1. Preparation of benzo[d][1,3]dioxol-5-yl ((3aS,4S,6R,6aR)-6-(4-chloro-7H-pyrrolo[2,3-d]pyrimidin-7-yl)-2,2,3a-trimethyltetrahydrofuro[3,4-d][1,3]dioxol-4-yl)methanone (49a)

To a mixture of compound 26b (1 g, 2.52 mmol, 1 eq.) in THF (10 mL) was added compound Int-7 (0.5 M, 15.12 mL, 3 eq.) at 25° C. under N₂. The mixture was stirred at 25° C. for 0.5 h under N₂. TLC showed the compound 26b was consumed. The mixture was quenched by saturated NaHCO₃ solution (30 mL). The mixture was extracted with EtOAc (10 mL×3). The combined organic layers were dried over Na₂SO₄, filtered and concentrated. The residue was purified by column chromatography (SiO₂, petroleum ether/ethyl acetate=100/1 to 30/1). Compound 49a (900 mg, 1.97 mmol, 78.00% yield) was obtained as a yellow solid. ¹H NMR (400 MHz, CHLOROFORM-d) δ=8.69 (s, 1H), 8.07 (d, J=3.5 Hz, 1H), 7.79 (dd, J=1.8, 7.9 Hz, 1H), 7.61 (d, J=1.8 Hz, 1H), 6.93 (d, J=8.3 Hz, 1H), 6.71 (d, J=3.9 Hz, 1H), 6.63 (d, J=0.9 Hz, 1H), 6.10 (s, 2H), 5.60 (s, 1H), 4.64 (d, J=1.3 Hz, 1H), 1.82 (s, 3H), 1.46 (s, 3H), 1.34 (s, 3H); TLC (SiO₂, petroleum ether/ethyl acetate=2/1): R_f=0.7.

Step 2. Preparation of (R)-benzo[d][1,3]dioxol-5-yl ((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methanol (49b)

To a mixture of compound 49a (200 mg, 436.81 umol, 1 eq.) in toluene (2 mL) was added DIBAL-H (1 M, 873.62 uL, 2 eq.) at −70° C. under N₂. The mixture was stirred at −70° C. for 0.5 h under N₂. TLC showed the compound 49a was consumed. The mixture was quenched by water (0.5 mL), 15% NaOH solution (0.5 mL), water (0.5 mL) and the mixture was stirred for 10 min. The mixture was dried over MgSO₄, filtered and concentrated. The residue was purified by prep-TLC (SiO₂, petroleum ether/ethyl acetate=1/1). Compound 49b (190 mg, 413.15 umol, 94.58% yield) was obtained as a white solid. ¹H NMR (400 MHz, CHLOROFORM-d) δ=8.67 (s, 1H), 7.33 (d, J=3.8 Hz, 1H), 6.93 (d, J=1.6 Hz, 1H), 6.89-6.84 (m, 1H), 6.79-6.74 (m, 1H), 6.67 (d, J=3.7 Hz, 1H), 6.24 (d, J=2.4 Hz, 1H), 5.95 (s, 2H), 4.73 (dd, J=2.8, 8.7 Hz, 1H), 4.67 (d, J=2.3 Hz, 1H), 4.15-4.09 (m, 1H), 2.31 (d, J=2.8 Hz, 1H), 1.86 (s, 3H), 1.68 (s, 3H), 1.44 (s, 3H); TLC (SiO₂, petroleum ether/ethyl acetate=1/1): R_f=0.4.

Step 3. Preparation of O—((R)-benzo[d][1,3]dioxol-5-yl((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methyl)S-methyl carbonodithioate (49c)

A mixture of compound 49b (150 mg mg, 326.17 umol, 1 eq.), CS₂ (1.74 g, 22.83 mmol, 1.38 mL, 70 eq.) and MeI (3.24 g, 22.83 mmol, 1.42 mL, 70 eq.) in THF (3 mL) was stirred at 0° C. for 0.5 h under N₂. NaH (27.40 mg, 684.96 umol, 60% purity, 2.1 eq.) was added at 0° C. under N₂. The mixture was stirred at 0° C. for 0.5 h. LCMS showed the compound 49b was consumed and the desired MS was observed. The mixture was quenched by saturated NH₄Cl solution (10 mL), extracted with EtOAc (5 mL×3). The combined organic layers were dried over Na₂SO₄, filtered and concentrated. The residue was purified by prep-TLC (SiO₂, petroleum ether/ethyl acetate=5/1). Compound 49c (160 mg, crude) was obtained as a white solid. ¹H NMR (400 MHz, CHLOROFORM-d) δ=8.69 (s, 1H), 7.30 (br d, J=3.8 Hz, 2H), 6.74 (s, 1H), 6.69 (s, 2H), 6.51 (d, J=9.7 Hz, 1H), 6.30-6.18 (m, 1H), 5.92 (s, 2H), 4.84 (s, 1H), 4.60-4.48 (m, 1H), 2.58 (s, 3H), 1.71 (s, 3H), 1.66 (s, 3H), 1.45 (s, 3H); LCMS: (M+H⁺): 550.1; TLC (SiO₂, petroleum ether/ethyl acetate=5/1): R_f=0.5.

Step 4. Preparation of 7-((3aR,4R,6R,6aR)-6-(benzo[d][1,3]dioxol-5-ylmethyl)-2,2,6a-trimethyltetrahydrofuro[3,4-d][1,3]dioxol-4-yl)-4-chloro-7H-pyrrolo[2,3-d]pyrimidine (49d) and 7-((3aR,4R,6R,6aR)-6-(benzo[d][1,3]dioxol-5-ylmethyl)-2,2,6a-trimethyltetrahydrofuro[3,4-d][1,3]dioxol-4-yl)-7H-pyrrolo[2,3-d]pyrimidine (49e)

A mixture of compound 49c (150 mg mg, 272.70 umol, 1 eq.), Bu₃SnH (396.87 mg, 1.36 mmol, 360.79 uL, 5 eq.) and AIBN (134.34 mg, 818.11 umol, 3 eq.) in toluene (2 mL) was stirred at 120° C. for 0.5 h. LCMS showed the compound 49c was consumed and the desired MS was observed. The mixture was concentrated. The residue was purified by prep-TLC (SiO₂, petroleum ether/ethyl acetate=3/1). Compound 49d (45 mg, 101.38 umol, 37.18% yield) was obtained as a white solid. Compound 1f (20 mg, crude) was obtained as yellow oil. LCMS of cpd. 49d: (M+H⁺): 444.0; LCMS of cpd. 49e: (M+H⁺): 410.0; TLC (SiO₂, petroleum ether/ethyl acetate=3/1): R_f(cpd. 1e)=0.4 & R_f(cpd. 1f)=0.3.

Step 5. Preparation of 7-((3aR,4R,6R,6aR)-6-(benzo[d][1,3]dioxol-5-ylmethyl)-2,2,6a-trimethyltetrahydrofuro[3,4-d][1,3]dioxol-4-yl)-7H-pyrrolo[2,3-d]pyrimidin-4-amine (49f)

A mixture of compound 49d (45 mg, 101.38 umol, 1 eq.) in NH₃.H₂O (1.82 g, 12.98 mmol, 2 mL, 25% purity, 128.06 eq.) and dioxane (2 mL) was stirred at 100° C. for 12 h. TLC showed the compound 49d was consumed. The mixture was concentrated. The crude product was used for next step without further purification. Compound 49f (43 mg, crude) was obtained as a yellow solid. LCMS: (M+H⁺): 425.1; TLC (SiO₂, petroleum ether/ethyl acetate=5/1): R_f=0.0.

Step 6. Preparation of (2R,3S,4R,5R)-5-(4-amino-7H-pyrrolo[2,3-d]pyrimidin-7-yl)-2-(benzo[d][1,3]dioxol-5-ylmethyl)-3-methyltetrahydrofuran-3,4-diol (49)

A mixture of compound 49f (40 mg, 94.24 umol, 1 eq.) in HCl/MeOH (4 M, 2 mL, 84.89 eq.) was stirred at 25° C. for 1 h. LCMS showed the compound 49f was consumed. The mixture was concentrated. The residue was purified by prep-HPLC (column: Waters Xbridge 150*25 5 u; mobile phase: [water (0.04% NH₃H₂O+10 mM NH₄HCO₃)-ACN]; B %: 5%-25%, 10 min). Compound 49 (2.43 mg, 6.26 umol, 6.65% yield, LCMS 99.063% purity) was obtained as a white solid. 1H NMR (400 MHz, DMSO-d₆) δ=8.04 (s, 1H), 7.44 (d, J=3.5 Hz, 1H), 7.00 (br s, 2H), 6.75-6.67 (m, 2H), 6.66-6.59 (m, 2H), 5.97 (d, J=7.7 Hz, 1H), 5.88 (dd, J=0.8, 5.4 Hz, 2H), 5.33 (d, J=6.8 Hz, 1H), 4.82 (s, 1H), 4.37 (t, J=7.3 Hz, 1H), 3.93 (dd, J=3.4, 10.7 Hz, 1H), 2.88-2.72 (m, 2H), 1.25 (s, 3H); $^1$H NMR (400 MHz, DMSO-d$_6$+D$_2$O) δ=8.02 (s, 1H), 7.42 (d, J=3.7 Hz, 1H), 6.73-6.57 (m, 4H), 5.95 (d, J=7.7 Hz, 1H), 5.84 (d, J=3.7 Hz, 2H), 4.35 (d, J=7.7 Hz, 1H), 3.92 (dd, J=5.0, 9.4 Hz, 1H), 2.82-2.72 (m, 2H), 1.25 (s, 3H); LCMS: (M+H$^+$): 385.0; LCMS purity 99.063%; HPLC purity: 100.00%.
Example 50. (2R,3S,4R,5R)-5-(4-amino-7H-pyrrolo[2,3-d]pyrimidin-7-yl)-2-(3,4-dichlorobenzyl)-3-methyltetrahydrofuran-3,4-diol (50)
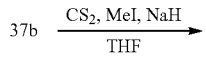
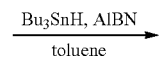
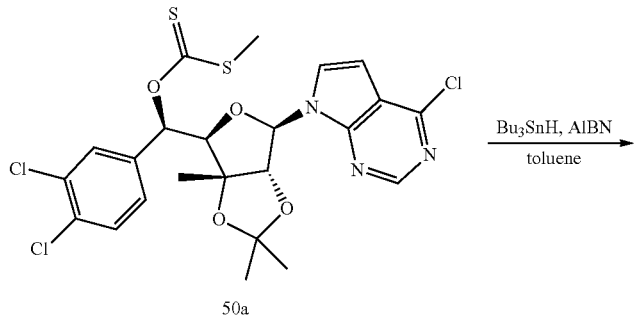
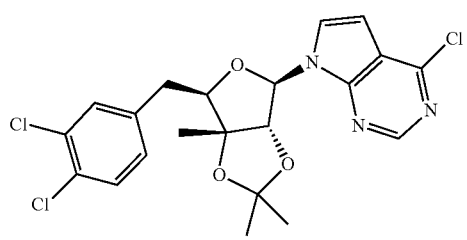
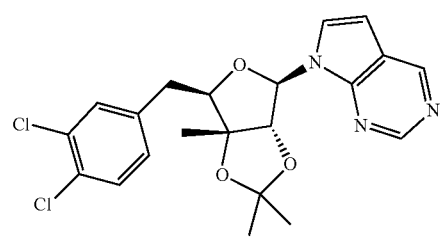
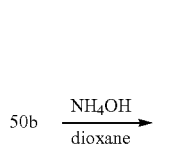
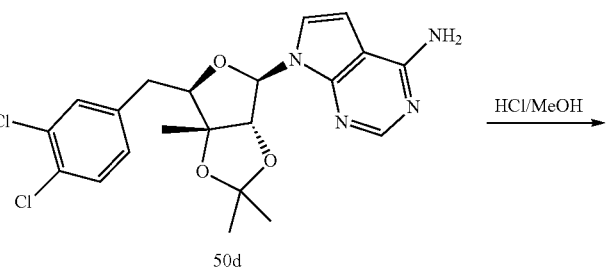
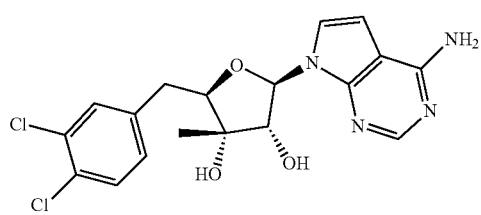
Ex. 50

Step 1. Preparation of O—((R)-((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)(3,4-dichlorophenyl)methyl)S-methyl carbonodithioate (50a)

To a solution of compound 37b (150 mg, 309.43 umol, 1 eq.) in THF (3 mL) was added $CS_2$ (1.65 g, 21.66 mmol, 1.31 mL, 70 eq.) and MeI (3.07 g, 21.66 mmol, 1.35 mL, 70 eq.). The mixture was stirred at 0° C. for 10 min. The mixture was added NaH (25.99 mg, 649.81 umol, 60% purity, 2.1 eq.) and stirred at 0° C. for 0.5 h. LC-MS showed compound 37b was consumed. Several new peaks were shown on LC-MS and desired compound was detected. The reaction mixture was concentrated under reduced pressure to remove solvent. The residue was diluted with $H_2O$ (15 mL) and extracted with EtOAc (15 mL×3). The combined organic layers were washed with brine (25 mL×2), dried over $Na_2SO_4$, filtered and concentrated under reduced pressure to give a residue. The residue was purified by prep-TLC ($SiO_2$, Petroleum ether/Ethyl acetate=3/1) and based on TLC (Petroleum ether/Ethyl acetate=3/1, $R_f$=0.61). The compound 50a (150 mg, 240.79 umol, 77.82% yield, 92.29% purity) was obtain as a white solid. TLC (Petroleum ether: Ethyl acetate=3:1) $R_f$=0.61; LCMS1: (M+H$^+$): 575.7; LCMS2: (M+H$^+$): 575.8, LCMS purity 92.29%.

Step 2. Preparation of 4-chloro-7-((3aR,4R,6R,6aR)-6-(3,4-dichlorobenzyl)-2,2,6a-trimethyltetrahydrofuro[3,4-d][1,3]dioxol-4-yl)-7H-pyrrolo[2,3-d]pyrimidine (50b) and 7-((3aR,4R,6R,6aR)-6-(3,4-dichlorobenzyl)-2,2,6a-trimethyltetrahydrofuro[3,4-d][1,3]dioxol-4-yl)-7H-pyrrolo[2,3-d]pyrimidine (50c)

To a solution of compound 50a (70 mg, 121.75 umol, 1 eq.) in toluene (1 mL) was added AIBN (6.00 mg, 36.53 umol, 0.3 eq.) and $Bu_3SnH$ (220.00 mg, 755.86 umol, 200.00 uL, 6.21 eq.) under $N_2$ at 25° C. The mixture was stirred at 110° C. for 1 h. LC-MS showed no compound 50a was remained. Several new peaks were shown on LC-MS and desired compound 50b and 50c were detected. The reaction mixture was concentrated under reduced pressure to remove solvent. The residue was purified by prep-TLC ($SiO_2$, Petroleum ether: Ethyl acetate=3:1) and based on TLC (Petroleum ether:Ethyl acetate=3:1, $R_f$(cpd. 50b)=0.54, $R_f$(cpd. 50c)=0.21). Compound 50b (40 mg, crude) was obtained as a colourless oil. Compound 50c (10 mg, crude) was obtained as a colourless oil. LCMS of cpd. 50b: (M+H$^+$): 470.1; LCMS of cpd. 50c: (M+H$^+$): 434.0, LCMS purity 79.33%.

Step 3. Preparation of 7-((3aR,4R,6R,6aR)-6-(3,4-dichlorobenzyl)-2,2,6a-trimethyltetra hydrofuro[3,4-d][1,3]dioxol-4-yl)-7H-pyrrolo[2,3-d]pyrimidin-4-amine (50d)

To a solution of compound 50b (40 mg, 85.33 umol, 1 eq.) in dioxane (3 mL) was added $NH_3.H_2O$ (2.73 g, 19.47 mmol, 3 mL, 25% purity, 228.19 eq.) at 25° C. The mixture was sealed and stirred at 100° C. for 10 h (30 psi). LC-MS showed compound 50b was consumed completely and one main peak with desired mass was detected. The reaction mixture was concentrated under reduced pressure to remove solvent. Compound 50d (40 mg, crude) was used into the next step without further purification as a yellow solid. LCMS: (M+H$^+$): 449.3.

Step 4. Preparation of (2R,3S,4R,5R)-5-(4-amino-7H-pyrrolo[2,3-d]pyrimidin-7-yl)-2-(3,4-dichlorobenzyl)-3-methyltetrahydrofuran-3,4-diol (50)

To a solution of compound 50d (80 mg, 178.04 umol, 1 eq.) was added HCl/MeOH (4 M, 4.64 mL, 104.24 eq.) and stirred at 25° C. for 5 min. LC-MS showed no compound 50d was remained. Several new peaks were shown on LC-MS and desired compound 50 was detected. The reaction mixture was added $NH_3.H_2O$ adjusted pH around 8 and concentrated under reduced pressure to remove solvent at 25° C. The residue was purified by prep-HPLC (basic condition: column: Waters Xbridge 150*25 5u; mobile phase: [water (0.04% $NH_3H_2O$+10 mM $NH_4HCO_3$) -CAN]; B %: 10%-40%, 10 min). Compound 50 (20.04 mg, 48.84 umol, 27.43% yield, 99.75% purity) was obtained as a white solid. LCMS1: (M+H$^+$): 409.3; $^1$H NMR (400 MHz, DMSO-d$_6$) δ=8.05 (s, 1H), 7.42-7.49 (m, 3H), 7.17 (dd, J=8.38, 1.98 Hz, 1H), 7.00 (s, 2H), 6.63 (d, J=3.75 Hz, 1H), 5.98 (d, J=7.72 Hz, 1H), 5.37 (d, J=6.84 Hz, 1H), 4.88 (s, 1H), 4.42 (t, J=7.39 Hz, 1H), 4.00 (dd, J=11.25, 3.09 Hz, 1H), 2.93-3.02 (m, 1H), 2.84-2.91 (m, 1H), 1.27 (s, 3H); $^1$H NMR (400 MHz, DMSO-d$_6$+D$_2$O) δ=8.03 (s, 1H), 7.37-7.45 (m, 3H), 7.16 (dd, J=8.27, 1.87 Hz, 1H), 6.63 (d, J=3.53 Hz, 1H), 5.96 (d, J=7.94 Hz, 1H), 4.39 (d, J=7.94 Hz, 1H), 3.99 (dd, J=10.80, 3.53 Hz, 1H), 2.78-3.00 (m, 2H), 1.27 (s, 3H); LCMS2: (M+H$^+$): 409.0, LCMS purity 99.75%; HPLC purity: 100.00%.

Example 51. (2R,3S,4R,5R)-2-(3,4-dichlorobenzyl)-3-methyl-5-(7H-pyrrolo[2,3-d]pyrimidin-7-yl)tetrahydrofuran-3,4-diol (51)

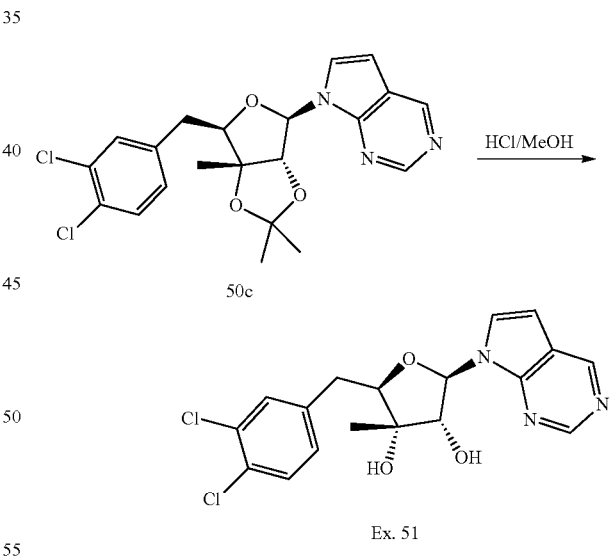

To a solution of compound 50c (20 mg, 46.05 umol, 1 eq.) was added HCl/MeOH (4 M, 1.20 mL, 104.24 eq.) and stirred at 25° C. for 5 min. LC-MS showed no compound 50c was remained. Several new peaks were shown on LC-MS and desired compound 51 was detected. The reaction mixture was added $NH_3.H_2O$ adjusted pH around 8 and concentrated under reduced pressure to remove solvent at 25° C. The residue was purified by prep-HPLC (basic condition: column: Waters Xbridge 150*25 5u; mobile phase: [water (0.04% $NH_3H_2O$+10 mM $NH_4HCO_3$)–ACN]; B %: 15%-45%, 10 min). Compound 51 (2.31 mg, 5.44 umol, 11.82% yield, 92.89% LCMS purity) was obtained as a white solid. LCMS1: (M+H⁺): 394.3; ¹H NMR (400 MHz, DMSO-$d_6$) δ=9.03 (s, 1H), 8.81 (s, 1H), 8.00 (d, J=3.75 Hz, 1H), 7.41-7.47 (m, 2H), 7.18 (dd, J=8.38, 1.98 Hz, 1H), 6.76 (d, J=3.75 Hz, 1H), 6.16 (d, J=7.94 Hz, 1H), 5.48 (d, J=6.84 Hz, 1H), 4.98 (s, 1H), 4.50 (t, J=7.28 Hz, 1H), 4.07 (dd, J=11.14, 3.20 Hz, 1H), 2.96-3.08 (m, 1H), 2.83-2.95 (m, 1H), 1.30 (s, 3H); ¹H NMR (400 MHz, DMSO-$d_6$+$D_2O$) δ=8.99 (s, 1H), 8.76 (s, 1H), 7.90 (d, J=3.95 Hz, 1H), 7.40 (d, J=7.89 Hz, 1H), 7.37 (s, 1H), 7.15 (d, J=8.33 Hz, 1H), 6.77 (d, J=3.51 Hz, 1H), 6.12 (d, J=8.33 Hz, 1H), 4.47 (d, J=7.89 Hz, 1H), 4.02-4.08 (m, 1H), 2.88-2.95 (m, 1H), 1.29 (s, 3H); LCMS2: (M+H⁺): 394.0, LCMS purity 92.89%; HPLC purity: 95.16%.

Example 52. (2R,3S,4R,5R)-2-(benzo[d][1,3]dioxol-5-ylmethyl)-3-methyl-5-(7H-pyrrolo[2,3-d]pyrimidin-7-yl)tetrahydrofuran-3,4-diol (52)

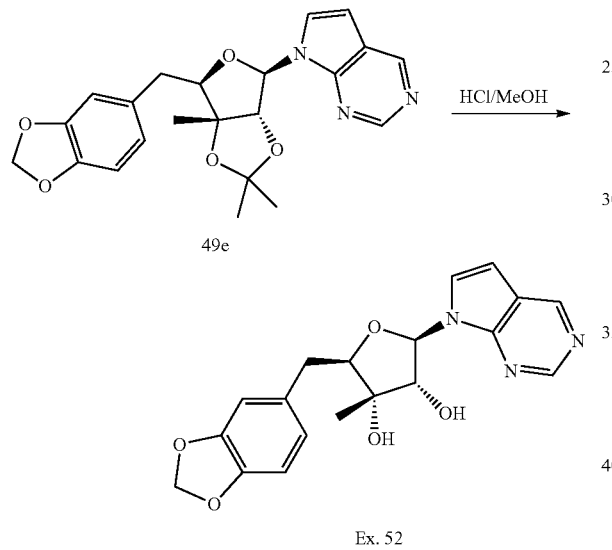

A mixture of 49e (20 mg, 48.85 umol, 1 eq.) in HCl/MeOH (4 M, 2 mL, 163.77 eq.) was stirred at 25° C. for 0.5 h. LCMS showed the compound 49e was consumed. The mixture was concentrated. The residue was purified by prep-HPLC (column: Waters Xbridge 150*25 5 u; mobile phase: [water (0.04% $NH_3H_2O$+10 mM $NH_4HCO_3$)–ACN]; B %: 10%-40%, 10 min). Compound 52 (5.25 mg, 14.08 umol, 28.83% yield, LCMS 99.078% purity) was obtained as a white solid. ¹H NMR (400 MHz, DMSO-$d_6$) δ=9.02 (s, 1H), 8.80 (s, 1H), 7.97 (d, J=3.7 Hz, 1H), 6.76 (d, J=3.7 Hz, 1H), 6.74-6.69 (m, 2H), 6.63 (d, J=8.1 Hz, 1H), 6.15 (d, J=7.8 Hz, 1H), 5.88 (d, J=4.3 Hz, 2H), 5.43 (br s, 1H), 4.93 (br s, 1H), 4.47 (d, J=7.7 Hz, 1H), 4.01 (dd, J=3.2, 10.8 Hz, 1H), 2.93-2.76 (m, 2H), 1.28 (s, 3H); ¹H NMR (400 MHz, DMSO-$d_6$+$D_2O$) δ=8.99 (d, J=2.3 Hz, 1H), 8.75 (d, J=2.1 Hz, 1H), 7.87 (d, J=2.8 Hz, 1H), 6.79-6.74 (m, 1H), 6.71-6.58 (m, 3H), 6.11 (dd, J=2.3, 7.8 Hz, 1H), 5.82 (br d, J=2.6 Hz, 2H), 4.43 (dd, J=2.8, 7.9 Hz, 1H), 2.86-2.74 (m, 2H), 1.27 (br s, 3H); LCMS: (M+H⁺): 370.1; LCMS purity 99.078%; HPLC purity: 100.00%.

Example 53. (2R,3S,4R,5R)-5-(4-aminopyrrolo[2,3-d]pyrimidin-7-yl)-3-methyl-2-(7-quinolyloxymethyl)tetrahydrofuran-3,4-diol (53)

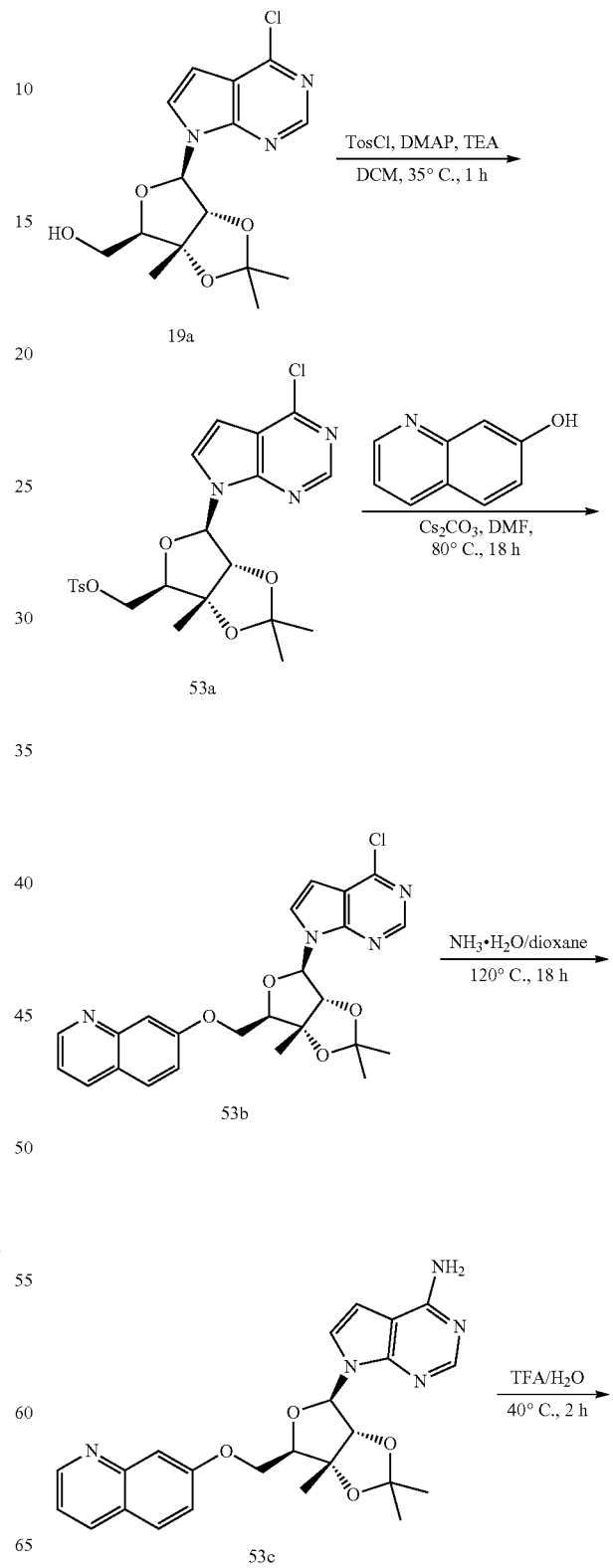

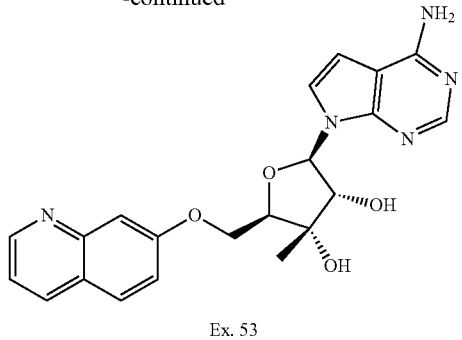

Ex. 53

Step 1. Preparation of [(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methyl 4-methylbenzenesulfonate (53a)

To a solution of TEA (0.12 mL, 0.88 mmol) and Tosyl chloride (112.2 mg, 0.59 mmol) in DCM (15.0 mL) was added [(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methanol (19a) (100.0 mg, 0.29 mmol) and DMAP (35.9 mg, 0.29 mmol). The reaction mixture was stirred at 35° C. for 1 h. LCMS showed the reaction was completed. The mixture was diluted with DCM (50.0 mL) and washed with brine (20.0 mL×3), dried over $Na_2SO_4$, filtered and concentrated in vacuum to give crude product which was purified silica gel column chromatography (DCM:MeOH=50:1 to afford [(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methyl 4-methylbenzenesulfonate (53a) (150.0 mg, 0.29 mmol, 99.1% yield. LCMS [M+H]: 494.1.

Step 2. Preparation of 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]quinoline (53b)

To a solution of [(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methyl 4-methylbenzenesulfonate (53a) (150.0 mg, 0.30 mmol) in DMF (10.0 mL) was added $Cs_2CO_3$ (296.8 mg, 0.91 mmol) and quinolin-7-ol (44.1 mg, 0.30 mmol). The reaction mixture was stirred at 80° C. for 16 h under $N_2$. The reaction mixture was concentrated in vacuum and diluted with EtOAc (10.0 ml). The mixture was washed with brine (10.0 mL×2), dried over $Na_2SO_4$, filtered and concentrated in vacuum to give crude product which was purified by pre-TLC (MeOH:DCM=1:15) to afford 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]quinoline (53b) (30.0 mg, 0.06 mmol, 19.9% yield). LCMS [M+H]: 466.9).

Step 3. Preparation of 7-[(3aR,4R,6R,6aR)-2,2,3a-trimethyl-4-(7-quinolyloxymethyl)-6,6a-dihydro-4H-furo-[3,4-d][1,3]dioxol-6-yl]pyrrolo[2,3-d]pyrimidin-4-amine (53c)

A solution of 7-[[(3aR,4R,6R)-6-(4-chloropyrrolo[2,3-d]pyrimidin-7-yl)-2,2,3a-trimethyl-6,6a-dihydro-4H-furo[3,4-d][1,3]dioxol-4-yl]methoxy]quinoline (30.0 mg, 0.06 mmol) in 1,4-Dioxane (5.0 mL) and Ammonium hydroxide (5.0 mL, 129.81 mmol) was stirred at 120° C. for 18 h in a sealed tube. TLC (PE:EA=1:1, $R_f$=0.1) showed the reaction was completed. The reaction mixture was concentrated in vacuum to 7-[(3aR,4R,6R,6aR)-2,2,3a-trimethyl-4-(7-quinolyloxymethyl)-6,6a-dihydro-4H-furo-[3,4-d][1,3]dioxol-6-yl]pyrrolo[2,3-d]pyrimidin-4-amine (53c) (29.9 mg, 0.07 mmol) which was used to the next step directly.

Step 4. Preparation of (2R,3S,4R,5R)-5-(4-aminopyrrolo[2,3-d]pyrimidin-7-yl)-3-methyl-2-(7-quinolyloxymethyl)tetrahydrofuran-3,4-diol (53)

A mixture of 7-[(3aR,4R,6R,6aR)-2,2,3a-trimethyl-4-(7-quinolyloxymethyl)-6,6a-dihydro-4H-furo-[3,4-d][1,3]dioxol-6-yl]pyrrolo[2,3-d]pyrimidin-4-amine (29.9 mg, 0.07 mmol), Water (3.0 mL) and TFA (0.2 mL, 2.73 mmol) was stirred at 40° C. for 2 h. LCMS showed the reaction was completed. The reaction mixture was purified by prep-HPLC, eluted with MeCN in $H_2O$ (0.1% $NH_3.H_2O$) from 10.0% to 95.0% to give (2R,3S,4R,5R)-5-(4-aminopyrrolo[2,3-d]pyrimidin-7-yl)-3-methyl-2-(7-quinolyloxymethyl)tetrahydrofuran-3,4-diol (Ex. 53) (3.0 mg, 0.007 mmol, 11.0% yield) as a white solid. LCMS [M+H]: 408.2). $^1$H NMR (400 MHz, DMSO-$d_6$) δ 8.66 (s, 1H), 8.29 (s, 1H), 7.79 (d, J=3.6 Hz 1H), 7.60 (d, J=8.4 Hz, 1H), 6.94-6.98 (m, 2H), 6.77 (d, J=3.2 Hz, 1H), 6.56 (s, 2H), 6.29 (d, J=8.4 Hz, 1H), 5.22-5.55 (m, 2H), 4.48 (d, J=8.0 Hz, 1H), 4.21-4.29 (m, 3H), 2.64 (s, 3H), 1.31 (s, 3H). $^1$H NMR (400 MHz, DMSO-$d_6$+$D_2O$) δ 8.66 (s, 1H), 8.30 (s, 1H), 7.77 (d, J=3.2 Hz 1H), 7.63 (d, J=8.8 Hz, 1H), 6.97-6.99 (m, 2H), 6.78 (d, J=3.2 Hz, 1H), 6.29 (d, J=7.6 Hz, 1H), 4.49 (d, J=8.0 Hz, 1H), 4.14-4.27 (m, 3H), 2.65 (s, 3H), 1.32 (s, 3H).

Example 54. (2R,3S,4R,5R)-3-methyl-5-(4-methylpyrrolo[2,3-d]pyrimidin-7-yl)-2-(7-quinolyloxymethyl)tetrahydrofuran-3,4-diol (54)

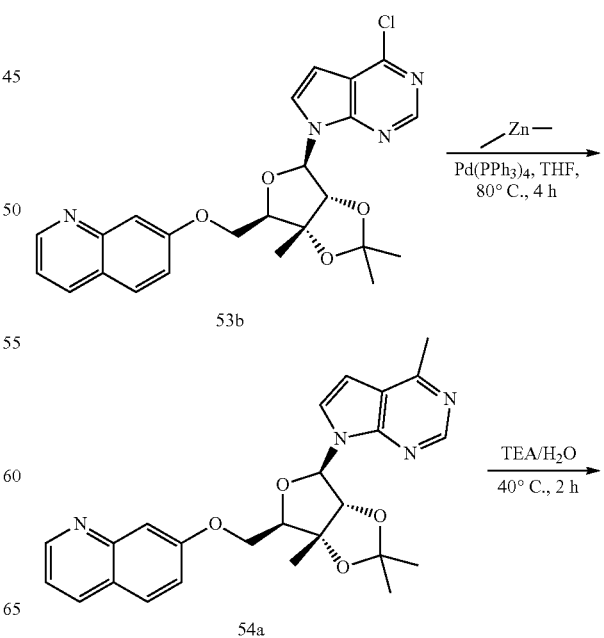

-continued

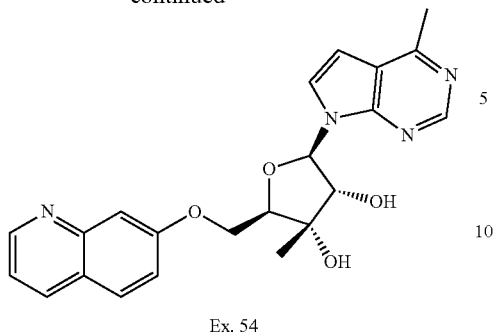

Ex. 54

Step 1. Preparation of 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]quinoline (54a)

To a solution of 7-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methoxy]quinoline (53b) (80.0 mg, 0.17 mmol) in THF (5.0 mL) was added Tetrakis(triphenylphosphine)palladium (19.8 mg, 0.02 mmol), Dimethylzinc (1.71 mL, 1.71 mmol). The reaction mixture was stirred at 80° C. for 4 h under $N_2$. LCMS showed the reaction was completed. The reaction mixture was poured into $NH_4Cl$ aqueous (20.0 mL) and extracted with EA (30.0 mL×3), dried over $Na_2SO_4$, filtered, concentrated in vacuum to give crude product which was purified by silica gel column chromatography (PE:EA=10:1) to afford 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]quinoline (54a) (72.0 mg, 0.15 mmol, 88.5% yield) as a solid. LCMS [M+H]: 447.2.

Step 2. Preparation of give (2R,3S,4R,5R)-3-methyl-5-(4-methylpyrrolo[2,3-d]pyrimidin-7-yl)-2-(7-quinolyloxymethyl)tetrahydrofuran-3,4-diol (54)

A mixture of 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]quinoline (54a) (72.0 mg, 0.15 mmol), Water (0.60 mL) and TFA (0.38 mL) was stirred at 40° C. for 2 h. LCMS showed the reaction was completed. The reaction mixture was purified by prep-HPLC, eluted with MeCN in $H_2O$ (0.1% $NH_3.H_2O$) from 10.0% to 95.0% to give (2R,3S,4R,5R)-3-methyl-5-(4-methylpyrrolo[2,3-d]pyrimidin-7-yl)-2-(7-quinolyloxymethyl)tetrahydrofuran-3,4-diol (Ex. 54) (26.0 mg, 0.06 mmol, 42.1% yield) as a white solid. LCMS [M+H]: 407.2. $^1$H NMR (400 MHz, DMSO-$d_6$) δ 8.83-8.84 (d, J=2.4 Hz, 1H), 8.67 (s, 1H), 8.30 (d, J=8 Hz, 1H), 7.92 (d, J=9.2 Hz, 1H), 7.83 (d, J=4 Hz, 1H), 7.49 (s, 1H), 7.34-7.41 (m, 2H), 6.78 (d, J=3.6 Hz, 1H), 6.31 (d, J=8.4 Hz, 1H), 6.06 (d, J=6 Hz, 2H), 4.51-4.53 (m, 1H), 4.34-4.36 (m, 2H), 4.26 (d, J=4.0 Hz, 1H), 2.65 (d, J=10.2 Hz, 3H), 1.34 (s, 3H). $^1$H NMR (400 MHz, DMSO-$d_6$+$D_2O$) δ 8.83 (s, 1H), 8.67 (s, 1H), 8.30-8.32 (m, 1H), 7.93-7.96 (m, 1H), 7.80 (d, J=3.2 Hz, 1H), 7.49 (s, 1H), 7.37-7.43 (m, 2H), 6.78 (d, J=3.2 Hz, 1H), 6.30-6.33 (m, 1H), 4.53 (d, J=8.0 Hz, 1H), 4.32-4.38 (m, 2H), 4.28 (s, 1H), 2.67 (s, 3H), 1.33 (s, 3H).

Example 55. (2R,3S,4R,5R)-2-[(2-amino-3-bromo-7-quinolyl) oxymethyl]-3-methyl-5-(4-methylpyrrolo[2,3-d]pyrimidin-7-yl)tetrahydrofuran-3,4-diol (55)

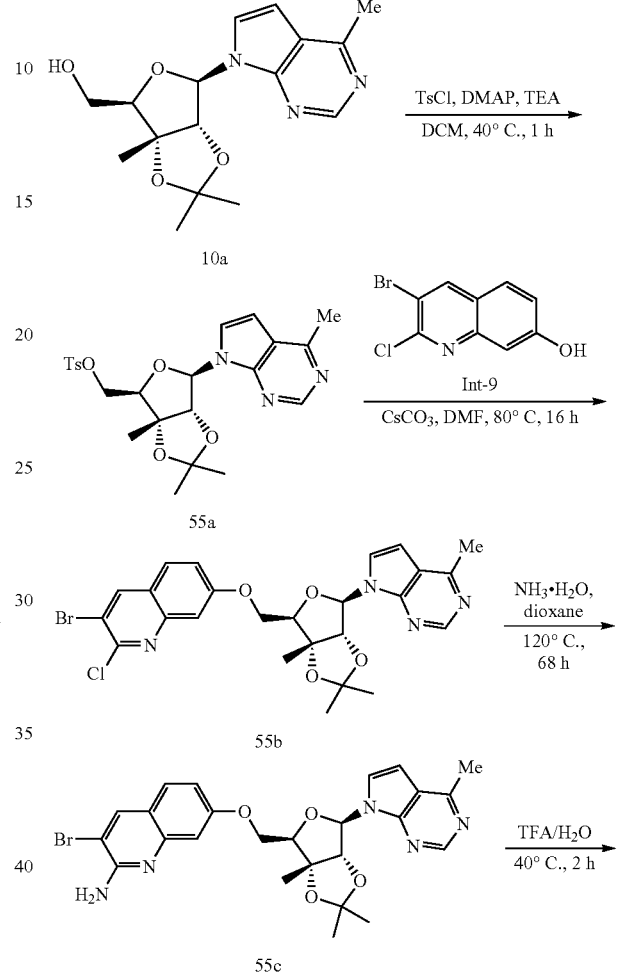

Step 1. Preparation of [(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methyl 4-methylbenzenesulfonate (55a)

To a solution of TEA (0.46 mL, 3.29 mmol) and Tosyl chloride (417.88 mg, 2.19 mmol) in DCM (7.0 mL) was added [(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methanol (10a) (350.0 mg, 1.10 mmol) and DMAP (66.9 mg, 0.55 mmol). The reaction mixture was stirred at 40° C. for 1 h. TLC (EA:PE=1:1, $R_f$=0.5) showed the reaction was completed. The mixture was diluted with DCM (50.0 mL) and washed with brine (20.0 mL×3), dried over Na$_2$SO$_4$, filtered and concentrated in vacuum to give crude product which was purified by silica gel column chromatography (EA:PE=1:2) to afford [(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methyl 4-methylbenzenesulfonate (55a) (476.0 mg, 0.98 mmol, 89.4% yield) as a white solid. LCMS [M+H]: 474.1.

Step 2. 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-2-chloro-quinoline (55b)

To a solution of [(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methyl 4-methylbenzenesulfonate (55a) (175.0 mg, 0.37 mmol) in DMF (2.0 mL) was added Cs$_2$CO$_3$ (361.2 mg, 1.11 mmol) and 2-bromo-3-chloro-quinolin-7-ol (Int-9) (95.5 mg, 0.37 mmol). The reaction mixture was stirred at 80° C. for 16 h under N$_2$. LCMS showed the reaction was completed. The reaction mixture was concentrated in vacuum and diluted with EtOAc (10.0 ml). The mixture was washed with brine (10.0 mL×2), dried over Na$_2$SO$_4$, filtered and concentrated in vacuum to give crude product which was purified by silica gel column chromatography (EA:PE=1:1) to afford 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-2-chloro-quinoline (55b) (75.0 mg, 0.10 mmol, 27.2% yield) as a white solid. LCMS [M+H]: 559.1.

Step 3. Preparation of 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-quinolin-2-amine (55c)

A solution of 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-2-chloro-quinoline (55b) (95.0 mg, 0.17 mmol) in 1,4-Dioxane (1.0 mL) and Ammonium hydroxide (2.8 mL, 73.26 mmol) was stirred at 140° C. for 68 h in a sealed tube. LCMS showed the reaction was done and 26.0% of SM was left. The reaction mixture was concentrated in vacuum to give crude product 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-quinolin-2-amine (55c) (110.0 mg) as a yellow solid which was used to the next step directly. LCMS [M+H]: 540.1

Step 4. Preparation of (2R,3S,4R,5R)-2-[(2-amino-3-bromo-7-quinolyl) oxymethyl]-3-methyl-5-(4-methylpyrrolo[2,3-d]pyrimidin-7-yl)tetrahydrofuran-3,4-diol (55)

A solution of 7-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methoxy]-3-bromo-quinolin-2-amine (110.0 mg, 0.20 mmol) in Water (1.0 mL) and TFA (1.5 mL, 20.19 mmol) was stirred at 40° C. for 2 h. LCMS showed the reaction was completed. The reaction mixture was purified by prep-HPLC, eluted with MeCN in H$_2$O (0.1% NH$_3$.H$_2$O) from 10.0% to 95.0% to give (2R,3S,4R,5R)-2-[(2-amino-3-bromo-7-quinolyl) oxymethyl]-3-methyl-5-(4-methylpyrrolo[2,3-d]pyrimidin-7-yl)tetrahydrofuran-3,4-diol (Ex. 55) (11.1 mg, 0.02 mmol, 10.8% yield) as a white solid. LCMS [M+H]: 500.1. $^1$H NMR (400 MHz, DMSO-d$_6$) δ 8.66 (s, 1H), 8.29 (s, 1H), 7.79 (d, J=3.6 Hz 1H), 7.60 (d, J=8.4 Hz, 1H), 6.94-6.98 (m, 2H), 6.77 (d, J=3.2 Hz, 1H), 6.56 (s, 2H), 6.29 (d, J=8.4 Hz, 1H), 5.22-5.55 (m, 2H), 4.48 (d, J=8.0 Hz, 1H), 4.21-4.29 (m, 3H), 2.64 (s, 3H), 1.31 (s, 3H). $^1$H NMR (400 MHz, DMSO-d$_6$+D$_2$O) δ8.66 (s, 1H), 8.30 (s, 1H), 7.77 (d, J=3.2 Hz 1H), 7.63 (d, J=8.8 Hz, 1H), 6.97-6.99 (m, 2H), 6.78 (d, J=3.2 Hz, 1H), 6.29 (d, J=7.6 Hz, 1H), 4.49 (d, J=8.0 Hz, 1H), 4.14-4.27 (m, 3H), 2.65 (s, 3H), 1.32 (s, 3H).

Example 56. (2R,3S,4R,5R)-5-(4-amino-7H-pyrrolo[2,3-d]pyrimidin-7-yl)-2-((R)-(4-chloro-3-methylphenyl)(hydroxy)methyl)-3-methyltetrahydrofuran-3,4-diol (56)

Example 56, an off-white solid, was prepared with a similar synthesis of Ex. 26 except for substituting 4-chlorobenzenemagnesium bromide with Int-8 in step 3. $^1$H NMR (500 MHz, Methanol-d$_4$) δ 8.11 (s, 1H), 7.40 (s, 1H), 7.30 (m, 2H), 7.27 (d, J=3.7 Hz, 1H), 6.60 (d, J=3.6 Hz, 1H), 5.85 (d, J=7.9 Hz, 1H), 5.01 (d, J=3.6 Hz, 1H), 4.67 (d, J=7.9 Hz, 1H), 4.37 (d, J=3.7 Hz, 1H), 2.36 (s, 3H), 1.17 (s, 3H). LCMS (M+H$^+$): 404.96/406.9.

Example 57. (2R,3S,4R,5R)-2-((R)-(4-chloro-3-methylphenyl)(hydroxy)methyl)-3-methyl-5-(4-methyl-7H-pyrrolo[2,3-d]pyrimidin-7-yl)tetrahydrofuran-3,4-diol (57)

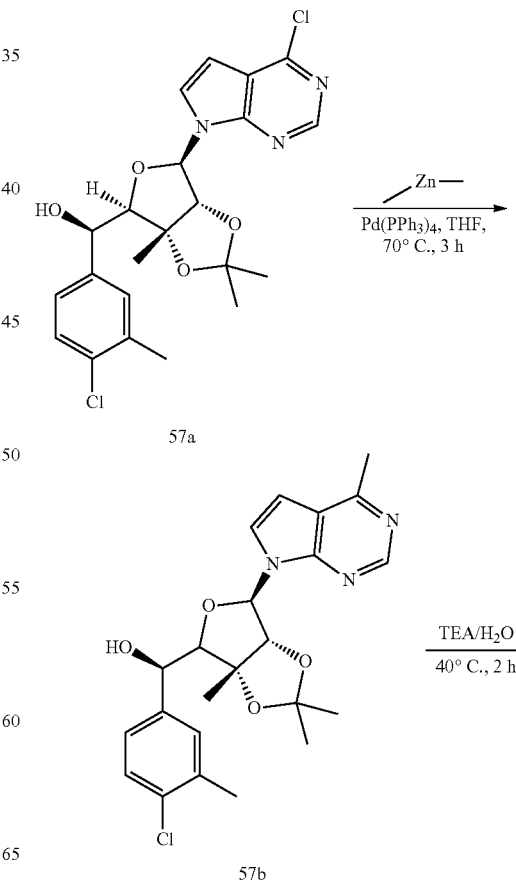

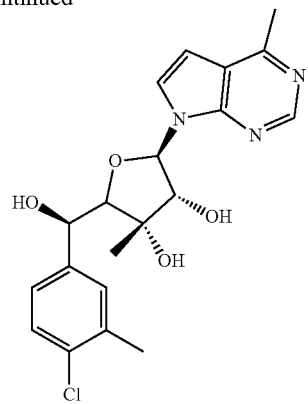

Ex. 57

Step 1. Preparation of (R)-[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]-(4-chloro-3-methyl-phenyl)methanol (57b)

A 4 mL vial with septum containing (R)-[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]-(4-chloro-3-methyl-phenyl)methanol (57a) (64 mg, 0.14 mmol) and palladium; triphenylphosphane (8.02 mg, 0.01 mmol) under nitrogen was charged with THF (1 mL) and purged with nitrogen for 10 min. The vial was then charged with Dimethylzinc (0.3 mL, 0.61 mmol) and heated at 70° C. for 3 h. Complete by LCMS. The reaction mixture was quenched by dropwise addition of sat. NaHCO$_3$ (5 drops) at rt under nitrogen with vigorous stirring. The reaction mixture was diluted with water and extracted with EtOAc three times. The organic layers were combined, washed with brine, dried over Na$_2$SO$_4$ and filtered. The filtrate was concentrated under reduced pressure and purified on a 12 g silica gel column chromatography using hexane/EtOAc (0-85%, wet-loaded in DCM) to yield (R)-[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]-(4-chloro-3-methyl-phenyl)methanol (57b) (27 mg, 0.0608 mmol, 44.1% yield) as a white solid. LCMS M+H$^+$ Found: 443.69/444.01, $^1$H NMR (500 MHz, Chloroform-d$_3$) δ 8.81 (s, 1H), 7.28 (m, 2H), 7.16 (d, J=8.2 Hz, 1H), 6.22 (m, 1H), 4.78 (t, J=10.8 Hz, 1H), 4.65 (m, 1H), 4.18 (d, J=8.3 Hz, 1H), 2.94 (s, 1H), 2.36 (s, 3H), 1.83 (s, 3H), 1.68 (s, 3H), 1.51 (s, 3H), 1.42 (s, 3H).

Step 2. Preparation of (2R,3S,4R,5R)-2-((R)-(4-chloro-3-methylphenyl)(hydroxy)methyl)-3-methyl-5-(4-methyl-7H-pyrrolo[2,3-d]pyrimidin-7-yl)tetrahydrofuran-3,4-diol (57)

To (R)-[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]-(4-chloro-3-methyl-phenyl)methanol (57b) (27 mg, 0.06 mmol) in Methanol (1 mL) were added a few drops of conc. HCl at 0° C. The reaction was stirred at rt. LCMS showed no remaining starting material and the reaction was concentrated under reduced pressure. The crude was diluted with EtOAc, cooled to 0° C. and carefully neutralized with sat. aq. NaHCO$_3$. The organic layer was separated and the aqueous was extracted with EtOAc twice. The combined organic layers were washed with brine, dried over Na$_2$SO$_4$, filtered and concentrated under vacuum. The crude was purified on a 12 g silica gel column using CH$_2$C$_2$/CH$_2$C$_2$:MeOH:NH$_3$ (0 to 60% of solvent B) to give (2R,3S,4R,5R)-2-[(R)-(4-chloro-3-methyl-phenyl)-hydroxy-methyl]-3-methyl-5-(4-methylpyrrolo[2,3-d]pyrimidin-7-yl)tetrahydrofuran-3,4-diol (13.8 mg, 0.03417 mmol, 57% yield) as an off-white solid. LCMS M+H+: 403.76/404.01. $^1$H NMR (500 MHz, DMSO-d$_6$) δ 8.64 (s, 1H), 7.85 (d, J=3.8 Hz, 2H), 7.33 (d, J=2.0 Hz, 1H), 7.25 (d, J=8.2 Hz, 2H), 7.21 (dd, J=2.0, 8.5 Hz, 1H), 6.76 (d, J=3.7 Hz, 2H), 6.06 (d, J=8.2 Hz, 2H), 5.89 (d, J=4.6 Hz, 1H), 5.29 (d, J=6.9 Hz, 2H), 4.83 (s, 1H), 4.76 (dd, J=4.7, 7.1 Hz, 1H), 4.43 (t, J=7.5 Hz, 1H), 4.00 (d, J=7.1 Hz, 1H), 2.65 (s, 3H), 2.23 (s, 3H), 1.26 (s, 3H).

Example 58. (2R,3S,4R,5R)-2-((R)-(3,4-dichlorophenyl)(hydroxy)methyl)-3-methyl-5-(4-methyl-7H-pyrrolo[2,3-d]pyrimidin-7-yl)tetrahydrofuran-3,4-diol (58)

Example 58, a white solid, was prepared with a similar synthesis of Ex. 57 except for substituting 57a with 37b in step 1. $^1$H NMR (500 MHz, Methanol-d$_4$) δ 8.65 (s, 1H), 7.67 (d, J=3.8 Hz, 1H), 7.61 (d, J=2.0 Hz, 1H), 7.43 (d, J=8.4 Hz, 1H), 7.37 (dd, J=2.0, 8.4 Hz, 1H), 6.75 (d, J=3.7 Hz, 1H), 6.07 (d, J=7.9 Hz, 1H), 4.98 (d, J=5.0 Hz, 1H), 4.69 (d, J=7.9 Hz, 1H), 4.29 (d, J=5.0 Hz, 1H), 2.73 (s, 3H), 1.27 (s, 3H).

Example 64. (2R,3S,4R,5R)-2-[[4-chloro-2-(hydroxymethyl)phenyl]methyl]-3-methyl-5-(4-methylpyrrolo[2,3-d]pyrimidin-7-yl)tetrahydrofuran-3,4-diol (64)

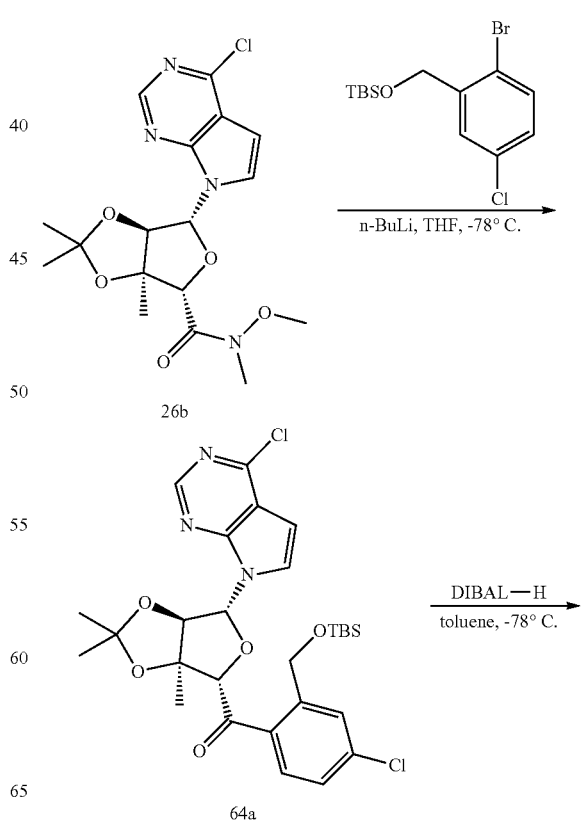

64a

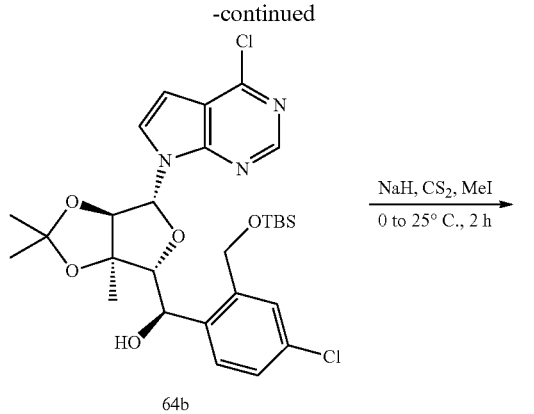

64b

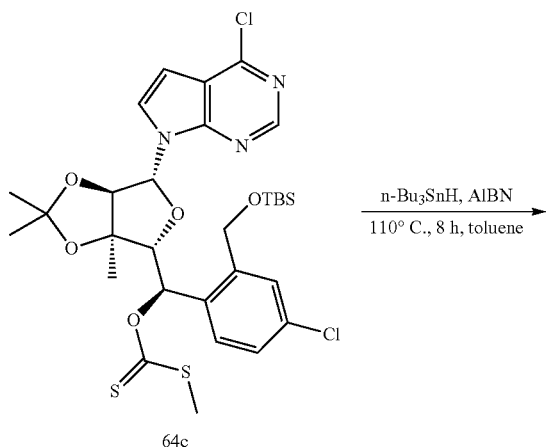

64c

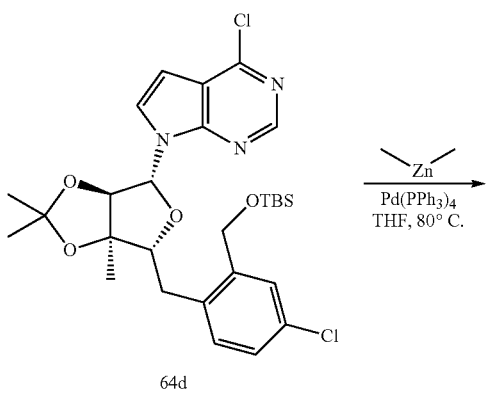

64d

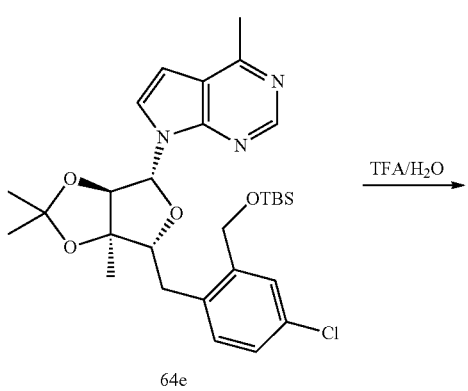

64e

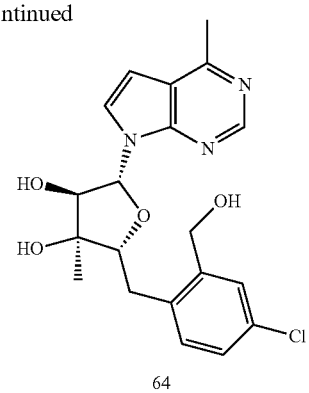

64

Step 1. Preparation of [(3aS,4S,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]-[2-[[tert-butyl(dimethyl)silyl]oxymethyl]-4-chloro-phenyl]methanone (64a)

To a solution of (2-bromo-5-chloro-phenyl)methoxy-tert-butyl-dimethyl-silane (8.46 g, 25.2 mmol) in dry THF (208 mL) was added n-BuLi (12.6 mL, 20.2 mmol) at −78° C. and stirred for 5 min under $N_2$. 26b (4.0 g, 10.1 mmol) in dry THF (10 mL) was added and stirred at −78° C. for 5 min. TLC (PE:EA=3:1, $R_f$=0.5) showed the reaction was complete. The reaction mixture was poured into $NH_4Cl$ aqueous and extracted with EA (300 mL×3), and the solvent was concentrated under reduced pressure to give a crude product which was purified by silica gel column chromatography (PE:EA=5:1) to give 64a (3.09 g, 5.11 mmol, 50.7% yield) as a white solid. LCMS [M+H]: 592.2

Step 2. Preparation of (R)-[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]-[2-[[tert-butyl(dimethyl)silyl]oxymethyl]-4-chloro-phenyl]methanol (64b)

To a solution of 64a (3.0 g, 5.1 mmol) in Toluene (30 mL) was added DIBAL-H (9.5 mL, 15.2 mmol) at −78° C. and stirred for 1 h under $N_2$. TLC (PE:EA=5:1, $R_f$=0.4) showed the reaction was complete. The reaction mixture was poured into $NH_4Cl$ aqueous (300 mL) and extracted with EA (300 mL×3). The solvent was concentrated under reduced pressure to give a crude product which was purified by silica gel column chromatography (PE:EA=5:1) to give 64b (2.50 g, 4.12 mmol, 81.39% yield) as a white solid. LCMS [M+H]: 594.2

Step 3. Preparation of O—[(R)-[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]-[2-[[tert-butyl(dimethyl)silyl]oxymethyl]-4-chloro-phenyl]methyl]methylsulfanylmethanethioate (64c)

To a solution of 64b (400 mg, 0.67 mmol) in THF (10 mL) was added NaH (48.4 mg, 1.21 mmol) and stirred at 0° C. for 0.5 h. $CS_2$ (153.7 mg, 2.0 mmol) was added and stirred at 0° C. for 0.5 h, then $CH_3I$ (191 mg, 1.35 mmol) was added and stirred at room temperature for 1 h. TLC (PE:EA=3:1, $R_f$=0.7) showed the reaction was complete. The reaction mixture was poured into NH₄Cl aqueous (50 mL) and extracted with EA (50 mL×3). The solvent was concentrated under reduced pressure to give a crude product which was purified by silica gel column chromatography (PE:EA=20:1) to give 64c (267 mg, 0.38 mmol, 57% yield) as a white solid. ¹H NMR (400 MHz, DMSO-d₆) δ 8.93 (s, 1H), 8.14 (d, J=3.6 Hz, 1H), 7.52-7.65 (m, 3H), 6.99 (d, J=3.6 Hz, 1H), 6.43-6.47 (m, 2H), 5.30 (s, 1H), 5.15 (d, J=14.8 Hz, 1H), 4.59-4.65 (m, 2H), 2.88 (s, 3H), 1.99 (s, 3H), 1.83 (s, 3H), 1.61 (s, 3H), 0.95 (s, 9H), 0.00 (s, 3H), -0.10 (s, 3H).

Step 4. Preparation of [2-[[(3aR,4R,6R,6aR)-6-(4-chloropyrrolo[2,3-d]pyrimidin-7-yl)-2,2,3a-trimethyl-6,6a-dihydro-4H-furo[3,4-d][1,3]dioxol-4-yl]methyl]-5-chloro-phenyl]methoxy-tert-butyl-dimethyl-silane (64d)

To a solution of 64c (430 mg, 0.63 mmol) and AIBN (103 mg, 0.63 mmol) in Toluene (20 mL) was added Tributyltin (183 mg, 0.63 mmol) under N₂, and the reaction mixture was stirred at 115° C. for 18 h under N₂. LCMS showed the reaction was complete. The reaction mixture was concentrated under reduced pressure and purified by silica gel column chromatography (PE:EA=20:1) to give 64d (260 mg, 0.44 mmol, 70% yield) as a solid. LCMS [M+H]: 576.2

Step 5. Preparation of [2-[[(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methyl]-5-chloro-phenyl]methoxy-tert-butyl-dimethyl-silane (64e)

To a solution of 64d (150 mg, 0.26 mmol) and Tetrakis(triphenylphosphine)palladium (30 mg, 0.03 mmol) in THF (10 mL) was added dimethylzine (2.6 mL, 2.59 mmol), the reaction mixture was stirred at 80° C. for 3 h. LCMS showed the reaction was complete. The reaction was poured into NH₄Cl (50 mL) aqueous and extracted with EA (50 mL×3). The solvent was concentrated under reduced pressure to give a crude product which was purified by reverse phase combi flash (neutral condition) to give 64e (110 mg, 0.19 mmol, 74.5% yield) as a white solid. LCMS [M+H]: 558.2

Step 4. Preparation of (2R,3S,4R,5R)-2-[[4-chloro-2-(hydroxymethyl)phenyl]methyl]-3-methyl-5-(4-methylpyrrolo[2,3-d]pyrimidin-7-yl)tetrahydrofuran-3,4-diol (64)

A solution of 64e (110 mg, 0.19 mmol) in Water (3 mL) and TFA (2 mL, 27 mmol) was stirred at 40° C. for 1 h. LCMS showed the reaction was complete. The solvent was concentrated under reduced pressure and purified by prep-HPLC (0.1% NH₃.H₂O), eluted with H₂O:CH₃CN from 90:10 to 5:95 to give 64 (41 mg, 0.10 mmol, 51% yield) as a white solid. LCMS [M+H]: 404.1. ¹H NMR (400 MHz, DMSO-d₆) δ 8.64 (s, 1H), 7.90 (d, J=3.6 Hz, 1H), 7.33 (s, 1H), 7.10 (d, J=1.2 Hz, 2H), 6.80 (d, J=3.6 Hz, 1H), 6.10 (d, J=7.6 Hz, 1H), 5.40 (d, J=6.8 Hz, 1H), 5.21 (t, J=5.6 Hz, 1H), 4.96 (s, 1H), 4.44-4.57 (m, 3H), 4.01-4.05 (m, 1H), 2.89-2.91 (m, 2H), 2.66 (s, 3H), 1.33 (s, 3H). ¹H NMR (400 MHz, DMSO-d₆+D₂O) δ 8.64 (s, 1H), 7.87 (d, J=3.6 Hz, 1H), 7.33 (s, 1H), 7.11 (d, J=1.6 Hz, 2H), 6.81 (d, J=7.6 Hz, 1H), 6.10 (d, J=7.6 Hz, 1H), 4.45-4.56 (m, 3H), 4.04 (d, J=6.4 Hz, 1H), 2.89 (d, J=6.8 Hz, 2H), 2.67 (s, 3H), 1.34 (s, 3H).

Example 66. (2R,3S,4R,5R)-5-(4-amino-7H-pyrrolo[2,3-d]pyrimidin-7-yl)-2-((S)-(3,4-dichlorophenyl)(hydroxy)methyl)-3-methyltetrahydrofuran-3,4-diol (66)

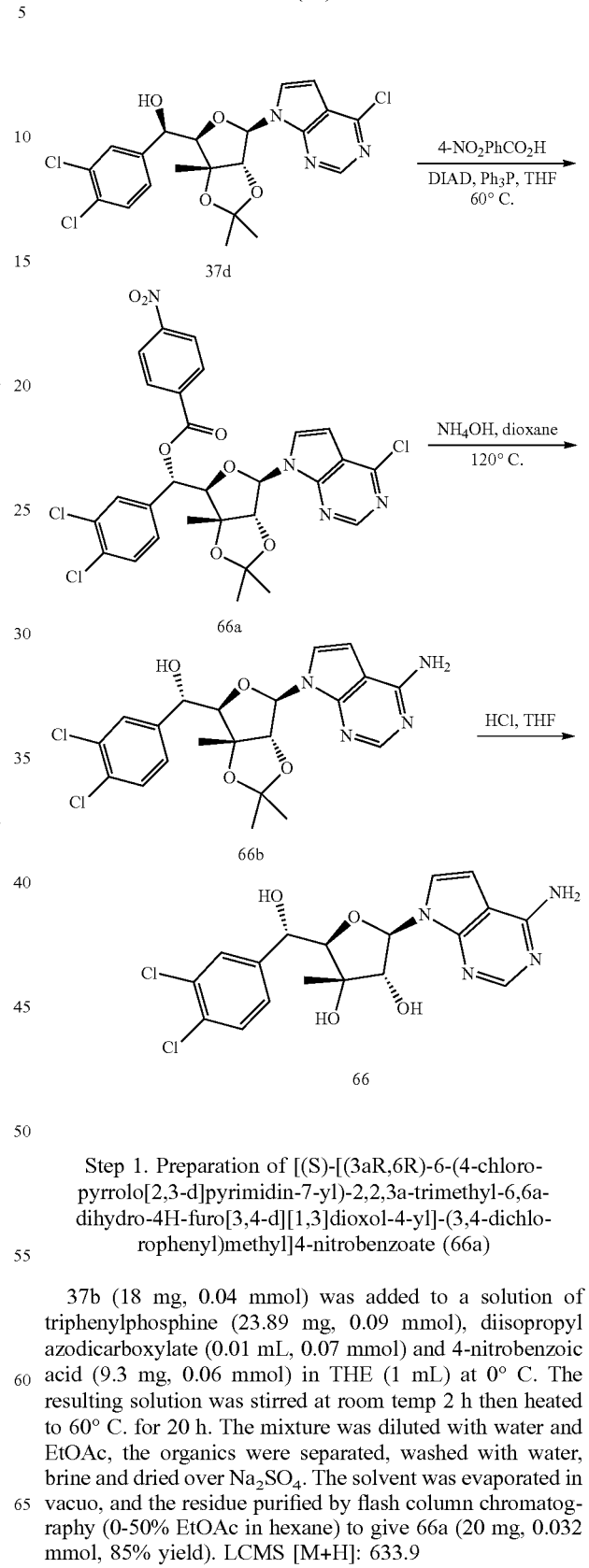

Step 1. Preparation of [(S)-[(3aR,6R)-6-(4-chloropyrrolo[2,3-d]pyrimidin-7-yl)-2,2,3a-trimethyl-6,6a-dihydro-4H-furo[3,4-d][1,3]dioxol-4-yl]-(3,4-dichlorophenyl)methyl]4-nitrobenzoate (66a)

37b (18 mg, 0.04 mmol) was added to a solution of triphenylphosphine (23.89 mg, 0.09 mmol), diisopropyl azodicarboxylate (0.01 mL, 0.07 mmol) and 4-nitrobenzoic acid (9.3 mg, 0.06 mmol) in THF (1 mL) at 0° C. The resulting solution was stirred at room temp 2 h then heated to 60° C. for 20 h. The mixture was diluted with water and EtOAc, the organics were separated, washed with water, brine and dried over Na₂SO₄. The solvent was evaporated in vacuo, and the residue purified by flash column chromatography (0-50% EtOAc in hexane) to give 66a (20 mg, 0.032 mmol, 85% yield). LCMS [M+H]: 633.9

Step 2. Preparation of (R)-[(3aR,6R,6aR)-6-(4-aminopyrrolo[2,3-d]pyrimidin-7-yl)-2,2,3a-trimethyl-6,6a-dihydro-4H-furo[3,4-d][1,3]dioxol-4-yl]-(3,4-dichlorophenyl)methanol (66b)

Into a sealable tube was placed 66a (22 mg, 0.03 mmol) and ammonium hydroxide (0.26 mL, 6.85 mmol) and 1,4-Dioxane (1 mL). The reaction was heated to 120° C. overnight, cooled to rt, and the solvent evaporated in vacuo to give crude 66b (19 mg, 0.041 mmol, 119% yield) which was used in the next step without further purification. LCMS [M+H]: 464.9

Step 3. Preparation of (2R,3S,4R,5R)-5-(4-amino-7H-pyrrolo[2,3-d]pyrimidin-7-yl)-2-((S)-(3,4-dichlorophenyl)(hydroxy)methyl)-3-methyltetrahydrofuran-3,4-diol (66)

Into a vial was placed 66b (20 mg, 0.04 mmol) in THE (1 mL) followed by 4N HCl (0.11 mL, 0.44 mmol) and the reaction was stirred overnight. Additional 4N HCl (0.11 mL, 0.44 mmol) added and the reaction was stirred overnight. LCMS shows that the reaction was complete. Saturated aqueous NaHCO$_3$ was added until the solution was slightly basic. The mixture was extracted with DCM (3 mL), the organics were washed with brine and dried over MgSO$_4$. The solvent was evaporated in vacuo, and the residue was purified by flash column chromatography (0-40% EtOAc/hexanes) to afford 66 (7.2 mg, 0.017 mmol, 40% yield). LCMS [M+H]: 424.9. 1H NMR (500 MHz, DMSO-d$_6$) δ 8.08 (s, 1H), 7.55 (d, J=2.0 Hz, 1H), 7.53-7.43 (m, 2H), 7.36-7.23 (m, 2H), 7.14 (s, 2H), 6.59 (d, J=3.6 Hz, 1H), 5.79 (d, J=8.1 Hz, 1H), 5.28 (d, J=7.1 Hz, 1H), 4.80 (d, J=8.6 Hz, 1H), 4.77 (s, 1H), 4.47 (t, J=7.6 Hz, 1H), 3.98 (d, J=1.3 Hz, 1H), 1.45 (s, 3H).

Example 67. (2R,3S,4R,5R)-3-methyl-2-[(3-methylimidazo[1,2-a]pyridin-7-yl)oxymethyl]-5-(4-methylpyrrolo[2,3-d]pyrimidin-7-yl)tetrahydrofuran-3,4-diol (67)

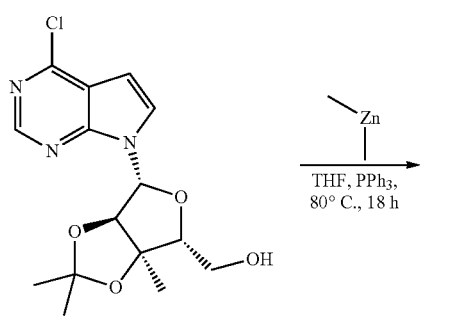

19a

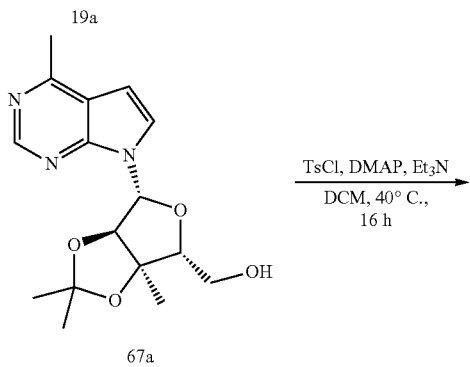

67a

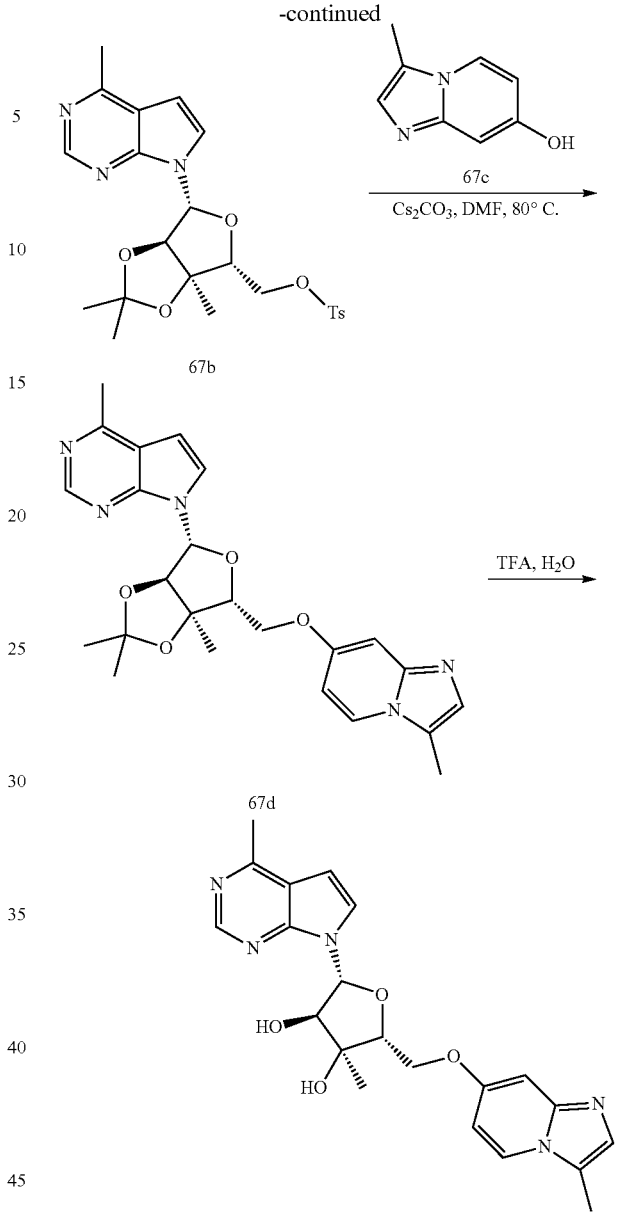

Step 1. Preparation of [(3aR,4R,6R,6aR)-2,2,3a-trimethyl-6-(4-methylpyrrolo[2,3-d]pyrimidin-7-yl)-6,6a-dihydro-4H-furo[3,4-d][1,3]dioxol-4-yl]methanol (67a)

To a mixture of 19a (350 mg, 1.03 mmol) and Pd(PPh$_3$)$_4$ (119 mg, 0.10 mmol) in THF (10 mL) was added Dimethylzine (983.2 mg, 10.30 mmol) dropwise under N$_2$ atmosphere. The reaction was stirred at 80° C. for 3 hours. TLC (PE:EA=10:1) showed the reaction was complete. The mixture was poured into NH$_4$Cl aqueous (30 mL) and extracted with EA (30 mL×3). The organic phases were combined, dried over Na$_2$SO$_4$, filtered and concentrated under vacuum. The residue was purified by silica gel column chromatography (PE:EA=50:1 to 5:1) to give 67a (300 mg, 0.81 mmol, 78% yield) as a white solid. LCMS: [M+H]: 320.2.

Step 2. Preparation of [(3aS,4S,6S,6aS)-2,2,3a-trimethyl-6-(4-methylpyrrolo[2,3-d]pyrimidin-7-yl)-6,6a-dihydro-4H-furo[3,4-d][1,3]dioxol-4-yl]methyl 4-methylbenzenesulfonate (67b)

To a solution of 67a (300 mg, 0.94 mmol), TEA (0.39 mL, 2.82 mmol) and DMAP (57.4 mg, 0.47 mmol) in DCM (20 mL) was added Tosyl chloride (358 mg, 1.88 mmol) and the reaction mixture was stirred at 40° C. for 16 h. TLC (PE:EA=1:1, $R_f$=0.4) showed the reaction was complete. The mixture was poured into $H_2O$/DCM washed by $H_2O$ and brine, purified by silica gel chromatography (PE: EA=10:1 to 2:1) to afford (67b) (220 mg, 0.44 mmol, 46.5% yield) as a white solid. LCMS: [M+H]: 474.1.

Step 3. Preparation of 4-methyl-7-[(3aR,4R,6R,6aR)-2,2,3a-trimethyl-4-[(3-methylimidazo[1,2-a]pyridin-7-yl)oxymethyl]-6,6a-dihydro-4H-furo[3,4-d][1,3]dioxol-6-yl]pyrrolo[2,3-d]pyrimidine (67d)

To a solution of 67b (60 mg, 0.13 mmol) in DMF (2 mL), were added 67c (prepared according to WO 2018/065365; 18.8 mg, 0.13 mmol) and $Cs_2CO_3$ (124 mg, 0.38 mmol) and the reaction mixture was stirred at 80° C. for 16 h under $N_2$ atmosphere. LCMS showed the reaction was complete. The reaction was concentrated to dryness and the residue was taken up in EtOAc (10 mL) and the organic layer was washed with water (2×10 mL) then saturated brine solution (1×20 mL). The organic layers were separated, dried ($MgSO_4$) and concentrated to give crude (67d) (60 mg, 0.11 mmol, 89.5% yield). LCMS: [M+H]: 450.4.

Step 4. Preparation of (2R,3S,4R,5R)-3-methyl-2-[(3-methylimidazo[1,2-a]pyridin-7-yl)oxymethyl]-5-(4-methylpyrrolo[2,3-d]pyrimidin-7-yl)tetrahydrofuran-3,4-diol (67)

To a solution of 67d (100 mg, 0.18 mmol) in water (3 mL) was added 2,2,2-trifluoroacetic acid; TFA (3.43 mL, 44.5 mmol), and the mixture was stirred at 25° C. for 90 min. LCMS showed the reaction was complete. The residue was purified by pre-HPLC, eluted with $CH_3CN$ in $H_2O$ (0.1% $NH_4OH$) from 5% to 95% to give (2R,3S,4R,5R)-3-methyl-2-[(3-methylimidazo[1,2-a]pyridin-7-yl)oxymethyl]-5-(4-methylpyrrolo[2,3-d]pyrimidin-7-yl)tetrahydrofuran-3,4-diol (27 mg, 0.06 mmol, 37% yield) as a light yellow solid. LCMS: [M+H]: 410.2.

$^1$H NMR (400 MHz, DMSO-$d_6$+$D_2O$): δ 8.66 (s, 1H), 8.25-8.27 (m, 1H), 7.77-7.78 (m, 1H), 7.33-7.34 (m, 1H), 7.08-7.09 (m, 1H), 6.89-6.91 (m, 1H), 6.77-6.78 (m, 1H), 6.27-6.29 (m, 1H), 4.48-4.50 (m, 1H), 4.27-4.29 (m, 2H), 4.22-4.24 (m, 1H), 2.65 (s, 3H), 2.43 (s, 3H), 1.32 (s, 3H).

The examples listed below either were prepared, or can be prepared, using methods analogous to those described above.

TABLE B

| Ex. # | Structures | Synthesis similar to Ex. # | Spectra Data |
|---|---|---|---|
| 59 | 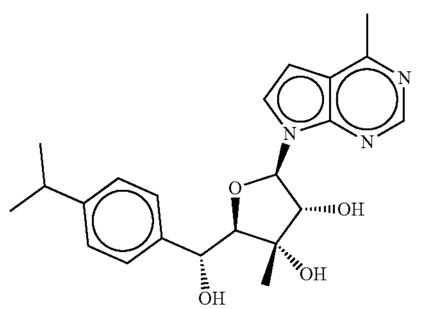 | Ex. 10 and Ex. 47 | 1H NMR (500 MHz, Methanol-d4) δ 8.66 (s, 1H), 7.68 (d, J = 3.8 Hz, 1H), 7.38 (d, J = 8.0 Hz, 2H), 7.19 (d, J = 8.0 Hz, 2H), 6.75 (d, J = 3.7 Hz, 1H), 6.09 (d, J = 7.8 Hz, 1H), 5.01 (d, J = 4.5 Hz, 1H), 4.62 (s, 1H), 4.39 (d, J = 4.5 Hz, 1H), 2.87 (h, J = 6.9 Hz, 1H), 2.74 (s, 3H), 1.24 (s, 3H), 1.23 (d, 6H). LCMS (MH$^+$): 398.0/398.9. |
| 60 | 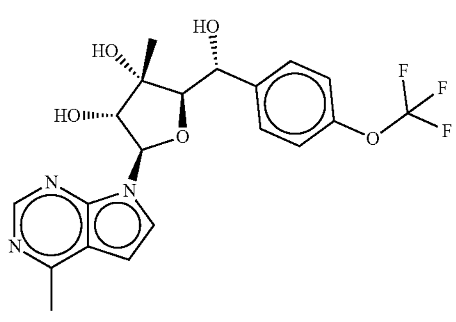 | Ex. 10 and Ex. 47 | 1H NMR (500 MHz, DMSO-d6) δ 8.62 (s, 1H), 7.85 (d, J = 3.8 Hz, 1H), 7.54-7.38 (m, 2H), 7.29-7.14 (m, 2H), 6.75 (d, J = 3.7 Hz, 1H), 6.07 (d, J = 8.1 Hz, 1H), 5.96 (d, J = 4.6 Hz, 1H), 5.29 (d, J = 7.2 Hz, 1H), 4.84 (d, J = 3.3 Hz, 2H), 4.41 (t, J = 7.7 Hz, 1H), 4.03 (d, J = 7.1 Hz, 1H), 2.63 (s, 3H), 1.24 (s, 3H). LCMS (MH$^+$): 439.9. |

TABLE B-continued

Synthesis of Additional Examples

| Ex. # | Structures | Synthesis similar to Ex. # | Spectra Data |
|---|---|---|---|
| 61 | 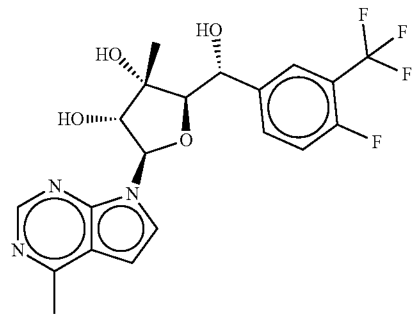 | Ex. 10 and Ex. 47 | 1H NMR (500 MHz, DMSO-d6) δ 8.63 (s, 1H), 7.89 (d, J = 3.6 Hz, 1H), 7.70 (d, J = 6.8 Hz, 2H), 7.35 (t, J = 9.9 Hz, 1H), 6.74 (d, J = 3.6 Hz, 1H), 6.04 (d, J = 8.2 Hz, 1H), 5.98 (d, J = 4.6 Hz, 1H), 5.33 (d, J = 7.0 Hz, 1H), 4.96-4.84 (m, 2H), 4.48 (t, J = 7.3 Hz, 1H), 3.92 (d, J = 8.0 Hz, 1H), 2.63 (s, 3H), 1.31 (s, 3H). LCMS (MH+): 441.9. |
| 62 | 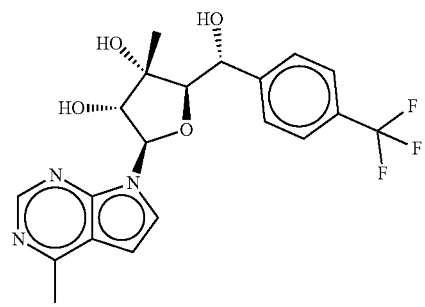 | Ex. 10 and Ex. 47 | 1H NMR (500 MHz, DMSO-d6) δ 8.63 (s, 1H), 7.87 (d, J = 3.7 Hz, 1H), 7.59 (s, 4H), 6.76 (d, J = 3.7 Hz, 1H), 6.13-5.98 (m, 2H), 5.30 (d, J = 6.5 Hz, 1H), 4.97-4.81 (m, 2H), 4.49-4.35 (m, 1H), 4.06 (d, J = 7.1 Hz, 1H), 2.64 (s, 3H), 1.25 (s, 3H). LCMS (MH+): 423.9. |
| 63 | 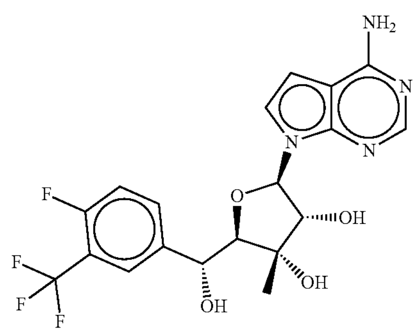 | Ex. 47 | 1H NMR (500 MHz, DMSO-d6) δ 8.04 (s, 1H), 7.73 (t, J = 7.7 Hz, 2H), 7.42 (d, J = 3.6 Hz, 1H), 7.41-7.34 (m, 1H), 7.06 (s, 2H), 6.57 (d, J = 3.6 Hz, 1H), 6.48 (s, 1H), 5.84 (d, J = 8.2 Hz, 1H), 5.25 (d, J = 7.3 Hz, 1H), 4.95-4.85 (m, 1H), 4.79 (s, 1H), 4.46 (t, J = 7.7 Hz, 1H), 3.97 (d, J = 7.0 Hz, 1H), 1.21 (s, 3H). LCMS (MH+): 442.9. |
| 65 | 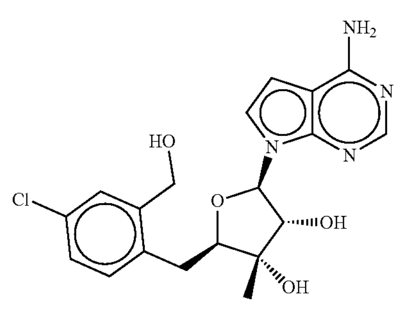 | Ex. 64, Ex. 10. | 1H NMR (400 MHz, DMSO-d6) δ 8.03 (s, 1 H), 7.44 (d, J = 3.6 Hz, 1 H), 7.34 (s, 1H), 7.11 (s, 2 H), 7.00 (br, 2 H), 6.63 (d, J = 3.6 Hz, 1 H), 5.95 (d, J = 7.6 Hz, 1H), 5.33 (d, J =7.2 Hz, 1 H), 5.21 (t, J = 5.2 Hz, 1 H), 4.88 (s, 1 H), 4.45-4.57(m, 2 H), 4.37 (t, J = 7.2 Hz, 1 H), 3.97 (t, J = 7.2 Hz, 1 H), 2.85 (d, J = 6.8 Hz, 2 H), 1.31 (s, 3 H). LCMS (MH+): 405.12/407.1. |

TABLE B-continued

Synthesis of Additional Examples

| Ex. # | Structures | Synthesis similar to Ex. # | Spectra Data |
|---|---|---|---|
| 68 | 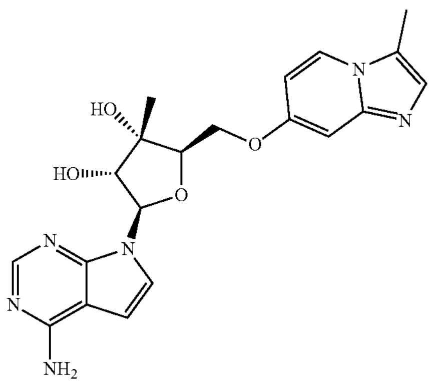 [SMILES: Cc1cnc2cc(OC[C@H]3O[C@@H](n4ccc5c(N)ncnc54)[C@H](O)[C@]3(C)O)ccn12] | Ex. 67, Ex. 47 | 1H NMR (400 MHz, DMSO-d6 + D2O): δ 8.14-8.16 (m, 1H), 8.05-8.06 (m, 1H), 7.39-7.40 (m, 1H), 7.18-7.19 (m, 1H), 7.00-7.01 (m, 1H), 6.73-6.75 (m, 1H), 6.60-6.62 (m, 1H), 6.15-6.16 (m, 1H), 4.39-4.41 (m, 1H), 4.16-4.19 (m, 3H), 2.41 (s, 3H), 1.30 (s, 3H). LCMS (MH+): 411.2. |
| 73 | 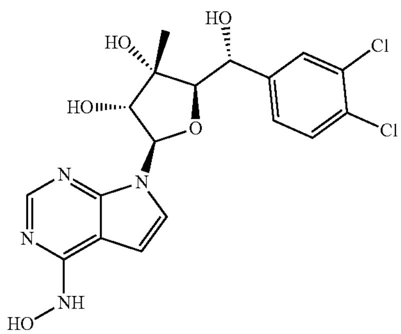 [SMILES: C[C@@]1(O)[C@@H]([C@H](O)c2ccc(Cl)c(Cl)c2)O[C@@H](n2ccc3c(NO)ncnc32)[C@@H]1O] | Ex. 46 | |

Biochemical Assay Protocol

Compounds were solubilized and 3-fold diluted in 100% DMSO. These diluted compounds were further diluted in the assay buffer (50 mM Tris-HCl, pH 8.5, 50 mM NaCl, 5 mM MgCl$_2$, 0.01% Brij35, 1 mM DTT, 1% DMSO) for 10-dose IC$_{50}$ mode at a concentration 10-fold greater than the desired assay concentration. Standard reactions were performed in a total volume of 50 in assay buffer, with histone H2A (5 µM final) as substrate. To this was added the PRMT5/MEP50 complex diluted to provide a final assay concentration of 5 nM and the compounds were allowed to preincubate for 15 to 20 minutes at room temperature. The reaction was initiated by adding S-[3H-methyl]-adenosyl-L-methionine (PerkinElmer) to final concentration of 1 M. Following a 60 minutes incubation at 30° C., the reaction was stopped by adding 100 µL of 20% TCA. Each reaction was spotted onto filter plate (MultiScreen FB Filter Plate, Millipore), and washed 5 times with PBS buffer, Scintillation fluid was added to the filter plate and read in a scintillation counter. IC$_{50}$ values were determined by fitting the data to the standard 4 parameters with Hill Slope using GraphPad Prism software.

Cellular Assay Protocol

Cell Treatment and Western Blotting for Detecting Symmetric Di-Methyl Arginine (sDMA) and Histone H3R8 Dimethyl Symmetric (H3R8me2s) Marks Initial Compounds Screening in A549 Cells:

Compounds were dissolved in DMSO to make 10 mM stock and further diluted to 0.1, and 1 mM. A549 cells were maintained in PRMI 1640 (Corning Cellgro, Catalog #: 10-040-CV) medium supplemented with 10% v/v FBS (GE Healthcare, Catalog #: SH30910.03). One day before experiment, 1.25×10$^5$ cells were seeded in 6 well plate in 3 mL medium and incubated overnight. The next day, medium was changed and 3 uL of compound solution was added (1:1,000 dilution, 0.1 and 1 uM final concentration; DMSO concentration: 0.1%), and incubated for 3 days. Cells incubated with DMSO was used as a vehicle control. Cells were washed once with PBS, trypsinized in 150 uL 0.25% Trypsin (Corning, Catalog #: 25-053-CI), neutralized with 1 mL complete medium, transferred to microCentrifuge tubes and collected. Cell pellet was then resuspended in 15 uL PBS, lysed in 4% SDS, and homogenized by passing through homogenizer column (Omega Biotek, Catalog #: HCR003). Total protein concentrations were determined by BCA assay (ThermoFisher Scientific, Catalog #: 23225). Lysates were mixed with 5× Laemmli buffer and boiled for 5 min. Forty ug of total protein was separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20 (TBST) for 1 hour at room temperature (RT), and incubated with primary antibodies (sDMA: Cell signaling, Catalog #: 13222, 1:3,000; H3R8me2s: Epigentek, Catalog #: A-3706-100, 1:2,000; β-Actin: Abcam, Catalog #: ab8227, 1:10,000) in 5% dry milk in TBST at 4° C. for overnight. The next day, membranes were washed with TBST, 5×5 min, and incubated with HRP conjugated seconded antibody (GE Healthcare; Catalog #: NA934-1ML; 1:5,000) for 2 hours at RT, followed by 5×5 min washes with TBST, and incubation with ECL substrates (Bio-Rad, Catalog #: 1705061, 1705062). Chemiluminescent signal was captured with Fluochem HD2 imager (Proteinsimple) and analyzed by ImageJ.

To determine enzyme inhibition $IC_{50}$ values using Western Blot analysis, Granta cells were seeded at density of $5 \times 10^5$ cells/mL in 3 mL medium (PRMI+10% v/v FBS). Nine-point 3-fold serial dilutions of compound were added to cells (3 ul, 1:1,000 dilution, DMSO concentration was 0.1%; final top concentration was 10 or 1 uM, depending on compounds potency) and incubated for 3 days. Cells incubated with DMSO was used as a vehicle control. Cells were harvested and subjected to western blot analysis as described above. SmD3me2s and H3R8me2s bands were quantified by ImageJ. Signals were normalized to β-Actin and DMSO control. $IC_{50}$ values were calculated using Graphpad Prism.

Cell Proliferation Assay to Determine $IC_{50}$ on Granta-519 Cells

Granta-519 cells were maintained in PRMI 1640 (Corning Cellgro, Catalog #: 10-040-CV) medium supplemented with 10% v/v FBS (GE Healthcare, Catalog #: SH30910.03). Compounds were dissolved in DMSO to make 10 mM stocks and stored at −20° C. Nine-point, 3-fold serial dilutions were made with DMSO with top concentration at 1 mM (working stocks).

On day of experiment, compound working stocks were further diluted at 1:50 with fresh medium in 96 well plate, and 10 µL of diluted drugs were added to a new 96 well plate for proliferation assay. Cells growing at exponential phase were spun down at 1500 rpm for 4 min and resuspend in fresh medium to reach a density of $0.5 \times 10^6$ cells/ml. 200 ul of cells were added to 96 well plate containing diluted drugs and incubated for 3 days. DMSO was used a vehicle control.

One day 3, 10 µL of Cell Counting Kit-8 (CCK-8, Jojindo, CK04-13) solution was added to a new 96 well plate. Cells incubated with drugs for 3 days were resuspended by pipetting up and down, and 100 µL of cells were transferred to 96 well plate containing CCK-8 reagent to measure viable cells. Plates were incubated in $CO_2$ incubator for 2 hours and OD450 values were measured with a microplate reader (iMark microplate reader, Bio-Rad).

For re-plating, compound working stocks were diluted at 1:50 with fresh medium and 10 µL of diluted drugs were added to a new 96 well plate. Cells from Day 3 plate (50 ul) were added to 96 well plate containing fresh drug and additional 150 µL of fresh medium was added to reach 200 µL volume. Plate was returned to $CO_2$ incubator and incubated for 3 more days. Viable cells measurement and re-plating were repeated on day 6, and the final viable cells measurement was taken on day 10.

Percentage of viable cells, relative to DMSO vehicle control, were calculated and plotted in Graphpad Prism ([Inhibitor] vs. normalized response–Variable slope) to determine proliferation $IC_{50}$ values on day 10.

Examples in Table A (above) will have an $IC_{50}$ in the PRMT5 assay of less than 200 µM. Biological activity for exemplary compounds of the disclosure are reported in Table C.

TABLE C

Biochemical and cellular potency (in Granta-519 cell line)

| Ex# | PRMT5 $IC_{50}$ µM | PRMT5 $IC_{50}$ N | sDMA $IC_{50}$ µM | sDMA $IC_{50}$ N | Prolif. $IC_{50}$ µM | Prolif. $IC_{50}$ N |
|---|---|---|---|---|---|---|
| 1 | 0.00075 | 2 | 0.015 | 1 | 0.04 | 1 |
| 2 | 0.0019 | 1 | 0.021 | 1 | | |
| 3 | 0.0016 | 1 | 0.0442 | 1 | | |
| 4 | 0.0087 | 1 | | | | |
| 6 | 0.00085 | 1 | 0.001 | 1 | 0.03 | 1 |
| 10 | 0.0011 | 1 | | | | |
| 12 | 0.0005 | 1 | 0.001 | 1 | | |
| 17 | 0.9 | 1 | 1 | 1 | 200 | 1 |
| 19 | 1.44 | 1 | | | | |
| 20 | 14.3 | 1 | | | | |
| 21 | 7.84 | 1 | | | | |
| 22 | 0.126 | 1 | 60 | 1 | | |
| 26 | 0.0048 | 1 | 0.0514 | 1 | 0.66 | 2 |
| 32 | 0.01 | 1 | | | | |
| 37 | 0.428 | 1 | | | | |
| 40 | 14.1 | 1 | | | | |
| 41 | 200 | 1 | | | | |
| 42 | 9.1 | 1 | | | | |
| 43 | 0.825 | 1 | | | | |
| 44 | 3.48 | 1 | | | | |
| 45 | 11.5 | 1 | | | | |
| 46 | 0.092 | 1 | | | | |
| 47 | 0.0015 | 3 | 0.031 | 3 | 0.075 | 3 |
| 49 | 0.229 | 1 | | | | |
| 50 | 0.017 | 1 | 9 | 1 | | |
| 51 | 0.404 | 1 | | | | |
| 53 | 0.0058 | 1 | | | | |
| 54 | 0.198 | 1 | | | | |
| 55 | 0.0008 | 1 | 0.0051 | 1 | | |
| 56 | 0.068 | 1 | 0.203 | 1 | | |
| 57 | 0.011 | 1 | 0.913 | 1 | | |
| 58 | 0.011 | 1 | 3.16 | 1 | 10 | 1 |
| 59 | 0.399 | 1 | | | | |
| 60 | 0.368 | 1 | | | | |
| 61 | 0.016 | 1 | | | | |
| 62 | 0.007 | 1 | 0.415 | 1 | | |
| 63 | 0.003 | 1 | 0.071 | 2 | 0.231 | 1 |
| 64 | 1.61 | 1 | | | | |
| 65 | 0.413 | 1 | | | | |
| 66 | 0.707 | 1 | | | | |
| 67 | 0.001 | 1 | 0.046 | 2 | | |
| 68 | 0.0009 | 1 | | | | |

FaSSIF Solubility of Example 48

Compounds were first dispersed in freshly prepared FaSSIF (http://biorelevant.com/site_media/upload/documents/How_to_make_FaSSIf_FeSSIF_and_FaSSGF.pdf) buffer in 1 mg/mL respectively, and the standard samples were prepared by preparing 1 mg/mL of test compounds in DMSO. The compounds were then sufficient mixed by vortex mixer for 30 sec, and agitated at 25° C. using 300 rpm form 4 hour in thermo mixer. After incubation, the prepared samples were centrifuged at 10000 rpm for 10 min to remove the undissolved solid, the resulting supernatants were applied to HPLC. The actual concentrations of the compounds were evaluated by measuring the peak area, and the solubility (S) of compounds was calculated according to following equation:

$$S = C_{smp} = C_{std} * (A_{smp}/A_{std}) * (V_{std}/V_{smp})$$

Where C is the sample concentration in µg/mL, A is the peak area, and V is the injection volume.

Warfarin (10-25 µg/mL), Atovaquone (<2 µg/mL) and Nimesulide (100-200 µg/mL) are positive controls in this experiment.

Example 48 was measured to have a FaSSIF solubility of 206 µg/mL.

In Vivo Pharmacokinetic Properties of Example 47.

In a rat (SD, male, non-fasted) non-crossover PK study, Example 47 was dosed at 1 mg/kg (DMA: 20% HPBCD=5:

95, solution) via i.v. administration (N=3) and 1 mg/kg (0.5% Na CMC+0.5% Tween80, solution) via oral gauge (p.o.) (N=3). It showed average $T_{1/2}$ of 4.1 hr, Vss of 3.1 L/kg, blood clearance of 8.8 mL/min/kg in the i.v. group; it showed average dose normalized AUC of 3246 ng*h*kg/mL/mg and >100% of oral bioavailability in the p.o. group.

In Vivo Pharmacodynamic Effect and Tumor Growth Inhibition of Example 47 in Granta-519 Mouse Xenograft Model.

Granta-519 cells was maintained in DMEM medium supplemented with 10% fetal bovine serum and 2 mM L-Glutamine at 37° C. in an atmosphere of 5% $CO_2$ in air. Cells in exponential growth phase were harvested and $1 \times 10^7$ cells in 0.1 mL of PBS with Matrigel (1:1) were injected subcutaneously at the right lower flank region of each mouse for tumor development. The treatments were started when the mean tumor size reaches approximately 300-400 mm³. Mice were assigned into groups using StudyDirector™ software (Studylog Systems, Inc. CA, USA) and one optimal randomization design (generated by either Matched distribution or Stratified method) that shows minimal group to group variation in tumor volume was selected for group allocation. Example 47 or vehicle (0.5% Na CMC+0.5% Tween80, suspension) were administered orally (QD for Example 47, QD for vehicle) at a dose of 30 mg/kg and 50 mg/kg for 19 and 16 days, respectively. Body weights and tumor size were measured every 3 to 4 days after randomization. Animals were euthanized 12 hours after last dosing, and blood and tumor samples were collected for analysis.

To measure sDMA levels in tumor samples, tumors from each mouse were weighted and homogenized in RIPA buffer supplemented with protease inhibitor (cOmplete™ EDTA-free Protease Inhibitor Cocktail, Roche). Lysate were centrifuged at 14,000 rpm for 30 min at 4° C. to remove debris. Total protein concentrations of lysate were determined by BCA assay (ThermoFisher Scientific, Catalog #: 23225). Equal amount of total proteins from each tumor were separated on SDS-PAGE gel, and sDMA levels were determined by WB as described previously.

Following this protocol, Example 47 showed an average of 46% (N=5) tumor growth inhibition at 30 mg/kg with body weight loss of 1%; an average of 79% tumor growth inhibition of at 50 mg/kg with body weight loss of 8%. It also showed >90% inhibition of sDMA at 30 mg/kg and no detectable sDMA at 50 mg/kg.

In addition, the present disclosure is directed to the following aspects:

1. A compound of Formula I:

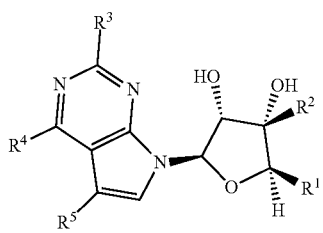

I or a pharmaceutically acceptable salt or solvate thereof, wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-$CO_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl;

$R^2$ is —$C_1$-$C_6$alkyl, —$C_1$-$C_6$haloalkyl, —$C_2$-$C_6$alkenyl, or —$C_2$-$C_6$alkynyl;

$R^3$ is H, halo, $NH_2$, or —$C_1$-$C_6$alkyl;

$R^4$ is halo, —$C_1$-$C_6$alkyl, —$C_1$-$C_6$alk-O—$C_1$-$C_6$alkyl, —$NR^6R^{6'}$, —$NHCONR^6R^{6'}$, —$NHC(S)NR^6R^{6'}$—NH—O—$R^6$, or —NH—$NR^6R^{6'}$;

$R^5$ is H, halo, —$C_1$-$C_6$alkyl, —$C_1$-$C_6$haloalkyl, —$C_2$-$C_6$alkenyl, —$C_2$-$C_6$alkynyl, or —$C_1$-$C_6$alk-OH; and $R^6$ and $R^{6'}$ are each independently H, $C_1$-$C_6$alkyl, or —$C_1$-$C_6$alk-O$C_1$-$C_6$alkyl;

or $R^6$ and $R^{6'}$, together with the atom to which they are attached, form a $C_2$-$C_6$heterocycloalkyl ring.

2. The compound of aspect 1 wherein $R^1$ is —$C_1$-$C_6$alk-O-heteroaryl.

3. The compound of aspect 2 wherein the —$C_1$-$C_6$alk-O-heteroaryl is ((2-amino-3-bromoquinolin-7-yl)oxy)methyl, ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, or ((indazol-6-yl)oxy)methyl.

4. The compound of aspect 1 wherein $R_1$ is —$C_1$-$C_6$alk-S-heteroaryl.

5. The compound of aspect 4 wherein the —$C_1$-$C_6$alk-S-heteroaryl is ((2-amino-3-bromoquinolin-7-yl)thio)methyl, ((2-amino-3-chloroquinolin-7-yl)thio)methyl, ((2-amino-3-fluoroquinolin-7-yl)thio)methyl, ((2-((cyclopropylmethyl)amino)quinolin-7-yl)thio)methyl, ((2-(methylamino)quinolin-7-yl)thio)methyl, ((2-aminoquinolin-7-yl)thio)methyl, ((indol-6-yl) thio)methyl, or ((indazol-6-yl)thio)methyl.

6. The compound of aspect 1 wherein $R_1$ is —$C_1$-$C_6$alk-NH-heteroaryl.

7. The compound of aspect 6 wherein the —$C_1$-$C_6$alk-NH-heteroaryl is ((2-amino-3-bromoquinolin-7-yl) amino)methyl, ((2-amino-3-chloroquinolin-7-yl) amino)methyl, ((2-amino-3-fluoroquinolin-7-yl) amino)methyl, ((2-((cyclopropylmethyl)amino) quinolin-7-yl)amino)methyl, ((2-(methylamino) quinolin-7-yl)amino)methyl, ((2-aminoquinolin-7-yl) amino)methyl, ((indol-6-yl) amino)methyl, or ((indazol-6-yl)amino)methyl.

8. The compound of aspect 1 wherein $R_1$ is —$C_0$-$C_6$alk-heteroaryl.

9. The compound of aspect 8 wherein the —$C_0$-$C_6$alk-heteroaryl is 2-(2-amino-3-bromoquinolin-7-yl)ethyl, 2-(2-amino-3-chloroquinolin-7-yl)ethyl, 2-(2-amino-3-fluoroquinolin-7-yl)ethyl, 2-(2-((cyclopropylmethyl) amino)quinolin-7-yl)ethyl, 2-(2-(methylamino)quinolin-7-yl)ethyl, 2-(2-aminoquinolin-7-yl)ethyl, (indol-6-yl)ethyl, or (indazol-6-yl)ethyl.

10. The compound of aspect 1 wherein R is —$C_1$-$C_6$alk-S—$C_1$-$C_6$alkyl.

11. The compound of aspect 10 wherein the —$C_1$-$C_6$alk-S—$C_1$-$C_6$alkyl is —$CH_2$—S—$CH_3$.

12. The compound of aspect 1 wherein R is —$C_1$-$C_6$alk-S—$C_1$-$C_6$alk-$CO_2$H.

13. The compound of aspect 12 wherein the —$C_1$-$C_6$alk-S—$C_1$-$C_6$alk-$CO_2$H is $CH_2$—S—$CH_2CH_2CH(NH_2)$—$CO_2$H.

14. The compound of aspect 1 wherein R is —$C_1$-$C_6$alk-O—$C_1$-$C_6$alkyl.

15. The compound of aspect 14 wherein the —$C_1$-$C_6$alk-O—$C_1$-$C_6$alkyl is —$CH_2$—O—$CH_3$.
16. The compound of aspect 1 wherein R is —$C_1$-$C_6$alk-O-aryl.
17. The compound of aspect 16 wherein the —$C_1$-$C_6$alk-O-aryl is —$CH_2$—O-phenyl, —$CH_2$—O-difluorophenyl, —$CH_2$—O-3,4-difluorophenyl, —$CH_2$—O-4-chlorophenyl, —$CH_2$—O-3-chloro-4-fluorophenyl, —$CH_2$—O-4-chloro-3-fluorophenyl, —$CH_2$—O-dichlorophenyl, —$CH_2$—O-3,4-dichlorophenyl, —$CH_2$—O-3-methyl-4-chlorophenyl, —$CH_2$—O-3-fluoro-4-trifluoromethylphenyl, —$CH_2$—O-3-(aminomethyl)phenyl, or —$CH_2$—O-3-(urea)phenyl.
18. The compound of aspect 1 wherein R is —$C_0$-$C_6$alk-$C_1$-$C_6$haloalkyl.
19. The compound of aspect 18 wherein the —$C_0$-$C_6$alk-$C_1$-$C_6$haloalkyl is —$CH_2$—Cl.
20. The compound of aspect 1 wherein $R^1$ is —$C_1$-$C_6$alk-aryl.
21. The compound of aspect 20 wherein the —$C_1$-$C_6$alk-aryl is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, or —CH(Me)(OH)-3-fluoro-4-trifluoromethylphenyl.
22. The compound of any one of aspects 1 to 21 wherein $R^2$ is —$C_1$-$C_6$alkyl, preferably methyl.
23. The compound of any one of aspects 1 to 21 wherein $R^2$ is —$C_1$-$C_6$haloalkyl, preferably —$CF_3$.
24. The compound of any one of aspects 1 to 21 wherein $R^2$ is —$C_2$-$C_6$alkenyl, preferably vinyl.
25. The compound of any one of aspects 1 to 21 wherein $R^2$ is —$C_2$-$C_6$alkynyl, preferably ethynyl.
26. The compound of any one of aspects 1 to 25 wherein $R^3$ is H.
27. The compound of any one of aspects 1 to 26 wherein $R^4$ is —$C_1$-$C_6$alkyl.
28. The compound of any one of aspects 1 to 26 wherein $R^4$ is —$C_1$-$C_6$alk-O—$C_1$-$C_6$alkyl.
29. The compound of any one of aspects 1 to 26 wherein $R^4$ is chloro, fluoro, bromo, or iodo.
30. The compound of any one of aspects 1 to 26 wherein $R^4$ is —$NR^6R^{6'}$, wherein $R^6$ and $R^{6'}$ are preferably both H.
31. The compound of any one of aspects 1 to 26 wherein $R^4$ is —$NHCONR^6R^{6'}$, wherein $R^6$ and $R^{6'}$ are preferably both —$C_1$-$C_6$alkyl.
32. The compound of any one of aspects 1 to 26 wherein $R^4$ is $NHC(S)NR^6R^{6'}$.
33. The compound of any one of aspects 1 to 26 wherein $R^4$ is —NH—O—$R^6$, wherein $R^6$ is preferably —$C_1$-$C_6$alkyl.
34. The compound of any one of aspects 1 to 26 wherein $R^4$ is —NH—$NR^6R^{6'}$, wherein $R^6$ and $R^{6'}$ are prefereably both —$C_1$-$C_6$alkyl or wherein $R^6$ is preferably —$C_1$-$C_6$alkyl and $R^{6'}$ is preferably H.
35. The compound of any one of aspects 1 to 34 wherein $R^5$ is H.
36. The compound of any one of aspects 1 to 34 wherein $R^5$ is halo, preferably fluoro.
37. The compound of any one of aspects 1 to 34 wherein $R^5$ is —$C_1$-$C_6$alkyl.
38. The compound of any one of aspects 1 to 34 wherein $R^5$ is —$C_1$-$C_6$haloalkyl.
39. The compound of any one of aspects 1 to 34 wherein $R^5$ is —$C_2$-$C_6$alkenyl, preferably vinyl.
40. The compound of any one of aspects 1 to 34 wherein $R^5$ is —$C_2$-$C_6$alkynyl, preferably ethynyl.
41. The compound of any one of aspects 1 to 34 wherein $R^5$ is —$C_1$-$C_6$alk-OH.
42. A pharmaceutical composition comprising a compound according to any one of aspects 1 to 41 and a pharmaceutically acceptable excipient.
43. A method of inhibiting a protein arginine methyltransferase 5 (PRMT5) enzyme, comprising: contacting the PRMT5 enzyme with an effective amount of a compound of any one of any one of aspects 1 to 41.
44. A method of treating a disease or disorder associated with aberrant PRMT5 activity in a subject comprising administering to the subject, a compound of any one of aspects 1 to 41.
45. The method of aspect 44, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).
46. A compound of Formula I:

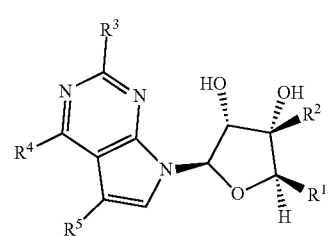

or a pharmaceutically acceptable salt or solvate thereof, wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-$CO_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, —$C_1$-$C_6$alk-NH-heteroaryl, or —C(O)NH-aryl;

$R^2$ is —$C_1$-$C_6$alkyl, —$C_1$-$C_6$haloalkyl, —$C_2$-$C_6$alkenyl, or —$C_2$-$C_6$alkynyl;

$R^3$ is H, halo, $NH_2$, or —$C_1$-$C_6$alkyl;

$R^4$ is halo, —$C_1$-$C_6$alkyl, —$C_1$-$C_6$alk-O—$C_1$-$C_6$alkyl, —$NR^6R^{6'}$, —$NHCONR^6R^{6'}$, —$NHC(S)NR^6R^{6'}$, —NH—O—$R^6$, or —NH—$NR^6R^{6'}$;

$R^5$ is H, halo, —$C_1$-$C_6$alkyl, —$C_1$-$C_6$haloalkyl, —$C_2$-$C_6$alkenyl, —$C_2$-$C_6$alkynyl, or —$C_1$-$C_6$alk-OH; and $R^6$ and $R^{6'}$ are each independently H, $C_1$-$C_6$alkyl, or —$C_1$-$C_6$alk-$OC_1$-$C_6$alkyl;

or $R^6$ and $R^{6'}$, together with the atom to which they are attached, form a $C_3$-$C_6$heterocycloalkyl ring.

47. The compound of aspect 46 wherein $R^1$ is —$C_1$-$C_6$alk-O-heteroaryl.

48. The compound of aspect 47 wherein the —$C_1$-$C_6$alk-O-heteroaryl is ((2-amino-3-bromoquinolin-7-yl)oxy)methyl, ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, 2-(methoxyamino)quinolin-7-yl)oxy)methyl, ((quinolin-7-yl)oxy)methyl, or ((indazol-6-yl)oxy)methyl.

49. The compound of aspect 46 wherein $R_1$ is —$C_1$-$C_6$alk-S-heteroaryl.

50. The compound of aspect 49 wherein the —$C_1$-$C_6$alk-S-heteroaryl is ((2-amino-3-bromoquinolin-7-yl)thio)methyl, ((2-amino-3-chloroquinolin-7-yl)thio)methyl, ((2-amino-3-fluoroquinolin-7-yl)thio)methyl, ((2-((cyclopropylmethyl)amino)quinolin-7-yl)thio)methyl, ((2-(methylamino)quinolin-7-yl)thio)methyl, ((2-aminoquinolin-7-yl)thio)methyl, ((indol-6-yl) thio)methyl, or ((indazol-6-yl)thio)methyl.

51. The compound of aspect 46 wherein $R_1$ is —$C_1$-$C_6$alk-NH-heteroaryl.

52. The compound of aspect 51 wherein the —$C_1$-$C_6$alk-NH-heteroaryl is ((2-amino-3-bromoquinolin-7-yl) amino)methyl, ((2-amino-3-chloroquinolin-7-yl) amino)methyl, ((2-amino-3-fluoroquinolin-7-yl) amino)methyl, ((2-((cyclopropylmethyl)amino) quinolin-7-yl)amino)methyl, ((2-(methylamino) quinolin-7-yl)amino)methyl, ((2-aminoquinolin-7-yl) amino)methyl, ((indol-6-yl) amino)methyl, or ((indazol-6-yl)amino)methyl.

53. The compound of aspect 46 wherein $R_1$ is —$C_0$-$C_6$alk-heteroaryl.

54. The compound of aspect 53 wherein the —$C_0$-$C_6$alk-heteroaryl is 2-(2-amino-3-bromoquinolin-7-yl)ethyl, 2-(2-amino-3-chloroquinolin-7-yl)ethyl, 2-(2-amino-3-fluoroquinolin-7-yl)ethyl, 2-(2-((cyclopropylmethyl) amino)quinolin-7-yl)ethyl, 2-(2-(methylamino)quinolin-7-yl)ethyl, 2-(2-aminoquinolin-7-yl)ethyl, (indol-6-yl)ethyl, or (indazol-6-yl)ethyl.

55. The compound of aspect 46 wherein R is —$C_1$-$C_6$alk-S—$C_1$-$C_6$alkyl.

56. The compound of aspect 55 wherein the —$C_1$-$C_6$alk-S—$C_1$-$C_6$alkyl is —$CH_2$—S—$CH_3$.

57. The compound of aspect 46 wherein R is —$C_1$-$C_6$alk-S—$C_1$-$C_6$alk-$CO_2$H.

58. The compound of aspect 57 wherein the —$C_1$-$C_6$alk-S—$C_1$-$C_6$alk-$CO_2$H is —$CH_2$—S—$CH_2CH_2$CH($NH_2$)—$CO_2$H.

59. The compound of aspect 46 wherein R is —$C_1$-$C_6$alk-O—$C_1$-$C_6$alkyl.

60. The compound of aspect 59 wherein the —$C_1$-$C_6$alk-O—$C_1$-$C_6$alkyl is —$CH_2$—O—$CH_3$.

61. The compound of aspect 46 wherein R is —$C_1$-$C_6$alk-O-aryl.

62. The compound of aspect 61 wherein the —$C_1$-$C_6$alk-O-aryl is —$CH_2$—O-phenyl, —$CH_2$—O-difluorophenyl, —$CH_2$—O-3,4-difluorophenyl, —$CH_2$—O-4-chlorophenyl, —$CH_2$—O-3-chloro-4-fluorophenyl, —$CH_2$—O-4-chloro-3-fluorophenyl, —$CH_2$—O-dichlorophenyl, —$CH_2$—O-3,4-dichlorophenyl, —$CH_2$—O-3-methyl-4-chlorophenyl, —$CH_2$—O-3-fluoro-4-trifluoromethylphenyl, —$CH_2$—O-3-(aminomethyl)phenyl, or —$CH_2$—O-3-(urea)phenyl.

63. The compound of aspect 46 wherein R is —$C_0$-$C_6$alk-$C_1$-$C_6$haloalkyl.

64. The compound of aspect 63 wherein the —$C_0$-$C_6$alk-$C_1$-$C_6$haloalkyl is —$CH_2$—Cl.

65. The compound of aspect 46 wherein $R^1$ is —$C_1$-$C_6$alk-aryl.

66. The compound of aspect 65 wherein the —$C_1$-$C_6$alk-aryl is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, benzo[d][1,3]dioxazol-5-ylmethyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(OH)-benzo[d][1,3]dioxazol-5-yl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH(F)-benzo[d][1,3]dioxazol-5-yl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH($NH_2$)-benzo[d][1,3]dioxazol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —CH(Me)-benzo[d][1,3]dioxazol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —C(Me)(OH)-benzo[d][1,3]dioxazol-5-yl, or —CH(Me)(OH)-3-fluoro-4-trifluoromethylphenyl.

67. The compound of aspect 66, wherein the —$C_1$-$C_6$alk-aryl is —CH(OH)-3,4-dichlorophenyl.

68. The compound of aspect 46 wherein $R^1$ is —C(O)NH-aryl.

69. The compounds of aspect 46 wherein the —C(O)NH-aryl is 3-(aminomethyl)phenyl-NH—C(O)—.
70. The compound of any one of aspects 46 to 69 wherein $R^2$ is —$C_1$-$C_6$alkyl, preferably methyl.
71. The compound of any one of aspects 46 to 69 wherein $R^2$ is —$C_1$-$C_6$haloalkyl, preferably —$CF_3$.
72. The compound of any one of aspects 46 to 69 wherein $R^2$ is —$C_2$-$C_6$alkenyl, preferably vinyl.
73. The compound of any one of aspects 46 to 69 wherein $R^2$ is —$C_2$-$C_6$alkynyl, preferably ethynyl.
74. The compound of any one of aspects 46 to 73 wherein $R^3$ is H.
75. The compound of any one of aspects 46 to 74 wherein $R^4$ is —$C_1$-$C_6$alkyl, preferably methyl.
76. The compound of any one of aspects 46 to 74 wherein $R^4$ is —$C_1$-$C_6$alk-O—$C_1$-$C_6$alkyl.
77. The compound of any one of aspects 46 to 74 wherein $R^4$ is chloro, fluoro, bromo, or iodo.
78. The compound of any one of aspects 46 to 74 wherein $R^4$ is —$NR^6R^{6'}$, wherein $R^6$ and $R^{6'}$ are preferably both H.
79. The compound of any one of aspects 46 to 74 wherein $R^4$ is —$NHCONR^6R^{6'}$, wherein $R^6$ and $R^{6'}$ are preferably both —$C_1$-$C_6$alkyl.
80. The compound of any one of aspects 46 to 74 wherein $R^4$ is —$NHC(S)NR^6R^{6'}$.
81. The compound of anyone aspects 46 to 74 wherein $R^4$ is —NH—O—$R^6$, wherein $R^6$ is preferably —$C_1$-$C_6$alkyl.
82. The compound of any one of aspects 46 to 74 wherein $R^4$ is —NH—$NR^6R^{6'}$, wherein $R^6$ and $R^{6'}$ are preferably both —$C_1$-$C_6$alkyl or wherein $R^6$ is preferably —$C_1$-$C_6$alkyl and $R^{6'}$ is preferably H.
83. The compound of any one of aspects 46 to 82 wherein $R^5$ is H.
84. The compound of any one of aspects 46 to 82 wherein $R^5$ is halo, preferably fluoro.
85. The compound of any one of aspects 46 to 82 wherein $R^5$ is —$C_1$-$C_6$alkyl.
86. The compound of any one of aspects 46 to 82 wherein $R^5$ is —$C_1$-$C_6$haloalkyl.
87. The compound of any one of aspects 46 to 82 wherein $R^5$ is —$C_2$-$C_6$alkenyl, preferably vinyl.
88. The compound of any one of aspects 46 to 82 wherein $R^5$ is —$C_2$-$C_6$alkynyl, preferably ethynyl.
89. The compound of any one of aspects 46 to 82 wherein $R^5$ is —$C_1$-$C_6$alk-OH.
90. A pharmaceutical composition comprising a compound according to any one of aspects 46 to 89 and a pharmaceutically acceptable excipient.
91. A method of inhibiting a protein arginine methyltransferase 5 (PRMT5) enzyme, comprising: contacting the PRMT5 enzyme with an effective amount of a compound of any one of any one of aspects 46 to 89.
92. A method of treating a disease or disorder associated with aberrant PRMT5 activity in a subject comprising administering to the subject, a compound of any one of aspects 46 to 89.
93. The method of aspect 92, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).
94. A compound of Formula I:

I or a pharmaceutically acceptable salt or solvate thereof, wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-$CO_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, —$C_1$-$C_6$alk-NH-heteroaryl, or —C(O)NH-aryl;

$R^2$ is —$C_1$-$C_6$alkyl, —$C_1$-$C_6$haloalkyl, —$C_2$-$C_6$alkenyl, or —$C_2$-$C_6$alkynyl;

$R^3$ is H, halo, $NH_2$, or —$C_1$-$C_6$alkyl;

$R^4$ is halo, —$C_1$-$C_6$alkyl, —$C_1$-$C_6$alk-O—$C_1$-$C_6$alkyl, —$NR^6R^{6'}$, —$NHCONR^6R^{6'}$, —$NHC(S)NR^6R^{6'}$, —NH—O—$R^6$, or —NH—$NR^6R^{6'}$;

$R^5$ is H, halo, —$C_1$-$C_6$alkyl, —$C_1$-$C_6$haloalkyl, —$C_2$-$C_6$alkenyl, —$C_2$-$C_6$alkynyl, or —$C_1$-$C_6$alk-OH; and $R^6$ and $R^{6'}$ are each independently H, $C_1$-$C_6$alkyl, or —$C_1$-$C_6$alk-$OC_1$-$C_6$alkyl;

or $R^6$ and $R^{6'}$, together with the atom to which they are attached, form a $C_3$-$C_6$heterocycloalkyl ring.

95. The compound of aspect 94 wherein $R^1$ is —$C_1$-$C_6$alk-O-heteroaryl.
96. The compound of aspect 95 wherein the —$C_1$-$C_6$alk-O-heteroaryl is ((2-amino-3-bromoquinolin-7-yl)oxy)methyl, ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, 2-(methoxyamino)quinolin-7-yl)oxy)methyl, ((quinolin-7-yl)oxy)methyl, or ((indazol-6-yl)oxy)methyl.
97. The compound of aspect 94 wherein $R_1$ is —$C_1$-$C_6$alk-S-heteroaryl.
98. The compound of aspect 97 wherein the —$C_1$-$C_6$alk-S-heteroaryl is ((2-amino-3-bromoquinolin-7-yl)thio)methyl, ((2-amino-3-chloroquinolin-7-yl)thio)methyl, ((2-amino-3-fluoroquinolin-7-yl)thio)methyl, ((2-((cyclopropylmethyl)amino)quinolin-7-yl)thio)methyl, ((2-(methylamino)quinolin-7-yl)thio)methyl, ((2-aminoquinolin-7-yl)thio)methyl, ((indol-6-yl) thio)methyl, or ((indazol-6-yl)thio)methyl.
99. The compound of aspect 94 wherein $R_1$ is —$C_1$-$C_6$alk-NH-heteroaryl.
100. The compound of aspect 99 wherein the —$C_1$-$C_6$alk-NH-heteroaryl is ((2-amino-3-bromoquinolin-7-yl) amino)methyl, ((2-amino-3-chloroquinolin-7-yl) amino)methyl, ((2-amino-3-fluoroquinolin-7-yl)

amino)methyl, ((2-((cyclopropylmethyl)amino) quinolin-7-yl)amino)methyl, ((2-(methylamino) quinolin-7-yl)amino)methyl, ((2-aminoquinolin-7-yl) amino)methyl, ((indol-6-yl) amino)methyl, or ((indazol-6-yl)amino)methyl.

101. The compound of aspect 94 wherein $R_1$ is —$C_0$-$C_6$alk-heteroaryl.

102. The compound of aspect 101 wherein the —$C_0$-$C_6$alk-heteroaryl is 2-(2-amino-3-bromoquinolin-7-yl)ethyl, 2-(2-amino-3-chloroquinolin-7-yl)ethyl, 2-(2-amino-3-fluoroquinolin-7-yl)ethyl, 2-(2-((cyclopropylmethyl)amino)quinolin-7-yl)ethyl, 2-(2-(methylamino)quinolin-7-yl)ethyl, 2-(2-aminoquinolin-7-yl)ethyl, (indol-6-yl)ethyl, or (indazol-6-yl)ethyl.

103. The compound of aspect 94 wherein R is —$C_1$-$C_6$alk-S—$C_1$-$C_6$alkyl.

104. The compound of aspect 103 wherein the —$C_1$-$C_6$alk-S—$C_1$-$C_6$alkyl is —$CH_2$—S—$CH_3$.

105. The compound of aspect 94 wherein R is —$C_1$-$C_6$alk-S—$C_1$-$C_6$alk-$CO_2$H.

106. The compound of aspect 105 wherein the —$C_1$-$C_6$alk-S—$C_1$-$C_6$alk-$CO_2$H is —$CH_2$—S—$CH_2CH_2CH(NH_2)$—$CO_2$H.

107. The compound of aspect 94 wherein R is —$C_1$-$C_6$alk-O—$C_1$-$C_6$alkyl.

108. The compound of aspect 107 wherein the —$C_1$-$C_6$alk-O—$C_1$-$C_6$alkyl is —$CH_2$—O—$CH_3$.

109. The compound of aspect 94 wherein $R^1$ is —$C_1$-$C_6$alk-O-aryl.

110. The compound of aspect 109 wherein the —$C_1$-$C_6$alk-O-aryl is —$CH_2$—O-phenyl, —$CH_2$—O-difluorophenyl, —$CH_2$—O-3,4-difluorophenyl, —$CH_2$—O-4-chlorophenyl, —$CH_2$—O-3-chloro-4-fluorophenyl, —$CH_2$—O-4-chloro-3-fluorophenyl, —$CH_2$—O-dichlorophenyl, —$CH_2$—O-3,4-dichlorophenyl, —$CH_2$—O-3-methyl-4-chlorophenyl, —$CH_2$—O-3-fluoro-4-trifluoromethylphenyl, —$CH_2$—O-3-(aminomethyl)phenyl, or —$CH_2$—O-3-(urea)phenyl.

111. The compound of aspect 94 wherein R is —$C_0$-$C_6$alk-$C_1$-$C_6$haloalkyl.

112. The compound of aspect 111 wherein the —$C_0$-$C_6$alk-$C_1$-$C_6$haloalkyl is —$CH_2$—Cl.

113. The compound of aspect 94 wherein R is —$C_1$-$C_6$alk-aryl.

114. The compound of aspect 113 wherein the —$C_1$-$C_6$alk-aryl is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, benzo[d][1,3]dioxazol-5-ylmethyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(OH)-benzo[d][1,3]dioxazol-5-yl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH(F)-benzo[d][1,3]dioxazol-5-yl, —CH(NH$_2$)-4-chlorophenyl, —CH(NH$_2$)-3,4-dichlorophenyl, —CH(NH$_2$)-3,4-difluorophenyl, —CH(NH$_2$)-3-fluoro-4-chlorophenyl, —CH(NH$_2$)-3-chloro-4-fluorophenyl, —CH(NH$_2$)-3-methyl-4-chlorophenyl, —CH(NH$_2$)-3-fluoro-4-trifluoromethylphenyl, —CH(NH$_2$)-benzo[d][1,3]dioxazol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —CH(Me)-benzo[d][1,3]dioxazol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —C(Me)(OH)-benzo[d][1,3]dioxazol-5-yl, or —CH(Me)(OH)-3-fluoro-4-trifluoromethylphenyl.

115. The compound of aspect 114, wherein the —$C_1$-$C_6$alk-aryl is —CH(OH)-3,4-dichlorophenyl.

116. The compound of aspect 94 wherein $R^1$ is —C(O)NH-aryl.

117. The compounds of aspect 94 wherein the —C(O)NH-aryl is 3-(aminomethyl)phenyl-NH—C(O)—.

118. The compound of any one of aspects 94 to 117 wherein $R^2$ is —$C_1$-$C_6$alkyl, preferably methyl.

119. The compound of any one of aspects 94 to 117 wherein $R^2$ is —$C_1$-$C_6$haloalkyl, preferably —$CF_3$.

120. The compound of any one of aspects 94 to 117 wherein $R^2$ is —$C_2$-$C_6$alkenyl, preferably vinyl.

121. The compound of any one of aspects 94 to 117 wherein $R^2$ is —$C_2$-$C_6$alkynyl, preferably ethynyl.

122. The compound of any one of aspects 94 to 121 wherein $R^3$ is H.

123. The compound of any one of aspects 94 to 122 wherein $R^4$ is —$C_1$-$C_6$alkyl, preferably methyl.

124. The compound of any one of aspects 94 to 122 wherein $R^4$ is —$C_1$-$C_6$alk-O—$C_1$-$C_6$alkyl.

125. The compound of any one of aspects 94 to 122 wherein $R^4$ is chloro, fluoro, bromo, or iodo.

126. The compound of any one of aspects 94 to 122 wherein $R^4$ is —$NR^6R^{6'}$, wherein $R^6$ and $R^{6'}$ are preferably both H.

127. The compound of any one of aspects 94 to 122 wherein $R^4$ is —$NHCONR^6R^{6'}$, wherein $R^6$ and $R^{6'}$ are preferably both —$C_1$-$C_6$alkyl.

128. The compound of any one of aspects 94 to 122 wherein $R^4$ is —$NHC(S)NR^6R^{6'}$.

129. The compound of any one of aspects 94 to 122 wherein $R^4$ is —NH—O—$R^6$, wherein $R^6$ is preferably —$C_1$-$C_6$alkyl.

130. The compound of any one of aspects 94 to 122 wherein $R^4$ is —NH—$NR^6R^{6'}$, wherein $R^6$ and $R^{6'}$ are preferably both —$C_1$-$C_6$alkyl or wherein $R^6$ is preferably —$C_1$-$C_6$alkyl and $R^{6'}$ is preferably H.

131. The compound of any one of aspects 94 to 130 wherein $R^5$ is H.

132. The compound of any one of aspects 94 to 130 wherein $R^5$ is halo, preferably fluoro.

133. The compound of any one of aspects 94 to 130 wherein $R^5$ is —$C_1$-$C_6$alkyl.

134. The compound of any one of aspects 94 to 130 wherein $R^5$ is —$C_1$-$C_6$haloalkyl.

135. The compound of any one of aspects 94 to 37 wherein $R^5$ is —$C_2$-$C_6$alkenyl, preferably vinyl.

136. The compound of any one of aspects 94 to 130 wherein $R^5$ is —$C_2$-$C_6$alkynyl, preferably ethynyl.

137. The compound of any one of aspects 94 to 130 wherein $R^5$ is —$C_1$-$C_6$alk-OH.

138. A pharmaceutical composition comprising a compound according to any one of aspects 94 to 137 and a pharmaceutically acceptable excipient.

139. A method of inhibiting a protein arginine methyltransferase 5 (PRMT5) enzyme, comprising: contacting the PRMT5 enzyme with an effective amount of a compound of any one of any one of aspects 94 to 137.

140. A method of treating a disease or disorder associated with aberrant PRMT5 activity in a subject comprising administering to the subject, a compound of any one of aspects 94 to 137.

141. The method of aspect 140, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

142. The method of aspect 140 or aspect 141, wherein the compound is administered in combination with one or more other agents.

143. A compound of Formula I:

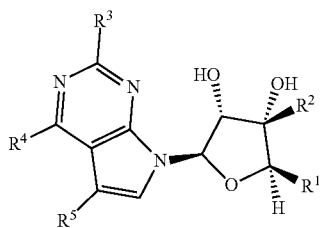

I or a pharmaceutically acceptable salt or solvate thereof, wherein $R^1$ is —$C_0$-$C_6$alk-$C_1$-$C_6$alkyl, —$C_0$-$C_6$alk-$C_1$-$C_6$haloalkyl, —$C_1$-$C_6$alk-O—$C_1$-$C_6$alkyl, —$C_1$-$C_6$alk-S—$C_1$-$C_6$alkyl, —$C_1$-$C_6$alk-S—$C_1$-$C_6$alk-$CO_2$H, —$C_1$-$C_6$alk-aryl, —$C_1$-$C_6$alk-O-aryl, —$C_1$-$C_6$alk-NH-aryl, —$C_1$-$C_6$alk-S-aryl, —$C_0$-$C_6$alk-heteroaryl, —$C_1$-$C_6$alk-O-heteroaryl, —$C_1$-$C_6$alk-S-heteroaryl, —$C_1$-$C_6$alk-NH-heteroaryl, or —C(O)NH-aryl;

$R^2$ is —$C_1$-$C_6$alkyl, —$C_1$-$C_6$haloalkyl, —$C_2$-$C_6$alkenyl, or —$C_2$-$C_6$alkynyl;

$R^3$ is H, halo, $NH_2$, or —$C_1$-$C_6$alkyl;

$R^4$ is H, halo, —$C_1$-$C_6$alkyl, —$C_1$-$C_6$alk-O—$C_1$-$C_6$alkyl, —$NR^6R^{6'}$, —$NHCONR^6R^{6'}$, —$NHC(S)NR^6R^{6'}$, —NH—O—$R^6$, or —NH—$NR^6R^{6'}$;

$R^5$ is H, halo, —$C_1$-$C_6$alkyl, —$C_1$-$C_6$haloalkyl, —$C_2$-$C_6$alkenyl, —$C_2$-$C_6$alkynyl, or —$C_1$-$C_6$alk-OH; and $R^6$ and $R^{6'}$ are each independently H, $C_1$-$C_6$alkyl, or —$C_1$-$C_6$alk-$OC_1$-$C_6$alkyl;

or $R^6$ and $R^{6'}$, together with the atom to which they are attached, form a $C_3$-$C_6$heterocycloalkyl ring.

144. The compound of aspect 143, or a pharmaceutically acceptable salt thereof, wherein $R^1$ is —$C_1$-$C_6$alk-O-heteroaryl.

145. The compound of aspect 144, or a pharmaceutically acceptable salt thereof, wherein the —$C_1$-$C_6$alk-O-heteroaryl is ((2-amino-3-bromoquinolin-7-yl)oxy)methyl, ((2-amino-3-chloroquinolin-7-yl)oxy)methyl, ((2-amino-3-fluoroquinolin-7-yl)oxy)methyl, ((2-((cyclopropylmethyl)amino)quinolin-7-yl)oxy)methyl, ((2-(methylamino)quinolin-7-yl)oxy)methyl, ((2-aminoquinolin-7-yl)oxy)methyl, ((indol-6-yl) oxy)methyl, (2-(methoxyamino)quinolin-7-yl)oxy)methyl, ((quinolin-7-yl)oxy)methyl, ((3-methylimidazo[1,2-a]pyridin-7-yl)oxy)methyl, or ((indazol-6-yl)oxy)methyl.

146. The compound of aspect 143, or a pharmaceutically acceptable salt thereof, wherein $R_1$ is —$C_1$-$C_6$alk-S-heteroaryl.

147. The compound of aspect 146, or a pharmaceutically acceptable salt thereof, wherein the —$C_1$-$C_6$alk-S-heteroaryl is ((2-amino-3-bromoquinolin-7-yl)thio)methyl, ((2-amino-3-chloroquinolin-7-yl)thio)methyl, ((2-amino-3-fluoroquinolin-7-yl)thio)methyl, ((2-((cyclopropylmethyl)amino)quinolin-7-yl)thio)methyl, ((2-(methylamino)quinolin-7-yl)thio)methyl, ((2-aminoquinolin-7-yl)thio)methyl, ((indol-6-yl) thio)methyl, or ((indazol-6-yl)thio)methyl.

148. The compound of aspect 143, or a pharmaceutically acceptable salt thereof, wherein $R_1$ is —$C_1$-$C_6$alk-NH-heteroaryl.

149. The compound of aspect 148, or a pharmaceutically acceptable salt thereof, wherein the —$C_1$-$C_6$alk-NH-heteroaryl is ((2-amino-3-bromoquinolin-7-yl)amino) methyl, ((2-amino-3-chloroquinolin-7-yl)amino) methyl, ((2-amino-3-fluoroquinolin-7-yl)amino) methyl, ((2-((cyclopropylmethyl)amino)quinolin-7-yl) amino)methyl, ((2-(methylamino)quinolin-7-yl)amino) methyl, ((2-aminoquinolin-7-yl)amino)methyl, ((indol-6-yl) amino)methyl, or ((indazol-6-yl)amino)methyl.

150. The compound of aspect 143, or a pharmaceutically acceptable salt thereof, wherein $R_1$ is —$C_0$-$C_6$alk-heteroaryl.

151. The compound of aspect 150, or a pharmaceutically acceptable salt thereof, wherein the —$C_0$-$C_6$alk-heteroaryl is 2-(2-amino-3-bromoquinolin-7-yl)ethyl, 2-(2-amino-3-chloroquinolin-7-yl)ethyl, 2-(2-amino-3-fluoroquinolin-7-yl)ethyl, 2-(2-((cyclopropylmethyl) amino)quinolin-7-yl)ethyl, 2-(2-(methylamino)quinolin-7-yl)ethyl, 2-(2-aminoquinolin-7-yl)ethyl, (indol-6-yl)ethyl, or (indazol-6-yl)ethyl.

152. The compound of aspect 143, or a pharmaceutically acceptable salt thereof, wherein $R^1$ is —$C_1$-$C_6$alk-S—$C_1$-$C_6$alkyl.

153. The compound of aspect 152, or a pharmaceutically acceptable salt thereof, wherein the —$C_1$-$C_6$alk-S—$C_1$-$C_6$alkyl is —$CH_2$—S—$CH_3$.

154. The compound of aspect 143, or a pharmaceutically acceptable salt thereof, wherein $R^1$ is —$C_1$-$C_6$alk-S—$C_1$-$C_6$alk-$CO_2$H.

155. The compound of aspect 154, or a pharmaceutically acceptable salt thereof, wherein the —$C_1$-$C_6$alk-S—$C_1$-$C_6$alk-$CO_2$H is —$CH_2$—S—$CH_2CH_2CH(NH_2)$—$CO_2$H.

156. The compound of aspect 143, or a pharmaceutically acceptable salt thereof, wherein $R^1$ is —$C_1$-$C_6$alk-O—$C_1$-$C_6$alkyl.

157. The compound of aspect 156, or a pharmaceutically acceptable salt thereof, wherein the —$C_1$-$C_6$alk-O—$C_1$-$C_6$alkyl is —$CH_2$—O—$CH_3$.

158. The compound of aspect 143, or a pharmaceutically acceptable salt thereof, wherein $R^1$ is —$C_1$-$C_6$alk-O-aryl.

159. The compound of aspect 158, or a pharmaceutically acceptable salt thereof, wherein the —$C_1$-$C_6$alk-O-aryl is —$CH_2$—O-phenyl, —$CH_2$—O-difluorophenyl, —$CH_2$—O-3,4-difluorophenyl, —$CH_2$—O-4-chlorophenyl, —$CH_2$—O-3-chloro-4-fluorophenyl, —$CH_2$—O-4-chloro-3-fluorophenyl, —$CH_2$—O-dichlorophenyl, —$CH_2$—O-3,4-dichlorophenyl, —$CH_2$—O-3-methyl-4-chlorophenyl, —$CH_2$—O-3-fluoro-4-trifluoromethylphenyl, —$CH_2$—O-3-(aminomethyl)phenyl, or —$CH_2$—O-3-(urea)phenyl.

160. The compound of aspect 143, or a pharmaceutically acceptable salt thereof, wherein $R^1$ is —$C_0$-$C_6$alk-$C_1$-$C_6$haloalkyl.

161. The compound of aspect 160, or a pharmaceutically acceptable salt thereof, wherein the —$C_0$-$C_6$alk-$C_1$-$C_6$haloalkyl is —$CH_2$—Cl.

162. The compound of aspect 143, or a pharmaceutically acceptable salt thereof, wherein $R^1$ is —$C_1$-$C_6$alk-aryl.

163. The compound of aspect 162, or a pharmaceutically acceptable salt thereof, wherein the —$C_1$-$C_6$alk-aryl is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, benzo[d][1,3]dioxazol-5-ylmethyl, —$CH_2$-(4-chloro-2-(hydroxymethyl)phenyl), —$CH_2$-(4-chloro-2-(aminomethyl)phenyl), —$CH_2$-(4-chloro-2-((methylamino)methyl)phenyl), —$CH_2$-4-trifluoromethylphenyl, —$CH_2$-4-(trifluoromethoxy)phenyl, —$CH_2$-4-fluoro-3-trifluoromethylphenyl, —$CH_2$-4-isopropylphenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(OH)-benzo[d][1,3]dioxazol-5-yl, —CH(OH)-(4-chloro-2-(hydroxymethyl)phenyl), —CH(OH)-(4-chloro-2-(aminomethyl)phenyl), —CH(OH)-(4-chloro-2-((methylamino)methyl)phenyl), —CH(OH)-4-trifluoromethylphenyl, —CH(OH)-4-(trifluoromethoxy)phenyl, —CH(OH)-4-fluoro-3-trifluoromethylphenyl, —CH(OH)-4-isopropylphenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH(F)-benzo[d][1,3]dioxazol-5-yl, —CH(F)-(4-chloro-2-(hydroxymethyl)phenyl), —CH(F)-(4-chloro-2-(aminomethyl)phenyl), —CH(F)-(4-chloro-2-((methylamino)methyl)phenyl), —CH(F)-4-trifluoromethylphenyl, —CH(F)-4-(trifluoromethoxy)phenyl, —CH(F)-4-fluoro-3-trifluoromethylphenyl, —CH(F)-4-isopropylphenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH($NH_2$)-benzo[d][1,3]dioxazol-5-yl, —CH($NH_2$)-(4-chloro-2-(hydroxymethyl)phenyl), —CH($NH_2$)-(4-chloro-2-(aminomethyl)phenyl), —CH($NH_2$)-(4-chloro-2-((methylamino)methyl)phenyl), —CH($NH_2$)-4-trifluoromethylphenyl, —CH($NH_2$)-4-(trifluoromethoxy)phenyl, —CH($NH_2$)-4-fluoro-3-trifluoromethylphenyl, —CH($NH_2$)-4-isopropylphenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —CH(Me)-benzo[d][1,3]dioxazol-5-yl, —CH(Me)-(4-chloro-2-(hydroxymethyl)phenyl), —CH(Me)-(4-chloro-2-(aminomethyl)phenyl), —CH(Me)-(4-chloro-2-((methylamino)methyl)phenyl), —CH(Me)-4-trifluoromethylphenyl, —CH(Me)-4-(trifluoromethoxy)phenyl, —CH(Me)-4-fluoro-3-trifluoromethylphenyl, —CH(Me)-4-isopropylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-3-methyl-4-chlorophenyl, —C(Me)(OH)-benzo[d][1,3]dioxazol-5-yl, —C(Me)(OH)-3-fluoro-4-trifluoromethylphenyl, —C(Me)(OH)-(4-chloro-2-(hydroxymethyl)phenyl), —C(Me)(OH)-(4-chloro-2-(aminomethyl)phenyl), —C(Me)(OH)-(4-chloro-2-((methylamino)methyl)phenyl), —C(Me)(OH)-4-trifluoromethylphenyl, —C(Me)(OH)-4-(trifluoromethoxy)phenyl, —C(Me)(OH)-4-fluoro-3-trifluoromethylphenyl, or —C(Me)(OH)-4-isopropylphenyl.

164. The compound of aspect 163, or a pharmaceutically acceptable salt thereof, wherein the —$C_1$-$C_6$alk-aryl is —CH(OH)-3,4-dichlorophenyl.

165. The compound of aspect 143, or a pharmaceutically acceptable salt thereof, wherein $R^1$ is —C(O)NH-aryl.

166. The compounds of aspect 165, or a pharmaceutically acceptable salt thereof, wherein the —C(O)NH-aryl is 3-(aminomethyl)phenyl-NH—C(O)—.

167. The compound of any one of aspects 143 to 166 wherein $R^2$ is —$C_1$-$C_6$alkyl, preferably methyl.

168. The compound of any one of aspects 143 to 166 wherein $R^2$ is —$C_1$-$C_6$haloalkyl, preferably —$CF_3$.

169. The compound of any one of aspects 143 to 166 wherein $R^2$ is —$C_2$-$C_6$alkenyl, preferably vinyl.

170. The compound of any one of aspects 143 to 166 wherein $R^2$ is —$C_2$-$C_6$alkynyl, preferably ethynyl.

171. The compound of any one of aspects 143 to 170 wherein $R^3$ is H.

172. The compound of any one of aspects 143 to 171 wherein $R^4$ is H.

173. The compound of any one of aspects 143 to 171 wherein $R^4$ is —$C_1$-$C_6$alkyl, preferably methyl.

174. The compound of any one of aspects 143 to 171 wherein $R^4$ is —$C_1$-$C_6$alk-O—$C_1$-$C_6$alkyl.

175. The compound of any one of aspects 143 to 171 wherein $R^4$ is chloro, fluoro, bromo, or iodo.

176. The compound of any one of aspects 143 to 171 wherein $R^4$ is —$NR^6R^{6'}$, wherein $R^6$ and $R^{6'}$ are preferably both H.

177. The compound of any one of aspects 143 to 171 wherein $R^4$ is —$NHCONR^6R^{6'}$, wherein $R^6$ and $R^{6'}$ are preferably both —$C_1$-$C_6$alkyl.

178. The compound of any one of aspects 143 to 171 wherein $R^4$ is —$NHC(S)NR^6R^{6'}$.

179. The compound of any one of aspects 143 to 171 wherein $R^4$ is —NH—O—$R^6$, wherein $R^6$ is preferably —$C_1$-$C_6$alkyl.

180. The compound of any one of aspects 143 to 171 wherein R⁴ is —NH—NR⁶R⁶', wherein R⁶ and R⁶' are preferably both —C₁-C₆alkyl or wherein R⁶ is preferably —C₁-C₆alkyl and R⁶' is preferably H.
181. The compound of any one of aspects 143 to 180 wherein R⁵ is H.
182. The compound of any one of aspects 143 to 180 wherein R⁵ is halo, preferably fluoro.
183. The compound of any one of aspects 143 to 180 wherein R⁵ is —C₁-C₆alkyl.
184. The compound of any one of aspects 143 to 180 wherein R⁵ is —C₁-C₆haloalkyl.
185. The compound of any one of aspects 143 to 180 wherein R⁵ is —C₂-C₆alkenyl, preferably vinyl.
186. The compound of any one of aspects 143 to 180 wherein R⁵ is —C₂-C₆alkynyl, preferably ethynyl.
187. The compound of any one of aspects 143 to 180 wherein R⁵ is —C₁-C₆alk-OH.
188. A pharmaceutical composition comprising a compound according to any one of aspects 143 to 187, or a pharmaceutically acceptable salt thereof, and a pharmaceutically acceptable excipient.
189. A method of inhibiting a protein arginine methyltransferase 5 (PRMT5) enzyme, comprising: contacting the PRMT5 enzyme with an effective amount of a compound of any one of aspects 143 to 187, or a pharmaceutically acceptable salt thereof.
190. A method of treating a disease or disorder associated with aberrant PRMT5 activity in a subject comprising administering to the subject, a compound of any one of aspects 143 to 187, or a pharmaceutically acceptable salt thereof.
191. The method of aspect 190, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).
192. The method of aspect 190 or aspect 191, wherein the compound, or a pharmaceutically acceptable salt thereof, is administered in combination with one or more other agents.

What is claimed:
1. A method of treating a disease in a subject comprising administering to the subject a compound, wherein said compound is a compound of formula I-C or formula I-D:

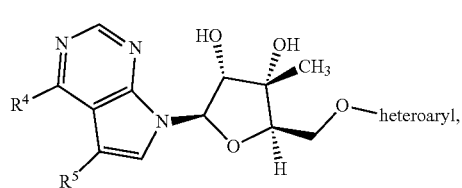

(I-C)

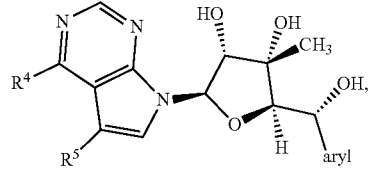

(I-D)

or a pharmaceutically acceptable salt thereof, wherein
R⁴ is —NR⁶R⁶', —NH—O—R⁶ or —NH—NR⁶R⁶';
R⁵ is H or F;
R⁶ and R⁶' are each independently H or —C₁-C₆alkyl;
heteroaryl is quinolinyl, substituted quinolinyl, indolyl, substituted indolyl, indazolyl, substituted indazolyl, imidazo[1,2-a]pyridinyl, or substituted imidazo[1,2-a]pyridinyl; and
aryl is phenyl or substituted phenyl; and
wherein the disease is adenoid cystic carcinoma (ACC), a myeloproliferative disorder, glioblastoma, primary central nervous system lymphoma, acute myeloid leukemia (AML), multiple myeloma (MM), myelodysplastic syndrome (MDS), breast cancer, fallopian tube cancer, ovarian cancer, prostate cancer, pancreatic cancer, or non-Hodgkin lymphoma.

2. The method according to claim 1, wherein R⁴ is NH₂, —NH—OH, —NH—O—CH₃ or —NH—NHCH₃.

3. The method according to claim 1, wherein aryl is -4-chlorophenyl, -3,4-dichlorophenyl, -3,4-difluorophenyl, -3-fluoro-4-chlorophenyl, -3-chloro-4-fluorophenyl, -3-methyl-4-chlorophenyl, -3-fluoro-4-trifluoromethylphenyl, or -4-fluoro-3-trifluoromethylphenyl.

4. The method according to claim 1, wherein said compound is
(2R,3S,4R,5R)-5-(4-amino-7H-pyrrolo[2,3-d]pyrimidin-7-yl)-2-(((2-aminoquinolin-7-yl)oxy)methyl)-3-methyltetrahydrofuran-3,4-diol or a pharmaceutically acceptable salt thereof;
(2R,3S,4R,5R)-5-(4-amino-5-fluoro-7H-pyrrolo[2,3-d]pyrimidin-7-yl)-2-(((2-aminoquinolin-7-yl)oxy)methyl)-3-methyltetrahydrofuran-3,4-diol or a pharmaceutically acceptable salt thereof;
(2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol or a pharmaceutically acceptable salt thereof;
(2R,3 S,4R,5R)-5-(4-amino-7H-pyrrolo[2,3-d]pyrimidin-7-yl)-3-methyl-2-((quinolin-7-yloxy)methyl)tetrahydrofuran-3,4-diol or a pharmaceutically acceptable salt thereof;
(2R,3 S,4R,5R)-5-(4-amino-7H-pyrrolo[2,3-d]pyrimidin-7-yl)-3-methyl-2-(((3-methylimidazo[1,2-a]pyridin-7-yl)oxy)methyl)tetrahydrofuran-3,4-diol or a pharmaceutically acceptable salt thereof;
(2R,3S,4R,5R)-5-(4-amino-7H-pyrrolo[2,3-d]pyrimidin-7-yl)-2-((R)-(4-chlorophenyl)(hydroxy)methyl)-3-methyltetrahydrofuran-3,4-diol or a pharmaceutically acceptable salt thereof;
(Z)-7-((2R,3R,4 S,5R)-5-((R)-(4-chlorophenyl)(hydroxy)methyl)-3,4-dihydroxy-4-methyltetrahydrofuran-2-yl)-3,7-dihydro-4H-pyrrolo[2,3-d]pyrimidin-4-one oxime or a pharmaceutically acceptable salt thereof;
(2R,3S,4R,5R)-5-(4-amino-7H-pyrrolo[2,3-d]pyrimidin-7-yl)-2-((R)-(3,4-dichlorophenyl)(hydroxy)methyl)-3-methyltetrahydrofuran-3,4-diol or a pharmaceutically acceptable salt thereof;

(2R,3S,4R,5R)-5-(4-amino-7H-pyrrolo[2,3-d]pyrimidin-7-yl)-2-((R)-(4-chloro-3-methyl phenyl)(hydroxy)methyl)-3-methyltetrahydrofuran-3,4-diol or a pharmaceutically acceptable salt thereof; or (2R,3S,4R,5R)-5-(4-amino-7H-pyrrolo[2,3-d]pyrimidin-7-yl)-2-((R)-(4-fluoro-3-(trifluoromethyl)phenyl)(hydroxy)methyl)-3-methyltetrahydrofuran-3,4-diol or a pharmaceutically acceptable salt thereof.

5. The method according to claim 1, wherein the compound is

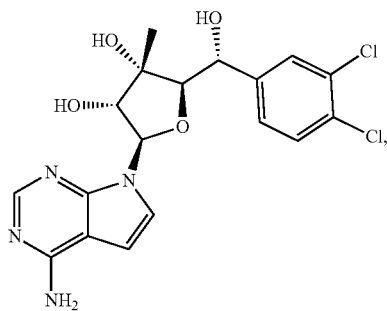 [SMILES: C[C@@]1(O)[C@@H]([C@H](O)c2ccc(Cl)c(Cl)c2)O[C@@H](n2ccc3c(N)ncnc32)[C@@H]1O]

or a pharmaceutically acceptable salt thereof.

6. The method of claim 1, wherein the disease is adenoid cystic carcinoma (ACC).

7. The method of claim 5, wherein the disease is adenoid cystic carcinoma (ACC).

8. The method of claim 1, wherein the disease is a myeloproliferative disorder.

9. The method of claim 5, wherein the disease is a myeloproliferative disorder.

10. The method of claim 1, wherein the disease is glioblastoma.

11. The method of claim 5, wherein the disease is glioblastoma.

12. The method of claim 1, wherein the disease is primary central nervous system lymphoma.

13. The method of claim 5, wherein the disease is primary central nervous system lymphoma.

14. The method of claim 1, wherein the disease is acute myeloid leukemia (AML).

15. The method of claim 5, wherein the disease is acute myeloid leukemia (AML).

16. The method of claim 1, wherein the disease is multiple myeloma (MM).

17. The method of claim 5, wherein the disease is multiple myeloma (MM).

18. The method of claim 1, wherein the disease is myelodysplastic syndrome (MDS).

19. The method of claim 5, wherein the disease is myelodysplastic syndrome (MDS).

20. The method of claim 1, wherein the disease is breast cancer.

21. The method of claim 5, wherein the disease is breast cancer.

22. The method of claim 1, wherein the disease is fallopian tube cancer.

23. The method of claim 5, wherein the disease is fallopian tube cancer.

24. The method of claim 1, wherein the disease is ovarian cancer.

25. The method of claim 5, wherein the disease is ovarian cancer.

26. The method of claim 1, wherein the disease is prostate cancer.

27. The method of claim 5, wherein the disease is prostate cancer.

28. The method of claim 1, wherein the disease is pancreatic cancer.

29. The method of claim 5, wherein the disease is pancreatic cancer.

30. The method of claim 1, wherein the disease is non-Hodgkin lymphoma.

31. The method of claim 5, wherein the disease is non-Hodgkin lymphoma.

32. The method of claim 1, wherein the compound is administered in combination with one or more other agents.

33. The method of claim 5, wherein the compound is administered in combination with one or more other agents.

34. The method of claim 32, wherein the other agent is a JAK kinase inhibitor, a BCL2 inhibitor, or a PARP inhibitor.

35. The method of claim 33, wherein the other agent is a JAK kinase inhibitor, a BCL2 inhibitor, or a PARP inhibitor.

36. The method of claim 34, wherein the JAK kinase inhibitor is ruxolitinib, and the BCL2 inhibitor is venetoclax.

37. The method of claim 35, wherein the JAK kinase inhibitor is ruxolitinib, and the BCL2 inhibitor is venetoclax.

* * * * *